(12) United States Patent
Milsom et al.

(10) Patent No.: US 10,662,429 B2
(45) Date of Patent: *May 26, 2020

(54) COMPOSITIONS AND METHODS TO TREATING HEMOGLOBINOPATHIES

(71) Applicant: THE CHILDREN'S MEDICAL CENTER CORPORATION, Boston, MA (US)

(72) Inventors: Michael Milsom, Dossenheim (DE); David A. Williams, Dover, MA (US); Richard Gregory, Brookline, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/366,900

(22) Filed: Mar. 27, 2019

(65) Prior Publication Data

US 2019/0316136 A1    Oct. 17, 2019

Related U.S. Application Data

(62) Division of application No. 15/306,527, filed as application No. PCT/US2015/027527 on Apr. 24, 2015, now Pat. No. 10,287,588.

(60) Provisional application No. 62/066,783, filed on Oct. 21, 2014, provisional application No. 61/984,247, filed on Apr. 25, 2014.

(51) Int. Cl.
| | | |
|---|---|---|
| C07H 21/04 | (2006.01) | |
| C12N 15/113 | (2010.01) | |
| A61K 35/28 | (2015.01) | |
| C12N 7/00 | (2006.01) | |

(52) U.S. Cl.
CPC .......... *C12N 15/1135* (2013.01); *A61K 35/28* (2013.01); *C12N 7/00* (2013.01); *C12N 15/113* (2013.01); *C12N 2310/141* (2013.01); *C12N 2310/3519* (2013.01); *C12N 2310/531* (2013.01); *C12N 2740/10032* (2013.01); *C12N 2740/10043* (2013.01)

(58) Field of Classification Search
None
See application file for complete search history.

(56) References Cited

U.S. PATENT DOCUMENTS

| | | |
|---|---|---|
| 5,928,638 A | 7/1999 | Uchida et al. |
| 9,228,185 B2 | 1/2016 | Orkin et al. |
| 9,885,041 B2 | 2/2018 | Orkin et al. |
| 2004/0259247 A1 | 12/2004 | Tuschl et al. |
| 2005/0227917 A1 | 10/2005 | Williams et al. |
| 2008/0051431 A1 | 2/2008 | Verhelle et al. |
| 2010/0273213 A1 | 10/2010 | Mineno et al. |
| 2011/0182867 A1 | 7/2011 | Orkin et al. |
| 2014/0018410 A1 | 1/2014 | Novobrantseva et al. |
| 2015/0132269 A1 | 5/2015 | Orkin et al. |

FOREIGN PATENT DOCUMENTS

| | | |
|---|---|---|
| EP | 1752536 A1 | 2/2007 |
| EP | 2334794 B1 | 11/2016 |
| EP | 2334794 B8 | 4/2017 |
| JP | 2006507841 A | 3/2006 |
| WO | 2009/007685 A2 | 1/2009 |
| WO | 2011/072086 A1 | 6/2011 |
| WO | 2012/073047 A2 | 6/2012 |
| WO | 2014/085593 A1 | 6/2014 |
| WO | 2015/065964 A1 | 5/2015 |
| WO | 2016/182893 A1 | 11/2016 |

OTHER PUBLICATIONS

Moffat et al., "A lentiviral RNAi library for human and mouse genes applied to an arrayed viral high-content screen." Cell 124(6):1283-1298 (2006).
Nemudryi et al., "TALEN and CRISPR/Cas Genome Editing Systems: Tools of Discovery" Acta Naturae, 6(3):19-40 (2014).
Neven et al., "A Mendelian predisposition to B-cell lymphoma caused by IL-10R deficiency," Blood 3713-3722 (2013).
Orkin et al., "Recent advances in globin research using genome-wide association studies and gene editing." Annals of the New York Academy of Sciences 1368 (1):5-10 (2016).
Papayannopoulou et al., "Erythroid progenitors circulating in the blood of adult individuals produce fetal hemoglobin in culture." Science 199(4335):1349-1350 (1978).
Pauling et al., "Sickle cell anemia a molecular disease." Science 110(2865):543-548 (1949).
Pembrey et al., "Fetal haemoglobin production and the sickle gene in the oases of Eastern Saudi Arabia." British journal of haematology 40(3):415-429 (1978).
Perrine "Fetal globin induction—can it cure beta thalassemia?" American Society of Hematology Education Program Book pp. 38-44 (2005).
Platt et al., "Mortality in sickle cell disease. Life expectancy and risk factors for early death." New England Journal of Medicine 330(23):1639-1644 (1994).
Purton et al., "All-trans retinoic acid enhances the long-term repopulating activity of cultured hematopoietic stem cells." Blood 95(2):470-477 (2000).
Renella et al. "Hematopoietic SIN lentiviral micro RNA-mediated silencing of BCL11A: pre-clinical evidence for a sickle cell disease gene-therapy trial." 120(21):Abstract 753 (2012).
Ridley et al., "Erythropoietin: A Review" J Natl Med Assoc., 86(2):129-135 (1994).
Rodriguez et al., "A bioavailability and pharmacokinetic study of oral and intravenous hydroxyurea." Blood 9 (5):1533-1541 (1998).
Rosenblum et al., "Peripheral blood erythroid progenitors from patients with sickle cell anemia: HPLC separation of hemoglobins and the effect of a HbF switching factor." Progress in Clinical and Biological Research 191:397-410 (1985).

(Continued)

*Primary Examiner* — Kimberly Chong
(74) *Attorney, Agent, or Firm* — Nixon Peabody LLP

(57) ABSTRACT

Embodiments herein provide specially designed synthetic BCL11A-targeting microRNAs for RNA polymerase II expression, and methods of use to treat hemoglobinopathies such as sickle cell disease or thalassemia by increasing the expression levels of fetal hemoglobin levels.

17 Claims, 56 Drawing Sheets

Specification includes a Sequence Listing.

(56) References Cited

OTHER PUBLICATIONS

Saiki et al., "Human EVI9, a homologue of the mouse myeloid leukemia gene, is expressed in the hematopoietic progenitors and down-regulated during myeloid differentiation of HL60 cells." Genomics 70(3):387-391 (2000).

Sankaran et al., "Developmental and species-divergent globin switching are driven by BCL11A." Nature 460(7259):1093-1097 (2009).

Sankaran et al., "Human fetal hemoglobin expression is regulated by the developmental stage-specific repressor BCL11A." Science 322(5909):1839-1843 (2008).

Sankaran et al., "Targeted therapeutic strategies for fetal hemoglobin induction." American Society of Hematology Education Program Book 2011(1):459-465 (2011).

Satterwhite et al., "The BCL11 gene family: involvement of BCL11A in lymphoid malignancies." Blood, 98(12):3413-3420 (2001).

Schopman et al. "Optimization of shRNA inhibitors by variation of the terminal loop sequence." Antiviral Research 86(2):204-211 (2010).

Sebastiani et al., "BCL11A enhancer haplotypes and fetal hemoglobin in sickle cell anemia." Blood Cells, Molecules, and Diseases 54(3):224-230 (2015).

Sedgewick et al., "BCL11A is a major HbF quantitative trait locus in three different populations with β-hemoglobinopathies." Blood Cells, Molecules, and Diseases 41(3):255-258 (2008).

Shen et al., "Modifcation of globin gene expression by RNA targeting strategies." Experimental Hematology, 35(8):1209-1218 (2007).

Takeuchi et al., "Redesign of extensive protein—DNA interfaces of meganucleases using iterative cycles of in vitro compartmentalization." PNAS 111(11):4061-4066 (2014).

Taymans et al., "Radiation hybrid mapping of chromosomal region 2p15-p16: integration of expressed and polymorphic sequences maps at the Carney complex (CNC) and Doyne honeycomb retinal dystrophy (DHRD) loci." Genomics 56(3):344-349 (1999).

Terasawa et al., "Synthetic pre-miRNA-based shRNA as potent RNAi triggers." Journal of Nucleic Acids (2011).

Thein "Genetic modifiers of the beta-haemoglobinopathies." British Journal of Hematology, 141(3):357-366 (2008).

Thein et al., "Discovering the genetics underlying foetal haemoglobin production in adults." British Journal of Haematology 145(4):455-467 (2009).

Thompson "Structure, Function, and Molecular Defects of Factor IX." Blood 67(3):565-72 (1986).

Uda et al., "Genome-wide association study shows BCL11A associated with persistent fetal hemoglobin and amelioration of the phenotype of β-thalassemia." PNAS 105(5):1620-1625 (2008).

Wang et al. "Genetic screens in human cells using the CRISPR/Cas9 system." Science 343(6166):80-84 (2013).

Wang et al. "Supplementary Material: Genetic screens in human cells using the CRISPR/Cas9 system." Science 343(6166):80-84 (2013).

Wang et al., "In Vivo Delivery Systems for Therapeutic Genome Editing" International Journal of Molecular Sciences 17(5):1-19 (2016).

Wang et al., "Selection of hyperfunctional siRNAs with improved potency and specificity." Nucleic Acids Research 37(22):e152 (2009).

White et al., "Factor VIII Gene and Hemophili A." Blood 73(1):1-12 (1989).

World Health Organization. "Sickle-cell anaemia. Report A59/9. Provisional agenda item 11.4." 59th World Health Assembly. www.who.int/gb/ebwha/pdf_files/WHA59/A59_9-en.pdf (2006).

Xu et al., "Correction of sickle cell disease in adult mice by interference with fetal hemoglobin silencing", Science 334(6058):993-996 (2011).

Xu et al., "Reactivation of silenced human HbF in adult mice by inactivation of BCL11A." Blood 116:Abstract 643 (2010).

Xu et al., "Transcriptional silencing of beta-globin by BCL11A involvs long-range interactions and cooperation with SOX6." Genes and Development 24(8):783-798 (2010).

Yin et al., "Bcl11a Causes p21 Cip1 Down-Regulation and Transplantable Leukemia in Nf1-Deficient Mice." Blood 110(11):2657-2657 (2007) [Abstract Only].

Akinsheye et al., "Fetal hemoglobin in sickle cell anemia." Blood 118(1):19-27 (2011).

Amaya et al., "Mi2β-mediated silencing of the fetal γ-globin gene in adult erythroid cells." Blood 121(17)3493-501 (2013).

Amendah et al., "Sickle cell disease-related pediatric medical expenditures in the U.S." American Journal of Preventive Medicine 38(4 Suppl):S550-S556 (2010).

Atweh et al., "Pharmacological induction of fetal hemoglobin in sickle cell disease and beta-thalassemia." Seminars in Hematology 38(4):367-73 (2001).

Bauer et al., "An Erythroid Enhancer of BCL11A Subject to Genetic Variation Determines Fetal Hemoglobin Level." Science 342(6155):253-257 (2013).

Bauer et al., "HbF-Associated Genetic Variation Marks an Erythroid Regulatory Element Essential for BCL11A Transcription and Subsequent Stage-Specific Globin Expression." Blood 120:828 (2012).

Bauer et al., "Hemoglobin switching's surprise: the versatile transcription factor BCL11A is a master repressor of fetal hemoglobin" Current Opinion in Genetics & Development 33:62-70 (2015).

Bauer et al., "Reawakening fetal hemoglobin: prospects for new therapies for the B-globin disorders." Blood 120(15):2945-2953 (2012).

Bauer et al., "Supplementary Material: An Erythroid Enhancer of BCL11A Subject to Genetic Variation Determines Fetal Hemoglobin Level." Science 342(6155):253-257 (2013).

Bjurström et al. "Reactivating fetal hemoglobin expression in human adult erythroblasts through BCL11A knockdown using targeted endonucleases." Molecular Therapy-Nucleic Acids 5:e351 (2016).

Boettcher et al., "Choosing the right tool for the job: RNAi, TALEN, or CRISPR." Molecular Cell 58(4):575-585 (2015).

Bohmer et al., "Identification of fetal nucleated red cells in co-cultures from fetal and adult peripheral blood: differential effects of serum on fetal and adult erythropoiesis." Prenatal Diagnosis 19(7):628-636 (1999).

Bunn "Reversing ontogeny." New Engl. J. Med. 328(2):129-131 (1993).

Canver et al., "BCL11A enhancer dissection by Cas9-mediated in situ saturating mutagenesis." Nature 527(7577)192-197 (2015).

Cao et al., "Recent advances in B-thalassemias." Pediatric Reports 3(2):65-71 (2011).

Chabchoub et al., "The facial dysmorphy in the newly recognised microdeletion 2p15-p16.1 refined to a 570 kb region in 2p15." Journal of Medical Genetics 45(3):189-192 (2008).

Coleman et al., "Sickle cell anemia: targeting the role of fetal hemoglobin in therapy." Clinical Pediatrics 46(5):386-391 (2007).

Cox et al., "Therapeutic genome editing: prospects and challenges" Nature Medicine 21(2):121-131 (2015).

Dixit et al., "Hydroxyurea in thalassemia intermedia—a promising therapy." Annals of Hematology 84(7):441-446 (2005).

Doench et al., "Rational design of highly active sgRNAs for CRISPR-Cas9-mediated gene inactivation." Nature Biotechnology 32(12):1262-1267 (2014).

Doench et al., "Supplementary Material: Rational design of highly active sgRNAs for CRISPR-Cas9-mediated gene inactivation." Nature Biotechnology 32(12):1262-1267 (2014).

Examination Search Report, dated May 11, 2018 in corresponding Canadian No. 2737180.

Fenaux "Inhibitors of DNA methylation: beyond myelodysplastic syndromes." Nature Reviews Clinical Oncology 2(S21):S36-S44 (2005).

Fischer et al., "Pulmonary Passage is a Major Obstacle for Intravenous Stem Cell Delivery: The Pulmonary First-Pass Effect" Stem Cells and Development 18(5):683-91 (2009).

Flanagan et al., "Hydroxycarbamide alters erythroid gene expression in children with sickle cell anaemia." British Journal of Haematology 157(2):240-248 (2012).

(56) References Cited

OTHER PUBLICATIONS

GeneCard for BCL11A, retrieved from http://www.genecards.org/cgi-bin/carddisp.pl?gene=BCL11A on Jun. 22, 2012.
Goffin et al., "DNA methyltransferase inhibitors—state of the art." Annals of Oncology 13(11):1699-716 (2002).
Goldberg et al., "Treatment of sickle cell anemia with hydroxyurea and erythropoietin." New England Journal of Medicine 323(6):366-372 (1990).
Hackam "Translating animal research into clinical benefit" BMJ 334:163-68 (2007).
Hancarova et al. "A patient with de novo 0.45 Mb deletion of 2p16.1: The role of BCL11A, PAPOLG, REL, and FLJ16341 in the 2p15-p16.1 microdeletion syndrome." American Journal of Medical Genetics Part A 161(4):865-870 (2013).
Harding et al., "Large animal models for stem cell therapy", Stem Cell Research & Therapy 4(23):1-9 (2013).
Hebbel et al., "The HDAC inhibitors trichostatin A and suberoylanilide hydroxamic acid exhibit multiple modalities of benefit for the vascular pathobiology of sickle transgenic mice." Blood 115(12):2483-2490 (2010).
Hendel et al., "Chemically modified guide RNAs enhance CRISPR-Cas genome editing in human primary cells." Nature Biotechnology 33(9):985-989 (2015).
Higgs et al., "Genetic complexity in sickle cell disease." PNAS 105(33):11595-11596 (2008).
Ho et al., "In vitro induction of fetal hemoglobin in human erythroid progenitor cells." Experimental Hematology 31(7):586-591 (2003).
Hsieh et al., "Allogeneic hematopoietic stem-cell transplantation for sickle cell disease." New England Journal of Medicine 361(24):2309-2317 (2009).
Jane et al., "Understanding fetal globin gene expression: a step towards effective HbF reactivation in haemoglobinopathies." British Journal of Haematology 102(2):415-423 (1998).
Kauf et al., "The cost of health care for children and adults with sickle cell disease." American Journal of Hematology 84(6):323-327 (2009).
Kirschner et al., "Genomic mapping of chromosomal region 2p15-p21 (D2S378-D2S391): integration of Genemap'98 within a framework of yeast and bacterial artificial chromosomes" Genomics 62(1):21-33 (1999).
Koshy et al., "2-deoxy 5-azacytidine and fetal hemoglobin induction in sickle cell anemia." Blood 96(7):2379-2384 (2000).
Labie "Le contrôle en trans de la production d'hémoglobine fœtale: une recherche qui dure depuis 20 ans." Hématologie 14(2):165-166 (2008).
Lettre et al., "DNA polymorphisms at the BCL11A, HBS1L-MYB, and beta-globin loci associate with fetal hemoglobin levels and pain crises in sickle cell disease." PNAS 105(33):11869-11874 (2008).
Liu et al., "Bcl11a is essential for normal lymphoid development." Nature Immunology 4(6):525-532 (2003).
Liu et al., "Functional studies of BCL11A: characterization of the conserved BCL11A-XL splice variant and its interaction with BCL6 in nuclear paraspeckles of germinal center B cells." Molecular Cancer 5(18):1-6 (2006).
Lulli et al., "MicroRNA-486-3p regulates γ-globin expression in human erythroid cells by directly modulating BCL11A." PLoS One 8(4):e60436 (2013).
Makala et al., "Fetal Hemoglobin Induction to Treat b-Hemoglobinopathies: From Bench to Bedside" J Hematol Transfus 2(2):1-2 (2014).
Martin-Subero et al., "Recurrent involvement of the REL and BCL11Aloci in classical Hodgkin lymphoma." Blood 99(4):1474-1477 (2002).
Matsuda et al., "Transcription factors LRF and BCL11A independently repress expression of fetal hemoglobin" Science 351(6270):285-289 (2016).
Menzel et al., "A QTL influencing F cell production maps to a gene encoding a zinc-finger protein on chromosome 2p15." Nature Genetics 39(10):1197-1199 (2007).
Migliaccio et al., "Influence of recombinant hematopoietins and of fetal bovine serum on the globin synthetic pattern of human BFUe." Blood 76(6):1150-1157 (1990).
GenBank Accession No. NM_022893.4. "*Homo sapiens* BAF chromatin remodeling complex subunit BCL11A (BCL11A), transcript variant 1, mRNA." https://www.ncbi.nlm.nih.gov/nuccore/NM_022893.4 (2019).

```
Bcl11a miR1 oligonucleotides:
Sense       (SEQ. ID. NO: 1)   ACGCTCGGCACAGAACACTCATGGATTctccatgtgtagagAATCCATGAGTGTTCTGTGCCGAG
Anti-sense  (SEQ. ID. NO: 2)   CGCACTCGGCACAGAACACTCATGGATTctctaccacatgagagAATCCATGAGTGTTCTGTGCGA Bcl11a miR2 oligonucleotides:
Sense       (SEQ. ID. NO: 3)   ACGCTCCAGAGGATGACGATTGTTTActccatgtgtagagTAAACAATCGTCATCCTCTGGag
Anti-sense  (SEQ. ID. NO: 4)   CGCActCCAGAGGATGACGATTGTTTActctaccacatggagTAAACAATCGTCATCCTCTGGa Italicized lower bases = shRNA loop
Bold and upper case bases = BCL11A targeting sequence for forming a shRNA
Underlined bases          = Cloning ends (synthetic)
```

FIG. 1

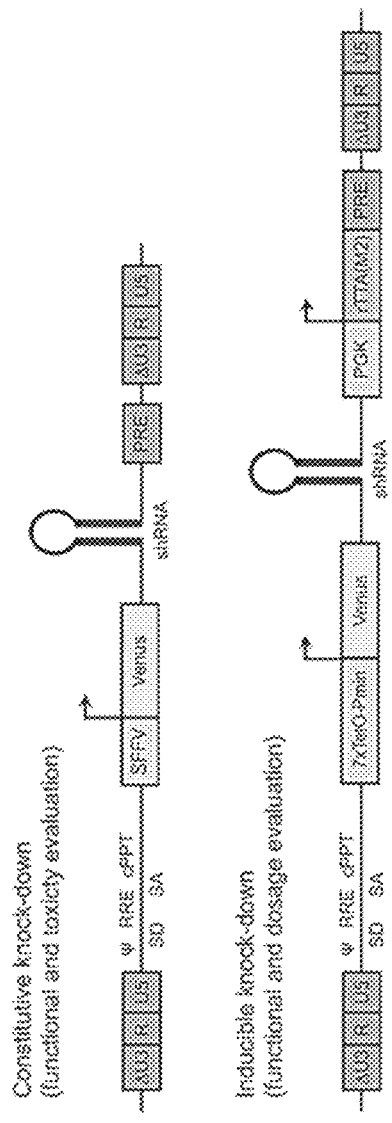

FIG. 2

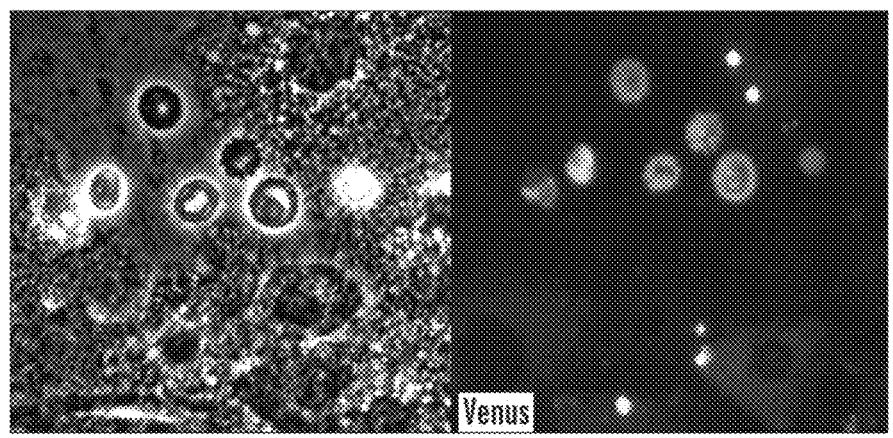
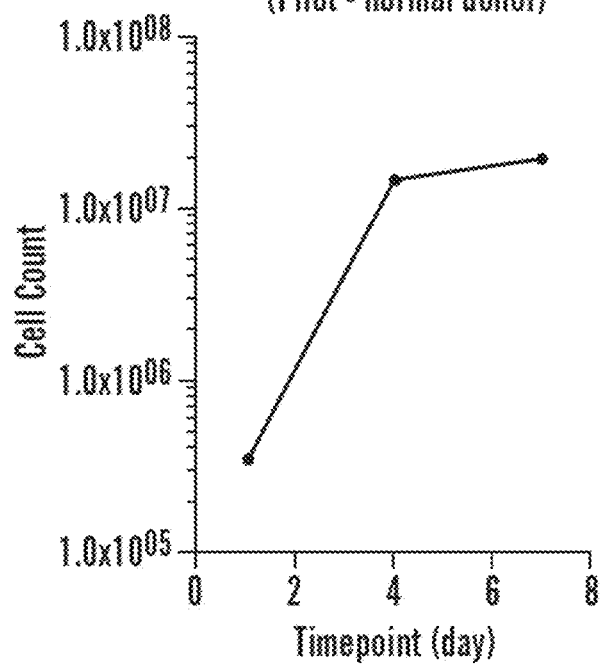
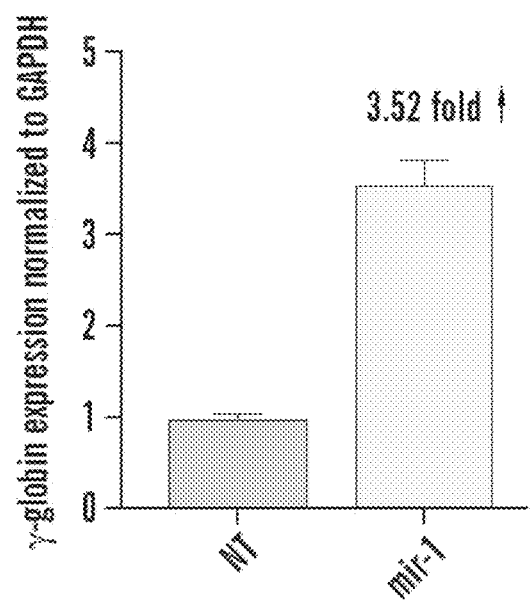
FIG. 5 (cont.)

Investigating potential toxicity of Bcl11a role in lymphoid development
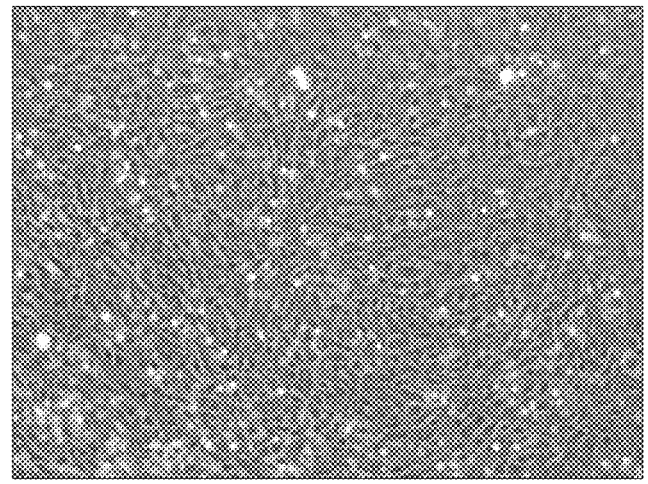
Venus-sorted hCD34 HSC on MS-5, 100x
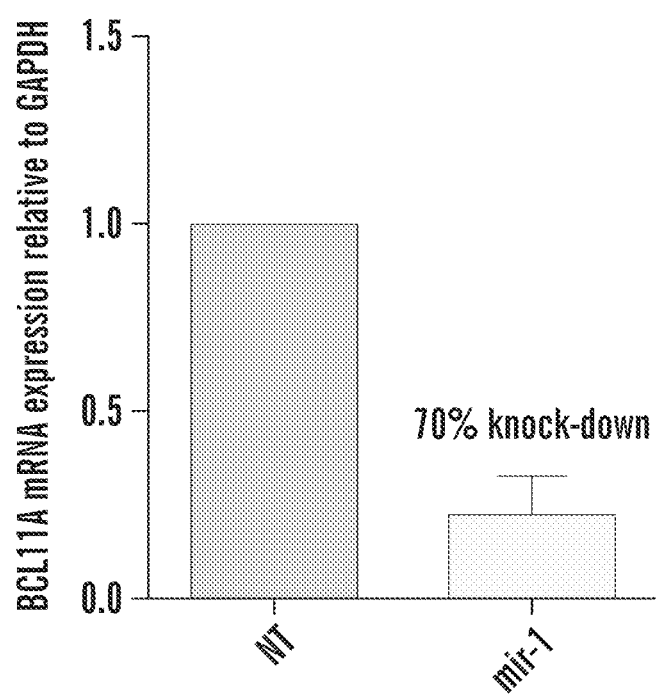
FIG. 7

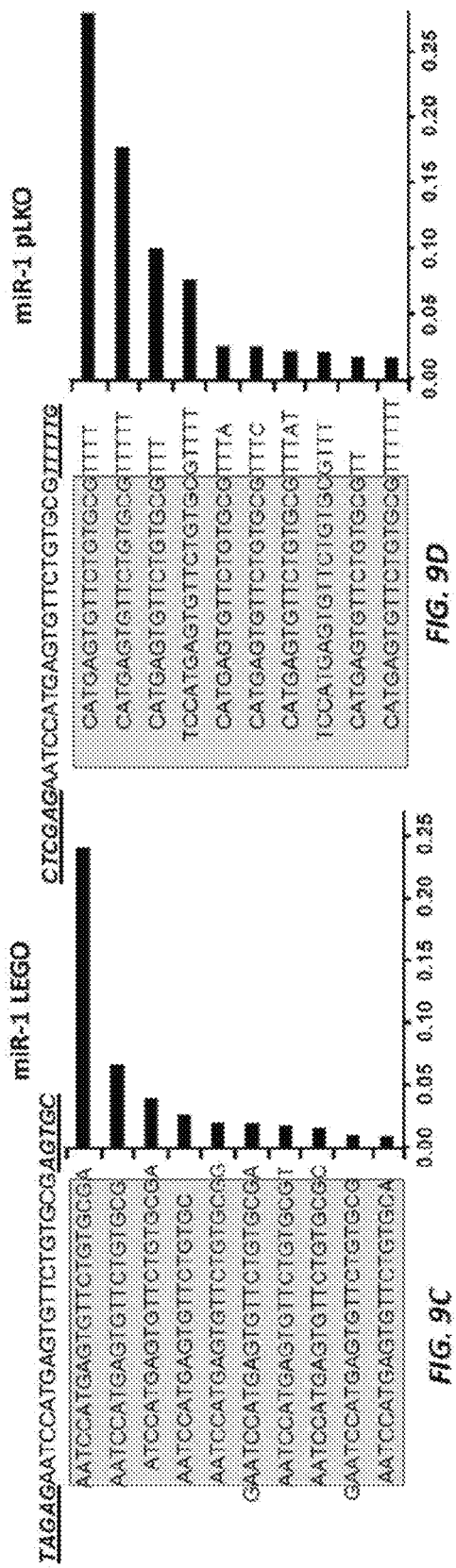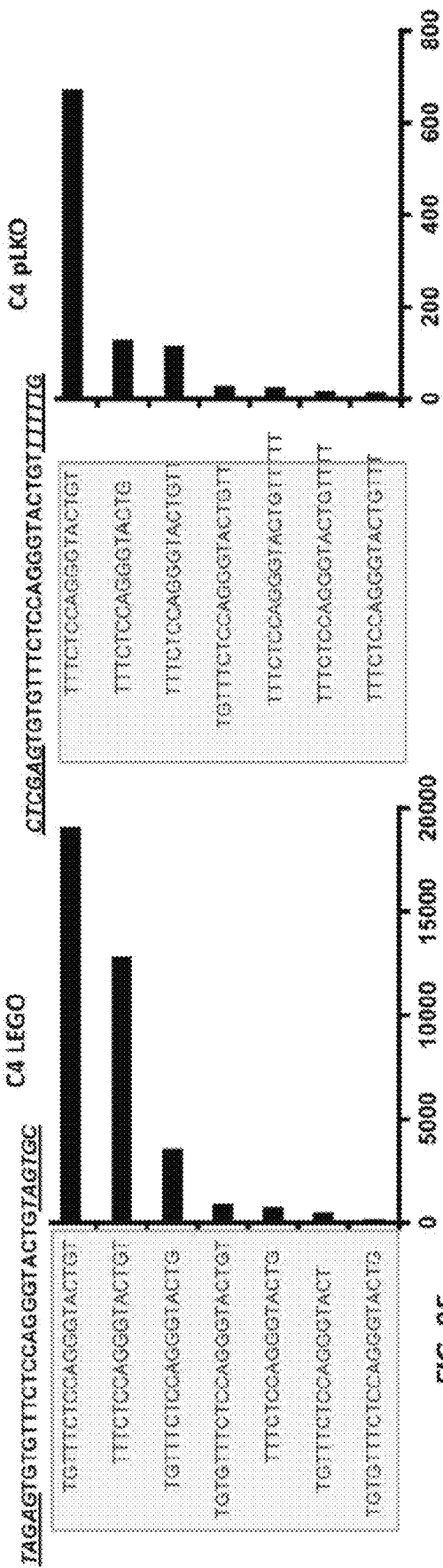

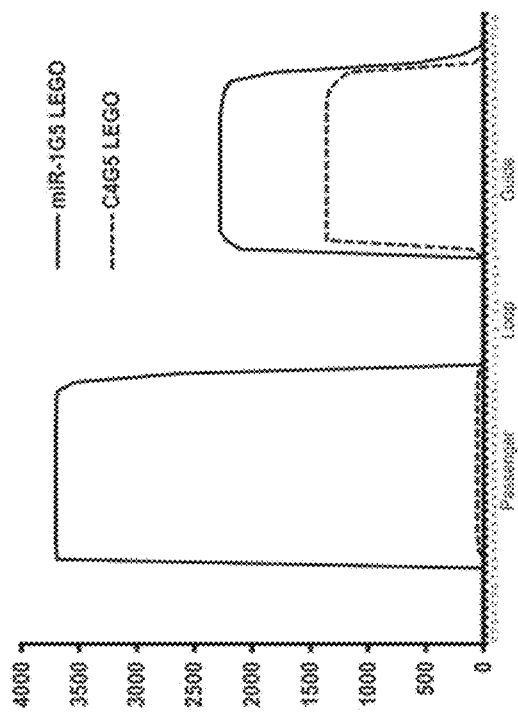
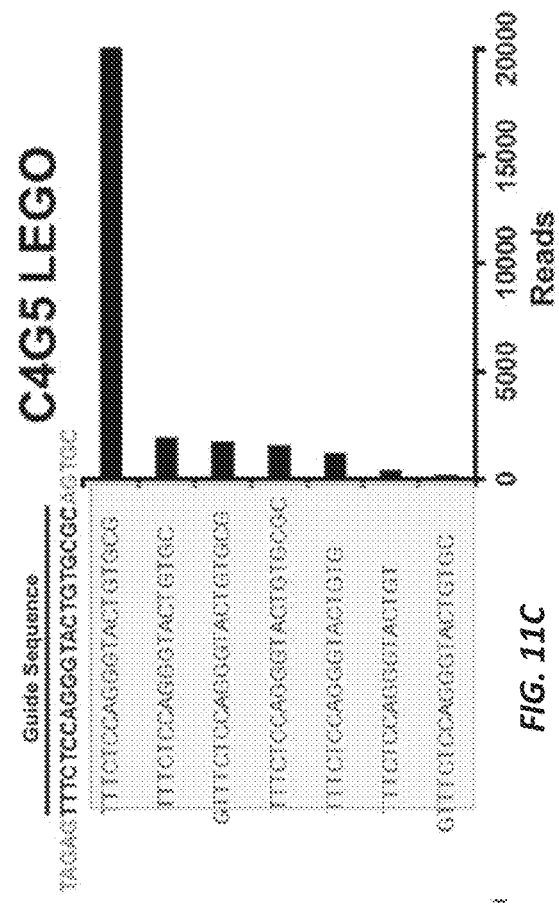
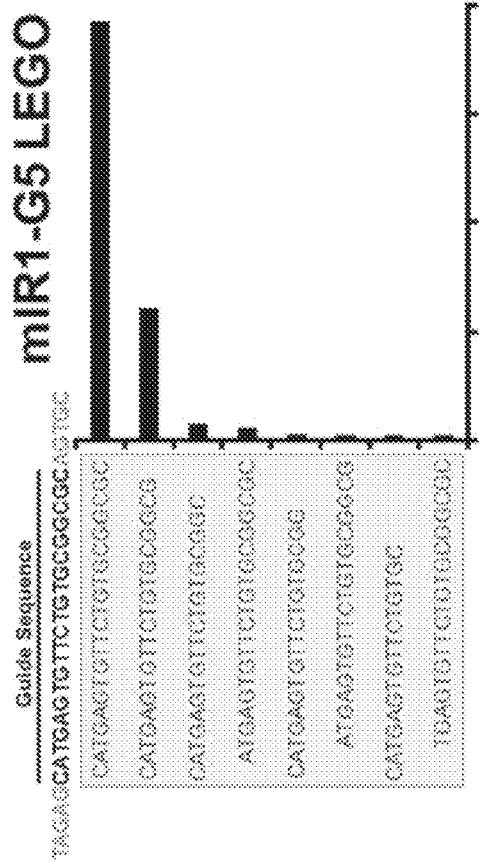
FIG. 11A
FIG. 11B
FIG. 11C

Candidates from the shRNA screen targeting Bcl11A using pLKO vector

| | Passenger | Loop | Guide | |
|---|---|---|---|---|
| miR1 | CGCACAGAACACTCATGGATT | ctccatgtggtagag | AATCCATGAGTGTTCTGTGCG | SEQ. ID. NO: 25 |
| E3 | TCGGAGACTCCAGACAATCGC | ctccatgtggtagag | GCCGATTGTCTGGAGTCTCCGA | SEQ. ID. NO: 26 |
| B5 | CCTCCAGGCAGCTCAAAGATC | ctccatgtggtagag | GATCTTTGAGCTGCCTGGAGG | SEQ. ID. NO: 27 |
| D8 | TTCTCTGTGCAACACGCACAGA | ctccatgtggtagag | TCTGTGCGTGTTGCAAGAGAA | SEQ. ID. NO: 28 |
| B11 | TCAGGACTAGGTGCAGAATGT | ctccatgtggtagag | ACATTCTGCACCTAGTCCTGA | SEQ. ID. NO: 29 |
| 50D12 | GATCGAGTGTTGAATAATGAT | ctccatgtggtagag | ATCATTATTCAACACTCGATC | SEQ. ID. NO: 30 |
| 50B11 | CACTGTCCACAGGAGAAGCCA | ctccatgtggtagag | TGGCTTCTCCTGTGGACAGTG | SEQ. ID. NO: 32 |
| 50A5 | CAGTACCCTGGAGAAACACAT | ctccatgtggtagag | ATGTGTTTCTCCAGGGTACTG | SEQ. ID. NO: 31 |
| 50C4 | ACAGTACCCTGGAGAAACACA | ctccatgtggtagag | TGTGTTTCTCCAGGGTACTGT | SEQ. ID. NO: 33 |

FIG. 12A

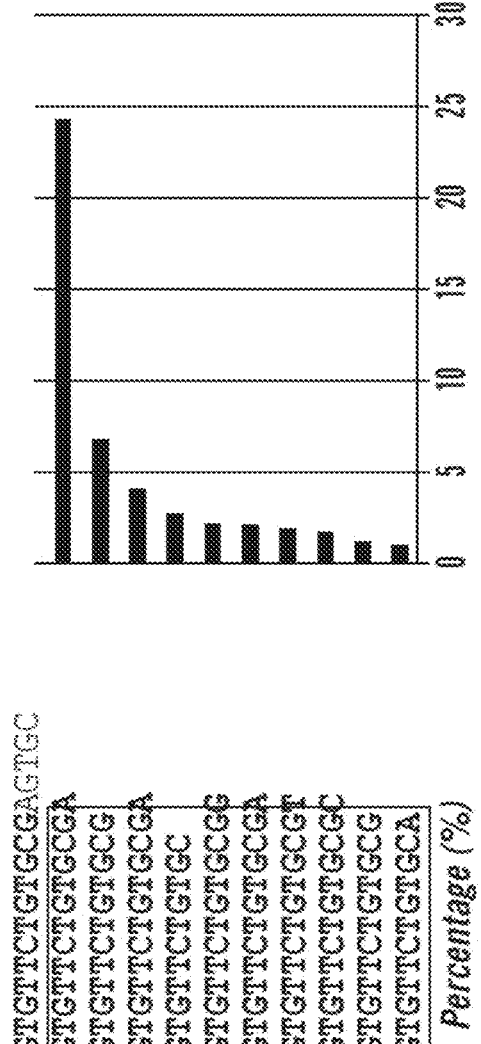
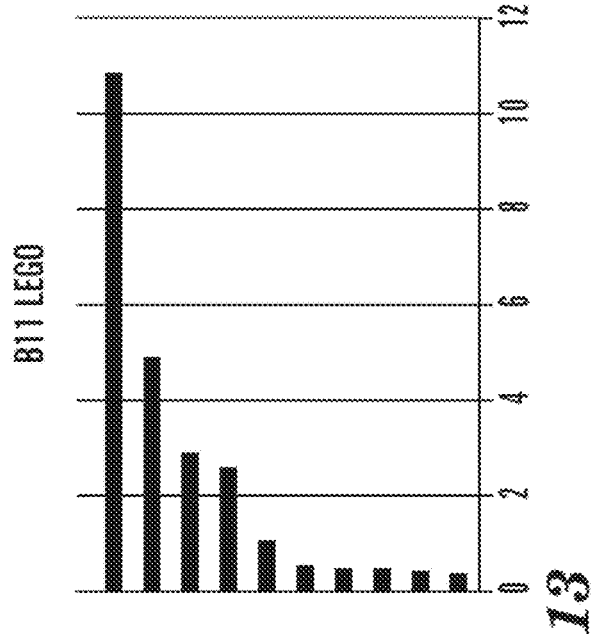
FIG. 13

Design of new shRNAs to mimic mature guide strands produced in pLKO vector

| | Passenger | Loop | Guide | |
|---|---|---|---|---|
| miR1G5 | gcgcCGCACAGAACACTCATGxxxx | ctccatgtggtagag | xxxxCATGAGTGTTCTGTGCGgcgc | SEQ. ID. NO: 34 |
| E3G5 | gcgcTCGGAGACTCCAGACAAxxxx | ctccatgtggtagag | xxxxTTGTCTGGAGTCTCCGAgcgc | SEQ. ID. NO: 35 |
| B5G5 | gcgcCCTCCAGGCAGCTCAAAxxxx | ctccatgtggtagag | xxxxTTTGAGCTGCCTGGAGGgcgc | SEQ. ID. NO: 36 |
| D8G5 | gcgcTTCTCTTGCAACACGCAxxxx | ctccatgtggtagag | xxxxTGCGTGTTGCAAGAGAAgcgc | SEQ. ID. NO: 37 |
| B11G5 | gcgcTCAGGACTAGGTGCAGAxxxx | ctccatgtggtagag | xxxxTCTGCACCTAGTCCTGAgcgc | SEQ. ID. NO: 38 |
| 50D12G5 | gcgcGATCGAGTGTTGAATAAxxxx | ctccatgtggtagag | xxxxTTATTCAACACTCGATCgcgc | SEQ. ID. NO: 39 |
| 50B11G5 | gcgcCACTGTCCACAGGAGAAxxxx | ctccatgtggtagag | xxxxTTCTCCTGTGGACAGTGgcgc | SEQ. ID. NO: 41 |
| 50A5G5 | GCGGCAGTACCCTGGAGAAACxxxx | ctccatgtggtagag | xxxxGTTTCTCCAGGGTACTGgcgc | SEQ. ID. NO: 40 |
| 50C4G5 | gcgcACAGTACCCTGGAGAAAxxxx | ctccatgtggtagag | xxxxTTTCTCCAGGGTACTGTgcgc | SEQ. ID. NO: 42 |

*FIG. 14A*

Differential processing in pol-III shRNA vectors and pol-II microRNA adapted shRNA vectors

Legend:
- REFERENCE
- PLKO
- LEGO
- MODLEGO miR1
AATCCATGAGTGTCTGTGCG
CATGAGTGTTCTGTGGTTTT
AATCCATGAGTGTGTGCGA
CATGAGTGTTCTGTGCCGC

E3
GCGATTGTGGAGTCTCCGA
ATTGTCTGGAGTCTCCG
GCGATTGTGGAGTCTCCGA
TGTCTGGAGTCTCCGA

D8
TCTGTGCGTGTTGCAAGAGAA
TGTGCGTGTTGCAAGAATTTT
TCTGTGCGTGTTGCAAGAGA
TGCGTGTTGCAAGAGAAGCG

B11
ACATTCGCACTAGTCTGA
TCTGCACCTAGTCCTGATT
ACATTCGCACTAGTCCTG
TCTGCACCTAGTCCTGAGGC

B5
GATCTTTGAGCTGCCGGAGG
TTTGAGCTGCCTGGAGGTT
GATCTTTGAGCTGCCGGAGGA
TTTGAGCTGCCTGGAGGGCA

XLC4
TGTGTTCTCCAGGGTACTGT
TTTCTCCAGGGTACTGT
TGTGTTCTCCAGGGTACTGT
TTTCTCCAGGGTACTGTGCG

XLA5
ATGTGTTCTCCAGGGTACTG
TGTTTCTCCAGGGTACTGTT
ATGTGTTCTCCAGGGTACTG
TTTCTCCAGGGTACTGGCGCA

*FIG. 18*

BCL11A knockdown with sequences in both SFFV and LCR backbones in CD34 differentiated erythroid cells.

| ShRNA | SEQUENCE | |
|---|---|---|
| Mir1 | CGCACAGAACACTCATGATTctccatgtggtagagAATCCATGAGTGTTCTGTGCG | SEQ. ID. NO: 25 |
| E3G5 | GCGCTCGGAGACTCCAGACAActccatgtggtagagTTGTCTGGAGTCTCCGAGgc | SEQ. ID. NO: 35 |
| D8G5 | GCGCTTCTCTTGCAACACGCActccatgtggtagagTGCGTGTTGCAAGAGAAgcgc | SEQ. ID. NO: 37 |
| C4G5 | GCGCACAGTACCCTGGAGAAActccatgtggtagagTTTCTCCAGGGTACTGTgcgc | SEQ. ID. NO: 42 |
| D12G5 | GCGGGATCGAGTGTTGAATAActccatgtggtagagTTATTCAACACTCGATCgcgc | SEQ. ID. NO: 39 |
| D12 | GATCGAGTGTTGAATAATGATctccatgtggtagagATCATTATTCAACACTCGATC | SEQ. ID. NO: 30 |
| A5 | CAGTACCCTGGAGAAACACATctccatgtggtagagATGTGTTTCTCCAGGGTACTG | SEQ. ID. NO: 31 |
| NT | CAACAAGATGAAGAGCACCAActccatgtggtagagTTGGTGCTCTTCATCTTGTTG | SEQ. ID. NO: 45 |

*FIG. 30*

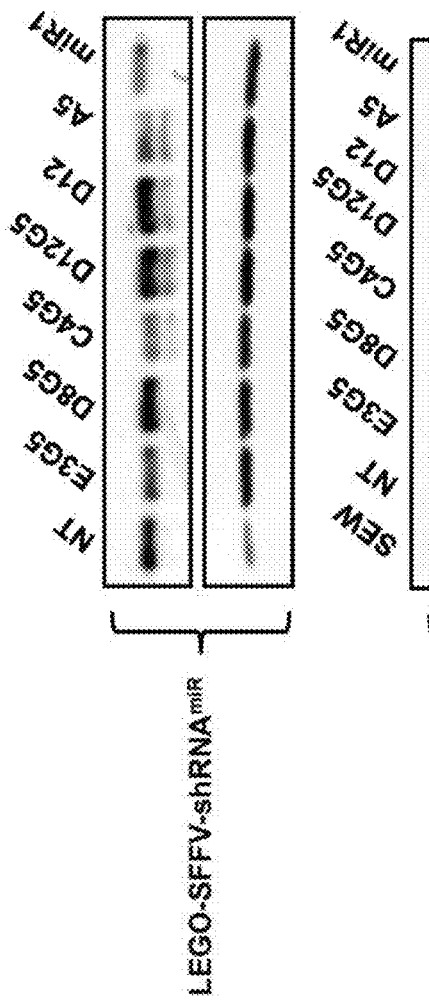

*FIG. 31*

SEQUENCE LISTING

<160> NUMBER OF SEQ ID NOS: 325

<210> SEQ ID NO 1
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgctcgcac agaacactca tggattctcc atgtggtaga gaatccatga gtgttctgtg    60
cgag                                                                 64

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgcactcgca cagaacactc atggattctc taccacatgg agaatccatg agtgttctgt    60
gcga                                                                 64

<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acgctccaga ggatgacgat tgtttactcc atgtggtaga gtaaacaatc gtcatcctct    60
ggag                                                                 64

<210> SEQ ID NO 4
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgcactccag aggatgacga ttgtttactc taccacatgg agtaaacaat cgtcatcctc    60
tgga                                                                 64

```
<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgcttcgga gactccagac aatcgcctcc atgtggtaga ggcgattgtc tggagtctcc    60
gaag                                                                 64

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cgcacttcgg agactccaga caatcgcctc taccacatgg aggcgattgt ctggagtctc    60
cgaa                                                                 64

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acgctttctc ttgcaacacg cacagactcc atgtggtaga gtctgtgcgt gttgcaagag    60
aaag                                                                 64

<210> SEQ ID NO 8
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgcactttct cttgcaacac gcacagactc taccacatgg agtctgtgcg tgttgcaaga    60
gaaa                                                                 64

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
acgctacagt accctggaga aacacactcc atgtggtaga gtgtgtttct ccagggtact    60
gtag                                                                 64

<210> SEQ ID NO 10
<211> LENGTH: 64
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
cgcactacag taccctggag aaacacactc taccacatgg agtgtgtttc tccagggtac    60
tgta                                                                 64

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acgctcaaca agatgaagag caccaactcc atgtggtaga gttggtgctc ttcatcttgt    60
tgag                                                                 64

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgcactcaac aagatgaaga gcaccaactc taccacatgg agttggtgct cttcatcttg    60
ttga                                                                 64

<210> SEQ ID NO 13
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
acgctgcgct cggagactcc agacaactcc atgtggtaga gttgtctgga gtctccgagc    60
gcag                                                                 64

<210> SEQ ID NO 14
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgcactgcgc tcggagactc cagacaactc taccacatgg agttgtctgg agtctccgag    60
cgca                                                                 64

<210> SEQ ID NO 15
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 15
acgctgcgct tctcttgcaa cacgcactcc atgtggtaga gtgcgtgttg caagagaagc    60
gcag    64

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgcactgcgc ttctcttgca acacgcactc taccacatgg agtgcgtgtt gcaagagaag    60
cgca    64

<210> SEQ ID NO 17
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acgctgcgca cagtaccctg gagaaactcc atgtggtaga gtttctccag ggtactgtgc    60
gcag    64

<210> SEQ ID NO 18
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgcactgcgc acagtaccct ggagaaactc taccacatgg agtttctcca gggtactgtg    60
cgca    64

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
taagcttgat atcgaattcc    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gctctagaac tagtggatcc    20

<210> SEQ ID NO 21

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttgccggcat ggtgagcaag ggcgagg                                          27

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tagcggccgc ttacttgtac agctcgtcc                                       29

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgctcgagca tgcatctaga gg                                              22

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttgcggccgc cggccgcgct taatgcgccg ctacag                               36

<210> SEQ ID NO 25
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgcacagaac actcatggat tctccatgtg gtagagaatc catgagtgtt ctgtgcg        57

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcggagactc cagacaatcg cctccatgtg gtagaggcga ttgtctggag tctccga        57

<210> SEQ ID NO 27
<211> LENGTH: 57
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctccaggca gctcaaagat cctccatgtg gtagaggatc tttgagctgc ctggagg      57

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttctcttgca acacgcacag actccatgtg gtagagtctg tgcgtgttgc aagagaa      57

<210> SEQ ID NO 29
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tcaggactag gtgcagaatg tctccatgtg gtagagacat tctgcaccta gtcctga      57

<210> SEQ ID NO 30
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gatcgagtgt tgaataatga tctccatgtg gtagagatca ttattcaaca ctcgatc      57

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagtaccctg gagaaacaca tctccatgtg gtagagatgt gtttctccag ggtactg      57

<210> SEQ ID NO 32
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cactgtccac aggagaagcc actccatgtg gtagagtggc ttctcctgtg gacagtg      57

<210> SEQ ID NO 33
<211> LENGTH: 57
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 33
acagtaccct ggagaaacac actccatgtg gtagagtgtg tttctccagg gtactgt        57

<210> SEQ ID NO 34
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcgccgcaca gaacactcat gctccatgtg gtagagcatg agtgttctgt gcggcgc        57

<210> SEQ ID NO 35
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgctcggag actccagaca actccatgtg gtagagttgt ctggagtctc cgagcgc        57

<210> SEQ ID NO 36
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcgccctcca ggcagctcaa actccatgtg gtagagtttg agctgcctgg agggcgc        57

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcgcttctct tgcaacacgc actccatgtg gtagagtgcg tgttgcaaga gaagcgc        57

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcgctcagga ctaggtgcag actccatgtg gtagagtctg cacctagtcc tgagcgc        57

<210> SEQ ID NO 39
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 39
gcgcgatcga gtgttgaata actccatgtg gtagagttat tcaacactcg atcgcgc          57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcgccagtac cctggagaaa cctccatgtg gtagaggttt ctccagggta ctggcgc          57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcgccactgt ccacaggaga actccatgtg gtagagttct cctgtggaca gtggcgc          57

<210> SEQ ID NO 42
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcgcacagta ccctggagaa actccatgtg gtagagtttc tccagggtac tgtgcgc          57

<210> SEQ ID NO 43
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
acgctcgcac agaacactca tggattctcc atgtggtaga gaatccatga gtgttctgtg      60
cgag                                                                    64

<210> SEQ ID NO 44
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgcactcgca cagaacactc atggattctc taccacatgg agaatccatg agtgttctgt      60
gcga                                                                    64

<210> SEQ ID NO 45
```

```
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caacaagatg aagagcacca actccatgtg gtagagttgg tgctcttcat cttgttg        57

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgcacagaac actcatggat t                                               21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ccagaggatg acgattgttt a                                               21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tcggagactc cagacaatcg c                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctccaggca gctcaaagat c                                               21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tcaggactag gtgcagaatg t                                               21

<210> SEQ ID NO 51
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttctcttgca acacgcacag a                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gatcgagtgt tgaataatga t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cagtaccctg gagaaacaca t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cactgtccac aggagaagcc a                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
acagtaccct ggagaaacac a                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
caacaagatg aagagcacca a                                              21

<210> SEQ ID NO 57
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 57
gcgccgcaca gaacactcat g                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gcgctcggag actccagaca a                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcgccctcca ggcagctcaa a                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gcgctcagga ctaggtgcag a                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gcgcgatcga gtgttgaata a                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gcgccagtac cctggagaaa c                                              21

<210> SEQ ID NO 63
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 63
gcgccactgt ccacaggaga a                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gcgcttctct tgcaacacgc a                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcgcacagta ccctggagaa a                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cgcacagaac actcatggat t                                              21

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
acgctcgcac agaacactca tggatt                                         26

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ctccatgtgg tagag                                                     15

<210> SEQ ID NO 69
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 69
gaagcagagg acaagttccc a                                              21

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tcaccaccat ggagaaggc                                                 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gctaagcagt tggtggtgca                                                20

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tggatgatct caagggcac                                                 19

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcagtggtat ctggaggaca                                                20

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctgaggagaa gtctgccgtt a                                              21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
            primer

<400> SEQUENCE: 75
agcatcagga gtggacagat                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acccagaaga ctgtggatgg                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ttcagctcag ggatgacctt                                               20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
cggagactcc agacaatcgc                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
ctccaggcag ctcaaagatc                                               20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
tctcttgcaa cacgcacaga                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 81
caggactagg tgcagaatgt                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
atcgagtgtt gaataatgat                                              20

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
gtaccctgga gaaacacat                                               19

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
actgtccaca ggagaagcca                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
cagtaccctg gagaaacaca                                              20

<210> SEQ ID NO 86
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccggcgcaca gaacactcat ggattctcga gaatccatga gtgttctgtg cgttttt     57

<210> SEQ ID NO 87
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 87
cgctcgcaca gaacactcat ggattctcca tgtggtagag aatccatgag tgttctgtgc    60
gagtg                                                                65

<210> SEQ ID NO 88
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cgctgcgccg cacagaacac tcatgctcca tgtggtagag catgagtgtt ctgtgcggcg    60
cagtg                                                                65

<210> SEQ ID NO 89
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ccggacagta ccctggagaa acacactcga gtgtgtttct ccagggtact gtttttt      57

<210> SEQ ID NO 90
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cgctacagta ccctggagaa acacactcca tgtggtagag tgtgtttctc cagggtactg    60
tagtg                                                                65

<210> SEQ ID NO 91
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cgctgcgcac agtaccctgg agaaactcca tgtggtagag tttctccagg gtactgtgcg    60
cagtg                                                                65

<210> SEQ ID NO 92
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccggttctct tgcaacacgc acagactcga gtctgtgcgt gttgcaagag aattttt      57

<210> SEQ ID NO 93
```

```
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cgctttctct tgcaacacgc acagactcca tgtggtagag tctgtgcgtg ttgcaagaga    60
aagtg                                                                65

<210> SEQ ID NO 94
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cgctgcgctt ctcttgcaac acgcactcca tgtggtagag tgcgtgttgc aagagaagcg    60
cagtg                                                                65

<210> SEQ ID NO 95
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccgggatcga gtgttgaata atgatctcga gatcattatt caacactcga tctttttt     57

<210> SEQ ID NO 96
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cgctgatcga gtgttgaata atgatctcca tgtggtagag atcattattc aacactcgat    60
cagtg                                                                65

<210> SEQ ID NO 97
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cgctgcgcga tcgagtgttg aataactcca tgtggtagag ttattcaaca ctcgatcgcg    60
cagtg                                                                65

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 98
tggcctgtgg agtaaggtca a                                              21

<210> SEQ ID NO 99
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other
<220> FEATURE:
<221> NAME/KEY: modified_base
<222> LOCATION: (28)..(47)
<223> OTHER INFORMATION: a, c, t, g, unknown or other

<400> SEQUENCE: 99
nnnnnnnnnn nnnnnnnnnn nctcgagnnn nnnnnnnnnn nnnnnnnttt tt            52

<210> SEQ ID NO 100
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(24)
<223> OTHER INFORMATION: a, c, t, g, unknown or other
<220> FEATURE:
<221> NAME/KEY: modified_base
<222> LOCATION: (31)..(51)
<223> OTHER INFORMATION: a, c, t, g, unknown or other

<400> SEQUENCE: 100
aaaannnnnn nnnnnnnnnn nnnnctcgag nnnnnnnnnn nnnnnnnnnn n             51

<210> SEQ ID NO 101
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(25)
<223> OTHER INFORMATION: a, c, t, g, unknown or other
<220> FEATURE:
<221> NAME/KEY: modified_base
<222> LOCATION: (41)..(60)
<223> OTHER INFORMATION: a, c, t, g, unknown or other

<400> SEQUENCE: 101
ccggnnnnnn nnnnnnnnnn nnnnnctcca tgtggtagag nnnnnnnnnn nnnnnnnnnn    60
cggc                                                                 64

<210> SEQ ID NO 102
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (5)..(24)
<223> OTHER INFORMATION: a, c, t, g, unknown or other
<220> FEATURE:
<221> NAME/KEY: modified_base
<222> LOCATION: (40)..(60)
<223> OTHER INFORMATION: a, c, t, g, unknown or other

<400> SEQUENCE: 102
gccgnnnnnn nnnnnnnnnn nnnnctctac cacatggagn nnnnnnnnnn nnnnnnnnnn    60
ccgg                                                                 64

<210> SEQ ID NO 103
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(25)
<223> OTHER INFORMATION: a, c, t, g, unknown or other
<220> FEATURE:
<221> NAME/KEY: modified_base
<222> LOCATION: (32)..(52)
<223> OTHER INFORMATION: a, c, t, g, unknown or other

<400> SEQUENCE: 103
ccggnnnnnn nnnnnnnnnn nnnnnctcga gnnnnnnnnn nnnnnnnnnn nnttttg       58

<210> SEQ ID NO 104
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(15)
<223> OTHER INFORMATION: a, c, t, g, unknown or other
<220> FEATURE:
<221> NAME/KEY: modified_base
<222> LOCATION: (23)..(33)
<223> OTHER INFORMATION: a, c, t, g, unknown or other

<400> SEQUENCE: 104
gcccnnnnnn nnnnntcttg aannnnnnnn nnngggcct                           39

<210> SEQ ID NO 105
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tagagaatcc atgagtgttc tgtgcgagtg c                                   31

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aatccatgag tgttctgtgc ga                                              22

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
aatccatgag tgttctgtgc g                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atccatgagt gttctgtgcg a                                               21

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aatccatgag tgttctgtgc                                                 20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aatccatgag tgttctgtgc gg                                              22

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gaatccatga gtgttctgtg cga                                             23

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
aatccatgag tgttctgtgc gt                                             22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aatccatgag tgttctgtgc gc                                             22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gaatccatga gtgttctgtg cg                                             22

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
aatccatgag tgttctgtgc a                                              21

<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctcgagaatc catgagtgtt ctgtgcgttt ttg                                 33

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
catgagtgtt ctgtgcgttt t                                              21

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
catgagtgtt ctgtgcgttt tt                                             22

```
<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
catgagtgtt ctgtgcgttt                                                      20

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tccatgagtg ttctgtgcgt ttt                                                  23

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
catgagtgtt ctgtgcgttt a                                                    21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
catgagtgtt ctgtgcgttt c                                                    21

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
catgagtgtt ctgtgcgttt at                                                   22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tccatgagtg ttctgtgcgt tt                                                   22
```

```
<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
catgagtgtt ctgtgcgtt                                                   19

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
catgagtgtt ctgtgcgttt ttt                                              23

<210> SEQ ID NO 127
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tagagtgtgt ttctccaggg tactgtagtg c                                     31

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgtttctcca gggtactgt                                                   19

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tttctccagg gtactgt                                                     17

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tgtttctcca gggtactg                                                    18
```

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgtgtttctc cagggtactg t                                             21

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tttctccagg gtactg                                                   16

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133 tgtttctccca gggtact                                                 17

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tgtgtttctc cagggtactg                                               20

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ctcgagtgtg tttctccagg gtactgtttt ttg                                33

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tttctccagg gtactgtt                                                 18

<210> SEQ ID NO 137

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tgtttctcca gggtactgtt                                                      20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
tttctccagg gtactgtttt t                                                    21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tttctccagg gtactgtttt                                                      20

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tttctccagg gtactgttt                                                       19

<210> SEQ ID NO 141
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(29)
<223> OTHER INFORMATION: a, c, t, g, unknown or other
<220> FEATURE:
<221> NAME/KEY: modified_base
<222> LOCATION: (45)..(65)
<223> OTHER INFORMATION: a, c, t, g, unknown or other

<400> SEQUENCE: 141
gccacgctnn nnnnnnnnn nnnnnnnnnc tccatgtggt agagnnnnn nnnnnnnnnn            60 nnnnnagtgc g                                                               71

<210> SEQ ID NO 142
<211> LENGTH: 31
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 142
tagagcatga gtgttctgtg cggcgcagtg c                                          31

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
catgagtgtt ctgtgcggcg c                                                     21

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
catgagtgtt ctgtgcggcg                                                       20

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
catgagtgtt ctgtgcggc                                                        19

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atgagtgttc tgtgcggcgc                                                       20

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
catgagtgtt ctgtgcgg                                                         18

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 148
atgagtgttc tgtgcggcg                                           19

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
catgagtgtt ctgtgc                                              16

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tgagtgttct gtgcggcgc                                           19

<210> SEQ ID NO 151
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tagagtttct ccagggtact gtgcgcagtg c                             31

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tttctccagg gtactgtgcg                                          20

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tttctccagg gtactgtgc                                           19

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
gtttctccag ggtactgtgc g                                        21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tttctccagg gtactgtgcg c                                        21

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tttctccagg gtactgtg                                            18

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gtttctccag ggtactgtgc                                          20

<210> SEQ ID NO 158
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ctcgagaatc catgagtgtt ctgtgcgttt tt                            32

<210> SEQ ID NO 159
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctcgagtctg tgcgtgttgc aagagaattt ttg                           33

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 160
tgtgcgtgtt gcaagagaat ttt                                          23

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgtgcgtgtt gcaagagaat tt                                           22

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tgtgcgtgtt gcaagagaat t                                            21

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tgtgcgtgtt gcaagagaat tttg                                         24

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 164
tgtgngtgtt gcaagagaat ttt                                          23

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tgtgcgtgtt gcaagagaat                                              20

<210> SEQ ID NO 166
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 166
tgtgcgtgtt gcaagagaat tttt                                              24

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 167
tgtgngtgtt gcaagagaat tt                                                22

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, g, unknown or other

<400> SEQUENCE: 168
tgtgngtgtt gcaagagaat t                                                 21

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tgtgcgtgtt gcaagagaat ttta                                              24

<210> SEQ ID NO 170
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ctcgaggcga ttgtctggag tctccgattt t                                      31

<210> SEQ ID NO 171
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
attgtctgga gtctccg                                                      17
```

```
<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
attgtctgga gtctccga                                                 18

<210> SEQ ID NO 173
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
attgtctgga gtctcc                                                   16

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gattgtctgg agtctccga                                                19

<210> SEQ ID NO 175
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ttgtctggag tctccg                                                   16

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
attgtctgga gtctccgatt                                               20

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ttgtctggag tctccga                                                  17
```

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gattgtctgg agtctccg                                                     18

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gattgtctgg agtctccgat t                                                 21

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
attgtctgga gtctccgat                                                    19

<210> SEQ ID NO 181
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ctcgagacat tctgcaccta gtcctgattt tt                                     32

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ttctgcacct agtcctgatt                                                   20

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ttctgcacct agtcctgatt tt                                                22

```
<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ttctgcacct agtcctgat                                                    19

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ttctgcacct agtcctgatt t                                                 21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
attctgcacc tagtcctgat t                                                 21

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ttctgcacct agtcctgatc                                                   20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ttctgcacct agtcctgata                                                   20

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttctgcacct agtcctgatt ttt                                               23

<210> SEQ ID NO 190
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
attctgcacc tagtcctgat ttt                                              23

<210> SEQ ID NO 191
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ttctgcacct agtcctga                                                    18

<210> SEQ ID NO 192
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ctcgagtgtg tttctccagg gtactgtttt tt                                    32

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tttctccagg gtactgtttt tt                                               22

<210> SEQ ID NO 194
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ctcgagatgt gtttctccag ggtactgttt tt                                    32

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tgtttctcca gggtactgtt tt                                               22

<210> SEQ ID NO 196
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tgtttctcca gggtactgtt t                                          21

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
tgtttctcca gggtactgtt ttt                                        23

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tgtttctcca gggtactgta                                            20

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
tgtttctcca gggtactgtt a                                          21

<210> SEQ ID NO 200
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ctcgaggatc tttgagctgc ctggaggttt tt                              32

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tttgagctgc ctggaggtt                                             19

<210> SEQ ID NO 202
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 202
tttgagctgc ctggaggttt a                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tttgagctgc ctggaggttt c                                              21

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tttgagctgc ctggaggttc                                                20

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tttgagctgc ctggaggttt ttt                                            23

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tctttgagct gcctggaggt tttt                                           24

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tttgagctgc ctggaggt                                                  18

<210> SEQ ID NO 208
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 208
tttgagctgc ctggaggtta                                                    20

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
tttgagctgc ctggaggttt at                                                 22

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
tttgagctgc ctggaggttt tg                                                 22

<210> SEQ ID NO 211
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
tagagtctgt gcgtgttgca agagaaagtg cg                                      32

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
tctgtgcgtg ttgcaagaga                                                    20

<210> SEQ ID NO 213
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
tctgtgcgtg ttgcaagaga aa                                                 22

<210> SEQ ID NO 214
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 214
tctgtgcgtg ttgcaagaga a                                              21

<210> SEQ ID NO 215
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tctgtgcgtg ttgcaag                                                   17

<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tctgtgcgtg ttgcaagag                                                 19

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tctgtgcgtg ttgcaaga                                                  18

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ctgtgcgtgt tgcaagaga                                                 19

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ctgtgcgtgt tgcaagagaa a                                              21

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 220
ctgtgcgtgt tgcaagagaa                                           20

<210> SEQ ID NO 221
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tctgtgcgtg ttgcaa                                               16

<210> SEQ ID NO 222
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
tagaggcgat tgtctggagt ctccgaagtg c                              31

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gcgattgtct ggagtctccg a                                         21

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
cgattgtctg gagtctccga                                           20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gcgattgtct ggagtctccg aa                                        22

<210> SEQ ID NO 226
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 226
ggcgattgtc tggagtctcc ga                                           22

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
cgattgtctg gagtctccga a                                            21

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cgattgtctg gagtctccg                                               19

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gcgattgtct ggagtctccg                                              20

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
cgattgtctg gagtctccga att                                          23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggcgattgtc tggagtctcc gaa                                          23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 232
cgattgtctg gagtctccga agt                                          23

<210> SEQ ID NO 233
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tagagacatt ctgcacctag tcctgaagtg c                                 31

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
acattctgca cctagtcctg a                                            21

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
acattctgca cctagtcctg aa                                           22

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
acattctgca cctagtcctg aat                                          23

<210> SEQ ID NO 237
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
acattctgca cctagtcctg ac                                           22

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
```
acattctgca cctagtcctg at                                                22

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
gacattctgc acctagtcct gaat                                              24

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
acattctgca cctagtcctg                                                   20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
cattctgcac ctagtcctga                                                   20

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
acattctgca cctagtcctg aaa                                               23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
acattctgca cctagtcctg aac                                               23

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gtttctccag ggtactgt                                               18

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tgtgtttctc cagggtact                                              19

<210> SEQ ID NO 246
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tgtttctcca gggtac                                                 16

<210> SEQ ID NO 247
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tagagatgtg tttctccagg gtactgagtg c                                31

<210> SEQ ID NO 248
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
atgtgtttct ccagggtac                                              19

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
atgtgtttct ccagggtact gag                                         23

<210> SEQ ID NO 250
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tgtgtttctc cagggtactg ag                                          22

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
atgtgtttct ccagggtact gatt                                           24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
atgtgtttct ccagggtact gaat                                           24

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
atgtgtttct ccagggtact                                                20

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tgtgtttctc cagggtactg a                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atgtgtttct ccagggtact g                                              21

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
atgtgtttct ccagggtact ga                                             22

```
<210> SEQ ID NO 257
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tagaggatct ttgagctgcc tggaggagtg c                                  31

<210> SEQ ID NO 258
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gatctttgag ctgcctggag ga                                            22

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gatctttgag ctgcctggag g                                             21

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gatctttgag ctgcctggag gat                                           23

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
atctttgagc tgcctggagg a                                             21

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gatctttgag ctgcctggag gt                                            22
```

```
<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gatctttgag ctgcctggag gatt                                          24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gatctttgag ctgcctggag gaat                                          24

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gatctttgag ctgcctggag gaa                                           23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
atctttgagc tgcctggagg aat                                           23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gatctttgag ctgcctggag gac                                           23

<210> SEQ ID NO 268
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
catgagtgtt ctgtgcg                                                  17

<210> SEQ ID NO 269
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tagagtgcgt gttgcaagag aagcgcagtg cg                                     32

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
tgcgtgttgc aagagaagcg                                                   20

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tgcgtgttgc aagagaagcg c                                                 21

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tgcgtgttgc aagagaagc                                                    19

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
tgcgtgttgc aagagaagcg ca                                                22

<210> SEQ ID NO 274
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tgcgtgttgc aagagaag                                                     18

<210> SEQ ID NO 275
<211> LENGTH: 21
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gtgcgtgttg caagagaagc g                                           21

<210> SEQ ID NO 276
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tgcgtgttgc aagaga                                                 16

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tgcgtgttgc aagagaagcg catt                                        24

<210> SEQ ID NO 278
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tgcgtgttgc aagagaagcg cagt                                        24

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gtgcgtgttg caagagaagc gc                                          22

<210> SEQ ID NO 280
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tagagttgtc tggagtctcc gagcgcagtg c                                31

<210> SEQ ID NO 281
<211> LENGTH: 16
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 281
tgtctggagt ctccga                                                        16

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 282
ttgtctggag tctccgagcg                                                    20

<210> SEQ ID NO 283
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 283
gttgtctgga gtctccga                                                      18

<210> SEQ ID NO 284
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 284
gtctggagtc tccgagc                                                       17

<210> SEQ ID NO 285
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 285
gtctggagtc tccgag                                                        16

<210> SEQ ID NO 286
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 286
tagagtctgc acctagtcct gagcgcagtg c                                       31

<210> SEQ ID NO 287
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 287
tctgcaccta gtcctgagcg c                                              21

<210> SEQ ID NO 288
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tctgcaccta gtcctgagcg ca                                             22

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tctgcaccta gtcctgagcg                                                20

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
tctgcaccta gtcctgagc                                                 19

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
tctgcaccta gtcctgagcg catt                                           24

<210> SEQ ID NO 292
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
tctgcaccta gtcctg                                                    16

<210> SEQ ID NO 293
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 293
tctgcaccta gtcctgagcg caat                                              24

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
tctgcaccta gtcctgag                                                     18

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tctgcaccta gtcctgagcg cag                                               23

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ctgcacctag tcctgagcgc                                                   20

<210> SEQ ID NO 297
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tagagtttct ccagggtact gtgcgcagtg cg                                     32

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gtttctccag ggtactgtgc gc                                                22

<210> SEQ ID NO 299
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 299
gtttctccag ggtactgtg                                                     19

<210> SEQ ID NO 300
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
tagaggtttc tccagggtac tggcgcagtg cg                                      32

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
tttctccagg gtactggcgc a                                                  21

<210> SEQ ID NO 302
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gtttctccag ggtactggcg ca                                                 22

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gtttctccag ggtactggcg                                                    20

<210> SEQ ID NO 304
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tttctccagg gtactggcg                                                     19

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 305
tttctccagg gtactggcgc                                               20

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gtttctccag ggtactggcg c                                             21

<210> SEQ ID NO 307
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gtttctccag ggtactggc                                                19

<210> SEQ ID NO 308
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
tttctccagg gtactggcgc ag                                            22

<210> SEQ ID NO 309
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gtttctccag ggtactgg                                                 18

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tttctccagg gtactggcgc att                                           23

<210> SEQ ID NO 311
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 311
tagagtttga gctgcctgga gggcgcagtg cg                                    32

<210> SEQ ID NO 312
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
tttgagctgc ctggagggcg ca                                               22

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tttgagctgc ctggagggcg                                                  20

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tttgagctgc ctggagggcg c                                                21

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
tttgagctgc ctggagggc                                                   19

<210> SEQ ID NO 316
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tttgagctgc ctggagg                                                     17

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
tttgagctgc ctggagggcg catt                                                          24

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tttgagctgc ctggaggg                                                                 18

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
tttgagctgc ctggagggcg caat                                                          24

<210> SEQ ID NO 320
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tttgagctgc ctggag                                                                   16

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tttgagctgc ctggagggcg cag                                                           23

<210> SEQ ID NO 322
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(23)
<223> OTHER INFORMATION: a, c, u, g, unknown or other
<220> FEATURE:
<221> NAME/KEY: modified_base
<222> LOCATION: (30)..(50)
<223> OTHER INFORMATION: a, c, u, g, unknown or other

<400> SEQUENCE: 322
ggnnnnnnnn nnnnnnnnnn nnncucgagn nnnnnnnnnn nnnnnnnnnn uuuu                         54

<210> SEQ ID NO 323
<211> LENGTH: 104

```
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (25)..(45)
<223> OTHER INFORMATION: a, c, u, g, unknown or other
<220> FEATURE:
<221> NAME/KEY: modified_base
<222> LOCATION: (61)..(81)
<223> OTHER INFORMATION: a, c, u, g, unknown or other

<400> SEQUENCE: 323
ccuggccucc ugcagugcca cgcunnnnnn nnnnnnnnnn nnnnncucca ugugguagag      60
nnnnnnnnnn nnnnnnnnnn nagugcggca caugcuuacc agcu                     104

<210> SEQ ID NO 324
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
tagagtctgt gcgtgttgca agagaaagtg c                                    31

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gacattctgc acctagtcct gat                                             23
```

COMPOSITIONS AND METHODS TO TREATING HEMOGLOBINOPATHIES

CROSS REFERENCED TO RELATED APPLICATIONS

This Application is a Divisional Application of U.S. application Ser. No. 15/306,527, filed on Oct. 25, 2016, which is a U.S.C. 371 National Stage Application of International Application No. PCT/US2015/027527 filed on Apr. 24, 2015, which designates the United States, and which claims the benefit under 35 U.S.C. § 119(e) of U.S. Provisional Application No: 61/984,247, filed on filed Apr. 25, 2014, and U.S. Provisional Application No. 62/066,783, filed on Oct. 21, 2014, the contents of each application are incorporated herein by reference in their entirety.

GOVERNMENT SUPPORT

This invention was made with Government support under Grant No.: 5U01HL117720-03 awarded by the National Institutes of Health. The Government has certain rights in the invention.

TECHNICAL FIELD

Embodiments disclosed herein relate to compositions and methods for the treatment of hemoglobinopathies. More particularly, the embodiments relate to compositions and methods of increasing fetal hemoglobin in a cell by selective knockdown of the endogenous BCL11A.

BACKGROUND

Hemoglobinopathies, including sickle cell disease/anemia (SCD) and thalassemia (THAL), are the most prevalent inherited monogenic disorders in the human. Approximately 5% of the world's population carries a globin gene mutation. The World Health Organization estimates that each year about 300,000 infants are born with major hemoglobin disorders. SCD has segregated to populations from sub-Saharan Africa, India, Saudi Arabia, and Mediterranean countries, where up to 2% of all children are born with the condition, due to the survival advantage against malarial transmission conferred by a heterozygous sickle β-globin βS) mutation (WHO Report on Sickle-cell anaemia—A59.9. Fifty-ninth World Health Assembly—Provisional agenda item 114: United Nations; 2006:1-5). Due to historic and/or recent migration, increasing numbers of patient populations can now be found in developed countries, and public health implications of SCD are significant (Kauf et al., American Journal of Hematology. 2009; 84:323-327; Amendah et al., American Journal of Preventive Medicine. 2010; 38:S550-556). In the United States of America, median survival of patients having a hemoglobinopathy was estimated in 1994 to be 42 years for men and 48 years for women (Platt et al., New England Journal of Medicine. 1994; 330:1639-1644). At a molecular level, SCD was the first disease to be linked to a molecular alteration (Pauling et al., Science. 1949; 110:543-548). A single nucleotide mutation results in glutamic acid to valine substitution by at position 6 of the β-globin protein. This modification results in the polymerization of the molecule in deoxygenated conditions, and subsequent "sickling" of the erythrocyte ultimately leading to anemia by hemolysis and acute and chronic vaso-occlusive and ischemic complications affecting multiple organs, including kidney, brain, lung, and others). Although preventive measures (including the chemoprophylactic agent hydroxyurea) have led to moderate reduction in the burden of selected patient groups, at present, the only available curative therapy for SCD is allogeneic hematopoietic stem cell transplantation (HSCT) (Hsieh et al., New England Journal of Medicine. 2009; 361:2309-2317; Hsieh et al., Blood; Electronic pre-publication Jun. 31, 2011). HSCT has unfortunately been associated in the SCD and THAL setting with significant mortality and morbidity, which is due in part to pre-HSCT transfusion-related iron overload, graft-versus-host disease, and high doses of chemotherapy/radiation required for pre-transplant conditioning of the host, among others.

New molecular therapies are being developed. For example, U.S. Pat. No. 8,383,604 describes that the BCL11A as a key regulator of the globin genes during development. In particular, BCL11A promotes the transitional switch from the expression of fetal hemoglobin genes to the expression of adult hemoglobin genes during fetal development. Supression of BCL11A reduces this transitional switch and maintains a significantly higher expression of the fetal hemoglobin genes post fetal development. The higher amount of fetal hemoglobin genes expressed ameliorates the symptoms associated with various hemoglobinopathies.

SUMMARY

In particular illustrative embodiments, the present invention provides, in part, improved compositions and methods for achieving gene therapy in hematopoietic cells and hematopoietic precursor cells, including erythrocytes, erythroid progenitors, and embryonic stem cells. The invention further provides improved gene therapy methods for treating hematopoietic-related disorders.

The goal is to efficiently knock-down BCL11A in cells derived from transduced, engraftable hematopoietic stem cells. Success at induction of γ-globin and thus simultaneous increase in HbF and reduction in mutant HbS depends on the quantitative reduction of BCL11A transcript and protein. The inventors have embedded a BCL11A shRNA in a mir223 loop. This approach allows the BCL11A shRNA to be transcribed via polymerase II (PolII) promoters instead of the polymerase III promoters. This allows exploitation of the microRNA-biogenesis pathway to generate siRNAs that target BCL11A expression in engraftable HSCs. Lentiviral transgenes arc engineered to express shRNAs that mimic primary microRNAs (pri-miRNAs) and are sequentially processed by the endogenous Microprocessor and Dicer complexes to generate small interfering RNAs (siRNAs) with sequence complementarity to the BCL11A messenger RNA (mRNA).

In one aspect, compositions and methods are provided that efficiently knock-down BCL11A in cells derived from transduced, engraftable hematopoietic stem cells. In one embodiment, a quantitative reduction of BCL11A transcript and protein induces γ-globin production, and thus simultaneous increase in HbF and reduction in mutant HbS. In a particular embodiment, a BCL11A shRNA is embedded in a mir223 loop. In particular embodiments, a lentivirus is engineered to express shRNAs that mimic pri-miRNAs that are sequentially processed by the endogenous Microprocessor and Dicer complexes to generate siRNAs with sequence complementarity to the BCL11A mRNA.

Accordingly, in various illustrative embodiments, the present specification provides, in part, a synthetic BCL11A microRNA comprising a first BCL11A segment, a loop segment, and a second BCL11A segment arranged in tandem in a 5' to 3' direction, wherein the loop segment is between and directly linked to the first and second BCL11A segments, and wherein the second BCL11A segment is complementary to the first BCL11A segment such that the first and second BCL11A segments base pair to form a hairpin loop with the loop segment forming the loop portion of the hairpin loop thus formed.

In one embodiment of any one of the synthetic BCL11A microRNA described herein, the first and second BCL11A segments are about 18 to 25 nucleotides long. The first BCL11A segment is derived from a BCL11A sequence and gives rise to the passenger strand during shRNA processing to a duplex siRNA and the second BCL11A segment is complementary to first BCL11A segment, wherein the second BCL11A segment gives rise to the guide strand that is incorporated into the RNA Interference Specificity Complex (RISC) for RNA interference or BCL11A gene silencing.

In one embodiment of any one of the synthetic BCL11A microRNA described herein, the first and second BCL11A segments contain sequences that are derived from BCL11A mRNA sequence.

In one embodiment of any one of the synthetic BCL11A microRNA described herein, the first BCL11A segment starts with a -GCGC- at the 5' end and the second BCL11A segment ends with a -GCGC- at the 3' end.

In one embodiment of any one of the synthetic BCL11A microRNA described herein, the first BCL11A segment further consist a -GCGC- at the 5' end and the second BCL11A segment ends with a -GCGC- at the 3' end.

In one embodiment of any one of the synthetic BCL11A microRNA described herein, the first BCL11A segment starts with a -GCGA-, -TCTG-, or -TG- at the 5' end and the second BCL11A segment is complementary to first BCL11A segment.

In one embodiment of any one of the synthetic BCL11A microRNA described herein, the first BCL11A segment further consist a -GCGA-, -TCTG-, or -TG- at the 5' end.

In one embodiment of any one of the synthetic BCL11A microRNA described herein, the second BCL11A segment ends with a -TTTT- at the 3' end.

In one embodiment of any one of the synthetic BCL11A microRNA described herein, the synthetic BCL11A microRNA comprise a nucleotide sequence selected from the group consisting of SEQ ID NOS:1-10,13-18, 25-44.

In one embodiment of any one of the synthetic BCL11A microRNA described herein, the synthetic BCL11A microRNA comprises a nucleotide sequence or a segment therefrom described in this disclosure.

In one embodiment of any one of the synthetic BCL11A microRNA described herein, the synthetic BCL11A microRNA consists of a nucleotide sequence selected from the group consisting of SEQ ID NOS:1-10,13-18, 25-44.

In one embodiment of any one of the synthetic BCL11A microRNA described herein, the synthetic BCL11A microRNA consist essentially of a nucleotide sequence selected from the group consisting of SEQ ID NOS:1-10,13-18, 25-44.

In one embodiment of any one of the synthetic BCL11A microRNA described herein, the first BCL11A segment is selected from the group consisting of CGCACAGAACACTCATGGATT (SEQ. ID. NO: 46; derived from BCL11A miR1 oligo described herein), CCAGAGGATGACGATTGTTTA (SEQ. ID. NO: 47; derived from BCL11A miR2 oligo described herein), TCGGAGACTCCAGACAATCGC (SEQ. ID. NO: 48; derived from BCL11A E3 oligo or shRNA1 or E3 described herein), CCTCCAGGCAGCTCAAAGATC, (SEQ. ID. NO: 49; derived from shRNA2 or B5 described herein), TCAGGACTAGGTGCAGAATGT (SEQ. ID. NO: 50; derived from shRNA4 or B11 described herein), TTCTCTTGCAACACGCACAGA (SEQ. ID. NO: 51; derived from BCL11A D8 oligo or shRNA3 or D8 described herein), GATCGAGTGTTGAATAATGAT (SEQ. ID. NO: 52; derived from shRNA5 or 50D12 of D12 described herein), CAGTACCCTGGAGAAACACAT (SEQ. ID. NO: 53; derived from shRNA5 or 50A5 described herein), CACTGTCCACAGGAGAAGCCA (SEQ. ID. NO: 54; derived from shRNA7 or 50B11 described herein), ACAGTACCCTGGAGAAACACA (SEQ. ID. NO: 55; derived from BCL11A XLC4, shRNA8 and 50C4 described herein), CAACAAGATGAAGAGCACCAA (SEQ. ID. NO: 56; derived from BCL11A Non-targeting oligos described herein), gcgcCGCACAGAACACTCATG (SEQ. ID. NO: 57; derived from miR1G5 oligo described herein), GCGCTCGGAGACTCCAGACAA (SEQ. ID. NO: 58; derived from E3G5 or E3 mod oligo or shRNA1mod described herein), gcgcCCTCCAGGCAGCTCAAA (SEQ. ID. NO: 59; derived from B5G5 or shRNA2mod described herein); gcgcTCAGGACTAGGTGCAGA (SEQ. ID. NO: 60; derived from B11G5 or shRNA4mod described herein); gcgcGATCGAGTGTTGAATAA (SEQ. ID. NO: 61; derived from 50D12G5, D12G4 or shRNA5mod described herein); gcgcCAGTACCCTGGAGAAAC (SEQ. ID. NO: 62; derived from 50A5G5 or shRNA6mod described herein); gcgcCACTGTCCACAGGAGAA (SEQ. ID. NO: 63; derived from 50B11G5 or shRNA7mod described herein); GCGCTTCTCTTGCAACACGCA (SEQ. ID. NO: 64; derived from BCL11A D8G5 or D8 mod or shRNA3mod described herein), GCGCACAGTACCCTGGAGAAA (SEQ. ID. NO: 65; derived from BCL11A C4G5, or C4 mod or shRNA8mod described herein), CGCACAGAACACTCATGGATT (SEQ. ID. NO: 66; derived from BCL11A D12G5-2 described herein), and ACGCTCGCACAGAACACTCATGGATT (SEQ. ID. NO: 67; derived from BCL11A D12G5-2 described herein).

In one embodiment of any one of the synthetic BCL11A microRNA described herein, the loop segment is derived from a microRNA. In one embodiment, the microRNA is a hematopoietic specific microRNA. For examples, miR-142, miR-155, miR-181 and miR-223.

In one embodiment of any one of the synthetic BCL11A microRNA described herein, the microRNA is miR223.

In one embodiment of any one of the synthetic BCL11A microRNA described herein, the loop segment is ctccatgtggtagag (SEQ ID NO:68).

Accordingly, in one aspect, the present specification provides an isolated nucleic acid molecule comprising a nucleotide sequence selected from the group consisting of SEQ ID NOS:1-10,13-18, 25-44, or a synthetic BCL11A microRNA described herein.

Accordingly, in one aspect, the present specification provides a composition comprising at least one nucleic acid molecule comprising a nucleotide sequence selected from the group consisting of SEQ ID NOS:1-10,13-18, 25-44, or a synthetic BCL11A microRNA described herein.

Accordingly, in one aspect, the present specification provides a composition comprising at least a vector comprising a nucleic acid molecule comprising a nucleotide sequence selected from the group consisting of SEQ ID NOS:1-10, 13-18, 25-44, or a synthetic BCL11A microRNA described herein.

In one embodiment of any isolated nucleic acid molecule described, the molecule comprises the nucleotide sequence of SEQ ID NO:1.

In one embodiment of any isolated nucleic acid molecule described, the molecule comprises the nucleotide sequence of SEQ ID NO:2.

In one embodiment of any isolated nucleic acid molecule described, the molecule comprises the nucleotide sequence of SEQ ID NO:3.

In one embodiment of any isolated nucleic acid molecule described, the molecule comprises the nucleotide sequence of SEQ ID NO:4.

In one embodiment of any isolated nucleic acid molecule described, the molecule comprises the nucleotide sequence of SEQ ID NO:5.

In one embodiment of any isolated nucleic acid molecule described, the molecule comprises the nucleotide sequence of SEQ ID NO:6.

In one embodiment of any isolated nucleic acid molecule described, the molecule comprises the nucleotide sequence of SEQ ID NO:7.

In one embodiment of any isolated nucleic acid molecule described, the molecule comprises the nucleotide sequence of SEQ ID NO:8.

In one embodiment of any isolated nucleic acid molecule described, the molecule comprises the nucleotide sequence of SEQ ID NO:9.

In one embodiment of any isolated nucleic acid molecule described, the molecule comprises the nucleotide sequence of SEQ ID NO:10.

In one embodiment of any isolated nucleic acid molecule described, the molecule comprises the nucleotide sequence of SEQ ID NO:13.

In one embodiment of any isolated nucleic acid molecule described, the molecule comprises the nucleotide sequence of SEQ ID NO:14.

In one embodiment of any isolated nucleic acid molecule described, the molecule comprises the nucleotide sequence of SEQ ID NO:15.

In one embodiment of any isolated nucleic acid molecule described, the molecule comprises the nucleotide sequence of SEQ ID NO:16.

In one embodiment of any isolated nucleic acid molecule described, the molecule comprises the nucleotide sequence of SEQ ID NO:17.

In one embodiment of any isolated nucleic acid molecule described, the molecule comprises the nucleotide sequence of SEQ ID NO:18.

In one embodiment of any isolated nucleic acid molecule described, the molecule comprises the nucleotide sequence of SEQ ID NO:25.

In one embodiment of any isolated nucleic acid molecule described, the molecule comprises the nucleotide sequence of SEQ ID NO:26.

In one embodiment of any isolated nucleic acid molecule described, the molecule comprises the nucleotide sequence of SEQ ID NO:27.

In one embodiment of any isolated nucleic acid molecule described, the molecule comprises the nucleotide sequence of SEQ ID NO:28.

In one embodiment of any isolated nucleic acid molecule described, the molecule comprises the nucleotide sequence of SEQ ID NO:29.

In one embodiment of any isolated nucleic acid molecule described, the molecule comprises the nucleotide sequence of SEQ ID NO:30.

In one embodiment of any isolated nucleic acid molecule described, the molecule comprises the nucleotide sequence of SEQ ID NO:31.

In one embodiment of any isolated nucleic acid molecule described, the molecule comprises the nucleotide sequence of SEQ ID NO:32.

In one embodiment of any isolated nucleic acid molecule described, the molecule comprises the nucleotide sequence of SEQ ID NO:33.

In one embodiment of any isolated nucleic acid molecule described, the molecule comprises the nucleotide sequence of SEQ ID NO:34.

In one embodiment of any isolated nucleic acid molecule described, the molecule comprises the nucleotide sequence of SEQ ID NO:35.

In one embodiment of any isolated nucleic acid molecule described, the molecule comprises the nucleotide sequence of SEQ ID NO:36.

In one embodiment of any isolated nucleic acid molecule described, the molecule comprises the nucleotide sequence of SEQ ID NO:37.

In one embodiment of any isolated nucleic acid molecule described, the molecule comprises the nucleotide sequence of SEQ ID NO:38.

In one embodiment of any isolated nucleic acid molecule described, the molecule comprises the nucleotide sequence of SEQ ID NO:39.

In one embodiment of any isolated nucleic acid molecule described, the molecule comprises the nucleotide sequence of SEQ ID NO:40.

In one embodiment of any isolated nucleic acid molecule described, the molecule comprises the nucleotide sequence of SEQ ID NO:41.

In one embodiment of any isolated nucleic acid molecule described, the molecule comprises the nucleotide sequence of SEQ ID NO:42.

In one embodiment of any isolated nucleic acid molecule described, the molecule comprises the nucleotide sequence of SEQ ID NO:43.

In one embodiment of any isolated nucleic acid molecule described, the molecule comprises the nucleotide sequence of SEQ ID NO:44.

In one aspect, the present specification provides a vector comprising at least one nucleic acid molecule comprising a nucleotide sequence selected from the group consisting of SEQ ID NOS:1-10,13-18, 25-44 or a synthetic BCL11A microRNA described herein.

In one embodiment of any vector described, the vector further comprises a spleen focus-forming virus promoter, a tetracycline-inducible promoter, or a β-globin locus control region and a β-globin promoter. The promoter provide for targeted expression of the nucleic acid molecule therein or the synthetic BCL11A microRNA therein.

In one aspect, the present specification provides a host cell comprising a vector which comprises at least one nucleic acid molecule comprising a nucleotide sequence selected from the group consisting of SEQ ID NOS:1-10,13-18, 25-44, or a synthetic BCL11A microRNA described herein.

In one embodiment of any host cell described herein, the host cell is an embryonic stem cell, a somatic stem cell, a progenitor cell, a bone marrow cell, a hematopoietic stem cell, or a hematopoietic progenitor cell. In one embodiment, the host cell is isolated from a subject. In one embodiment, the host cell is isolated from a subject who has been diagnosed with a hemoglobinopathy. Diagnosis can be made by any method known in the art. For example, by genetic testing, by RT-PCR, and by blood cytology.

In one embodiment of any host cell described herein, the host cell is an erythrocyte.

In one aspect, the present specification provides a host cell comprising a vector or a bacterium which comprises at least one nucleic acid molecule comprising a nucleotide sequence selected from the group consisting of SEQ ID NOS:1-10, 13-18, 25-44, or a synthetic BCL11A microRNA described herein.

In one aspect, the present specification provides a host cell comprising a virus which comprises at least one nucleic acid molecule comprising a nucleotide sequence selected from the group consisting of SEQ ID NOS:1-10,13-18, 25-44, or a synthetic BCL11A microRNA described herein.

In one embodiment of any virus or vector described herein, the virus is a lentivirus.

In one embodiment of any vector or virus described herein, the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (Hy), bovine immune deficiency virus (BIV), and simian immunodeficiency virus (SIV).

Accordingly, one aspect of, the present specification provides methods for increasing fetal hemoglobin levels expressed by a cell, comprising the steps of contacting an embryonic stem cell, a somatic stem cell, a progenitor cell, a bone marrow cell, a hematopoietic stem cell, or a hematopoietic progenitor cell with an effective amount of a composition described herein or an effective amount of at least isolated nucleic acid molecule described herein, whereby fetal hemoglobin expression is increased in the cell, or its progeny, relative to the cell prior to such contacting. In some embodiments, the composition comprises at least one vector or cell comprising at least one nucleic acid molecule comprising the nucleotide sequence selected from the group consisting of SEQ ID NOS:1-10,13-18, 25-44, or a synthetic BCL11A microRNA described herein. In one embodiment, the method further comprises providing a sample of stem or progenitor cells for the contacting. In one embodiment, the sample of cells comprises CD34+ selected cells. In one embodiment, the composition comprises a mixture of the nucleotide sequences selected from the group consisting of SEQ ID NOS:1-10,13-18, 25-44. For example, the composition has 2-5 different nucleotide sequences selected from the group consisting of SEQ ID NOS:1-10, 13-18, 25-44. For example, the composition comprises SEQ ID NOS: 34, 37, 39, 41 and 43.

In one aspect, the present specification provides methods of treating, or reducing a risk of developing, a hemoglobinopathy, e.g., SCD and THAL, in a subject. The methods can include selective knockdown of the BCL11A gene in the hematopoietic stem cells of subjects or individuals. These subjects are at risk of developing, a hemoglobinopathy.

In one embodiment of any method described, the selective knockdown of the BCL11A gene in the hematopoietic stem cells comprises using an isolated nucleic acid molecule comprising a nucleotide sequence of SEQ ID NOS:1-10,13-18, 25-44 or using a vector (e.g. a viral vector) comprising a nucleic acid molecule comprising any one of the nucleotide sequence of SEQ ID NOS:1-10,13-18, 25-44, or a synthetic BCL11A microRNA described herein.

In one embodiment of any method described, the selective knockdown of the BCL11A gene in the hematopoietic stem cells comprises contacting the hematopoietic stem cells with a composition which comprises at least an isolated nucleic acid molecule comprising the nucleotide sequence of SEQ ID NOS:1-10,13-18, 25-44, or with a composition which comprises at least a vector (e.g. a viral vector) comprising a nucleic acid molecule comprising any one of the nucleotide sequence of SEQ ID NOS:1-10,13-18, 25-44, or a synthetic BCL11A microRNA described herein. In one embodiment, the hematopoietic stem cells are isolated prior the contacting.

In one embodiment of any method described, the selective knockdown of the BCL11A gene in the hematopoietic stem cells occurs in vivo, in vitro, or ex vivo. In a further embodiment, the hematopoietic progenitor cell being targeted for selective knockdown is of the erythroid lineage.

In one embodiment of any method described, the contacting of the hematopoietic stem cells with any of the composition described herein occurs in vivo, in vitro, or ex vivo. In a further embodiment, the hematopoietic progenitor cell being contacted is of the erythroid lineage.

In one embodiment of any method described, the contacting of the hematopoietic stem cells with any of the composition described herein occurs in vivo, in vitro, or ex vivo.

In other embodiments of any method described, selective knockdown of the BCL11A gene occurs in an embryonic stem cell, a somatic stem cell, a progenitor cell, a bone marrow cell in addition to a hematopoietic stem cell, or a hematopoietic progenitor cell. In one embodiment, an embryonic stem cell, a somatic stem cell, a progenitor cell, or a bone marrow cell is contacted with the described composition. The embryonic stem cell, the somatic stem cell, the progenitor cell, or the bone marrow cell is isolated prior the contacting. In one embodiment, the contacting of the embryonic stem cell, the somatic stem cell, the progenitor cell, or the bone marrow cell with any of the composition described herein occurs in vivo, in vitro, or ex vivo.

In other embodiments of any method described, the hematopoietic stem cells are collected from peripheral blood, cord blood, chorionic villi, amniotic fluid, placental blood, or bone marrow.

In other embodiments of any method described, the embryonic stem cell, somatic stem cell, progenitor cell, or bone marrow cell is collected from peripheral blood, cord blood, chorionic villi, amniotic fluid, placental blood, or bone marrow.

In one aspect, the present specification provides a method of treating, or reducing a risk of developing, a hemoglobinopathy in a subject, the method comprising: administering to the subject a therapeutically effective amount of one or more isolated nucleic acid molecule described herein, a virus or a vector described herein, or a cell described herein, thereby treating, or reducing the risk of developing, the hemoglobinopathy in the subject, wherein the virus, the vector or cell comprises at least one nucleic acid molecule comprising the nucleotide sequence selected from the group consisting of SEQ ID NOS:1-10,13-18, 25-44, or a synthetic BCL11A microRNA described herein. For example, the effective amount of one or more isolated nucleic acid molecule described herein, a virus or a vector described herein, or a cell described herein are injected directly into the bone marrow of the subject.

In one aspect, the present specification provides a method of treating, or reducing a risk of developing, a hemoglobinopathy in a subject, the method comprising contacting a population of hematopoietic stem cells in vitro or ex vivo with a composition described herein or with at least one or more isolated nucleic acid molecule described herein, a virus or a vector described herein, and implanting or administering the contacted hematopoietic stem cells or the progeny cells thereof to the subject. In one embodiment, the contacted hematopoietic stem cells or the progeny cells engrafts in the subject. In one embodiment, the contacted hematopoietic stem cells or the progeny cells thereof are implanted with prostaglandin E2 and/or antioxidant N-acetyl-L-cysteine (NAC) to promote the engraftments of the contacted cells.

In one aspect, the present specification provides a method of treating, or reducing a risk of developing, a hemoglobinopathy in a subject, the method comprising expressing at least one synthetic BCL11A microRNA described herein in an embryonic stem cell, a somatic stem cell, a progenitor cell, a bone marrow cell, a hematopoietic stem cell, or a hematopoietic progenitor cell of the subject wherein the expression is ex vivo or in vitro, and implanting or administering the cell into the subject.

In one aspect, the present specification provides a method for increasing fetal hemoglobin levels expressed by a cell, the method comprising expressing at least one synthetic BCL11A microRNA described herein in an embryonic stem cell, a somatic stem cell, a progenitor cell, a bone marrow cell, a hematopoietic stem cell, or a hematopoietic progenitor cell of a subject wherein the expression is ex vivo or in vitro or in vivo. In one embodiment, the expression is by contacting the cells with an effective amount of a composition described herein or an effective amount of at least isolated nucleic acid molecule described herein.

In one aspect, the present specification provides a method for decreasing BCRLLA levels expressed by a cell, the method comprising expressing at least one synthetic BCL11A microRNA described herein in an embryonic stem cell, a somatic stem cell, a progenitor cell, a bone marrow cell, a hematopoietic stem cell, or a hematopoietic progenitor cell of a subject wherein the expression is ex vivo or in vitro or in vivo. In one embodiment, the expression comprises the steps of contacting an embryonic stem cell, a somatic stem cell, a progenitor cell, a bone marrow cell, a hematopoietic stem cell, or a hematopoietic progenitor cell with an effective amount of a composition described herein or an effective amount of at least isolated nucleic acid molecule described herein, whereby fetal hemoglobin expression is increased in the cell, or its progeny, relative to the cell prior to such contacting. In some embodiments, the composition comprises at least one vector or cell comprising at least one nucleic acid molecule comprising the nucleotide sequence selected from the group consisting of SEQ ID NOS:1-10,13-18, 25-44, or a synthetic BCL11A microRNA described herein.

In a further embodiment of any methods described herein, the hematopoietic stem cell or hematopoietic progenitor cell being contacted is of the erythroid lineage.

In one embodiment of any methods described herein, the hematopoietic stem cell or hematopoietic progenitor cell is collected from peripheral blood, cord blood, chorionic villi, amniotic fluid, placental blood, or bone marrow.

In a further embodiment of any methods described herein, the recipient subject is treated with chemotherapy and/or radiation prior to implantation of the contacted or transfected cells.

In one embodiment, the chemotherapy and/or radiation is to reduce endogenous stem cells to facilitate engraftment of the implanted cells.

In one aspect, the present specification provides a method of treating, or reducing a risk of developing a hemoglobinopathy in a subject, the method comprising providing hematopoietic stem cells from the subject, contacting the hematopoietic stem cells in vitro or ex vivo with a composition described herein or with at least one or more isolated nucleic acid molecule described herein, a virus or a vector described herein, and implanting or re-administering the contacted hematopoietic stem cells back into the same subject. In one embodiment, the contacted hematopoietic stem cells or the progeny cells engrafts in the subject.

In one aspect of any method, the contacted hematopoietic stem cells, embryonic stem cells, somatic stem cells, progenitor cells, bone marrow cells, or the progeny cells thereof are treated ex vivo with prostaglandin E2 and/or antioxidant N-acetyl-L-cysteine (NAC) to promote subsequent engraftment in a recipient subject.

In one aspect of any method, the population of hematopoietic stem cells or host cells is obtained from a subject at risk of developing a hemoglobinopathy or has been diagnose with a hemoglobinopathy.

In one aspect of any method, the population of hematopoietic stem cells is autologous or allogeneic to the subject.

In one aspect of any method, the population of hematopoietic stem cells or host cells is ex vivo expanded in culture prior to contacting with a composition described herein or with at least one or more isolated nucleic acid molecule described herein, a virus or a vector described herein.

In one aspect of any method, the population of hematopoietic stem cells or host cells is ex vivo expanded in culture after to contacting with a composition described herein or with at least one or more isolated nucleic acid molecule described herein, a virus or a vector described herein.

In one aspect of any method, the contacted population of hematopoietic stem cells or host cells is pre-differentiated ex vivo in culture prior to implanting into a subject.

In one aspect of any method, the contacted hematopoietic stem cells are expanded in vitro or ex vivo prior to administering into the subject. In one aspect of any method, the contacted hematopoietic stem cells are cryopreserved prior to administering into the subject. In another aspect of any method, the contacted hematopoietic stem cells are expanded in vitro or ex vivo and cryopreserved prior to administering into the subject. In another aspect of any method, the contacted hematopoietic stem cells are expanded in vitro or ex vivo after cryopreservation prior to administering into the subject.

In one aspect of any method, the subject is a human. In one aspect of any method, the subject is diagnosed with a hemoglobinopathy.

In one aspect of any method, the method further comprises of selecting a subject diagnosed with a hemoglobinopathy or a subject at risk of developing a hemoglobinopathy.

In one aspect of any method, the hemoglobinopathy is sickle cell disease (SCD) or thalassemia (THAL). For example, β-thalassemias.

In one aspect of the method, the method further comprising administering to the subject a therapy comprising oxygen, hydroxyurea, folic acid, or a blood transfusion.

In one aspect, the present specification provides a method of treating, or reducing a risk of developing, a hemoglobinopathy in a subject, the method comprising expressing in vivo at least one synthetic BCL11A microRNA described herein in the subject.

In one aspect of any method, the in vivo expression occurs in an embryonic stem cell, a somatic stem cell, a progenitor cell, a bone marrow cell, a hematopoietic stem cell, or a hematopoietic progenitor cell.

In one aspect of any method, the embryonic stem cell, somatic stem cell, progenitor cell, bone marrow cell, hematopoietic stem cell, or hematopoietic progenitor cell is autologous or allogeneic to the subject.

In one aspect of any method, the embryonic stem cell, somatic stem cell, progenitor cell, bone marrow cell, hematopoietic stem cell, or hematopoietic progenitor cell expressing the at least one synthetic BCL11A microRNA described herein is expanded in vitro or ex vivo prior to administering into the subject. In a further embodiment, the progenitor cell, bone marrow cell, hematopoietic stem cell and hematopoietic progenitor cell is of the erythroid lineage.

In one aspect of any method, the embryonic stem cell, somatic stem cell, progenitor cell, bone marrow cell, hematopoietic stem cell, or hematopoietic progenitor cell expressing the at least one synthetic BCL11A microRNA described herein is cryopreserved prior to administering into the subject.

In another aspect of any method, the embryonic stem cell, somatic stem cell, progenitor cell, bone marrow cell, hematopoietic stem cell, or hematopoietic progenitor cell expressing the at least one synthetic BCL11A microRNA described herein is expanded in vitro or ex vivo and cryopreserved prior to administering into the subject.

In another aspect of any method, the embryonic stem cell, somatic stem cell, progenitor cell, bone marrow cell, hematopoietic stem cell, or hematopoietic progenitor cell expressing the at least one synthetic BCL11A microRNA described herein is expanded in vitro or ex vivo after cryopreservation prior to administering into the subject.

In one aspect of any method, the at least one synthetic BCL11A microRNA is operably linked to a promoter and constructed in a vector for expression in a eukaryotic cell.

In one aspect of any method, the at least one synthetic BCL11A microRNA is expressed from a RNA II polymerase.

In one aspect of any method, the at least one synthetic BCL11A microRNA is not expressed from a RNA III polymerase.

In one aspect of any method, the promoter is selected from a group consisting of a spleen focus-forming virus promoter, a tetracycline-inducible promoter, or a β-globin locus control region and a β-globin promoter, or a hematopoietic specific promoter.

In one aspect of any method, the vector is a virus.

In one aspect of any method, the virus is a lentivirus.

In one aspect of any method, the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (ETAV), feline immunodeficiency virus (Fly), bovine immune deficiency virus (BIV), and simian immunodeficiency virus (SIV).

In one aspect of any method, the subject is an animal, human or non-human, and rodent or non-rodent. For example, the subject can be any mammal, e.g., a human, other primate, pig, rodent such as mouse or rat, rabbit, guinea pig, hamster, cow, horse, cat, dog, sheep or goat, or a non-mammal such as a bird.

In one aspect of any method, the method comprises obtaining a sample or a population of embryonic stem cells, somatic stem cells, progenitor cells, bone marrow cells, hematopoietic stem cells, or hematopoietic progenitor cells from the subject.

In one embodiment, the embryonic stem cells, somatic stem cells, progenitor cells, bone marrow cells, hematopoietic stem cells, hematopoietic progenitor cells are isolated from the host subject, transfected, cultured (optional), and transplanted back into the same host, i. e. an autologous cell transplant. In another embodiment, the embryonic stem cells, somatic stem cells, progenitor cells, bone marrow cells, hematopoietic stem cells, or hematopoietic progenitor cells are isolated from a donor who is an HLA-type match with a host (recipient) who is diagnosed with or at risk of developing a hemoglobinopathy. Donor-recipient antigen type-matching is well known in the art. The HLA-types include HLA-A, HLA-B, HLA-C, and HLA-D. These represent the minimum number of cell surface antigen matching required for transplantation. That is the transfected cells are transplanted into a different host, i.e., allogeneic to the recipient host subject. The donor's or subject's embryonic stem cells, somatic stem cells, progenitor cells, bone marrow cells, hematopoietic stem cells, or hematopoietic progenitor cells can be transfected with a vector or nucleic acid comprising the nucleic acid molecule described herein, the transfected cells are culture expanded, and then transplanted into the host subject. In one embodiment, the transplanted cells engrafts in the host subject. The transfected cells can also be cryopreserved after transfected and stored, or cryopreserved after cell expansion and stored.

As used herein, treating or reducing a risk of developing a hemoglobinopathy in a subject means to ameliorate at least one symptom of hemoglobinopathy. In one aspect, the invention features methods of treating, e.g., reducing severity or progression of, a hemoglobinopathy in a subject. In another aspect, the methods can also be used to reduce a risk of developing a hemoglobinopathy in a subject, delaying the onset of symptoms of a hemoglobinopathy in a subject, or increasing the longevity of a subject having a hemoglobinopathy. In one aspect, the methods can include selecting a subject on the basis that they have, or are at risk of developing, a hemoglobinopathy, but do not yet have a hemoglobinopathy, or a subject with an underlying hemoglobinopathy. Selection of a subject can include detecting symptoms of a hemoglobinopathy, a blood test, genetic testing, or clinical recordings. If the results of the test(s) indicate that the subject has a hemoglobinopathy, the methods also include administering the compositions described herein, thereby treating, or reducing the risk of developing, a hemoglobinopathy in the subject. For example, a subject who is diagnosis of SCD with genotype HbSS, HbS/β0 thalassemia, HbSD, or HbSO, and/or HbF<10% by electrophoresis.

As used herein, the term "hemoglobinopathy" refers to a condition involving the presence of an abnormal hemoglobin molecule in the blood. Examples of hemoglobinopathies include, but are not limited to, SCD and THAL. Also included are hemoglobinopathies in which a combination of abnormal hemoglobins is present in the blood (e.g., sickle cell/Hb-C disease). An exemplary example of such a disease includes, but is not limited to, SCD and THAL. SCD and THAL and their symptoms are well-known in the art and are described in further detail below. Subjects can be diagnosed as having a hemoglobinopathy by a health care provider, medical caregiver, physician, nurse, family member, or acquaintance, who recognizes, appreciates, acknowledges, determines, concludes, opines, or decides that the subject has a hemoglobinopathy.

The term "SCD" is defined herein to include any symptomatic anemic condition which results from sickling of red blood cells. Manifestations of SCD include: anemia; pain; and/or organ dysfunction, such as renal failure, retinopathy, acute-chest syndrome, ischemia, priapism, and stroke. As used herein the term "SCD" refers to a variety of clinical problems attendant upon SCD, especially in those subjects who are homozygotes for the sickle cell substitution in HbS.

Among the constitutional manifestations referred to herein by use of the term of SCD are delay of growth and development, an increased tendency to develop serious infections, particularly due to pneumococcus, marked impairment of splenic function, preventing effective clearance of circulating bacteria, with recurrent infarcts and eventual destruction of splenic tissue. Also included in the term "SCD" are acute episodes of musculoskeletal pain, which affect primarily the lumbar spine, abdomen, and femoral shaft, and which are similar in mechanism and in severity. In adults, such attacks commonly manifest as mild or moderate bouts of short duration every few weeks or months interspersed with agonizing attacks lasting 5 to 7 days that strike on average about once a year. Among events known to trigger such crises are acidosis, hypoxia, and dehydration, all of which potentiate intracellular polymerization of HbS (J. H. Jandl, Blood: Textbook of Hematology, 2nd Ed., Little, Brown and Company, Boston, 1996, pages 544-545).

As used herein, "THAL" refers to a hereditary disorder characterized by defective production of hemoglobin. In one embodiment, the term encompasses hereditary anemias that occur due to mutations affecting the synthesis of hemoglobins. In other embodiments, the term includes any symptomatic anemia resulting from thalassemic conditions such as severe or β-thalassemia, thalassemia major, thalassemia intermedia, α-thalassemias such as hemoglobin H disease. β-thalassemias are caused by a mutation in the β-globin chain, and can occur in a major or minor form. In the major form of β-thalassemia, children are normal at birth, but develop anemia during the first year of life. The mild form of β-thalassemia produces small red blood cells. Alpha-thalassemias are caused by deletion of a gene or genes from the globin chain.

By the phrase "risk of developing disease" is meant the relative probability that a subject will develop a hemoglobinopathy in the future as compared to a control subject or population (e.g., a healthy subject or population). For example, an individual carrying the genetic mutation associated with SCD, an A to T mutation of the β-globin gene, and whether the individual in heterozygous or homozygous for that mutation increases that individual's risk.

The term "inhibitory RNA" is meant to include a nucleic acid molecule that contains a sequence that is complementary to a target nucleic acid (e.g., a target microRNA) that mediates a decrease in the level or activity of the target nucleic acid. Non-limiting examples of inhibitory RNAs include interfering RNA, shRNA, siRNA, ribozymes, antagomirs, and antisense oligonucleotides. Methods of making inhibitory RNAs are described herein. Additional methods of making inhibitory RNAs are known in the art. In one embodiment, the BCL11A microRNA described herein is an inhibitory RNA that cause a decrease in the activity of BCL11A mRNA.

As used herein, "an interfering RNA" refers to any double stranded or single stranded RNA sequence, capable—either directly or indirectly (i.e., upon conversion) of inhibiting or down-regulating gene expression by mediating RNA interference. Interfering RNA includes, but is not limited to, small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family. As used herein, the phrase "post-transcriptional processing" refers to mRNA processing that occurs after transcription and is mediated, for example, by the enzymes Dicer and/or Drosha.

A "small interfering RNA" or "siRNA" as used herein refers to any small RNA molecule capable of inhibiting or down regulating gene expression by mediating RNA interference in a sequence specific manner. The small RNA can be, for example, about 18 to 21 nucleotides long. Each siRNA duplex is formed by a guide strand and a passenger strand. The endonuclease Argonaute 2 (Ago 2) catalyzes the unwinding of the siRNA duplex. Once unwound, the guide strand is incorporated into the RNA Interference Specificity Complex (RISC), while the passenger strand is released. RISC uses the guide strand to find the mRNA that has a complementary sequence leading to the endonucleolytic cleavage of the target mRNA.

Retroviruses are RNA viruses that utilize reverse transcriptase during their replication cycle. The term "retrovirus" refers to any known retrovirus (e.g., type c retroviruses, such as Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend, Murine Stem Cell Virus (MSCV) and Rous Sarcoma Virus (RSV)). "Retroviruses" of the invention also include human T cell leukemia viruses, HTLV-1 and HTLV-2, and the lentiviral family of retroviruses, such as Human Immunodeficiency Viruses, HIV-1, HIV-2, simian immunodeficiency virus (SW), feline immonodeficiency virus (FIV), equine immunodeficiency virus (EIV), and other classes of retroviruses.

The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, R, and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R and U5. The U3 region contains the enhancer and promoter elements. The U5 region is the sequence between the primer binding site and the R region and contains the polyadenylation sequence. The R (repeat) region is flanked by the U3 and U5 regions. The LTR composed of U3, R, and U5 regions, appears at both the both the 5' and 3' ends of the viral genome. In one embodiment of the invention, the promoter within the LTR, including the 5' LTR, is replaced with a heterologous promoter. Examples of heterologous promoters that can be used include, for example, a spleen focus-forming virus (SFFV) promoter, a tetracycline-inducible (TET) promoter, a β-globin locus control region and a β-globin promoter (LCR), and a cytomegalovirus (CMV) promoter.

The term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes, i.e., T-cells.

The term "R region" refers to the region within retroviral LTRs beginning at the start of the capping group (i.e., the start of transcription) and ending immediately prior to the start of the poly A tract. The R region is also defined as being flanked by the U3 and U5 regions. The R region plays an important role during reverse transcription in permitting the transfer of nascent DNA from one end of the genome to the other.

The term "promoter/enhancer" refers to a segment of DNA which contains sequences capable of providing both promoter and enhancer functions. For example, the long terminal repeats of retroviruses contain both promoter and enhancer functions. The enhancer/promoter may be "endogenous," "exogenous," or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

Unless otherwise defined, all technical terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control. Other features and advantages of the invention will be apparent from the following detailed description and figures, and from the claims.

DESCRIPTION OF DRAWINGS

FIG. 1 is a diagram of two embodiments of the disclosed synthetic BCL11A micro RNA: BCL11A miR1 and BCL11A miR2 oligonucleotides. The stem/loop structure is generated by the complementary sequences of the BCL11A targeting sequences (in bold upper case nucleotide bases) in the oligonucleotides. The BCL11A targeting sequences are the BCL11A segments. The stem/loop structure is then cloned in to a miR-223/miR-30 background (micro RNA background). The entire miRNA/shRNA structure is then cloned into a SFFV/LCR/TET cassette containing SIN lentiviral vector containing a transgene reporter (Venus).

FIG. 2 is a schematic diagram of lentiviral vector proviruses with SFFV, TET and LCR promoters.

FIG. 8A. Schematic representation of RNA polymerase III (pol III, U6 promoter, left side) and RNA polymerase II (pol II, SFFV promoter, right side) driven shRNA and miRNA(223) embedded shRNA cassettes, respectively. Both expression cassettes were engineered into lentivirus vectors. The various boxes represent the passenger strand, the guide strand, and the loop structure as indicated. The miRNA223 scaffold is represented with dotted line box. Different shRNA sequences targeting BCL11A were expressed in these two backbones and evaluated for knockdown efficiency.

FIG. 8B. High-throughput screening of multiple shRNA sequences targeting various regions in BCL11A mRNA (XL/L-shared isoform sequences, XL-unique coding sequences and the 3'-UTR of XL isoform, as indicated) for knockdown efficiency using pol III-based lentivirus vectors. Both induction of ε-γ by qPCR and induction of mCherry reporter by FACS (as a surrogate for epsilon-y induction in a reporter cell line) were used as a functional readout for BCL11A knockdown. Normalized expression of ε-γ mRNA relative to non-targeting control is plotted on y-axis and mean florescence intensity (MFI) of mCherry expression relative to un-transduced control is plotted on x-axis. The 11 shRNAs that were further tested are marked with circles.

FIGS. 8C and 8D. Comparison of knockdown efficiency of selected shRNAs in pol III-based and pol II-based systems. MEL cells were transduced with LKO vector or with LEGO vector to express the indicated shRNAs and the transduced cells were selected either in the presence of puromycin (LKO) or sorted for Venus expression (LEGO). miR1 shRNA previously reported by Sankaran et al. ( ). BCL11A protein levels are shown (FIG. 8C) by immunoblot with β-actin as control. XL and L show the position of each isoform of BCL11A protein. (FIG. 8D) Band intensity was analyzed using ImageJ software.

FIG. 8E. Fold induction of normalized expression of ε-γ compared to non-targeting control is measured by qPCR. Non-targeting shRNA transduced MEL cells were used and expression set to 1. Data represent mean±SD from a representative experiment of three independent experiments conducted in triplicates. *$P<0.05$, $P<0.01$, *$P<0.001$.

FIGS. 9A-9F are data collected from small RNA sequencing analysis which reveals differential processing between pol III vs pol II transcripts.

FIGS. 9A and 9B. Total RNA was isolated from transduced, sorted or puromycin selected MEL cells expressing either miR1 or C4 shRNA. The resulting RNA was then subjected to RNA deep-sequencing. Processed final guide and passenger strand sequence transcribed from (FIG. 9A) pol III (LKO) or (FIG. 9B) from pol II (LEGO) are represented on the x-axis and corresponding number of reads per million of total reads of each strand are plotted on the y-axis.

FIGS. 9C-9F. The sequences of processed variant guide strands of miR1 transcribed from (FIG. 9C) pol III promoter or (FIG. 9D) pol II promoter are plotted on the y-axis with the number of total reads plotted on the x-axis. The sequence of processed variant guide strand species of C4 transcribed from (FIG. 9E) pol III promoter or (FIG. 9F) pol II promoter are plotted on y-axis with the number of total reads plotted on x-axis.

FIG. 10A. mIR1 and C4 shRNAs were modified such that four 5' bases were deleted and GCGC was added on 3' end to yield modified shRNA termed miR1 G5 and C4G5.

FIG. 10B. Comparison of knockdown efficiency of modified and parent shRNA sequences. MEL cells were transduced with LEGO to express the indicated shRNAs via pol II promoter and transduced cells were sorted for Venus expression. BCL11A protein levels were measured by immunoblot with β-actin as a loading control. XL and L indicate position of these isoforms of BCL11A protein.

FIG. 10C. Immunoblot band intensity was analyzed using ImageJ software.

FIG. 10D. Fold induction of normalized expression compared to non-targeting control of ε-γ by modified/unmodified shRNA sequences measured by qPCR. Data represent mean±SD from a representative experiment of three independent experiments conducted in triplicate showing similar results. *P<0.05, **P<0.01.

FIGS. 11A-11C show the RNA sequencing analysis of four base-pairs modified shRNAs exhibit faithful processing.

FIG. 11A. Total small RNA was isolated from transduced, sorted MEL expressing modified miR1 and modified C4 shRNAs and sequenced. Frequency distribution of processed guide strand species of modified miR1 (miR1-G5 and C4G5) transcribed from pol II promoter are plotted on the y-axis with the proportion of reads per million total reads plotted on x-axis.

FIGS. 11B and 11C. The sequence of processed variant guide strand species of mIR1-G5 and C4-G5 are displayed on the y-axis and the frequency of reads are shown on the x-axis.

FIG. 12A. Candidates from the shRNA screen targeting BCL11A using pLKO vector.

FIG. 14A. Design of new shRNAs to mimic mature guide strands produced in pLKO vector. All shRNAs were modified such that four bases on the 5' were deleted and GCGC was added on 3' end to yield modified shRNA termed miR1G5, E3G5, B5G5, D8G5, B11G5, 50D12G5, 50B11G5, 50A5G5, 50C4G5. With incorporation of this shift, significant improvement was observed with E3G5, D8G5 and C4G5 regarding the BCL11A knockdown and epsilon-gamma induction. The "xxxx" represents the position of the 4-base pair (bp) frame shift that results in the 4-bases removed from the unmodified miR1, E3, B5, D8, B11, 50D12 (also referred to as D12), 50B11, 50A5 (also referred to as A5), and 50C4 (also referred to as C4).

FIG. 18 shows the differential processing in pol-III shRNA vectors and pol-II microRNA adapted shRNA vectors.

FIG. 19A. Schematic representation of LKO-U6-BCL11A-shRNA (left side) and LEGO-SFFV-BCL11A-shRNAmiR (right side). Both expression cassettes were engineered into lentiviral vectors as described in Material and Methods. The light grey boxes represent the sense strand; white boxes represent the antisense strand; dark grey boxes represent the loop structure and the miRNA223 scaffold is indicated by a dotted line. The hairpin structures are shown below. Different shRNA sequences targeting BCL11A were expressed in these two backbones and evaluated for knockdown efficiency.

FIG. 19B. High-throughput screening of multiple shRNA sequences targeting BCL11A mRNA for knockdown efficiency using pol III-based lentivirus vectors. Both induction of Hbb-y mRNA by qRT-PCR and induction of mCherry reporter by FACS (as a surrogate for ε-γ induction in a reporter cell line) were used as a functional readout for BCL11A knockdown. Normalized expression of Hbb-y mRNA relative to non-targeting control is plotted on y-axis and fold induction of mCherry expression (by mean fluorescence intensity, MFI) relative to non-transduced control is plotted on x-axis. The eight best performing shRNAs isolated from the screen were further tested and are labeled as 1 through 8.

FIG. 19C. Comparison of knockdown efficiency of selected shRNAs in pol III (U6)- and pol II (SFFV)-based systems. MEL cells were transduced with U6- (top panel) or with SFFV- (bottom panel) vectors to express the indicated shRNAs and the transduced cells were selected either in the presence of puromycin (pol III) or sorted for Venus expression (pol II). BCL11A protein levels are shown by immunoblot with β-actin as control. XL and L on left of panel denote the position of each isoform of BCL11A protein.

FIG. 19D. Fold induction of normalized expression of Hbb-y compared to non-targeting control measured by qPCR. Expression in non-targeting (NT) shRNA transduced MEL cells was set 1. Black bars represent the relative expression by U6 promoter driven shRNAs and white bars represent SFFV promoter driven shRNAs. Data represent mean±SD from a representative experiment of three independent experiments conducted in triplicates. *$P<0.05$.

FIG. 21A. SFFV-shRNAmiRs were modified by deleting the first four bases from the guide sequence and the addition of GCGC to the 3' end (shRNA modified)

FIG. 21B. Comparison of knockdown efficiency of modified and parental shRNAmiR sequences expressed from a SFFV-pol II promoter in MEL cells. BCL11A protein levels were measured in FACS sorted transduced cells by immunoblot with β-actin as a loading control. XL and L on the left of top panel indicate the position of these isoforms of BCL11A protein. PIII: pol III promoter vector; PII: pol II promoter vector; PIIM: pol II promoter vector containing modified shRNAmiR sequences.

FIG. 21C. Fold induction of Hbb-y compared to the non-targeting control by unmodified (white bars) and modified (shaded bars) shRNAmiR sequences measured by qRT-PCR. Data represent mean±SD. **$P<0.01$.

FIG. 21D. Northern blot analysis of total RNA extracted from cells transduced with multiple shRNAs and shRNAmiRs. Probes (20 nt) complementarity to the guide and passenger strands from positions 1 to 20 of shRNAs and shRNAmiRs were utilized to measure the abundance of processed small RNAs. A probe complementary to 5S RNA was used as an internal control to determine RNA loading. PIII: pol III promoter vector; PII: pol II promoter vector; PIIM: pol II promoter vector containing modified shRNAmiR sequences.

FIG. 21E. RNA-sequencing results of homogeneous populations of transduced MEL cells expressing shRNA1, 2, 3, 4, 7, or 8. The sequences of these RNAs were aligned to the corresponding reference guide strand sequence shown at the top of each panel. The sequences of different guide strand species are displayed on the y-axis and the frequency as percentage of aligned reads are shown on the x-axis.

FIG. 22A. CD34+ cells transduced with pol III or pol II vectors expressing different shRNAs with and without modification were selected either in the presence of puromycin (pol III) or sorted for Venus expression (pol II and pol II modified). BCL11A expression was measured by immunoblot with β-actin as a loading control on day 11 of differentiation.

FIG. 22B. Induction of γ-globin mRNA was determined on day 18 of differentiation by qRT-PCR. Data represents the percentage of γ-globin of total β-locus output (γ+β-globin) for pol III (black bars), pol II (white bars), and modified pol II (grey bars). *$p>0.05$; ***$p>0.001$.

FIG. 22C. Quantification and statistical analysis of erythroid differentiation markers (CD71, GpA) and enucleation were assessed by flow cytometry. CTRL: control vectors SFFV-shRNAmiRNT and SEW; PIII: pol III vectors; PII: pol II vectors; PIIM: pol II vectors containing modified shRNAmiR sequences. Data represents mean±SD from three independent experiments. ***$p>0.001$.

FIG. 22D. Hemoglobin F of cell lysates was measured by HPLC on day 18 of differentiation. The arrow indicates the HbF peaks and the percentage of HbF of total hemoglobin is shown below the chromatogram.

FIG. 22E. Correlation graph of γ-globin mRNA expression assessed by qRT-PCR versus HbF by HPLC. Black circles represent pol III vectors, open and grey circles represent pol II or modified shRNAmiRs, respectively. Correlation coefficient ($r^2$) is shown for all data.

FIG. 23A. Lineage negative bone marrow cells isolated from β-YAC mice (CD45.2) were transduced ex vivo with LeGO vectors expressing shRNAmiR* targeting BCL11A or a non-targeting control vector (SFF-shRNAmiRNT) and transplanted into lethally irradiated BoyJ recipients (CD45.1). Untransduced control cells were transplanted as control. Engraftment analysis was performed 4, 8 and 12 weeks post transplantation in peripheral blood and bone marrow, respectively. (n=4 mice per group)

FIG. 23B. The fraction of gene modified cells (Venus+ cells) in these mice was determined 4, 8 and 12 weeks post transplantation in peripheral blood and bone marrow.

FIG. 23C. Competitive transplants were performed using CD45.1 and CD45.2 donor cells transduced with the indicated vectors and transplanted into CD45.1/2 heterozygous mice (top panels). Alternatively a neutral vector encoding blue fluorescent protein (SFFV-BFP) was used to identify the competitor population in a CD45.1 donor into CD45.2 recipient setting (lower panels). Shown are representative dot blots of different mixed populations used for transplantation three days post transduction. The two competing vectors are indicated above each panel, the first one indicates the CD45.2 or SFFV-BFP transduced populations, respectively.

FIG. 23D. The contribution of gene modified cells in competitively repopulated mice was analyzed at 4 and 8 weeks post transplantation in peripheral blood (PB) or at week 12 in bone marrow (BM) and spleen (Spl). The relative contribution of gene modified cells transduced with the two competing vectors is shown. The first vector mentioned dominated the hematopoietic output. Each dot represents an individual recipient mouse.

FIG. 23E. A pairwise comparison of the bone marrow B-cell fraction within the transduced fraction of cells between BCL11A targeting vectors versus control vectors (SFF-shRNAmiRNT and SFFV-BFP, left panel). Similarly, the LSK content within transduced cell fractions was analyzed. Each dot represents an individual recipient. * and ** indicate p-values≤0.05 and 0.01, respectively.

FIG. 23F. Configuration of the LCR-shRNAmiR vector used for erythroid specific expression (details in text).

FIG. 23G. The in vivo expression profile of the LCR-vector was analyzed in various hematopoietic lineages 12 weeks after transplantation. The percentages of Venus+ cells in each mouse were normalized to CD71+/Ter119+ erythroid cells (n=4).

FIG. 23H. A competitive transplantation experiment as described in c and d was performed using the LCR or SFFV vectors expressing shRNAmiR*. Each dot represents an individual recipient.

FIG. 23I. Mobilized peripheral blood CD34+ cells were transduced with LCR-shRNAmiR*, 3 and 8 or a SFFV-GFP mock vector and subjected to erythroid differentiation in vitro. At day 7 after transduction the promoter activity of SFFV-GFP and LCR-vectors in different erythroid subpopulation was assessed. Representative flow diagrams are shown. Error bars in all figures=SD. Statistical analysis: t-test.

FIG. 24A. CD34+ HSPCs transduced with LCR-shRNAmiR 3, 8 or the SFFV-GFP mock vector were FACS-sorted for fluorescent reporter expression and BCL11A expression was measured by immunoblot with β-actin as a loading control on day 11 of differentiation.

FIG. 24B. Induction of γ-globin mRNA was determined on day 18 of differentiation by qRT-PCR. Data represents the percentage of γ/(γ+β) globin.

FIG. 24C. Quantification and statistical analysis of erythroid differentiation markers (CD71, GpA) and enucleation by flow cytometric analysis. CTRL: SFFV-GFP control vector; LCRM: Modified shRNAmiRs shown in FIG. 23A expressed via LCR promoter. Data represents mean±SD from three independent experiments.

FIG. 24D. HbF level of cell lysates was measured by HPLC on day 18 of differentiation. Arrows indicate the HbF peaks and the percentage of HbF of total hemoglobin is shown below the chromatogram.

FIG. 24E. Correlation graph of γ-globin induction by qRT-PCR versus HbF by HPLC. Error bars indicate±SD from three independent experiments.

FIG. 24F. Bone marrow CD34+ HSPCs were transduced with LCR-shRNAmiR3 or NT and transplanted into sublethally irradiated NSG-mice (n=3 per group). Untransduced cells were used as a control. Fourteen weeks later CD34 cells were isolated from the bone marrow of transplanted animals and subjected to erythroid differentiation in vitro for 14 days. Expression of γ-globin and β-globin was assessed in cells sorted for Venus reporter expression.

FIG. 30 shows the sequences used in both SFFV and LCR backbones for the knockdown of BCL11A in CD34+ differentiated erythroid cells.

FIG. 31 shows Western blots of the BCL11A knockdown in CD34+ differentiated erythroid cells.

DETAILED DESCRIPTION

Figure 3:
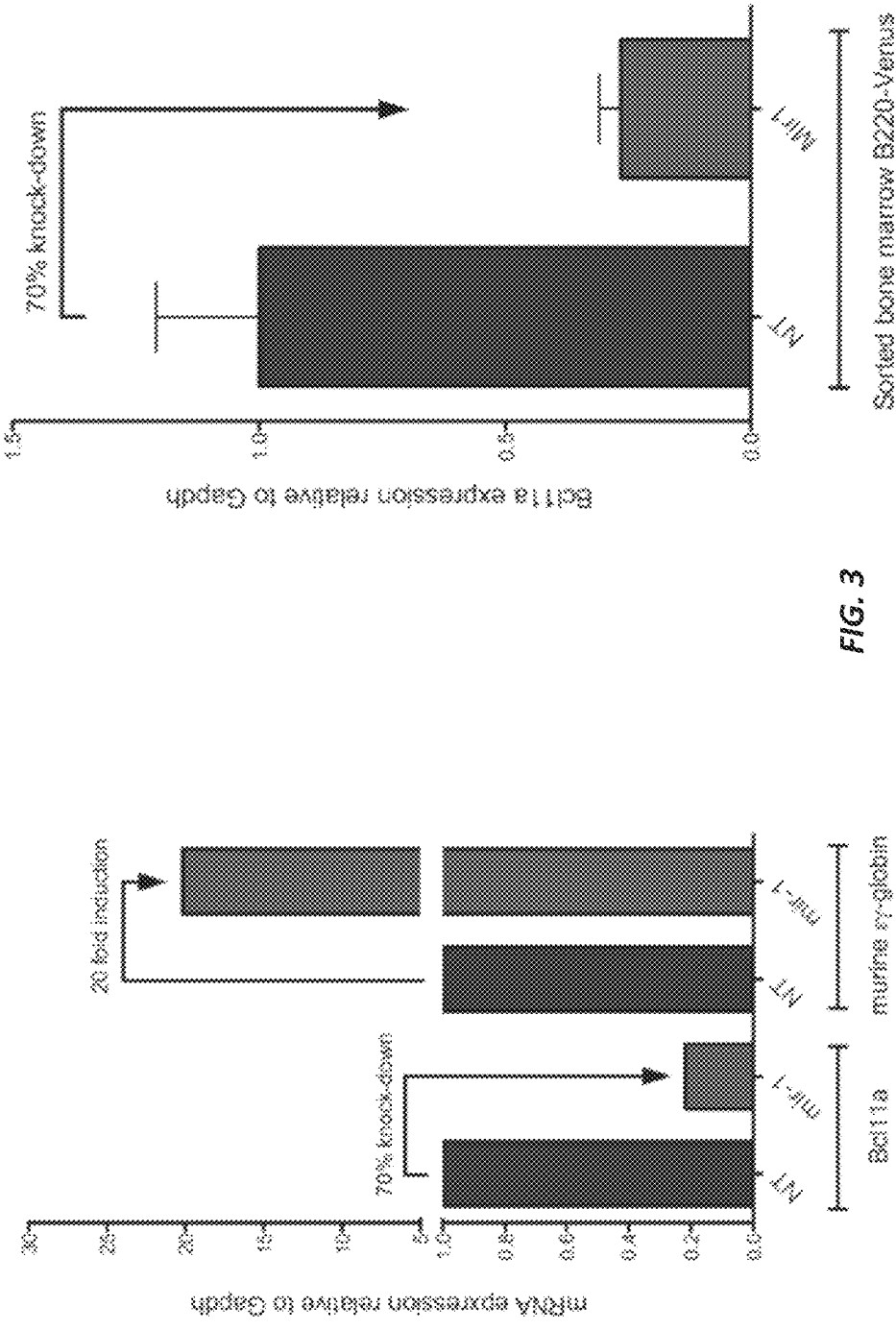
FIG. 3 is a panel of two bar graphs showing that SFFV-LV efficiently knocks down BCL11A and induces εγ-globin expression.

The disclosure described herein is based, in part, on development of lentiviral gene therapy vectors that selectively express the BCL11A-targeting shRNA in progeny of hematopoietic stem cells (HSC). Accordingly, the disclosure encompasses novel methods for the regulation of γ-globin expression in erythroid cells. More specifically, these activities can be harnessed in methods for the treatment of hemoglobinopathies, including SCD and THAL, by induction of γ-globin via inhibition of the BCL11A gene product. In particular embodiments, lentiviral gene therapy vectors that selectively express the BCL11A-targeting snRNA in progeny of HSCs, hematopoietic progenitor cells, or other stem cells such as embryonic cells are provided.

Normal adult hemoglobin comprises four globin proteins, two of which are alpha (α) proteins and two of which are beta (β) proteins. During mammalian fetal development, particularly in humans, the fetus produces fetal hemoglobin, which comprises two gamma (γ)-globin proteins instead of the two β-globin proteins. At some point during fetal development, a globin fetal switch occurs at which point erythrocytes in the fetus switch from making predominantly γ-globin to making predominantly β-globin. The developmental switch from production of predominantly fetal hemoglobin or HbF (α2γ2) to production of adult hemoglobin or HbA (α2β2) begins at about 28 to 34 weeks of gestation and continues shortly after birth until HbA becomes predominant. This switch results primarily from decreased transcription of the γ-globin genes and increased transcription of β-globin genes. On average, the blood of a normal adult contains only about 2% HbF, though residual HbF levels have a variance of over 20-fold in healthy adults (Atweh, Semin. Hematol. 38:367-73 (2001)).

Hemoglobinopathies encompass a number of anemias of genetic origin in which there is a decreased production and/or increased destruction (hemolysis) of red blood cells (RBCs). These also include genetic defects that result in the production of abnormal hemoglobins with a concomitant impaired ability to maintain oxygen concentration. Some such disorders involve the failure to produce normal β-globin in sufficient amounts, while others involve the failure to produce normal β-globin entirely. These disorders associated with the β-globin protein are referred to generally as hemoglobinopathies. For example, SCD results from a point mutation in the β-globin structural gene, leading to the production of abnormal (sickled) hemoglobin (HbS). HbS RBCs are more fragile than normal RBCs and undergo hemolysis more readily, leading eventually to anemia (Atweh, Semin. Hematol. 38(4):367-73 (2001)). THAL results from a partial or complete defect in the expression of the β-globin gene, leading to deficient or absent HbA.

The search for treatment aimed at reduction of globin chain imbalance in patients with hemoglobinopathies has focused on the pharmacologic manipulation of fetal HbF. The therapeutic potential of such approaches is demonstrated by observations that certain populations of adult patients with β chain abnormalities and higher than normal levels of HbF experience a milder clinical course of disease than patients with normal adult levels of HbF. For example, a group of Saudi Arabian sickle cell anemia patients who express 20-30% HbF have only mild clinical manifestations of the disease (Pembrey, et al., Br. J. Haematol. 40: 415-429 (1978)). It is now accepted that hemoglobinopathies, such as SCD and THAL, are ameliorated by increased HbF production (Jane et al., Br. J. Haematol. 102: 415-422 (1998); Bunn, N. Engl. J. Med. 328: 129-131 (1993)).

The transcriptional repressor BCL11A represents a therapeutic target for β-hemoglobinopathies. RNA interference was applied using pol III promoter-expressed short hairpin RNAs (shRNAs) to reduce BCL11A expression in hematopoietic cells. Knockdown of BCL11A in murine hematopoietic stem cells (HSCs) impaired long-term engraftment. To avoid HSC toxicity, the expression of BCL11A in erythroid cells was selectively suppressed via pol II promoter expressed microRNA adapted shRNAs (shRNAmiRs). With identical target matched sequences, markedly reduced knockdown was observed using pol II vectors due to 3-5 nt differences in the guide strands between the systems that strongly influence target knockdown. A corresponding 4 nt shift was engineered into guide strands of shRNAmiRs that surprisingly and unexpectedly improved the knockdown of BCL11A and derepression of Hbb-y, a functional homolog of the human γ-globin gene in a murine erythroid cell line. The modified shRNAmiRs were expressed in an erythroid-specific fashion to circumvented the adverse effects on murine HSC engraftment, and this led to efficient BCL11A knockdown and high levels of HbF in human CD34-derived erythroid cells. A strategy was developed for the prospective design of shRNAmiRs derived from pol III-expressed shRNA screens. This strategy constitutes an improved approach to genetic therapy in hemoglobinopathies and other diseases requiring lineage-specific expression of gene silencing sequences.

Retroviral and Lentiviral Vectors

In some embodiments, the present disclosure provides improved compositions and methods for treating hemoglobinopathies using retrovirus-based, e.g., lentivirus-based, gene delivery vectors that achieve sustained, high-level expression of transferred therapeutic genes in eythroid cells or erythroid precursor cells. In one embodiment of the invention, the vector comprises an artificial miRNA comprising targeting sequences to BCL11A cloned into the stem loop of the endogenouse miR-223 sequence (Amendola et al., Mol Ther 17:1039-52, 2009). The stem/loop structure of the present vectors are generated by complementary sequences of the oligonucleotides of SEQ ID NOs:1-18 and 25-44 disclosed herein. See FIGS. 1, 12A, 14A, 21A, and EXAMPLE 11. This stem/loop structure was cloned into a miR-223/miR-30 background. The entire miRNA/shRNA structure was then cloned into a cassette with a SFFV, TET, or LCR promoter containing self-inactivating (SIN) vector. Particular lentiviral vectors of the invention are described by Pawliuk et al. (2001) Science 294:2368 and Imren et al. (2002) PNAS 99:14380, incorporated by reference herein.

Accordingly, in one aspect, provided herein is a synthetic BCL11A microRNA comprising a first BCL11A segment, a loop segment, and a second BCL11A segment arranged in tandem in a 5' to 3' direction, wherein the loop segment is between and directly linked to the first and second BCL11A segments, and wherein the second BCL11A segment is complementary to the first BCL11A segment such that the first and second BCL11A segments base pair to form a hairpin loop with the loop segment forming the loop portion of the hairpin loop thus formed.

In one embodiment of any one of the synthetic BCL11A microRNA described herein, the first and second BCL11A segments are about 18 to 25 nucleotides long. The first BCL11A segment is derived from a BCL11A sequence and gives rise to the passenger strand during shRNA processing to a duplex siRNA and the second BCL11A segment is complementary to first BCL11A segment, wherein the second BCL11A segment gives rise to the guide strand that is incorporated into the RNA Interference Specificity Complex (RISC) for RNA interference or BCL11A gene silencing.

In one embodiment of any one of the synthetic BCL11A microRNA described herein, the first and second BCL11A segments are derived from BCL11A mRNA sequence.

In one embodiment of any one of the synthetic BCL11A microRNA described herein, the first BCL11A segment starts with a -GCGC- at the 5' end and the second BCL11A segment ends with a -GCGC- at the 3' end.

In one embodiment of any one of the synthetic BCL11A microRNA described herein, the first BCL11A segment further consist a -GCGC- at the 5' end and the second BCL11A segment ends with a -GCGC- at the 3' end.

In one embodiment of any one of the synthetic BCL11A microRNA described herein, the first BCL11A segment starts with a -GCGA-, -TCTG-, or -TG- at the 5' end and the second BCL11A segment is complementary to first BCL11A segment.

In one embodiment of any one of the synthetic BCL11A microRNA described herein, the first BCL11A segment further consist a -GCGA-, -TCTG-, or -TG- at the 5' end.

In one embodiment of any one of the synthetic BCL11A microRNA described herein, the second BCL11A segment ends with a -TTTT- at the 3' end.

In one embodiment of any one of the synthetic BCL11A microRNA described herein, the synthetic BCL11A microRNA comprise a nucleotide sequence selected from the group consisting of SEQ ID NOS:1-10,13-18, 25-44.

In one embodiment of any one of the synthetic BCL11A microRNA described herein, the synthetic BCL11A microRNA consists of a nucleotide sequence selected from the group consisting of SEQ ID NOS:1-10,13-18, 25-44.

In one embodiment of any one of the synthetic BCL11A microRNA described herein, the synthetic BCL11A microRNA consist essentially of a nucleotide sequence selected from the group consisting of SEQ ID NOS:1-10,13-18, 25-44.

In one embodiment of any one of the synthetic BCL11A microRNA described herein, the first BCL11A segment is selected from the group consisting of CGCACAGAACACTCATGGATT (SEQ. ID. NO: 46; derived from BCL11A miR1 oligo described herein), CCAGAGGATGACGATTGTTTA (SEQ. ID. NO: 47; derived from BCL11A miR2 oligo described herein), TCGGAGACTCCAGACAATCGC (SEQ. ID. NO: 48; derived from BCL11A E3 oligo or shRNA1 or E3 described herein), CCTCCAGGCAGCTCAAAGATC, (SEQ. ID. NO: 49; derived from shRNA2 or B5 described herein), TCAGGACTAGGTGCAGAATGT (SEQ. ID. NO: 50; derived from shRNA4 or B11 described herein), TTCTCTTGCAACACGCACAGA (SEQ. ID. NO: 51; derived from BCL11A D8 oligo or shRNA3 or D8 described herein), GATCGAGTGTTGAATAATGAT (SEQ. ID. NO: 52; derived from shRNA5 or 50D12 of D12 described herein), CAGTACCCTGGAGAAACACAT (SEQ. ID. NO: 53; derived from shRNA5 or 50A5 described herein), CACTGTCCACAGGAGAAGCCA (SEQ. ID. NO: 54; derived from shRNA7 or 50B11 described herein), ACAGTACCCTGGAGAAACACA (SEQ. ID. NO: 55; derived from BCL11A XLC4, shRNA8 and 50C4 described herein), CAACAAGATGAAGAGCACCAA (SEQ. ID. NO: 56; derived from BCL11A Non-targeting oligos described herein), gcgcCGCACAGAACACTCATG (SEQ. ID. NO: 57; derived from miR1G5 oligo described herein), GCGCTCGGAGACTCCAGACAA (SEQ. ID. NO: 58; derived from E3G5 or E3 mod oligo or shRNA1mod described herein), gcgcCCTCCAGGCAGCTCAAA (SEQ. ID. NO: 59; derived from B5G5 or shRNA2mod described herein); gcgcTCAGGACTAGGTGCAGA (SEQ. ID. NO: 60; derived from B11G5 or shRNA4mod described herein); gcgcGATCGAGTGTTGAATAA (SEQ. ID. NO: 61; derived from 50D12G5, D12G4 or shRNA5mod described herein); gcgcCAGTACCCTGGAGAAAC (SEQ. ID. NO: 62; derived from 50A5G5 or shRNA6mod described herein); gcgcCACTGTCCACAGGAGAA (SEQ. ID. NO: 63; derived from 50B11G5 or shRNA7mod described herein); GCGCTTCTCTTGCAACACGCA (SEQ. ID. NO: 64; derived from BCL11A D8G5 or D8 mod or shRNA3mod described herein), GCGCACAGTACCCTGGAGAAA (SEQ. ID. NO: 65; derived from BCL11A C4G5, or C4 mod or shRNA8mod described herein), CGCACAGAACACTCATGGATT (SEQ. ID. NO: 66; derived from BCL11A D12G5-2 described herein), and ACGCTCGCACAGAACACTCATGGATT (SEQ. ID. NO: 67; derived from BCL11A D12G5-2 described herein).

In one embodiment of any one of the synthetic BCL11A microRNA described herein, the loop segment is derived from a microRNA. In one embodiment, the microRNA is a hematopoietic specific microRNA. For examples, miR-142, miR-155, miR-181 and miR-223.

In one embodiment of any one of the synthetic BCL11A microRNA described herein, the microRNA is miR223.

In one embodiment of any one of the synthetic BCL11A microRNA described herein, the loop segment is ctccatgtggtagag (SEQ ID NO:68).

In one aspect, the present specification provides an isolated nucleic acid molecule comprising a nucleotide sequence selected from the group consisting of SEQ ID NOS:1-18, 25-44, or a synthetic BCL11A microRNA described herein.

Accordingly, in one aspect, the present specification provides a composition comprising at least one nucleic acid molecule comprising a nucleotide sequence selected from the group consisting of SEQ ID NOS:1-10,13-18, 25-44, or a synthetic BCL11A microRNA described herein.

Accordingly, in one aspect, the present specification provides a composition comprising at least a vector or a bacterium comprising a nucleic acid molecule comprising a nucleotide sequence selected from the group consisting of SEQ ID NOS:1-10,13-18, 25-44, or a synthetic BCL11A microRNA described herein.

In one aspect, the present specification provides a host cell comprising a vector or virus which comprises at least one nucleic acid molecule comprising a nucleotide sequence selected from the group consisting of SEQ ID NOS:1-10, 13-18, 25-44, or a synthetic BCL11A microRNA described herein.

In one aspect, the present specification provides a host cell comprising a vector, virus or a bacterium which comprises at least one nucleic acid molecule comprising a nucleotide sequence selected from the group consisting of SEQ ID NOS:1-10,13-18, 25-44, or a synthetic BCL11A microRNA described herein.

In one embodiment, the vector is a viral vector or a virus.

RNA interference (RNAi) mediated by short interfering RNAs (siRNA) or microRNAs (miRNA) is a powerful method for post-transcriptional regulation of gene expression. RNAi has been extensively used for the study of biological processes in mammalian cells and could constitute a therapeutic approach to human diseases in which selective modulation of gene expression would be desirable. Depending on the degree of complementarity between miRNA and target mRNA sequences, loss of gene expression occurs by inducing degradation of the cognate mRNA or by translational attenuation. Endogenous miRNAs are transcribed as primary transcripts and subsequently processed by the RNAse III enzyme Drosha, (1) to create a stem loop structure. Nuclear export and cleavage by Dicer generates a mature short double stranded molecule (siRNA) that is separated into guide and passenger strands. The guide strand is loaded into the RNA induced silencing complex (RISC), the effector complex mediating cleavage of target mRNAs with the functional guide strand binding to RISC proteins (2) while the passenger strand is degraded [reviewed in (3)]. The loading of guide versus passenger strands into RISC largely depends on the 5' end stability of the siRNA, with the less stable strand preferentially incorporated into RISC (4, 5), although the exact regulation in mammalian cells is incompletely understood. The 5' end of the guide strand contains the "seed region," which is critical for target identification (6, 7). Precise cleavage by Drosha and Dicer is critical for the generation of guide RNAs with defined seed regions that mediate efficient binding to the appropriate target mRNAs. Inaccurate processing results in binding to off-target molecules but a shift in cleavage sites also alters the nucleotide composition of duplex ends, which may have a profound effect on strand loading into RISC (8).

The inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. RNAi is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, at least 20%, at least 30%, at least 40%, at least 50%, at least 60%, at least 70%, at least 80%, at least 90%, at least 95%, at least 99%, or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. siRNA is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g., the BCL11A sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target BCL11A mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human BCL11A mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA. The Examples herein provide specific examples of RNA interfering agents, such as shRNA molecules that effectively target BCL11A mRNA.

Polymerase (pol) III driven short hairpin RNAs (shRNAs) are most commonly used in biological experimental settings. shRNAs mimic the structure of miRNA precursor intermediates, and thus bypass the first cleavage step mediated by Drosha. shRNAs can be abundantly expressed to provide efficient knockdown. However at high multiplicities of infection (MOI), oversaturation of the endogenous RNAi machinery has been reported in some cases to be associated with cytotoxic effects due to the dysregulation of endogenous miRNAs (9-11). Two components of microRNA processing, Exportin5 and Ago2, seem to limit the capacity of this pathway, and overexpression of these proteins results in increased knockdown capacity (12-15). Additionally, activation of innate immune responses triggered by small RNAs in a sequence specific as well as non-specific manner may mediate cytotoxic side effects (16, 17), reviewed in (18). These effects have resulted in increased mortality in mice in some experimental transgenic model systems reportedly as a direct side effect of shRNA over-expression (14, 19).

For clinical translation of RNAi based therapeutics, alternative expression systems utilizing polymerase II promoters will likely be required. This class of promoters allows for utilization of appropriate regulatory elements for lineage or even cell-type specific expression. It also could provide lower levels of expression compared to pol III promoters, which may obviate over-saturation of the processing machinery that have been reported in cells transduced at high MOIs). Complicating the use of pol II promoters for shRNA expression, requires embedding of the shRNA sequences into flanking sequences usually derived from endogenous miRNA precursors for efficient processing. shRNAs flanked by a miRNA scaffold mimic the structure of endogenous miRNAs (10, 20). To date, flanking regions derived from human miRNA-30 and miRNA-223 have been widely used for incorporation of recombinant shRNAs for expression in mammalian cells, and there have been numerous efforts to better understand and to improve this expression strategy (21). The latter miRNA has been shown to be particularly effective when used as scaffold for shRNA expression in hematopoietic cells and mediates substantial knockdown of target mRNAs as a result of efficient processing and low passenger strand activity in several hematopoietic cell types (21, 22).

In this disclosure, the inventors utilized BCL11A as a target to study the processing and optimization of shRNAmiRs for potential therapeutic applications. BCL11A is a validated therapeutic target for reactivation of γ-globin gene and therefore HbF expression in the major hemoglobinopathies, sickle cell disease (SCD) and β-thalassemias. Down modulation or genetic deletion of BCL11A relieves γ-globin repression (23) and inactivation of BCL11A in the erythroid lineage prevents SCD phenotype and organ toxicities in genetically engineered mice (24). The mouse embryonic Hbb-y gene is a functional homolog of the human γ-globin gene, and therefore serves as a convenient surrogate for assessment of the effect of BCL11A knockdown in murine erythroleukemia (MEL) cells. Initially we observed a markedly reduced efficiency of knockdown of BCL11A upon expression of shRNA using pol II-based as compared with pol III-based vectors. Pol III and pol II shRNAmiR designs typically incorporate 21 base target site matched sequences within the palindromic hairpin stem, but the transcripts from these two types of expression cassettes are expected to be processed differently (25). The pol II shRNAmiR transcripts enter the RNAi processing pathway upstream of Drosha processing, whereas the much shorter pol III products are expected to enter the pathway downstream of Drosha and to be cleaved only at the loop end by Dicer. Based upon the sequences of processed small RNAs derived from pol III and pol II promoters we observed that pol III shRNA cassettes and pol II shRNAmiR cassettes yielded different processed shRNAs with respect to the relative positioning of the 21 base target-matched sequences. Redesigned shRNAmiRs that mimicked the mature guide strand sequences produced by effective pol III-driven shRNAs led to enhancement in processing efficiency and inhibition of the target mRNA. Incorporation of these modifications into an erythroid-specific mammalian expression vector led to significant knockdown of BCL11A protein and re-induction of fetal hemoglobin. This strategy also avoided toxicity in the hematopoietic stem cell and B cell lineage compartments that accompanied pan-hematopoietic shRNA expression. In summary, the data demonstrate critical features of RNA processing relevant to the use of shRNA in different vector contexts, and also provide a strategy for lineage-specific gene knockdown that circumvents adverse consequences of widespread expression. Our findings have important implications for design of microRNA embedded shRNAs and their application in RNAi based gene therapy approaches.

In one embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small or short hairpin RNA (shRNA) in a pharmaceutically acceptable carrier to the cells in an organ of an individual. The shRNA is converted by the cells after transcription into siRNA capable of targeting, for example, BCL11A.

In one embodiment, the RNA interference agent is a nucleic acid molecule comprising the nucleotide sequence selected from the group consisting of SEQ ID NOS: 1-18, and 25-44, or a synthetic BCL11A microRNA described herein.

In one embodiment, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting BCL11A mRNA, may be delivered singly, or in combination with other RNA interference agents, e.g., siRNAs, such as, for example siRNAs directed to other cellular genes. BCL11A siRNAs may also be administered in combination with other pharmaceutical agents which are used to treat or prevent diseases or disorders associated with oxidative stress, especially respiratory diseases, and more especially asthma. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell. 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., a BCL11A coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif and selecting hits with at least 25%, 30%, 35%, 40%, 45%, 50%, 55%, 60%, 65%, 70% or 75% G/C content. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent, and GenSeq as well as commercially available oligosynthesis companies such as OLIGOENGINE®, may also be used to select siRNA sequences against EST libraries to ensure that only one gene is targeted.

Lentiviral vectors of the invention include, but are not limited to, human immunodeficiency virus (e.g., HIV-1, HIV-2), feline immunodeficiency virus (FIV), simian immunodeficiency virus (SIV), bovine immunodeficiency virus (BIV), and equine infectious anemia virus (EIAV). These vectors can be constructed and engineered using art-recognized techniques to increase their safety for use in therapy and to include suitable expression elements and therapeutic genes, such as those described below, which encode siRNAs for treating conditions including, but not limited to, hemoglobinopathies.

In consideration of the potential toxicity of lentiviruses, the vectors can be designed in different ways to increase their safety in gene therapy applications. For example, the vector can be made safer by separating the necessary lentiviral genes (e.g., gag and pol) onto separate vectors as described, for example, in U.S. Pat. No. 6,365,150, the contents of which are incorporated by reference herein. Thus, recombinant retrovirus can be constructed such that the retroviral coding sequence (gag, pol, env) is replaced by a gene of interest rendering the retrovirus replication defective. The replication defective retrovirus is then packaged into virions through the use of a helper virus or a packaging cell line, by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals.

A major prerequisite for the use of viruses as gene delivery vectors is to ensure the safety of their use, particularly with regard to the possibility of the spread of wild-type virus in the cell population. The development packaging cell lines, which produce only replication-defective retroviruses, has increased the utility of retroviruses for gene therapy, and defective retroviruses are well characterized for use in gene transfer for gene therapy purposes (for a review see Miller, A. D. (1990) Blood 76:271). Accordingly, in one embodiment of the invention, packaging cell lines are used to propagate vectors (e.g., lentiviral vectors) of the invention to increase the titer of the vector virus. The use of packaging cell lines is also considered a safe way to propagate the virus, as use of the system reduces the likelihood that recombination will occur to generate wild-type virus. In addition, to reduce toxicity to cells that caused by expression of packaging proteins, packaging systems can be use in which the plasmids encoding the packaging functions of the virus are only transiently transfected by, for example, chemical means.

In another embodiment, the vector can be made safer by replacing certain lentiviral sequences with non-lentiviral sequences. Thus, lentiviral vectors of the present disclosure may contain partial (e.g., split) gene lentiviral sequences and/or non-lentiviral sequences (e.g., sequences from other retroviruses) as long as its function (e.g., viral titer, infectivity, integration and ability to confer high levels and duration of therapeutic gene expression) are not substantially reduced. Elements which may be cloned into the viral vector include, but are not limited to, promoter, packaging signal, LTR(s), polypurine tracts, and a reverse response element (RRE).

In one embodiment of the disclosure, the LTR region is modified by replacing the viral LTR promoter with a heterologous promoter. In one embodiment, the promoter of the 5' LTR is replaced with a heterologous promoter. Examples of heterologous promoters which can be used include, but are not limited to, a spleen focus-forming virus (SFFV) promoter, a tetracycline-inducible (TET) promoter, a β-globin locus control region and a β-globin promoter (LCR), and a cytomegalovirus (CMV) promoter.

In some embodiments, the lentiviral vectors of the disclosure also include vectors which have been modified to improve upon safety in the use of the vectors as gene delivery agents in gene therapy. In one embodiment of the invention, an LTR region, such as the 3' LTR, of the vector is modified in the U3 and/or U5 regions, wherein a SIN vector is created. Such modifications contribute to an increase in the safety of the vector for gene delivery purposes. In one embodiment, the SIN vector of the invention comprises a deletion in the 3' LTR wherein a portion of the U3 region is replaced with an insulator element. The insulator prevents the enhancer/promoter sequences within the vector from influencing the expression of genes in the nearby genome, and vice/versa, to prevent the nearby genomic sequences from influencing the expression of the genes within the vector. In a further embodiment of the invention, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in the invention.

The promoter of the lentiviral vector can be one which is naturally (i.e., as it occurs with a cell in vivo) or non-naturally associated with the 5' flanking region of a particular gene. Promoters can be derived from eukaryotic genomes, viral genomes, or synthetic sequences. Promoters can be selected to be non-specific (active in all tissues) (e.g., SFFV), tissue specific (e.g., (LCR), regulated by natural regulatory processes, regulated by exogenously applied drugs (e.g., TET), or regulated by specific physiological states such as those promoters which are activated during an acute phase response or those which are activated only in replicating cells. Non-limiting examples of promoters in the present invention include the spleen focus-forming virus promoter, a tetracycline-inducible promoter, a β-globin locus control region and a β-globin promoter (LCR), a cytomegalovirus (CMV) promoter, retroviral LTR promoter, cytomegalovirus immediate early promoter, SV40 promoter, and dihydrofolate reductase promoter. The promoter can also be selected from those shown to specifically express in the select cell types which may be found associated with conditions including, but not limited to, hemoglobinopathies. In one embodiment of the invention, the promoter is cell specific such that gene expression is restricted to red blood cells. Erythrocyte-specific expression is achieved by using the human β-globin promoter region and locus control region (LCR).

Skilled practitioners will recognize that selection of the promoter to express the polynucleotide of interest will depend on the vector, the nucleic acid cassette, the cell type to be targeted, and the desired biological effect. Skilled practitioners will also recognize that in the selection of a promoter, the parameters can include: achieving sufficiently high levels of gene expression to achieve a physiological effect; maintaining a critical level of gene expression; achieving temporal regulation of gene expression; achieving cell type specific expression; achieving pharmacological, endocrine, paracrine, or autocrine regulation of gene expression; and preventing inappropriate or undesirable levels of expression. Any given set of selection requirements will depend on the conditions but can be readily determined once the specific requirements are determined. In one embodiment of the invention, the promoter is cell-specific such that gene expression is restricted to red blood cells. Erythrocyte-specific expression is achieved by using the human β-globin promoter region and locus control region (LCR).

Standard techniques for the construction of expression vectors suitable for use in the present invention are well-known to those of ordinary skill in the art and can be found in such publications as Sambrook et al. (1989) Molecular Cloning: A Laboratory Manual, 2nd Ed. Cold Spring Harbor, N.Y. A variety of strategies are available for ligating fragments of DNA, the choice of which depends on the nature of the termini of the DNA fragments and which choices can be readily made by the skilled artisan.

Gene therapy vectors of the present invention, such as the foregoing lentiviral vectors, can be used to express a variety of therapeutic siRNAs in transformed erythroid cells. In one embodiment, the siRNA of interest to be expressed in the vector is derived from a gene that can be used to treat a hemoglobinopathy, such as an siRNA to BCL11A.

Particular gene therapy constructs of the invention include, but are not limited to, those shown in FIG. 2. The three lentiviral vectors described herein are schematically shown with a stem of the shRNA containing BCL11A mRNA targeting sequence, while the loop is miR223-specific. All contain a fluorochrome marker (Venus) and are built into a self-inactivating (SIN) delta-U3 LEGO backbone (Ferhse Lab, Germany). A constitutive knock-down lentivirus, where the targeting shRNA is expressed via the very potent, ubiquitously expressed SFFV promoter, was used to assess functionality and toxicity of the targeting shRNA. An inducible knock-down lentivirus, where the shRNA is expressed via a PGK tetracycline inducible promoter, was used to assess functional, dose- and schedule-dependent effects of the targeting shRNA. A lineage-specific lentivirus, where the shRNA is expressed via a β-globin LCR promoter landscape (HS2/3 DNA hypersensitive sites, Naldini Lab, Italy) is a therapeutic option to validate in in vivo systems. The LTR regions further comprise a U3 and U5 region, as well as an R region. The U3 and U5 regions can be modified together or independently to create a vector which is self-inactivating, thus increasing the safety of the vector for use in gene delivery. The U3 and U5 regions can further be modified to comprise an insulator element.

The step of facilitating the production of infectious viral particles in the cells may be carried out using conventional techniques, such as standard cell culture growth techniques. If desired by the skilled practitioner, lentiviral stock solutions may be prepared using the vectors and methods of the present invention. Methods of preparing viral stock solutions are known in the art and are illustrated by, e.g., Y. Soneoka et al. (1995) Nucl. Acids Res. 23:628-633, and N. R. Landau et al. (1992) J. Virol. 66:5110-5113. In the method of producing a stock solution in the present invention, lentiviral-permissive cells (referred to herein as producer cells) are transfected with the vector system of the present invention. The cells are then grown under suitable cell culture conditions, and the lentiviral particles collected from either the cells themselves or from the cell media as described above. Suitable producer cell lines include, but are not limited to, the human embryonic kidney cell line 293, the equine dermis cell line NBL-6, and the canine fetal thymus cell line Cf2TH.

The step of collecting the infectious virus particles also can be carried out using conventional techniques. For example, the infectious particles can be collected by cell lysis, or collection of the supernatant of the cell culture, as is known in the art. Optionally, the collected virus particles may be purified if desired. Suitable purification techniques are well known to those skilled in the art.

Other methods relating to the use of viral vectors in gene therapy can be found in, e.g., Kay, M. A. (1997) Chest 111(6 Supp.):1385-1425; Ferry, N. and Heard, J. M. (1998) Hum. Gene Ther. 9:1975-81; Shiratory, Y. et al. (1999) Liver 19:265-74; Oka, K. et al. (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J. Hepatol. 23:746-58; Brody, S. L. and Crystal, R. G. (1994) Ann. N.Y. Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al. (2000) Nature 408:483-8.

Retroviral vectors, including lentiviral vectors, as described above or cells comprising the same, can be administered in vivo to subjects by any suitable route, as is well known in the art. The term "administration" refers to the route of introduction of a formulated vector into the body. For example, administration may be intravascular, intraarterial, intravenous, intramuscular, topical, oral, or by gene gun or hypospray instrumentation. Thus, administration can be direct to a target tissue or through systemic delivery. Administration can be direct injection into the bone marrow. Administration directly to the target tissue can involve needle injection, hypospray, electroporation, or the gene gun. See, e.g., WO 93/18759, which is incorporated by reference herein.

Alternatively, the retroviral vectors of the invention can be administered ex vivo or in vitro to cells or tissues using standard transfection techniques well known in the art.

In one embodiment, the retroviral vectors of the invention can also be transduced into host cells, including embryonic stem cells, somatic stem cells, or progenitor cells. Examples of progenitor host cells which can be transduced by the retroviral vectors of the invention include precursors of erythrocytes and hematopoietic stem cells. In another embodiment, the host cell is an erythrocyte. Transduced host cells can be used as a method of achieving erythroid-specific expression of the gene of interest in the treatment of hemoglobinopathies.

Another aspect of the invention pertains to pharmaceutical compositions of the lentiviral vectors of the invention. In one embodiment, the composition includes a lentiviral vector in a therapeutically effective amount sufficient to treat or reduce the risk of developing (e.g. ameliorate the symptoms of a hemoglobinopathy) and a pharmaceutically acceptable carrier. A "therapeutically effective amount" refers to an amount effective, at dosages and for periods of time necessary, to achieve the desired therapeutic result, such as treatment or prevention of a hemoglobinopathic condition. A therapeutically effective amount of lentiviral vector may vary according to factors such as the disease state, age, sex, and weight of the individual, and the ability of the lentiviral vector to elicit a desired response in the individual. Dosage regimens may be adjusted to provide the optimum therapeutic response. A therapeutically effective amount is also one in which any toxic or detrimental effects of the lentiviral vector are outweighed by the therapeutically beneficial effects. The potential toxicity of the lentiviral vectors of the invention can be assayed using cell-based assays or art recognized animal models and a therapeutically effective modulator can be selected which does not exhibit significant toxicity. In a preferred embodiment, a therapeutically effective amount of a lentiviral vector is sufficient to treat a hemoglobinopathy.

Sterile injectable solutions can be prepared by incorporating lentiviral vector in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

It is to be noted that dosage values may vary with the severity of the condition to be alleviated. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition. In one embodiment, the dosage is ranges from $10^3$-$10^8$ viral particles/50 kg weight. In other embodiments, the dosage is ranges from $10^3$-$10^5$ viral particles/50 kg weight, $10^4$-$10^6$ viral particles/50 kg weight, $10^5$-$10^7$ viral particles/50 kg weight, $10^3$-$10^8$ viral particles/50 kg weight. In one embodiment, the dosage is about $10^4$ viral particles/50 kg weight.

The amount of viral vector in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. However, for any given case, an appropriate "effective amount" can be determined by one of ordinary skill in the art using only routine experimentation.

The present invention contemplates, in particular embodiments, cells genetically modified to express the therapeutic polypeptides and inhibitory RNAs contemplated herein, for use in the treatment of hemoglobinopathies. As used herein, the term "genetically engineered" or "genetically modified" refers to the addition, deletion, or modification of the genetic material in a cell. The terms, "genetically modified cells," "modified cells," and, "redirected cells," are used interchangeably. In particular embodiments, cells transduced with vectors contemplated herein are genetically modified. As used herein, the term "gene therapy" refers to the introduction of extra genetic material in the form of DNA or RNA into the total genetic material in a cell that restores, corrects, or modifies the cell's physiology to provide a desired therapeutic outcome.

In various embodiments, the genetically modified cells contemplated herein are transduced in vitro or ex vivo with vectors of the invention, and optionally expanded ex vivo. The transduced cells are then administered to a subject in need of gene therapy.

Cells suitable for transduction and administration in the gene therapy methods contemplated herein include, but are not limited to stem cells, progenitor cells, and differentiated cells. In certain embodiments, the transduced cells are embryonic stem cells, bone marrow stem cells, umbilical cord stem cells, placental stem cells, mesenchymal stem cells, hematopoietic stem cells, erythroid progenitor cells, and erythroid cells.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

In some embodiments, the transduced cells are hematopoietic stem and/or progenitor cells isolated from bone marrow, umbilical cord blood, or peripheral circulation. In particular embodiments, the transduced cells are hematopoietic stem cells isolated from bone marrow, umbilical cord blood, or peripheral circulation.

In one embodiment, the hematopoietic cells are CD34+ cells.

In one embodiment, the hematopoietic cells are erythroid progenitor cells.

In one embodiment, the hematopoietic cells are erythroid cells.

Cells of the invention can be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic. An "isolated cell" refers to a cell that has been obtained from an in vivo tissue or organ and is substantially free of extracellular matrix.

Illustrative examples of genetically modified cells suitable for cell-based therapies contemplated herein include, but are not limited to: embryonic stem cells, bone marrow stem cells, umbilical cord stem cells, placental stem cells, mesenchymal stem cells, hematopoietic stem cells, hematopoietic progenitor cells, myeloid progenitors, erythroid progenitors, and other erythroid cells.

In preferred embodiments, cells suitable for cell-based therapies contemplated herein include, but are not limited to: hematopoietic stem or progenitor cells, proerythroblasts, basophilic erythroblasts, polychromatic erythroblasts, orthochromatic erythroblasts, polychromatic erythrocytes, and erythrocytes (RBCs), or any combination thereof.

Methods of Treating, or Reducing a Risk of Developing, a Hemoglobinopathy

The present invention provides improved compositions and methods for increasing HbF production in a cell, by administering vectors that inhibit expression of BCL11A. The data demonstrate that inhibition of BCL11A leads to increased expression from the γ-globin genes. As disclosed herein, it is an object of the present invention to provide compositions and methods for increasing fetal hemoglobin levels in a cell. In some embodiments, the cell is an embryonic stem cell, a somatic stem cell, a progenitor cell, a bone marrow cell, a hematopoietic stem cell, a hematopoietic progenitor cell or a progeny thereof.

Accordingly, one aspect of the invention provides methods for increasing fetal hemoglobin levels expressed by a cell, comprising the steps of contacting an embryonic stem cell, a somatic stem cell, a progenitor cell, a bone marrow cell, a hematopoietic stem cell, or a hematopoietic with an effective amount of a composition comprising at least a virus or vector comprising a nucleic acid molecule described herein, whereby the expression of BCL11A is reduced and the fetal hemoglobin expression is increased in the cell, or its progeny, relative to the cell prior to such contacting. In one embodiment, the vector or virus expresses an RNA interference agent which is a BCL11A microRNA which inhibits BCL11A, thereby reducing the expression of BCL11A.

In connection with contacting a cell with an inhibitor of BCL11A, "increasing the fetal hemoglobin levels" in a cell indicates that HbF is at least 5% higher in populations treated with a BCL11A inhibitor, than in a comparable, control population, wherein no BCL11A inhibitor is present. It is preferred that the percentage of HbF expression in a BCL11A inhibitor treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of a non-targeting oligonucleotide.

In some embodiments of any of the methods described herein, the subject is suspected of having, is at risk of having, or has a hemoglobinopathy, e.g., SCD or THAL. It is well within the skills of an ordinary practitioner to recognize a subject that has, or is at risk of developing, a hemoglobinopathy.

The subjects can also be those undergoing any of a variety of additional therapy treatments. Thus, for example, subjects can be those being treated with oxygen, hydroxyurea, folic acid, or a blood transfusion.

Methods of delivering RNA interference agents, e.g., an siRNA, or vectors containing an RNA interference agent, to the target cells, e.g., erythrocytes or other desired target cells, for uptake include injection of a composition containing the RNA interference agent, e.g., an siRNA, or directly contacting the cell, e.g., a erythrocyte, with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agent may be used simultaneously. In one preferred embodiment, only one siRNA that targets human BCL11A is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., BCL11A. The dose of the particular RNA interfering agent will be in an amount necessary to effect RNA interference, e.g., post translational gene silencing, of the particular target gene, thereby leading to inhibition of target gene expression or inhibition of activity or level of the protein encoded by the target gene.

In one embodiment of any methods described herein, the embryonic stem cell, somatic stem cell, progenitor cell, bone marrow cell, or hematopoietic progenitor cell, or hematopoietic stem cell (HSC) is contacted ex vivo or in vitro. In a specific embodiment, the cell being contacted is a cell of the erythroid lineage. In one embodiment, the composition inhibits BCL11A expression.

In one embodiment of any methods described herein, the embryonic stem cell, somatic stem cell, progenitor cell, bone marrow cell, or hematopoietic progenitor cell, or HSC is isolated from the subject prior to contacting with the composition described herein or contacting with the virus or vector carrying a nucleic acid molecule comprising a nucleic acid sequence selected from a group consisting of SEQ ID NOS:1-10,13-18, 25-44, or contacting with the virus or vector expressing a synthetic BCL11A microRNA described herein.

Mature blood cells have a finite lifespan and must be continuously replaced throughout life. Blood cells are produced by the proliferation and differentiation of a very small population of pluripotent hematopoietic stem cells (HSCs) that also have the ability to replenish themselves by self-renewal. HSCs are multipotent, self-renewing progenitor cells that develop from mesodermal hemangioblast cells. HSCs are the blood cells that give rise to all the other blood cells, that includes all the differentiated blood cells from the erythroid, lymphoid and myeloid lineages. HSCs are located in the adult bone marrow, peripheral blood, and umbilical cord blood.

During differentiation, the progeny of HSCs progress through various intermediate maturational stages, generating multi-potential hematopoietic progenitor cells and lineage-committed hematopoietic progenitor cells, prior to reaching maturity. Bone marrow (BM) is the major site of hematopoiesis in humans and, under normal conditions, only small numbers of HSCs and hematopoietic progenitor cells can be found in the peripheral blood (PB). Treatment with cytokines (in particular granulocyte colony-stimulating factor; G-CSF), myelosuppressive drugs used in cancer treatment, and compounds that disrupt the interaction between hematopoietic cells and BM stromal cells can rapidly mobilize large numbers of stem and progenitor cells into the circulation.

"Hematopoietic progenitor cell" as the term is used herein, refers to cells of a hematopoietic stem cell lineage that give rise to all the blood cell types including the myeloid (monocytes and macrophages, neutrophils, basophils, eosinophils, erythrocytes, megakaryocytes/platelets, dendritic cells), and the lymphoid lineages (T-cells, B-cells, NK-cells). A "cell of the erythroid lineage" indicates that the cell being contacted is a cell that undergoes erythropoeisis such that upon final differentiation it forms an erythrocyte or red blood cell (RBC). Such cells belong to one of three lineages, erythroid, lymphoid, and myeloid, originating from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage," as the term is used herein, comprise hematopoietic progenitor cells, rubriblasts, prorubricytes, erythroblasts, metarubricytes, reticulocytes, and erythrocytes.

In some embodiment of any methods described herein, the hematopoietic progenitor cell has at least one of the cell surface marker characteristic of hematopoietic progenitor cells: CD34+, CD59+, Thy1/CD90+, CD38$^{lo/-}$, and C-kit/CD117+. Preferably, the hematopoietic progenitor cells have several of these markers.

In some embodiment of any methods described herein, the hematopoietic progenitor cells of the erythroid lineage have the cell surface marker characteristic of the erythroid lineage: CD71 and Ter119.

In some embodiment of any methods described herein, the HSC has at least one of the cell surface marker characteristic of hematopoietic progenitor cells: CD34+, CD59+, Thy1/CD90+, CD38$^{lo/-}$, and C-kit/CD117+.

The HSCs, similar to the hematopoietic progenitor cells, are capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In one embodiment of any methods described herein, the hematopoietic stem cell or hematopoietic progenitor cell is collected from peripheral blood, cord blood, chorionic amniotic fluid, placental blood, or bone marrow.

In one embodiment of any methods described herein, the embryonic stem cell, somatic stem cell, progenitor cell, or bone marrow cell is collected from peripheral blood, cord blood, chorionic villi, amniotic fluid, placental blood, or bone marrow.

Peripheral blood progenitor cells (PBPC) have become the preferred source of hematopoetic progenitor cells for allogeneic and autologous transplantation because of technical ease of collection and shorter time required for engraftment. Traditionally, granulocyte-colony stimulating factor (G-CSF) has been used to stimulate more PBPC and release of hematopoetic progenitor cells from the bone marrow. Although regimens using G-CSF usually succeed in collecting adequate numbers of PBPC from healthy donors, 5%-10% will mobilize stem cells poorly and may require multiple large volume apheresis or bone marrow harvesting.

In some embodiments of any methods described herein, the embryonic stem cell, somatic stem cell, progenitor cell, bone marrow cell, or hematopoietic progenitor cell, or HSC is selected for the CD34+ surface marker prior to the contacting.

Accordingly, in one embodiment of any methods described herein, the isolated CD34+ embryonic stem cell, isolated CD34+ somatic stem cell, isolated CD34+ progenitor cell, isolated CD34+ bone marrow cell, isolated CD34+ hematopoietic progenitor cell, or isolated CD34+ HSC is contacted with the composition described herein or contacted with the virus or vector carrying a nucleic acid molecule comprising a nucleic acid sequence selected from a group consisting of SEQ ID NOS:1-10,13-18, 25-44, or contacted with the virus or vector expressing a synthetic BCL11A microRNA described herein.

In one embodiment of any methods described herein, the embryonic stem cell, somatic stem cell, progenitor cell, bone marrow cell, or hematopoietic progenitor cell, or HSC is cryopreserved prior to any contacting with the composition described herein or contacting with the virus or vector carrying a nucleic acid molecule comprising a nucleic acid sequence selected from a group consisting of SEQ ID NOS:1-10,13-18, 25-44, or contacting with the virus or vector expressing a synthetic BCL11A microRNA described herein.

In one embodiment of any methods described herein, the contacting is in vitro, ex vivo or in vivo.

In one embodiment of any methods described herein, the contacting is repeated at least once. That is, after the initial first contacting of the embryonic stem cell, somatic stem cell, progenitor cell, bone marrow cell, or hematopoietic progenitor cell, or HSC with the composition described herein or contacting with the virus or vector carrying a nucleic acid molecule comprising a nucleic acid sequence selected from a group consisting of SEQ ID NOS:1-10,13-18, 25-44, or contacting with the virus or vector expressing a synthetic BCL11A microRNA described herein, the cell is washed, and the washed cell is then contacted for a second time with the composition described herein or contacted with the virus or vector carrying a nucleic acid molecule comprising a nucleic acid sequence selected from a group consisting of SEQ ID NOS:1-10,13-18, 25-44, or contacted with the virus or vector expressing a synthetic BCL11A microRNA described herein.

In other embodiments, the contacting is repeated at least twice after the initial first contacting.

In one embodiment of any methods described herein, after the contacting, the contacted embryonic stem cell, somatic stem cell, progenitor cell, bone marrow cell, or hematopoietic progenitor cell, or HSC is cryopreserved prior to use, for example, ex vivo expansion and/or implantation into a subject.

In one embodiment of any methods described herein, after the contacting, the contacted embryonic stem cell, somatic stem cell, progenitor cell, bone marrow cell, or hematopoietic progenitor cell, or HSC is culture expanded ex vivo prior to use, for example, cryopreservation, and/or implantation/engraftment into a subject.

In one embodiment of any methods described herein, after the contacting, the contacted embryonic stem cell, somatic stem cell, progenitor cell, bone marrow cell, or hematopoietic progenitor cell, or HSC is differentiated in culture ex vivo prior to use, for example, cryopreservation, and/or implantation/engraftment into a subject.

In the context of cell ontogeny, the adjective "differentiated," or "differentiating" is a relative term. A "differentiated cell" is a cell that has progressed further down the developmental pathway than the cell it is being compared with. Thus, stem cells can differentiate to lineage-restricted precursor cells (such as a hematopoietic progenitor cell), which in turn can differentiate into other types of precursor cells further down the pathway (such as an erthyrocyte precursor), and then to an end-stage differentiated cell, such as an erthyrocyte, which plays a characteristic role in a certain tissue type, and may or may not retain the capacity to proliferate further.

In one embodiment, the inhibitor of BCL11A expression is a BCL11A specific RNA interference agent, or a vector encoding said BCL11A specific RNA interference agent. In one specific embodiment, the RNA interference agent comprises one or more of the nucleotide sequences of SEQ ID NOS:1-10,13-18, 25-44.

A "nucleic acid," as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), and locked nucleic acid (LNA). Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, microRNAi (miRNA), and antisense oligonucleotides.

As disclosed herein, it is an object of the present invention to provide a method for increasing fetal hemoglobin levels in a subject.

Accordingly, one aspect of the present invention provides a method for increasing fetal hemoglobin levels in a subject in need thereof, the method comprising the step of contacting a hematopoietic progenitor cell or a HSC in the subject with an effective amount of a composition comprising an inhibitor of BCL11A, whereby HbF expression is increased, relative to expression prior to such contacting. In one embodiment, the inhibitor of BCL11A is an RNA interference agent which comprises one or more of the nucleotide sequences of SEQ ID NOS:1-10,13-18, 25-44, or a synthetic BCL11A microRNA described herein.

In connection with contacting a cell in a subject with an inhibitor of BCL11A, "increasing HbF levels in a subject" indicates that HbF in the subject is at least 5% higher in populations treated with a BCL11A inhibitor, than a comparable, control population, wherein no BCL11A inhibitor is present. It is preferred that the fetal hemoglobin expression in a BCL11A inhibitor treated subject is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a comparable control treated subject. The term "comparable control treated subject" is used herein to describe a subject that has been treated identically, with the exception of the addition of a non-targeting oligonucleotide.

Accordingly, in one embodiment, the subject has been diagnosed with a hemoglobinopathy. In a further embodiment, the hemoglobinopathy is a SCD. As used herein, SCD can be sickle cell anemia, sickle-hemoglobin C disease (HbSC), sickle beta-plus-thalassaemia (HbS/β+), or sickle beta-zero-thalassaemia (HbS/β0). In another preferred embodiment, the hemoglobinopathy is THAL.

The treatment according to the present invention ameliorates one or more symptoms associated with the disorder by increasing the amount of fetal hemoglobin in the individual. Symptoms typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

In one embodiment, the hematopoietic progenitor cell or HSC is contacted ex vivo or in vitro, and the cell or its progeny is administered to the subject. In a further embodiment, the hematopoietic progenitor cell is a cell of the erythroid lineage.

In one embodiment, the hematopoietic progenitor cell or HSC is contacted with a composition comprising of an inhibitor of BCL11A and a pharmaceutically acceptable carrier or diluent. In one embodiment, the composition is administered by injection, infusion, instillation, or ingestion. In one embodiment, the composition is administered by direct injection into the bone marrow.

In one embodiment of any one method described, the gene therapy method is used to treat, prevent, or ameliorate a hemoglobinopathy is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease.

In various embodiments of any one method described, the retroviral vectors are administered by direct injection to a cell, tissue, or organ of a subject in need of gene therapy, in vivo. In various other embodiments of any one method described, cells are transduced in vitro or ex vivo with vectors of the invention, and optionally expanded ex vivo. The transduced cells are then administered to a subject in need of gene therapy.

A "subject," as used herein, includes any animal that exhibits a symptom of a monogenic disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., a hemoglobinopathy, that can be treated with the gene therapy vectors, cell-based therapeutics, and methods contemplated herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include animals that exhibit aberrant amounts (lower or higher amounts than a "normal" or "healthy" subject) of one or more physiological activities that can be modulated by gene therapy.

In one embodiment, as used herein "treatment" or "treating," includes any beneficial or desirable effect on the symptoms or pathology of a disease or pathological condition, and may include even minimal reductions in one or more measurable markers of the disease or condition being treated. In another embodiment, treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

In one embodiment, as used herein, "prevent," and similar words such as "prevented," "preventing" etc., indicate an approach for preventing, inhibiting, or reducing the likelihood of the occurrence or recurrence of, a disease or condition. In another embodiment, the term refers to delaying the onset or recurrence of a disease or condition or delaying the occurrence or recurrence of the symptoms of a disease or condition. In another embodiment, as used herein, "prevention" and similar words includes reducing the intensity, effect, symptoms and/or burden of a disease or condition prior to onset or recurrence of the disease or condition.

In one embodiment of any one method described, the method further comprises selecting a subject in need of the gene therapy described. For example, a subject exhibiting symptoms or cytology of a hemoglobinopathy is selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. Alternatively, the subject carries a genetic mutation that is associated with a hemoglobinopathy, a genetic mutation described herein. For example, a subject diagnosis of SCD with genotype HbSS, HbS/β0 thalassemia, HbSD, or HbSO, and/or with HbF<10% by electrophoresis.

In various embodiments of any one method described, a subject in need of gene therapy is administered a population of cells comprising an effective amount of genetically modified cells contemplated herein. That is a genetically modified cells that express one or more of the nucleotide sequences of SEQ ID NOS:1-10,13-18, 25-44, or a synthetic BCL11A microRNA described herein.

As used herein, the term "amount" refers to "an amount effective" or "an effective amount" of a virus or transduced therapeutic cell to achieve a beneficial or desired prophylactic or therapeutic result, including clinical results.

A "prophylactically effective amount" refers to an amount of a virus or transduced therapeutic cell effective to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a virus or transduced therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient).

In one embodiment, the present invention provides a method of providing a transduced cell to a subject that comprises administering, e.g., parenterally, one or more cells transduced with a vector contemplated herein into the subject. In one embodiment, the vector is one that carrys one or more of the nucleotide sequences of SEQ ID NOS:1-10, 13-18, 25-44, or a synthetic BCL11A microRNA described herein.

In a particular embodiment, a method of preventing, ameliorating, or treating a hemoglobinopathy in a subject is provided. The method comprises administering a population of cells comprising hematopoietic cells transduced with a vector contemplated herein. In one embodiment, the vector is one that carrys one or more of the nucleotide sequences of SEQ ID NOS:1-10,13-18, 25-44, or a synthetic BCL11A microRNA described herein.

In particular embodiments, a population of cells administered to a subject comprises hematopoietic stem or progenitor cells, proerythroblasts, basophilic erythroblasts, polychromatic erythroblasts, orthochromatic erythroblasts, polychromatic erythrocytes, and erythrocytes (RBCs), or any combination thereof, and any proportion of which may be genetically modified by the vectors contemplated herein. In one embodiment, the vector is one that carrys one or more of the nucleotide sequences of SEQ ID NOS:1-10,13-18, 25-44, or a synthetic BCL11A microRNA described herein.

The genetically modified cells may be administered as part of a bone marrow or cord blood transplant in an individual that has or has not undergone bone marrow ablative therapy. In one embodiment, genetically modified cells contemplated herein are administered in a bone marrow transplant to an individual that has undergone chemoablative or radioablative bone marrow therapy.

In one embodiment, a dose of genetically modified cells is delivered to a subject intravenously. In one embodiment, genetically modified hematopoietic cells are intravenously administered to a subject.

In particular embodiments, patients receive a dose of genetically modified cells, e.g., hematopoietic stem cells, of about $1 \times 10^5$ cells/kg, about $5 \times 10^5$ cells/kg, about $1 \times 10^6$ cells/kg, about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $5 \times 10^7$ cells/kg, about $1 \times 10^8$ cells/kg, or more in one single intravenous dose. In certain embodiments, patients receive a dose of genetically modified cells, e.g., hematopoietic stem cells, of at least $1 \times 10^5$ cells/kg, at least $5 \times 10^5$ cells/kg, at least $1 \times 10^6$ cells/kg, at least $2 \times 10^6$ cells/kg, at least $3 \times 10^6$ cells/kg, at least $4 \times 10^6$ cells/kg, at least $5 \times 10^6$ cells/kg, at least $6 \times 10^6$ cells/kg, at least $7 \times 10^6$ cells/kg, at least $8 \times 10^6$ cells/kg, at least $9 \times 10^6$ cells/kg, at least $1 \times 10^7$ cells/kg, at least $5 \times 10^7$ cells/kg, at least $1 \times 10^8$ cells/kg, or more in one single intravenous dose.

In an additional embodiment, patients receive a dose of genetically modified cells, e.g., hematopoietic stem cells, of about $1 \times 10^5$ cells/kg to about $1 \times 10^8$ cells/kg, about $1 \times 10^6$ cells/kg to about $1 \times 10^8$ cells/kg, about $1 \times 10^6$ cells/kg to about $9 \times 10^6$ cells/kg, about $2 \times 10^6$ cells/kg to about $8 \times 10^6$ cells/kg, about $2 \times 10^6$ cells/kg to about $8 \times 10^6$ cells/kg, about $2 \times 10^6$ cells/kg to about $5 \times 10^6$ cells/kg, about $3 \times 10^6$ cells/kg to about $5 \times 10^6$ cells/kg, about $3 \times 10^6$ cells/kg to about $4 \times 10^8$ cells/kg, or any intervening dose of cells/kg.

In various embodiments, the methods of the invention provide more robust and safe gene therapy than existing methods and comprise administering a population or dose of cells comprising about 5% transduced cells, about 10% transduced cells, about 15% transduced cells, about 20% transduced cells, about 25% transduced cells, about 30% transduced cells, about 35% transduced cells, about 40% transduced cells, about 45% transduced cells, or about 50% transduced cells, to a subject.

In one embodiment, the invention provides genetically modified cells, such as a stem cell, e.g., hematopoietic stem cell, with the potential to expand or increase a population of erythroid cells. In particular embodiments, hematopoietic stem cells are transduced with a vector of the invention and administered to an individual in need of therapy for hemoglobinopathy. Hematopoietic stem cells are the origin of erythroid cells and thus, are preferred. In one embodiment, the vector is one that carrys one or more of the nucleotide sequences of SEQ ID NOS:1-10,13-18, 25-44, or a synthetic BCL11A microRNA described herein.

As used herein, the term "pharmaceutically acceptable," and grammatical variations thereof, as they refer to compositions, carriers, diluents and reagents, are used interchangeably and represent that the materials are capable of administration to or upon a subject without the production of undesirable physiological effects such as nausea, dizziness, gastric upset, and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

In one embodiment of any methods described, as used herein, "administered" refers to the placement of an inhibitor of BCL11A into a subject by a method or route which results in at least partial localization of the inhibitor at a desired site. An agent which inhibits BCL11A can be administered by any appropriate route which results in effective treatment in the subject, i.e., administration results in delivery to a desired location in the subject where at least a portion of the composition delivered, i.e., at least one agent, which inhibits BCL11A, is active in the desired site for a period of time. The period of time the inhibitor is active depends on the half-life in vivo after administration to a subject, and can be as short as a few hours, e.g., at least 1 hour, at least 2 hours, at least 3 hours, at least 4 hours, at least 5 hours, at least 6 hours, at least 8 hours, at least 10 hours, at least 12 hours, at least 18 hours, at least 24 hours, to a few days, to as long as several years. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In one embodiment, the composition described herein, or the virus or vector carrying a nucleic acid molecule comprising a nucleic acid sequence selected from a group consisting of SEQ ID NOS:1-10,13-18, 25-44, or the virus or vector expressing a synthetic BCL11A microRNA described herein, is injected into the bone marrow.

In one embodiment, the hematopoietic progenitor cell or HSC from a subject needing treatment is contacted with a composition that inhibits BCL11A expression. In other embodiments, the composition comprises a virus or vector carrying a nucleic acid molecule comprising a nucleic acid sequence selected from a group consisting of SEQ ID NOS:1-10, 13-18, 25-44, or a virus or vector expressing a synthetic BCL11A microRNA described herein. The subject needing treatment is one diagnosed with a hemoglobinopathy such as SCD or THAL.

By "inhibits BCL11A expression" is meant that the amount of expression of BCL11A is at least 5% lower in populations treated with a BCL11A inhibitor, than a comparable, control population, wherein no BCL11A inhibitor is present. It is preferred that the percentage of BCL11A expression in a BCL11A inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no BCL11A inhibitor is added.

In one embodiment, the nucleic acid is a BCL11A specific RNA interference agent or a vector encoding the RNA interference agent. In one embodiment, the RNA interference agent comprises one or more of the nucleotide sequences of SEQ ID NOs:1-10, 13-18, 25-44.

As an example of a method of treatment of a subject or reducing the risk of developing a hemoglobinopathy in a subject, the method comprises administering to the subject a composition comprising modified engineered cells that comprise a vector carrying a nucleic acid sequence selected from the group consisting of SEQ ID NOS:1-10, 13-18 and 25-44, or a BCL11A microRNA described herein. In one embodiment, the method further comprises identifying a subject having a hemoglobinopathy or is at risk of developing a hemoglobinopathy. In another embodiment, the method further comprises selecting the identified subject having a hemoglobinopathy or is at risk of developing a hemoglobinopathy.

As another example of a method of treatment of a subject or reducing the risk of developing a hemoglobinopathy in a subject, the method comprises the following steps: mobilize the hematopoietic stem and hematopoietic progenitor cells in a subject; harvest and collect peripheral blood from the subject, positive selection of CD34+ cells from the peripheral blood, transduce or transfect the CD34+ selected cells in vitro with a vector carrying a nucleic acid sequence selected from the group consisting of SEQ ID NOS:1-10, 13-18 and 25-44, or a BCL11A microRNA described herein; wash the transduced CD34+ selected cells; and administer the cells into the subject. In one embodiment, the method further comprises identifying a subject having a hemoglobinopathy or is at risk of developing a hemoglobinopathy. In one embodiment, the method further comprises selecting the subject having a hemoglobinopathy or is at risk of developing a hemoglobinopathy. In another embodiment, the method further comprises expanding in culture the washed, transduced CD34+ selected cells in vitro prior to administering to the subject. In another embodiment, the method further comprises differentiating in culture the washed, transduced CD34+ selected cells in vitro prior to administering to the subject.

As another example of a method of treatment of a subject or reducing the risk of developing a hemoglobinopathy in a subject, the method comprises the following steps: mobilize the hematopoietic stem and hematopoietic progenitor cells in a donor subject; harvest and collect peripheral blood from the donor subject, positive selection of CD34+ cells from the peripheral blood, transduce or transfect the CD34+ selected cells in vitro with a vector carrying a nucleic acid sequence selected from the group consisting of SEQ ID NOS:1-10, 13-18 and 25-44, or a BCL11A microRNA described herein; wash the transduced CD34+ selected cells; and administer the cells into a recipient subject. In one embodiment, the method further comprises selecting a recipient subject having a hemoglobinopathy or is at risk of developing a hemoglobinopathy. In another embodiment, the method further comprises expanding in culture the washed, transduced CD34+ selected cells in vitro prior to administering to the recipient subject. In another embodiment, the method further comprises differentiating in culture the washed, transduced CD34+ selected cells in vitro prior to administering to the recipient subject.

As another example of a method of treatment of a subject or reducing the risk of developing a hemoglobinopathy in a subject, the method comprises the following steps: harvest and collect the blood from the bone marrow of a subject, positive selection of CD34+ cells from the bone marrow blood, transduce or transfect the CD34+ selected cells in vitro with a vector carrying a nucleic acid sequence selected from the group consisting of SEQ ID NOS:1-10, 13-18 and 25-44, or a BCL11A microRNA described herein; wash the transduced CD34+ selected cells; and administer the cells into the subject. In one embodiment, the method further comprises identifying a subject having a hemoglobinopathy or is at risk of developing a hemoglobinopathy. In one embodiment, the method further comprises selecting the subject having a hemoglobinopathy or is at risk of developing a hemoglobinopathy. In another embodiment, the method further comprises expanding in culture the washed, transduced CD34+ selected cells in vitro prior to administering to the subject. In another embodiment, the method further comprises differentiating in culture the washed, transduced CD34+ selected cells in vitro prior to administering to the subject.

As another example of a method of treatment of a subject or reducing the risk of developing a hemoglobinopathy in a subject, the method comprises the following steps: harvest and collect the blood from the bone marrow of a donor subject, positive selection of CD34+ cells from the bone marrow blood, transduce or transfect the CD34+ selected cells in vitro with a vector carrying a nucleic acid sequence selected from the group consisting of SEQ ID NOS:1-10, 13-18 and 25-44, or a BCL11A microRNA described herein; wash the transduced CD34+ selected cells; and administer the cells into a recipient subject. In one embodiment, the method further comprises identifying a recipient subject having a hemoglobinopathy or is at risk of developing a hemoglobinopathy. In one embodiment, the method further comprises selecting a recipient subject having a hemoglobinopathy or is at risk of developing a hemoglobinopathy. In another embodiment, the method further comprises expanding in culture the washed, transduced CD34+ selected cells in vitro prior to administering to the recipient subject. In another embodiment, the method further comprises differentiating in culture the washed, transduced CD34+ selected cells in vitro prior to administering to the recipient subject.

In one embodiment, the disclosure herein provides a modified engineered cell comprising a nucleic acid sequence selected from the group consisting of SEQ ID NOS:1-10, 13-18 and 25-44, or a BCL11A microRNA described herein.

In one embodiment, the disclosure herein provides a modified engineered cell that has been transduced or transfected with a vector comprising a nucleic acid sequence selected from the group consisting of SEQ ID NOS:1-10, 13-18 and 25-44, or a BCL11A microRNA described herein. In one embodiment, the vector is a lentivirus.

In one embodiment, the disclosure herein provides a method of treatment of a subject or reducing the risk of developing a hemoglobinopathy in a subject, the method comprises administering a modified engineered cell that has been transduced or transfected with a vector comprising a nucleic acid sequence selected from the group consisting of SEQ ID NOS:1-10, 13-18 and 25-44, or a BCL11A microRNA described herein. In one embodiment, the vector is a lentivirus.

In one embodiment, the disclosure herein provides a method of treatment of a subject or reducing the risk of developing a hemoglobinopathy in a subject, the method comprises administering a modified engineered cell comprising a nucleic acid sequence selected from the group consisting of SEQ ID NOS:1-10, 13-18 and 25-44, or a BCL11A microRNA described herein.

In one embodiment, the modified engineered cell is an embryonic stem cell, a somatic stem cell, a progenitor cell, a bone marrow cell, a hematopoietic stem cell, or a hematopoietic progenitor cell.

In one embodiment, the modified engineered cell is a cell that has been differentiated from an embryonic stem cell, a somatic stem cell, a progenitor cell, a bone marrow cell, a hematopoietic stem cell, or a hematopoietic progenitor cell.

In one embodiment, the modified engineered cell is a cell that has been differentiated into the erythroid lineage.

In one embodiment, the modified engineered cell is a cell that has been differentiated into an erythrocyte.

In one embodiment, the modified engineered cell is a CD34+ cell.

The present invention can be defined in any of the following numbered paragraphs.

[1] A synthetic BCL11A microRNA comprising a first BCL11A segment, a loop segment; and a second BCL11A segment arranged in tandem in a 5' to 3' direction, wherein the loop segment is between and directly linked to the first and second BCL11A segments, and wherein the second BCL11A segment is complementary to the first BCL11A segment so that the first and second BCL11A segments base pair to form a hairpin loop with the loop segment forming the loop portion of the hairpin loop thus formed.

[2] The synthetic BCL11A microRNA of paragraph 1, wherein the first and second BCL11A segments are about 18 to 25 nucleotides long.

[3] The synthetic BCL11A microRNA of paragraph 1 or 2, wherein the first BCL11A segment contains a sequence derived from a BCL11A mRNA sequence.

[4] The synthetic BCL11A microRNA of any one of paragraphs 1-3, wherein the first BCL11A segment is complementary to the second BCL11A segment.

[5] The synthetic BCL11A microRNA of any one of paragraphs 1-4, wherein the first BCL11A segment starts with a -GCGC- at the 5' end and the second BCL11A segment ends with a -GCGC- at the 3' end.

[6] The synthetic BCL11A microRNA of any one of paragraphs 1-5, wherein the first BCL11A segment is selected from the group consisting of CGCACAGAACACTCATGGATT (SEQ. ID. NO: 46; derived from BCL11A miR1 oligo described herein), CCAGAGGATGACGATTGTTTA (SEQ. ID. NO: 47; derived from BCL11A miR2 oligo described herein), TCGGAGACTCCAGACAATCGC (SEQ. ID. NO: 48; derived from BCL11A E3 oligo or shRNA1 or E3 described herein), CCTCCAGGCAGCTCAAAGATC, (SEQ. ID. NO: 49; derived from shRNA2 or B5 described herein), TCAGGACTAGGTGCAGAATGT (SEQ. ID. NO: 50; derived from shRNA4 or B11 described herein), TTCTCTTGCAACACGCACAGA (SEQ. ID. NO: 51; derived from BCL11A D8 oligo or shRNA3 or D8 described herein), GATCGAGTGTTGAATAATGAT (SEQ. ID. NO: 52; derived from shRNA5 or 50D12 of D12 described herein), CAGTACCCTGGAGAAACACAT (SEQ. ID. NO: 53; derived from shRNA5 or 50A5 described herein), CACTGTCCACAGGAGAAGCCA (SEQ. ID. NO: 54; derived from shRNA7 or 50B11 described herein), ACAGTACCCTGGAGAAACACA (SEQ. ID. NO: 55; derived from BCL11A XLC4, shRNA8 and 50C4 described herein), CAACAAGATGAAGAGCACCAA (SEQ. ID. NO: 56; derived from BCL11A Non-targeting oligos described herein), gcgcCGCACAGAACACTCATG (SEQ. ID. NO: 57; derived from miR1G5 oligo described herein); GCGCTCGGAGACTCCAGACAA (SEQ. ID. NO: 58; derived from E3G5 or E3 mod oligo or shRNA1mod described herein), gcgcCCTCCAGGCAGCTCAAA (SEQ. ID. NO: 59; derived from B5G5 or shRNA2mod described herein); gcgcTCAGGACTAGGTGCAGA (SEQ. ID. NO: 60; derived from B11G5 or shRNA4mod described herein); gcgcGATCGAGTGTTGAATAA (SEQ. ID. NO: 61; derived from 50D12G5, D12G4 or shRNA5mod described herein); gcgcCAGTACCCTGGAGAAAC (SEQ. ID. NO: 62; derived from 50A5G5 or shRNA6mod described herein); gcgcCACTGTCCACAGGAGAA (SEQ. ID. NO: 63; derived from 50B11G5 or shRNA7mod described herein); GCGCTCTCTTGCAACACGCA (SEQ. ID. NO: 64; derived from BCL11A D8G5 or D8 mod or shRNA3mod described herein), GCGCACAGTACCCTGGAGAAA (SEQ. ID. NO: 65; derived from BCL11A C4G5, or C4 mod or shRNA8mod described herein), CGCACAGAACACTCATGGATT (SEQ. ID. NO: 66; derived from BCL11A D12G5-2 described herein), and ACGCTCGCACAGAACACTCATGGATT (SEQ. ID. NO: 67; derived from BCL11A D12G5-2 described herein).

[7] The synthetic BCL11A microRNA of any one of paragraphs 1-6, wherein the loop segment is derived from a microRNA.

[8] The synthetic BCL11A microRNA of paragraph 7, wherein the microRNA is a hematopoietic specific microRNA.

[9] The synthetic BCL11A microRNA of paragraph 8, wherein the microRNA is miR223.

[10] The synthetic BCL11A microRNA of paragraph 9, wherein the loop segment is ctccatgtggtagag.

[11] The synthetic BCL11A microRNA of any one of paragraphs 1-10, wherein the microRNA comprising a nucleotide sequence selected from the group consisting of SEQ ID NOS:1-10, 13-18 and 25-44.

[12] A method of treating, or reducing a risk of developing, a hemoglobinopathy in a subject, the method comprising expressing in vivo at least one synthetic BCL11A microRNA of any one of paragraphs 1-11 in the subject.

[13] The method of paragraph 12, wherein the in vivo expression occurs in an embryonic stem cell, a somatic stem cell, a progenitor cell, a bone marrow cell, a hematopoietic stem cell, or a hematopoietic progenitor cell in the subject.

[14] A method of treating, or reducing a risk of developing, a hemoglobinopathy in a subject, the method comprising expressing at least one synthetic BCL11A microRNA of any one paragraphs 1-11 in an embryonic stem cell, a somatic stem cell, a progenitor cell, a bone marrow cell, a hematopoietic stem cell, or a hematopoietic progenitor cell of the subject wherein the expression is ex vivo, and implanting the cell into the subject.

[15] A method of increasing fetal hemoglobin levels expressed by a cell comprising expressing at least one synthetic BCL11A microRNA of any one paragraphs 1-11 in a cell, wherein the cell is an embryonic stem cell, a somatic stem cell, a progenitor cell, a bone marrow cell, a hematopoietic stem cell, or a hematopoietic progenitor cell.

[16] The method of any one paragraphs 12-15, wherein the at least one synthetic BCL11A microRNA is operably linked to a promoter and constructed in a vector for expression in a eukaryotic cell.

[17] The method of any one paragraphs 12-16, wherein the at least one synthetic BCL11A microRNA is expressed from a RNA II polymerase.

[18] The method of any one paragraphs 12-17, wherein the at least one synthetic BCL11A microRNA is not expressed from a RNA III polymerase.

[19] The method of paragraph 18, wherein the promoter is selected from a group consisting of a spleen focus-forming virus promoter, a tetracycline-inducible promoter, or a β-globin locus control region and a β-globin promoter.

[20] The method of any one paragraphs 16-19, wherein the vector is a virus.

[21] The method of paragraph 20, wherein the virus is a lentivirus.

[22] The method of paragraph 21, wherein the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (Fly), bovine immune deficiency virus (BIV), and simian immunodeficiency virus (SIV).

[23] An isolated nucleic acid molecule comprising the nucleotide sequence selected from the group consisting of SEQ ID NOS: 1-10, 13-18, and 25-44.

[24] The isolated nucleic acid molecule of paragraph 23, wherein the molecule comprises the nucleotide sequence of SEQ ID NO: 1.

[25] The isolated nucleic acid molecule of paragraph 23, wherein the molecule comprises the nucleotide sequence of SEQ ID NO: 2.

[26] The isolated nucleic acid molecule of paragraph 23, wherein the molecule comprises the nucleotide sequence of SEQ ID NO: 3.

[27] The isolated nucleic acid molecule of paragraph 23, wherein the molecule comprises the nucleotide sequence of SEQ ID NO: 4.

[28] The isolated nucleic acid molecule of paragraph 23, wherein the molecule comprises the nucleotide sequence of SEQ ID NO: 5.

[29] The isolated nucleic acid molecule of paragraph 23, wherein the molecule comprises the nucleotide sequence of SEQ ID NO: 6.

[30] The isolated nucleic acid molecule of paragraph 23, wherein the molecule comprises the nucleotide sequence of SEQ ID NO: 7.

[31] The isolated nucleic acid molecule of paragraph 23, wherein the molecule comprises the nucleotide sequence of SEQ ID NO: 8.

[32] The isolated nucleic acid molecule of paragraph 23, wherein the molecule comprises the nucleotide sequence of SEQ ID NO: 9.

[33] The isolated nucleic acid molecule of paragraph 23, wherein the molecule comprises the nucleotide sequence of SEQ ID NO: 10.

[34] The isolated nucleic acid molecule of paragraph 23, wherein the molecule comprises the nucleotide sequence of SEQ ID NO: 13.

[35] The isolated nucleic acid molecule of paragraph 23, wherein the molecule comprises the nucleotide sequence of SEQ ID NO: 14.

[36] The isolated nucleic acid molecule of paragraph 23, wherein the molecule comprises the nucleotide sequence of SEQ ID NO: 15.

[37] The isolated nucleic acid molecule of paragraph 23, wherein the molecule comprises the nucleotide sequence of SEQ ID NO: 16.

[38] The isolated nucleic acid molecule of paragraph 23, wherein the molecule comprises the nucleotide sequence of SEQ ID NO: 17.

[39] The isolated nucleic acid molecule of paragraph 23, wherein the molecule comprises the nucleotide sequence of SEQ ID NO: 18.

[40] The isolated nucleic acid molecule of paragraph 23, wherein the molecule comprises the nucleotide sequence of SEQ ID NO: 25.

[41] The isolated nucleic acid molecule of paragraph 23, wherein the molecule comprises the nucleotide sequence of SEQ ID NO: 26.

[42] The isolated nucleic acid molecule of paragraph 23, wherein the molecule comprises the nucleotide sequence of SEQ ID NO: 27.

[43] The isolated nucleic acid molecule of paragraph 23, wherein the molecule comprises the nucleotide sequence of SEQ ID NO: 28.

[44] The isolated nucleic acid molecule of paragraph 23, wherein the molecule comprises the nucleotide sequence of SEQ ID NO: 29.

[45] The isolated nucleic acid molecule of paragraph 23, wherein the molecule comprises the nucleotide sequence of SEQ ID NO: 30.

[46] The isolated nucleic acid molecule of paragraph 23, wherein the molecule comprises the nucleotide sequence of SEQ ID NO: 31.

[47] The isolated nucleic acid molecule of paragraph 23, wherein the molecule comprises the nucleotide sequence of SEQ ID NO: 33.

[48] The isolated nucleic acid molecule of paragraph 23, wherein the molecule comprises the nucleotide sequence of SEQ ID NO: 34.

[49] The isolated nucleic acid molecule of paragraph 23, wherein the molecule comprises the nucleotide sequence of SEQ ID NO: 35.

[50] The isolated nucleic acid molecule of paragraph 23, wherein the molecule comprises the nucleotide sequence of SEQ ID NO: 36.

[51] The isolated nucleic acid molecule of paragraph 23, wherein the molecule comprises the nucleotide sequence of SEQ ID NO: 37.

[52] The isolated nucleic acid molecule of paragraph 23, wherein the molecule comprises the nucleotide sequence of SEQ ID NO: 38.

[53] The isolated nucleic acid molecule of paragraph 23, wherein the molecule comprises the nucleotide sequence of SEQ ID NO: 39.

[54] The isolated nucleic acid molecule of paragraph 23, wherein the molecule comprises the nucleotide sequence of SEQ ID NO: 40.

[55] The isolated nucleic acid molecule of paragraph 23, wherein the molecule comprises the nucleotide sequence of SEQ ID NO:41.

[56] The isolated nucleic acid molecule of paragraph 23, wherein the molecule comprises the nucleotide sequence of SEQ ID NO: 42.

[57] The isolated nucleic acid molecule of paragraph 23, wherein the molecule comprises the nucleotide sequence of SEQ ID NO: 43.

[58] The isolated nucleic acid molecule of paragraph 23, wherein the molecule comprises the nucleotide sequence of SEQ ID NO: 44.

[59] A vector comprising the isolated nucleic acid molecule of paragraph 23.
[60] The vector of paragraph 59, wherein the vector further comprises a spleen focus-forming virus promoter, a tetracycline-inducible promoter, or a β-globin locus control region and a β-globin promoter.
[61] A host cell comprising the vector of paragraph 59 or 60.
[62] The cell of paragraph 61, wherein the cell is an embryonic stem cell, a somatic stem cell, a progenitor cell, a bone marrow cell, a hematopoietic stem cell, or a hematopoietic progenitor cell.
[63] The cell of paragraph 61, wherein the cell is an erythrocyte.
[64] A bacterium comprising the isolated nucleic acid molecule of paragraph 23.
[65] A virus comprising the isolated nucleic acid molecule of paragraph 23.
[66] The virus of paragraph 65, wherein the virus is a lentivirus.
[67] The virus of paragraph 66, wherein the lentivirus is selected from the group consisting of: human immunodeficiency virus type 1 (HIV-1), human immunodeficiency virus type 2 (HIV-2), caprine arthritis-encephalitis virus (CAEV), equine infectious anemia virus (EIAV), feline immunodeficiency virus (Hy), bovine immune deficiency virus (BIV), and simian immunodeficiency virus (SIV).
[68] A composition comprising an isolated nucleic acid molecule of any one of paragraphs 1-58, a vector of paragraphs 59 or 60, a host cell of any one of paragraphs 61-63, or a virus of any one of paragraphs 65-67.
[69] A composition comprising a vector of paragraphs 59 or 60, a host cell of any one of paragraphs 61-63, or a virus of any one of paragraphs 65-67.
[70] The composition of paragraph 68 or 69, further comprising a pharmaceutically acceptable carrier or diluent.
[71] A composition of any one of paragraphs 68-70 for use in the treatment or for reducing a risk of developing a hemoglobinopathy in a subject.
[72] A composition of any one of paragraphs 68-70 for use in the manufacture of medicament in treatment or for reducing a risk of developing, a hemoglobinopathy in a subject.
[73] A composition of any one of paragraphs 68-70 for use in increasing the fetal hemoglobin levels expressed by a cell.
[74] The composition of paragraph 73, wherein the cell is an embryonic stem cell, a somatic stem cell, a progenitor cell, a bone marrow cell, a hematopoietic stem cell, or a hematopoietic progenitor cell.
[75] A method of treating, or reducing a risk of developing, a hemoglobinopathy in a subject, the method comprising: administering to the subject a therapeutically effective amount of an isolated nucleic acid molecule of any one of paragraphs 1-58, a vector of paragraphs 59 or 60, a host cell of any one of paragraphs 61-63, or a virus of any one of paragraphs 65-67 to the subject, thereby treating, or reducing the risk of developing, the hemoglobinopathy in the subject.
[76] A method of treating, or reducing a risk of developing, a hemoglobinopathy in a subject, the method comprising: administering to the subject a therapeutically effective amount of a composition of any one of paragraphs 68-74 into the subject, thereby treating, or reducing the risk of developing, the hemoglobinopathy in the subject.
[77] A method of treating, or reducing a risk of developing a hemoglobinopathy in a subject, the method comprising increasing fetal hemoglobin levels expressed by a cell in the subject.
[78] The method of any one of paragraphs 75-77, the method further comprising selecting a subject having a hemoglobinopathy or is at risk of developing a hemoglobinopathy.
[79] The method of claim 78, wherein the hemoglobinopathy is sickle cell disease or thalassemia.
[80] The method of any one of paragraphs 75-80, the method further comprising administering to the subject a therapy comprising oxygen, hydroxyurea, folic acid, or a blood transfusion.

The invention is further described in the following examples, which do not limit the scope of the invention described in the claims.

EXAMPLES

Materials and Methods

The typical PCR reaction conditions are as follows: 1× reaction buffer (consist of $MgCl_2$ at 1.5 mM; 3.0 mM; 4.5 mM (final concentration)); 0.2 mM of each of dATP, dCTP, dGTP and dTTP; 25 pmol each primer; 50 ng template DNA; 3-10% (v/v) DMSO to melt structure (this is optional) in a total volume of 100 µl.

The following is the typical reaction conditions or setting on thermal cycler for the PCR reaction: 94° C. for 3-5 min, during this time add 1U DNA polymerase or set up reaction on ice and then put tubes into PCR machine when it gets up to 94° C.; followed by 25 cycles of 94° C. for 1 min; 60° C. for 1 min, and 70° C. for 1 min; and end with 4° C. till PCR samples arc used.

Example 1

Manufacturing Synthetic miRs

Three different synthetic miRs were constructed, two which target BCL11A at different sites and a third non-targeting to act as a control. Each of these miRs was inserted into a constitutive expressing vector, a TET-inducible vector, and an erythroid specific vector.

miRs are made by annealing complimentary oligonucleotides, which have 4 base pair 5' overlaps corresponding to the sticky end left by a restriction digest with BbsI.

```
BCL11A miR1 oligos:
Sense
                                           (SEQ ID NO: 1)
ACGCTCGCACAGAACACTCATGGATTctccatgtggtagagAATCCATGA

GTGTTCTGTGCGAG

Anti-sense
                                           (SEQ ID NO: 2)
CGCACTCGCACAGAACACTCATGGATTctctaccacatggagAATCCATG

AGTGTTCTGTGCGA

BCL11A miR2 oligos:
Sense
                                           (SEQ ID NO: 3)
ACGCTCCAGAGGATGACGATTGTTTActccatgtggtagagTAAACAATC GTCATCCTCTGGag
```

-continued

Anti-sense
(SEQ ID NO: 4)
CGCActCCAGAGGATGACGATTGTTTActctaccacatggagTAAACAAT

CGTCATCCTCTGGa

Non-targeting oligos:
Sense
(SEQ ID NO: 11)
ACGCTCAACAAGATGAAGAGCACCAActccatgtggtagagTTGGTGCTC

TTCATCTTGTTGAG

Anti-sense
(SEQ ID NO: 12)
CGCACTCAACAAGATGAAGAGCACCAActctaccacatggagTTGGTGCT

CTTCATCTTGTTGA

Oligonucleotide pairs were denatured and then re-annealed (as for oligo cassette in LM-PCR protocol) following which the cassette was purified using microcentrifuge concentration devices. In the meantime, plasmid O.6.pBKS (miR223) was digested with BbsI and purified by running out on an agarose gel (no treatment with alkaline phosphatase). Each oligo cassette was then ligated into the digested O.6.pBKS construct and transformed into competent bacteria (Stb13). Bacterial clones were picked and mini-prepped to prepare isolated vectors. The synthetic miRs were sequenced using primers miR223 SEQ FOR and miR223 SEQ REV using DMSO to melt structure.

miR223 SEQ FOR
(SEQ ID NO: 19)
TAAGCTTGATATCGAATTCC miR223 SEQ REV
(SEQ ID NO: 20)
GCTCTAGAACTAGTGGATCC

Example 2

Manufacture of Constitutive miR Vectors

Each miR was cloned into the LeGO-V2 lentiviral backbone such that Venus-miR expression is driven by the constitutive SFFV promoter.

Modification of the Venus cDNA. The Venus cDNA will be amplified via PCR to add a NaeI restriction site to the 5' end (as well as maintain a good Kozak consensus sequence) and a NotI site to the 3' end.

Venus NaeI FOR:
(SEQ ID NO: 21)
TTgccggcATGGTGAGCAAGGGCGAGG

Venus NotI REV:
(SEQ ID NO: 22)
TAgcggccgcTTACTTGTACAGCTCGTCC

The PCR products were run out on an agarose gel and then purified. The purified PCR product were TA-cloned into vector PCR 2.1 TOPO (INVITROGEN™) using the TA cloning kit. Bacterial clones were picked and DNA miniprepped. Using restriction digest analysis, clones were selected that a) contain the Venus PCR product (EcoRI digest) and b) contain the clone in an orientation where the NotI that was added is next to the NotI site in the polylinker (i.e., so that a NotI digest does not excise the PCR fragment, but instead just linearises the vector). These clones were then sequenced using M13Forward and Reverse primers.

Insertion of the miR sequences into the Venus-PCR 2.1 TOPO plasmid. The Venus-PCR 2.1 TOPO plasmid was digested with NotI, treated with calf intestinal alkaline phosphatase, then run out on an agarose gel and purified. The synthetic miR constructs were excised from the O.6.pBKS plasmid by double digest with NotI and PspOMI, following by purification by agarose gel extraction. The digested miR inserts were ligated into the Venus-PCR 2.1 TOPO plasmid and the ligation product was used to transform competent bacteria (Stb13). Individual bacterial clones were picked and mini-prepped. Plasmids that contain the miR insert in the correct orientation (i.e., yield the full fragment when digested with NotI and NaeI) were selected.

Insertion of the Venus-miR cassette into LeGO-V2. The Venus-miR cassette was excised from PCR 2.1 TOPO by double digestion with NotI and NaeI, followed by treatment with Klenow large fragment to blunt the NotI overhang. This cassette was purified by agarose gel extraction. LeGO-V2 or LeGO G2 was digested with BamHI and EcoRI, which released the Venus/eGFP cDNA. This linearized vector was treated with Klenow large fragment to blunt the EcoRI and BamHI overhangs, followed by purification of the vector by agarose gel electrophoresis. The purified Venus-miR cassette and the LeGO vector were ligated together, and the product was used to transform competent bacteria. Individual bacterial clones were picked and DNA mini-prepped. Clones that contain the insert in the correct orientation were selected and grown up and used in maxi preps to manufacture viral supernatant.

Example 3

Manufacture of Erythroid-specific miR Vectors

A polyadenylation signal was attached to the Venus-miR cassettes manufactured described above. The resulting Venus-miR-PolyA cassettes were inserted in the anti-sense orientation into the erythroid specific pRRL-HS3-HS2-B-globin lentiviral vector provided by Guilianna Ferrari.

Modification of the BGH polyadenylation signal. The BGH polyA signal was amplified via PCR to maintain the PspOMI restriction site at the 5' end and add NaeI and NotI sites to the 3' end.

BGHpA PspOMI FOR:
(SEQ ID NO: 23)
CGCTCGAGCATGCATCTAGAGG

BGHpA NaeI/NotI REV:
(SEQ ID NO: 24)
TTgcggccgccggcCGCGCTTAATGCGCCGCTACAG

The PCR products were run out on an agarose gel and then purified. The purified PCR product was TA-cloned into vector PCR 2.1 TOPO (INVITROGEN™) using the TA cloning kit. Bacterial clones were picked and DNA miniprepped. Using restriction digest analysis, clones were selected that contain the BGHpA PCR product (EcoRI digest and/or NotI/PspOMI double digest). These clones were sequenced using M13Forward and Reverse primers.

Insertion of the BGHpA sequence into the Venus-miR-PCR 2.1 TOPO plasmids manufactured described above. The BGHpA cassette was excised from PCR 2.1 TOPO by digestion with PspOMI and NotI following which the insert was purified by agarose gel extraction. The Venus-miR-PCR 2.1 TOPO constructs manufactured in step B2 above were digested with NotI and subsequently treated with calf intestinal alkaline phosphatase. The linearized Venus-miR-PCR 2.1 TOPO vector was purified by running out on an agarose gel. The BGHpA insert was ligated into the Venus-miR-PCR 2.1 TOPO vector and the product used to transform competent bacteria (Stb13). Individual bacterial clones will be picked and mini-prepped. Plasmids that contain the BGHpA sequence inserted in the correct orientation (yields the whole insert upon digestion with NaeI) were selected.

Insertion of the Venus-miR-BGHpA cassette into pRRL-HS3-HS2-B-globin vector. The Venus-miR-BGHpA cassettes were excised from PCR 2.1 TOPO by digestion with NaeI. These inserts were purified by agarose gel electrophoresis. The pRRL-HS3-HS2-B-globin vector was digested with EcoRV and treated with calf intestinal alkaline phosphatase. The linearized vector was purified by agarose gel electrophoresis. The Venus-miR-BGHpA cassettes were ligated into pRRL-HS3-HS2-B-globin and the ligation product used to transform competent bacteria. Individual bacterial clones were picked and mini-prepped. Plasmids that contain the Venus-miR-BGHpA cassettes in the correct orientation in the pRRL-HS3-HS2-B-globin vector were grown up for maxi prep in order that they can be used to generate lentiviral supernatant.

Example 4

In Vitro Cell RNA Interference Experiments are Performed as Follows.

Murine erythroleukemia cells kept in culture in IMDM with FCS were transduced on fibronectin with SFFV-LVs (NT=scrambled shRNA, miR-2=targeting shRNA) at MOI=2 and sorted for Venus fluorescence. Timepoint analyzed after transduction was day 7. Cells were >95% Venus positive and $10^6$ cells were collected and RNA extracted, cDNA was obtained by reverse transcription and real-time qPCR was performed for BCL11A and epsi-gamma globin mRNAs with Gapdh as an internal control transcript (FIG. 3). A standard curve method was employed to quantify expression.

In Vivo RNA Interference Experiments in Mice are Performed as Follows.

BojJ donor derived LSK HSCs were transplanted into lethally irradiated C57/BL6 mice after transduction on fibronectin with SFFV-LVs (NT=scrambled shRNA, miR-1=targeting shRNA) at MOI=2. Injected cell dose was 100,000 cells per mouse. Venus positive WBC carrying animals at 4 months were pooled (n=2) and bone marrow sorted for Venus fluorescence after viability stain (7-AAD) (FIG. 3). RNA extraction and qPCR was performed as above.

Example 5

LCR-LV

Figure 4:
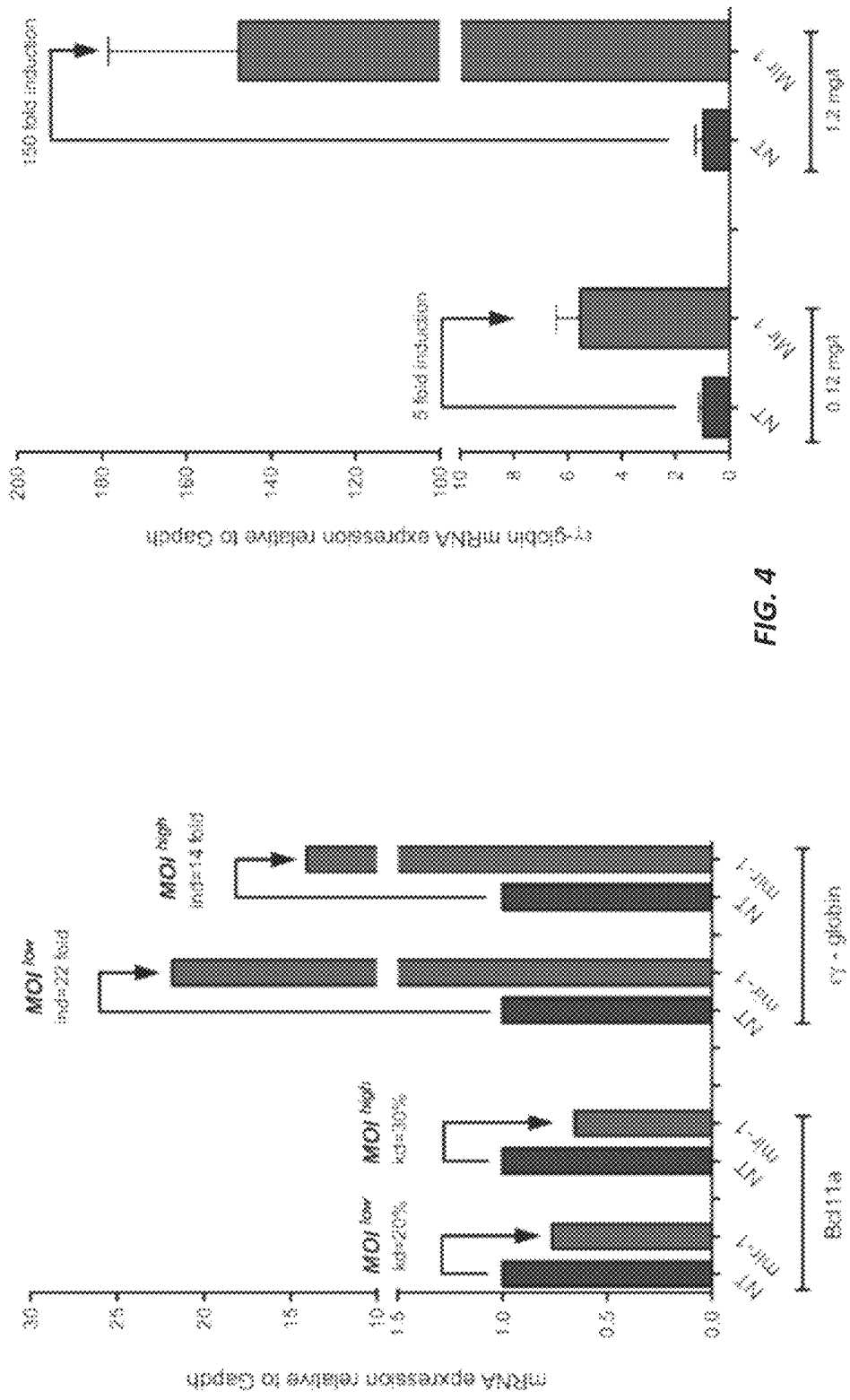
FIG. 4 is a panel of two bar graphs depicting that LCR/TET-LV efficiently knocks down BCL11A and induces εγ-globin expression.

Murine erythroleukemia cells kept in culture in IMDM with FCS were transduced on fibronectin with LCR-LVs (NT=scrambled shRNA, miR-1=targeting shRNA) at MOI=2 and MOI=100 and sorted for Venus fluorescence. Timepoint analyzed after transduction was day 7. Cells were >95% Venus positive and $10^6$ cells were collected and RNA extracted, cDNA was obtained by reverse transcription and real-time qPCR was performed for BCL11A and epsi-gamma globin mRNAs with Gapdh as an internal control transcript (FIG. 4). A standard curve method was employed to quantify expression.

TET-LV

Murine erythroleukemia cells kept in culture in IMDM with FCS were transduced on fibronectin with TET-LVs (NT=scrambled shRNA, miR-1=targeting shRNA) at MOI=2 and sorted for Venus fluorescence after exposure to doxycycline at differential concentrations. Timepoint analyzed after transduction was day 7. Cells were >95% Venus positive and $10^6$ cells were collected and RNA extracted, cDNA was obtained by reverse transcription and real-time qPCR was performed for epsi-gamma globin mRNA with Gapdh as an internal control transcript (FIG. 4). A standard curve method was employed to quantify expression.

Example 6

Figure 5:
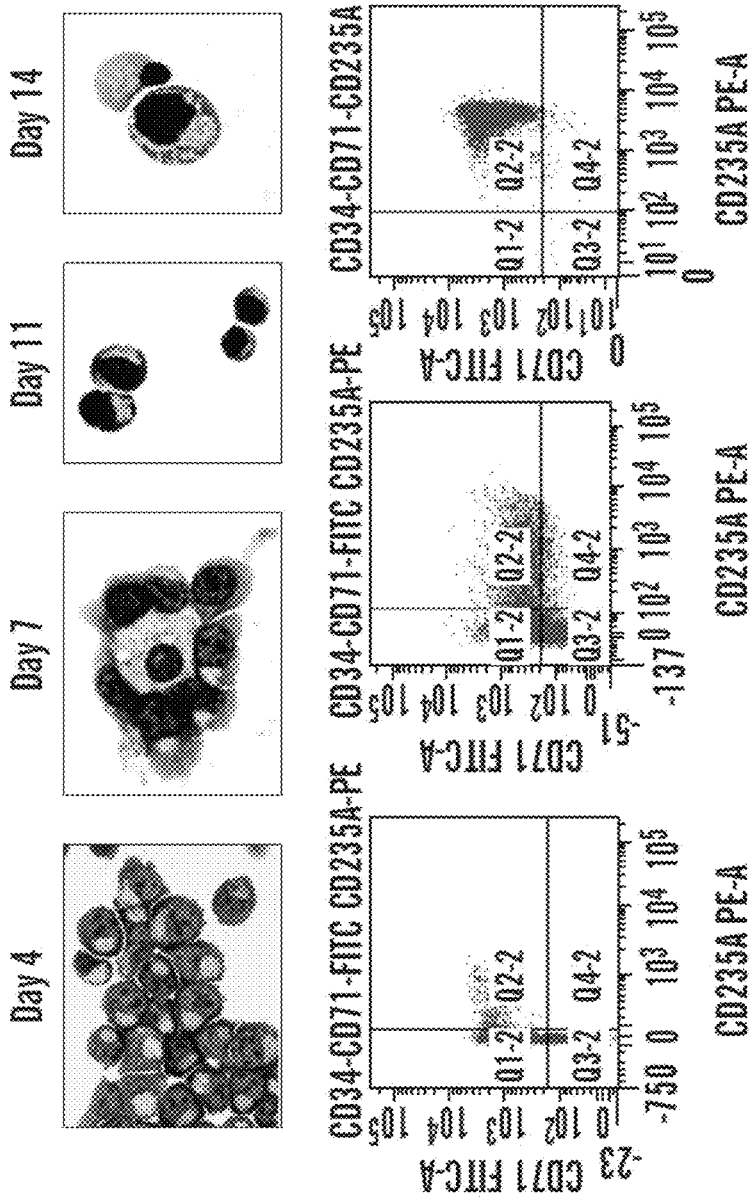
FIG. 5 is a panel of photomicrographs and graphs showing that transduced CD34+ HSC differentiate ex vivo into erythrocytes and express HbF.

Peripheral blood SOD-patient derived CD34+ circulating HSC were fractionated from discarded apheresis material (approximately 200 ml, $10^6$ CD34+ cells). Cells were transduced with SFFV-LVs (NT=scrambled shRNA, miR-1=targeting shRNA) at MOI=2 on fibronectin and differentiated as modified from Giarratana et al. (Nat Biotech 2005). Cells were analyzed maturational acquisition of erythroid surface markers (GPA, CD71) by flow cytometry. Erythroid cells sequentially acquire erythroblast and erythrocyte morpholosy and express Venus fluorescence. Cells are collected at terminal differentiation stage and RNA extracted and qPCR analysis performed to evaluate gamma-globin mRNA induction by miR-1 SFFV-IV compared to scrambled (NT) control (FIG. 5).

Example 7

Figure 6:
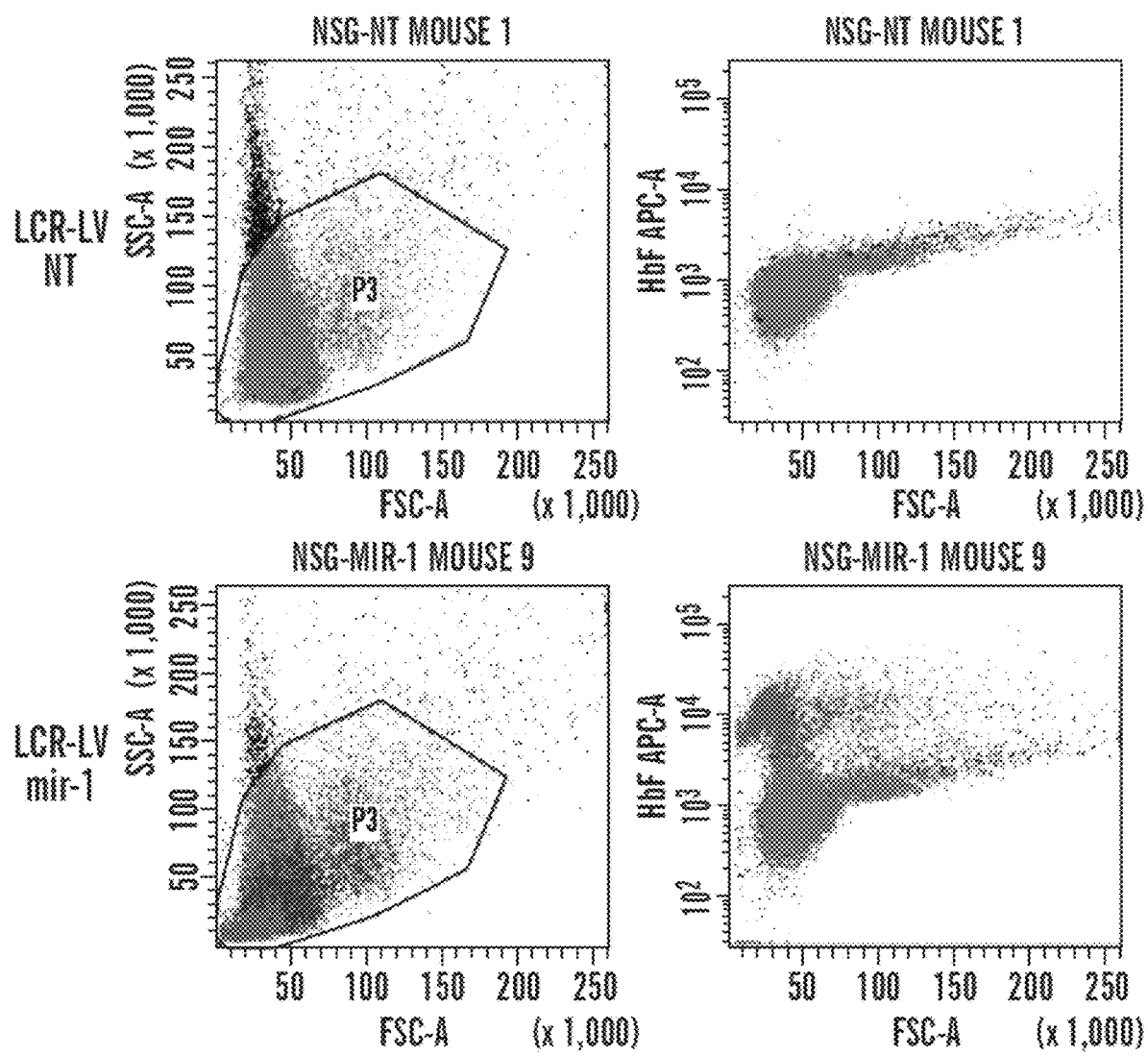
FIG. 6 is a panel of scatter plots depicting LCR-LV transduced CD34+ HSCs from patients with SCD transplanted into NSG mice.
Figure 6:
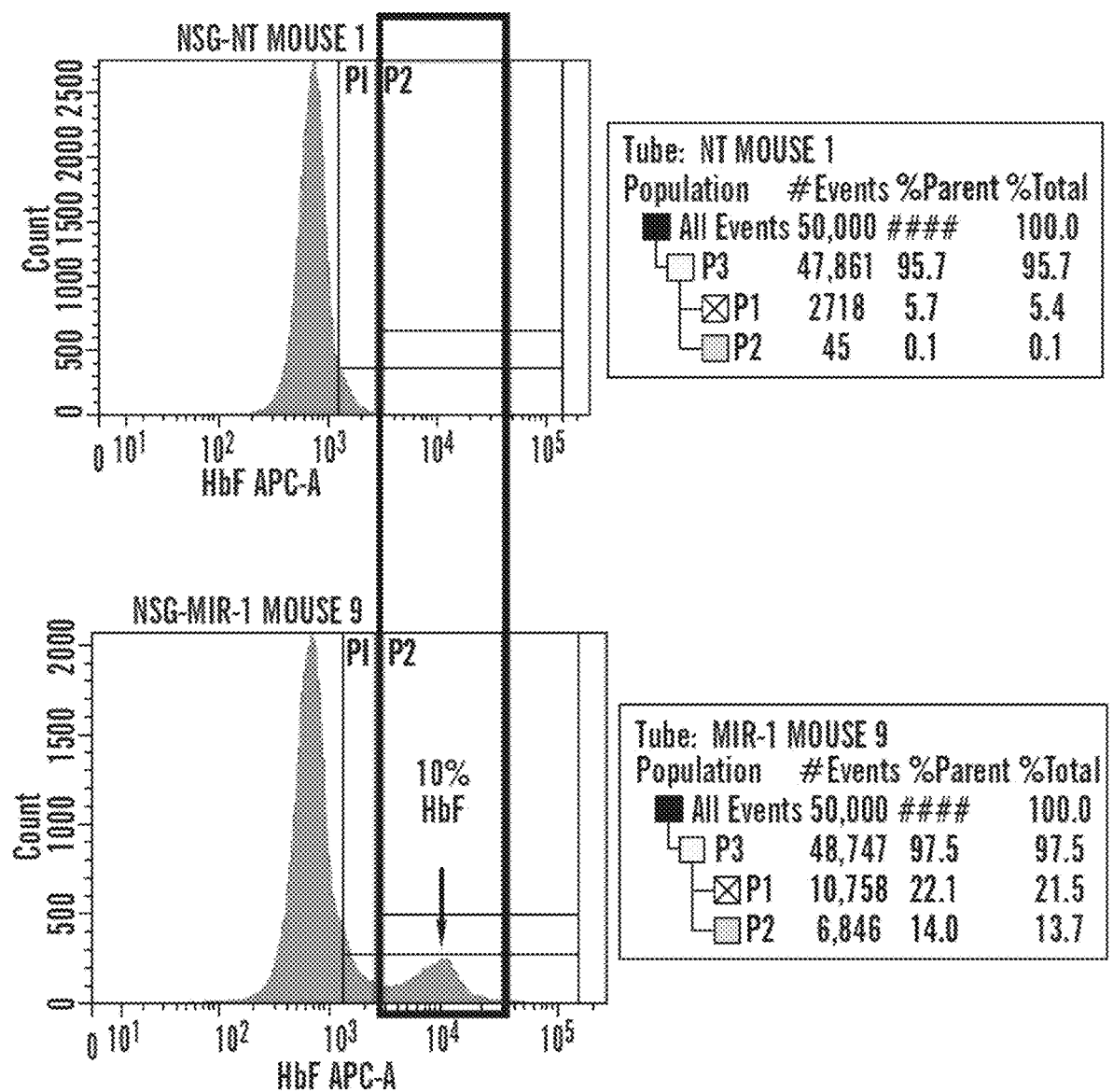

Peripheral blood SCD-patient derived CD34+ circulating HSC were fractionated from discarded apheresis material (approximately 200 ml, $10^6$ CD34+ cells). Cells were transduced with LCR-LVs (NT=scrambled shRNA, miR-1=targeting shRNA) at MOI=2 on fibronectin and injected at 30,000 cells/animal into sub-lethally irradiated NSG mice without prior sorting. Animals were bled at 4 weeks post-injection and RBCs fixed and permeabilized. HbF stain was performed and identified a LCR-LV-miR-1 animal with human HbF levels at 10% (FIG. 6).

Example 8

Figure 7:
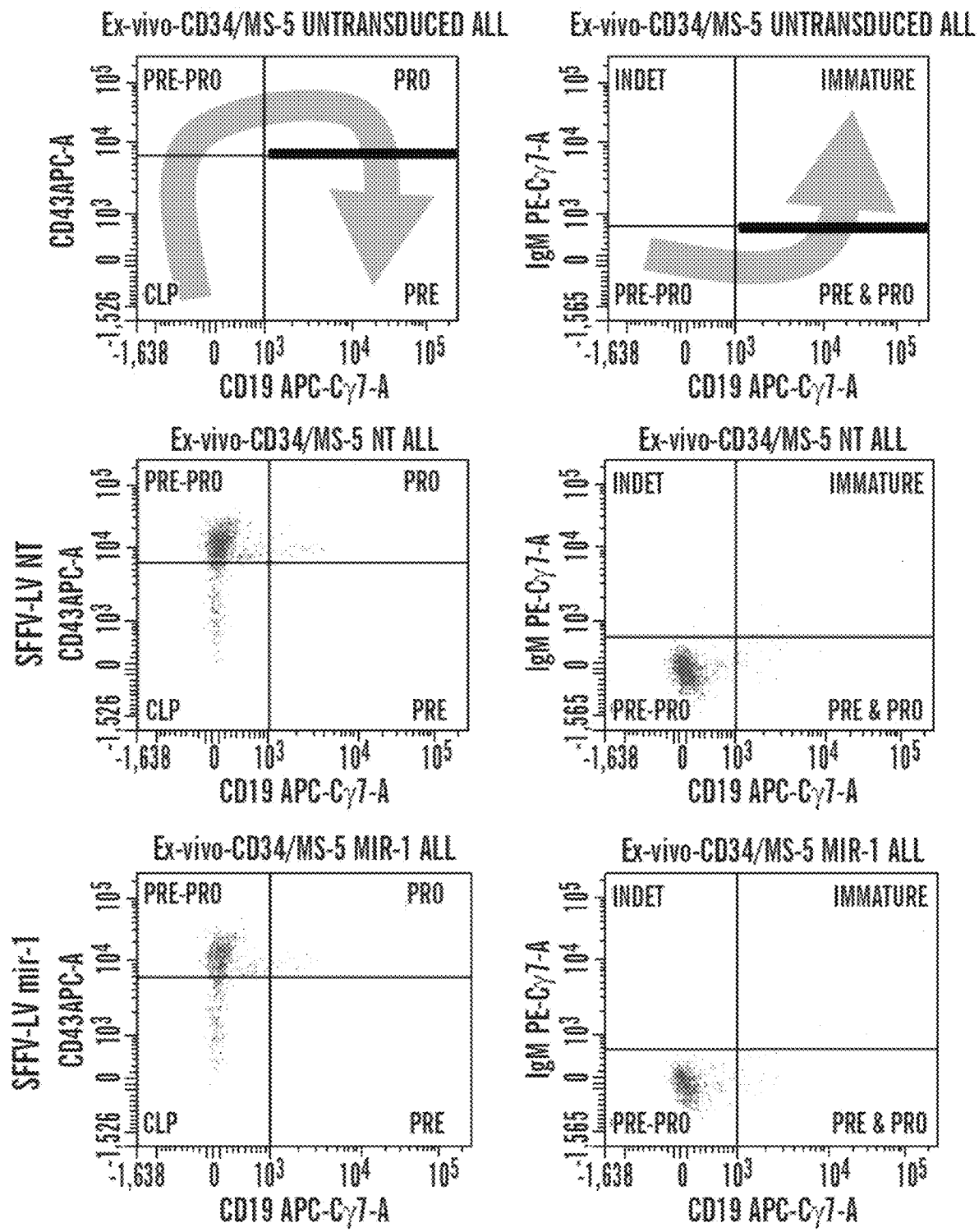
FIG. 7 is a panel of a photomicrograph and graphs showing the study of potential toxicity of BCL11A in lymphoid development.
Figure 8A:
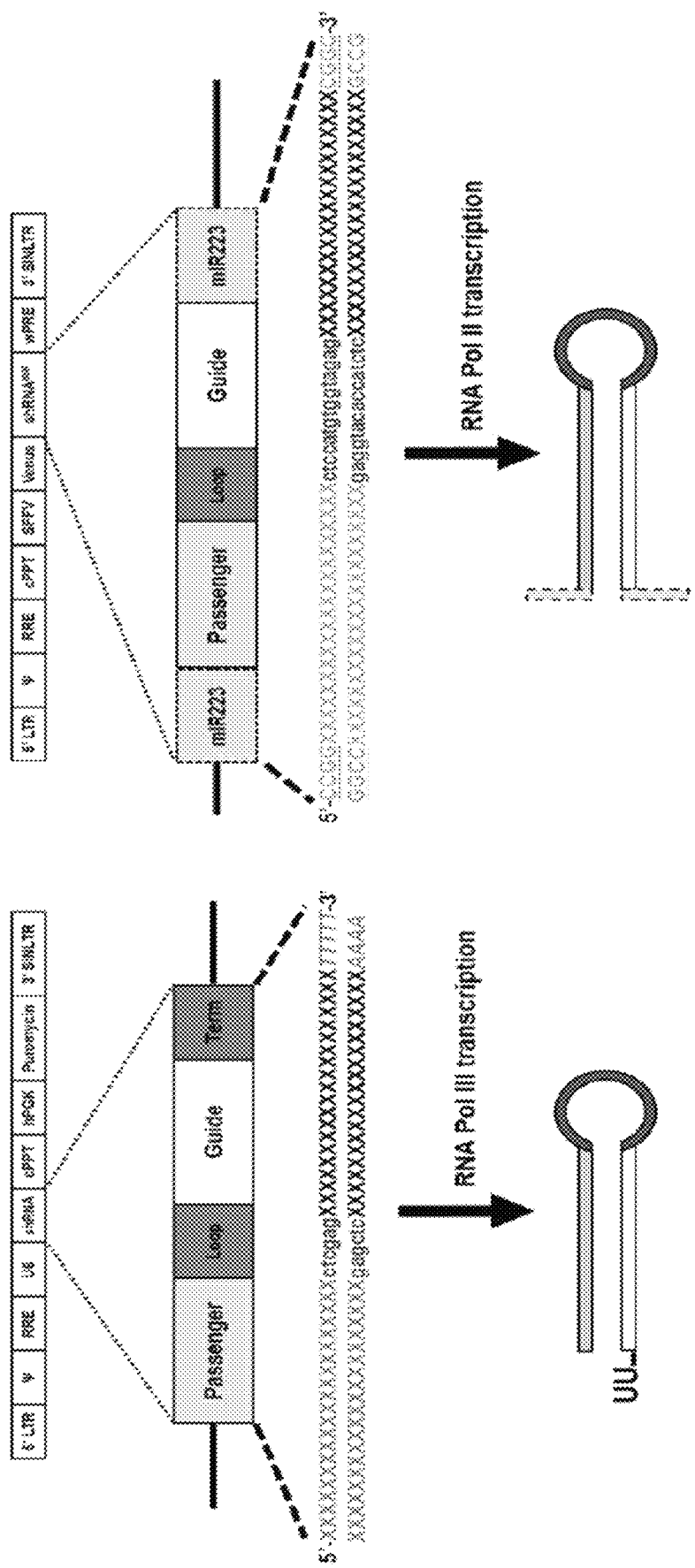
FIGS. 8A-8E show the screening and evaluation of shRNAs targeting BCL11A in pol III and pol II expression systems.
Figure 8B:
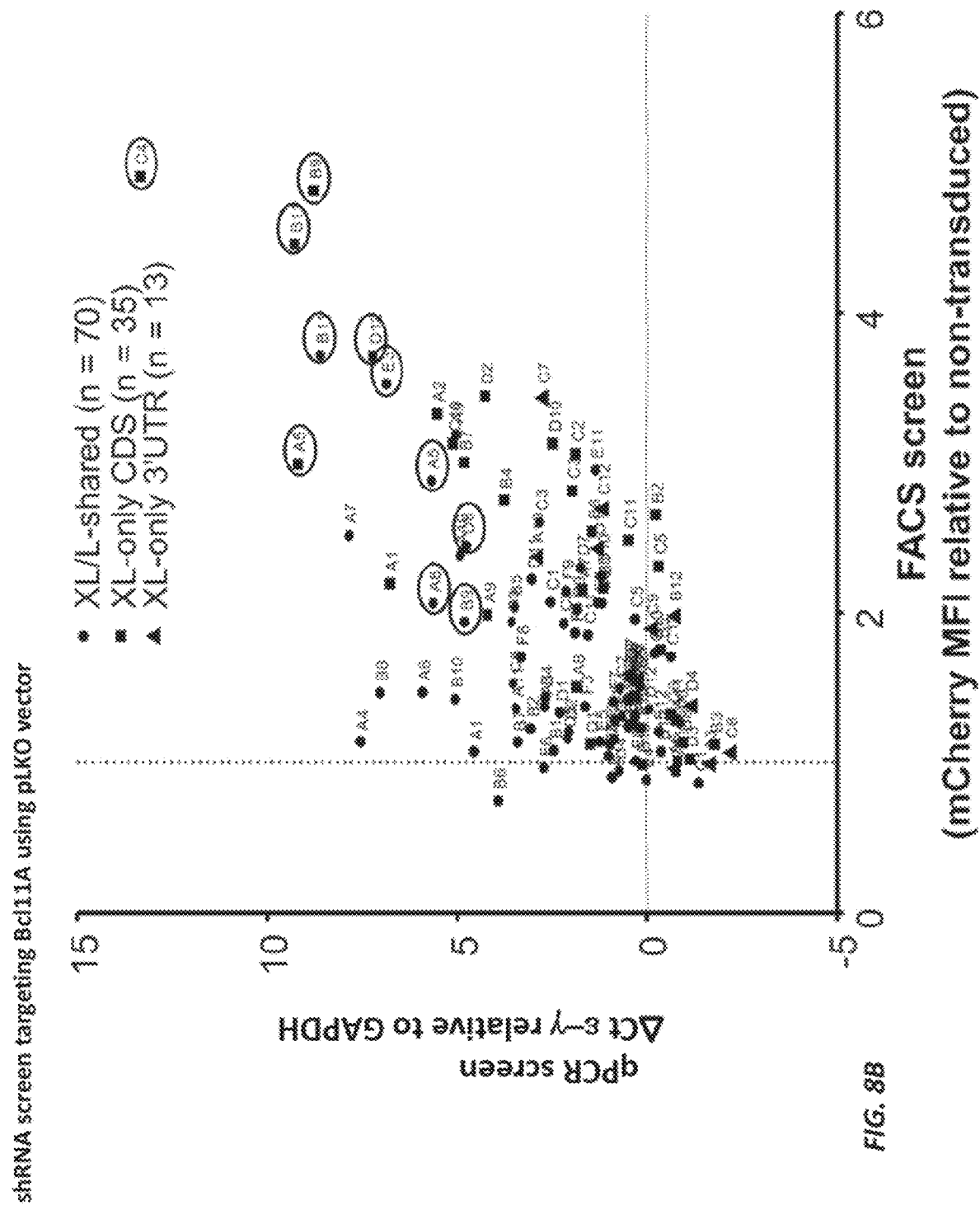
Figure 8C:
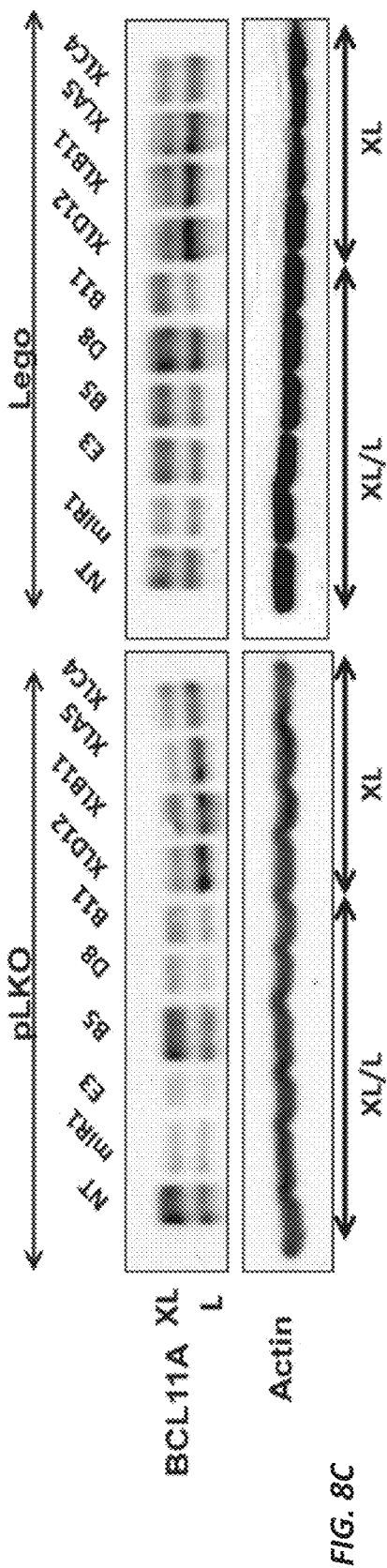
Figure 8D:
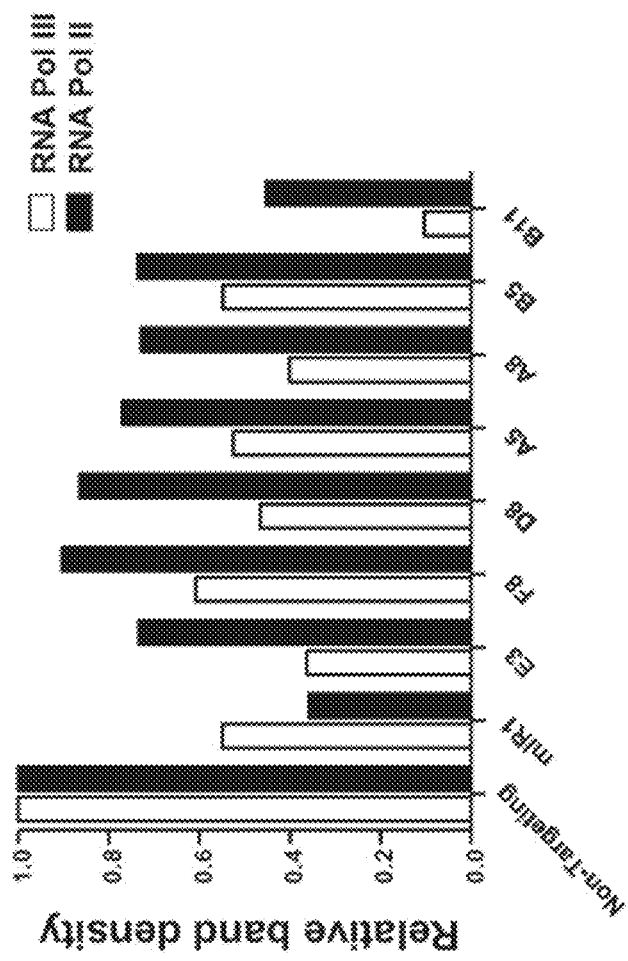
Figure 8E:
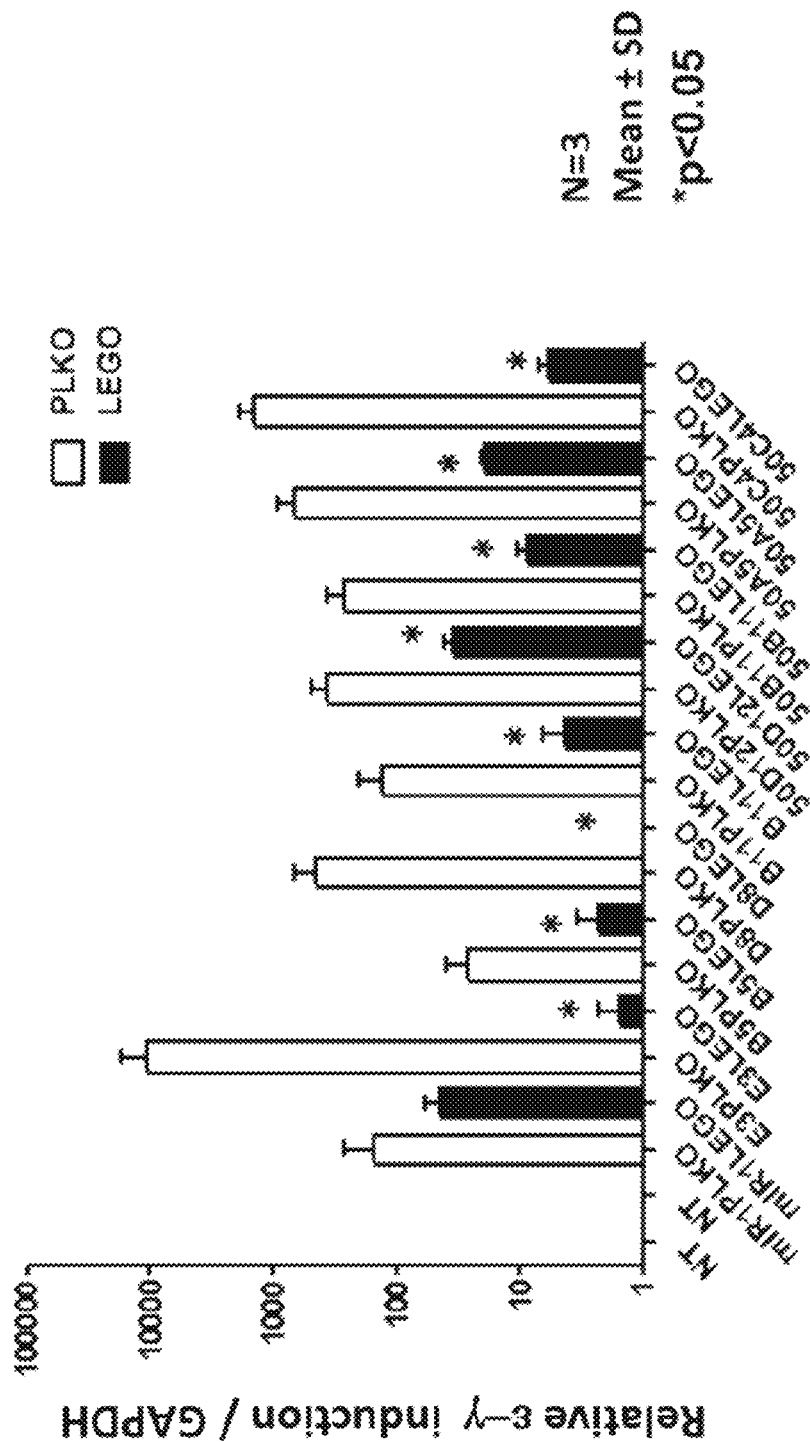
Figure 9B:
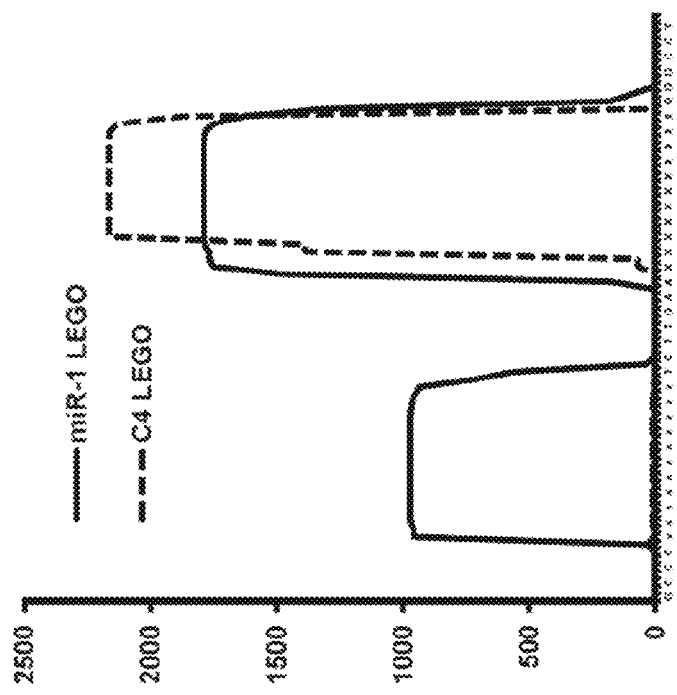
Figure 9A:
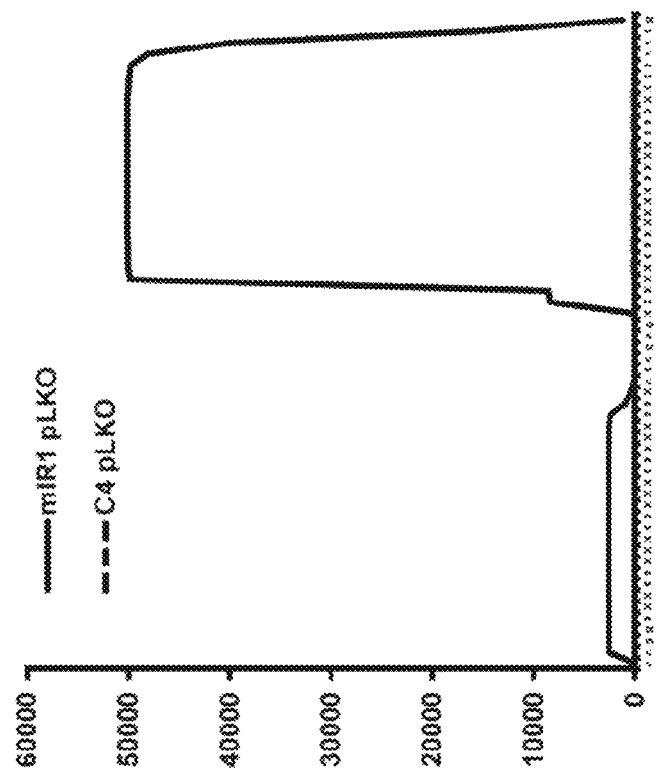
Figure 10A:
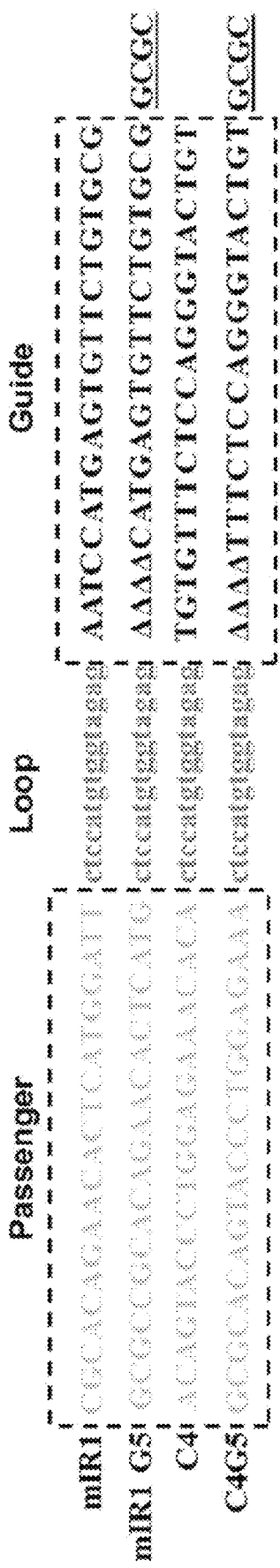
FIGS. 10A-10D show that modification of shRNA sequences leads to increased knockdown and improved guide vs passenger strand ratio.
Figure 10B:
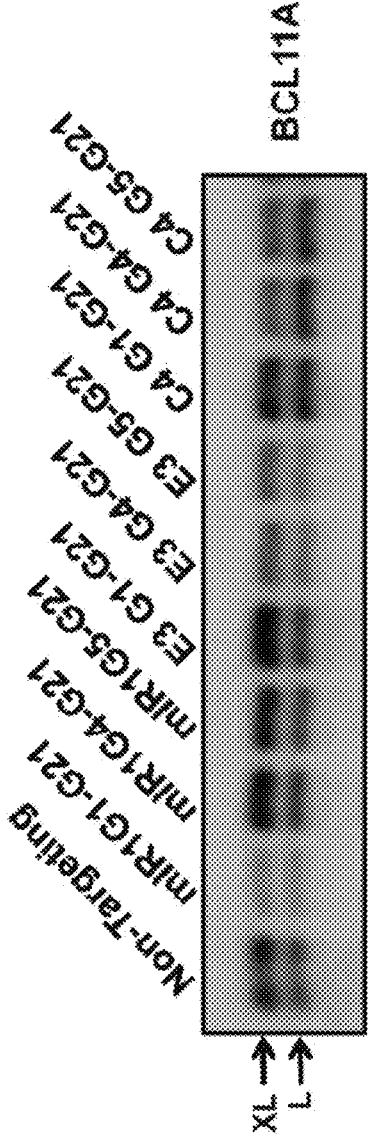
Figure 10C:
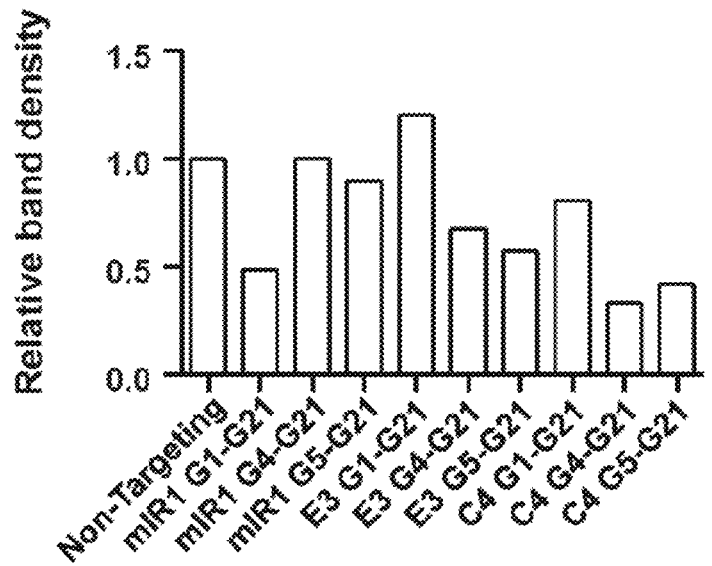
Figure 10D:
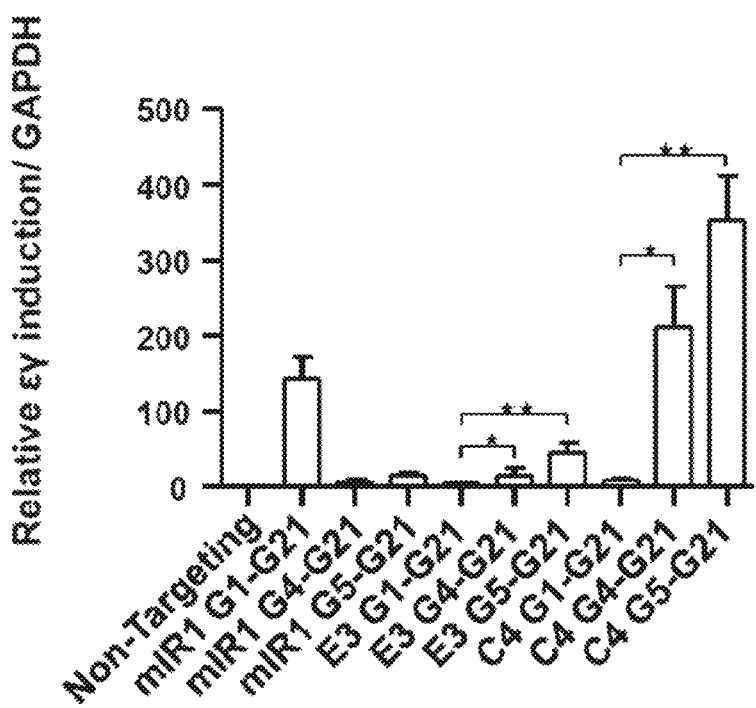
Figure 12B:
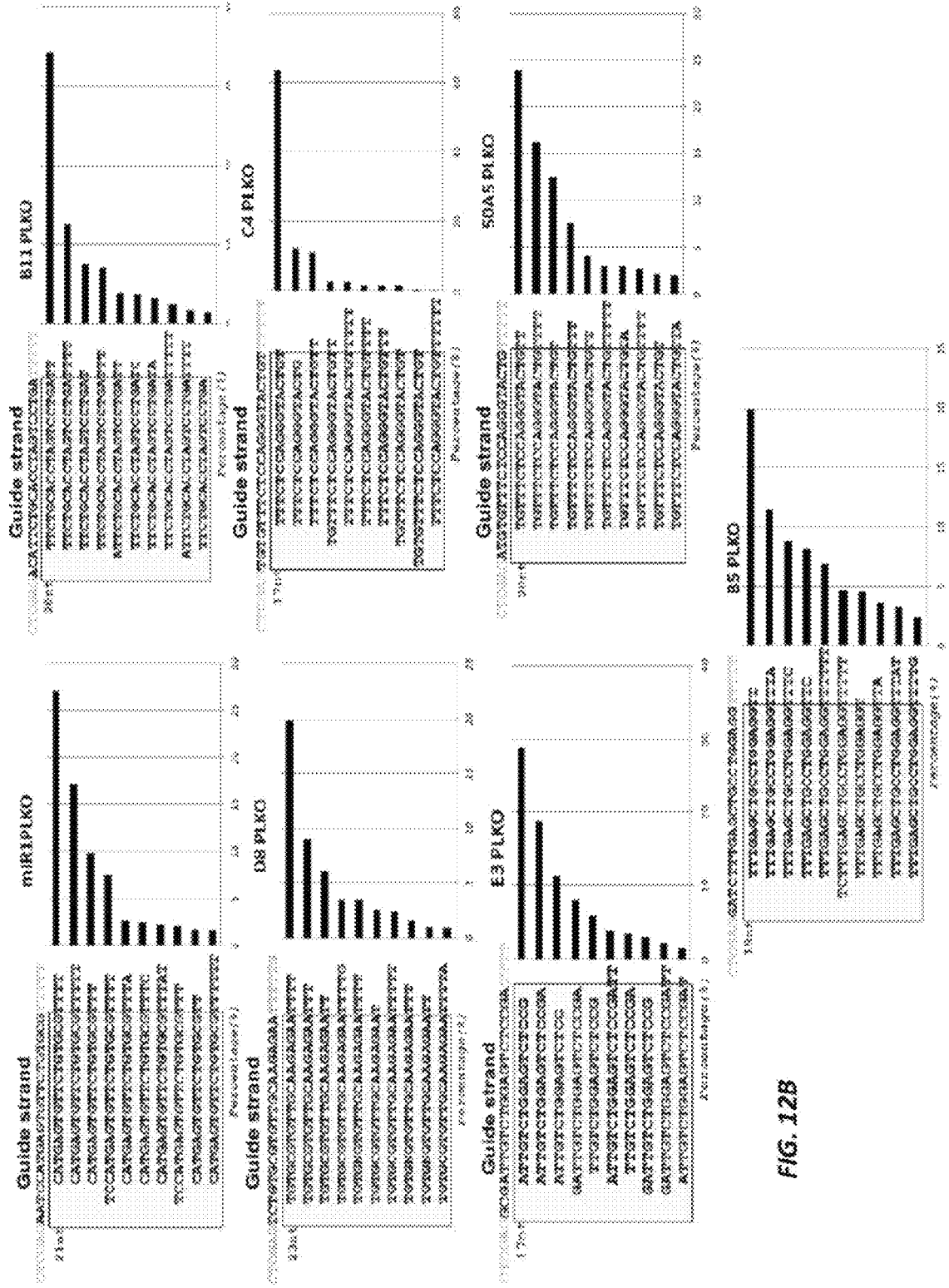
FIG. 12B. Guide strand sequence composition and distribution in PLKO. With pLKO constructs there is always a shift at the 5' end which may be due to extension of T rich sequence at the 3' end. The added T's are part of the pol III termination sequence. This shift in mature shRNA sequence indicates that during Dicer-mediated processing the 3' counting rule is dominant, meaning cleavage of the shRNA is initiated 21 nt from the 3'-end. This results in a 3 or 4 basepair shift at the 5'end and also in an identically shifted seed-region (bases 2-7 of the guide strand) which is for target recognition.
Figure 13:
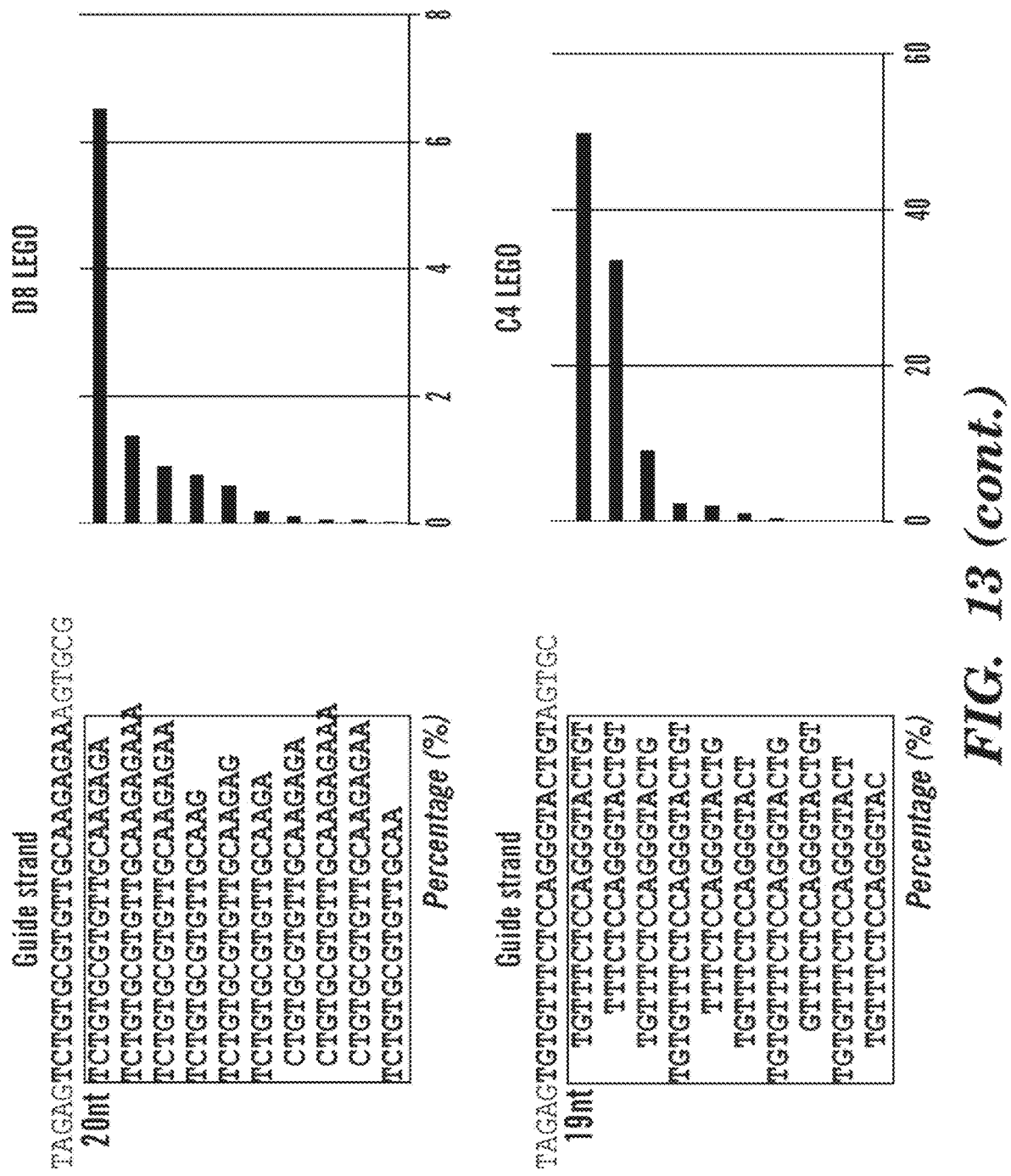
FIG. 13. Guide strand sequence composition and distribution in LEGO. Small RNA deep sequencing analysis reveals differential processing between pol III vs pol II transcripts. With lego constructs there is no shift at the 5' end and the guide strand is faithfully processed by dicer which results in the predicted product. Accordingly the final guide strand differs between pol III and pol II driven constructs.
Figure 13:
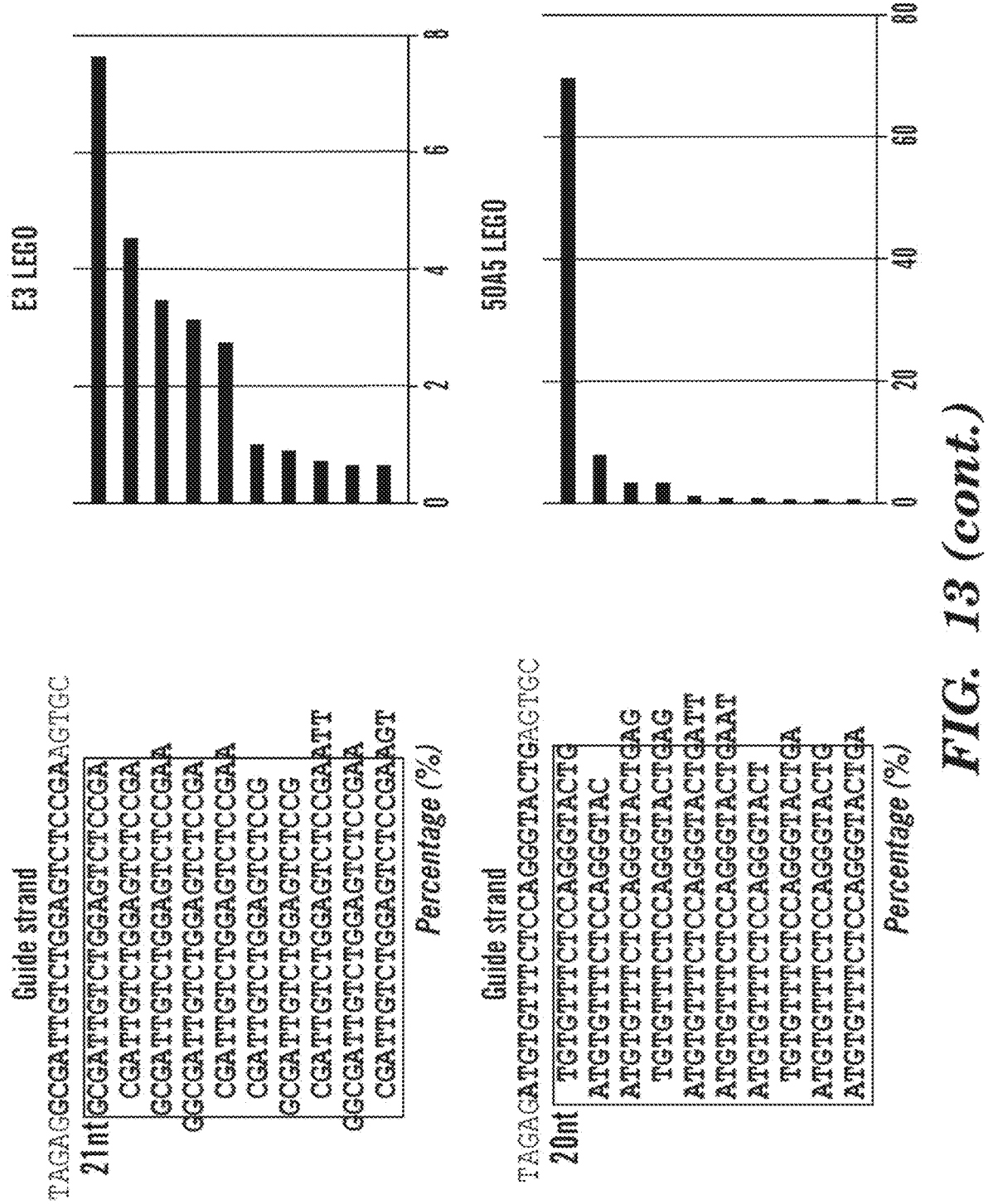
Figure 13:
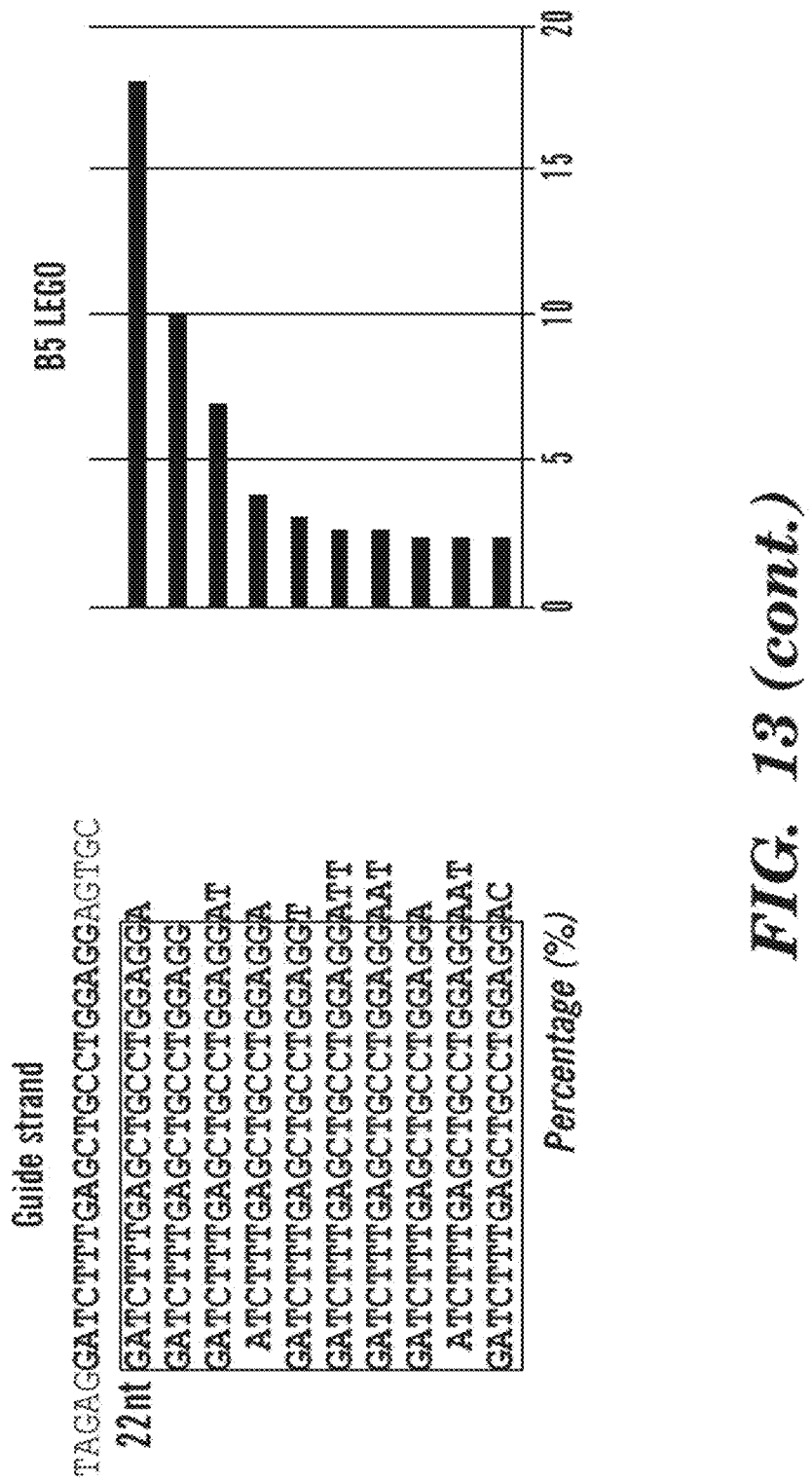
Figure 14B:
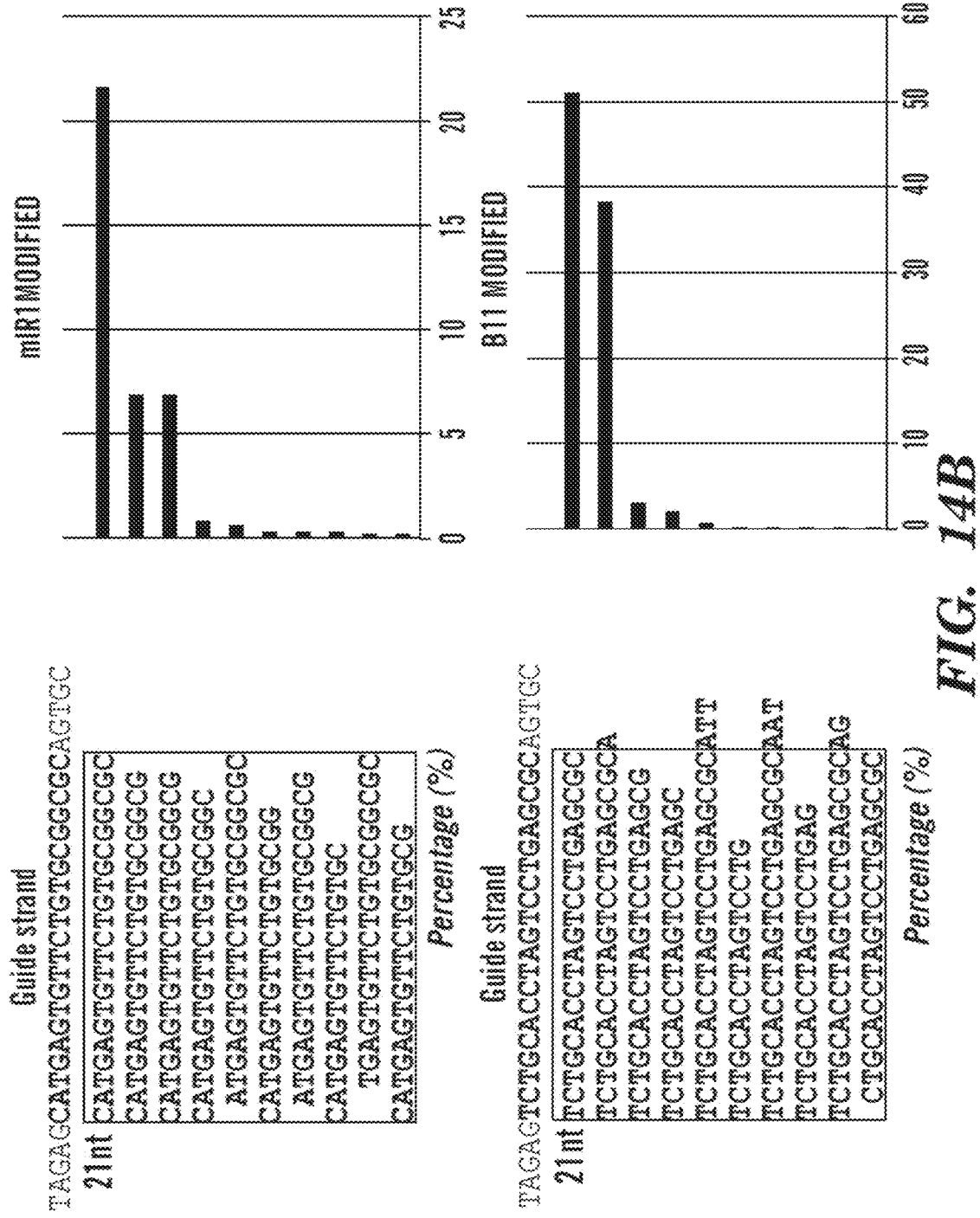
FIG. 14B. Guide strand sequence composition and distribution in modified LEGO. RNA deep sequencing analysis of modified shRNAs shows faithful processing with a 4 bp shift, which indicates that by introducing the shift we are able to perfectly mimic the product of pLKO-vectors. As pLKO vectors were used for screening of effective shRNAs, this modification mimics the precise mature product guide sequence when transferring the shRNA cassette into pol II driven backbones.
Figure 14B:
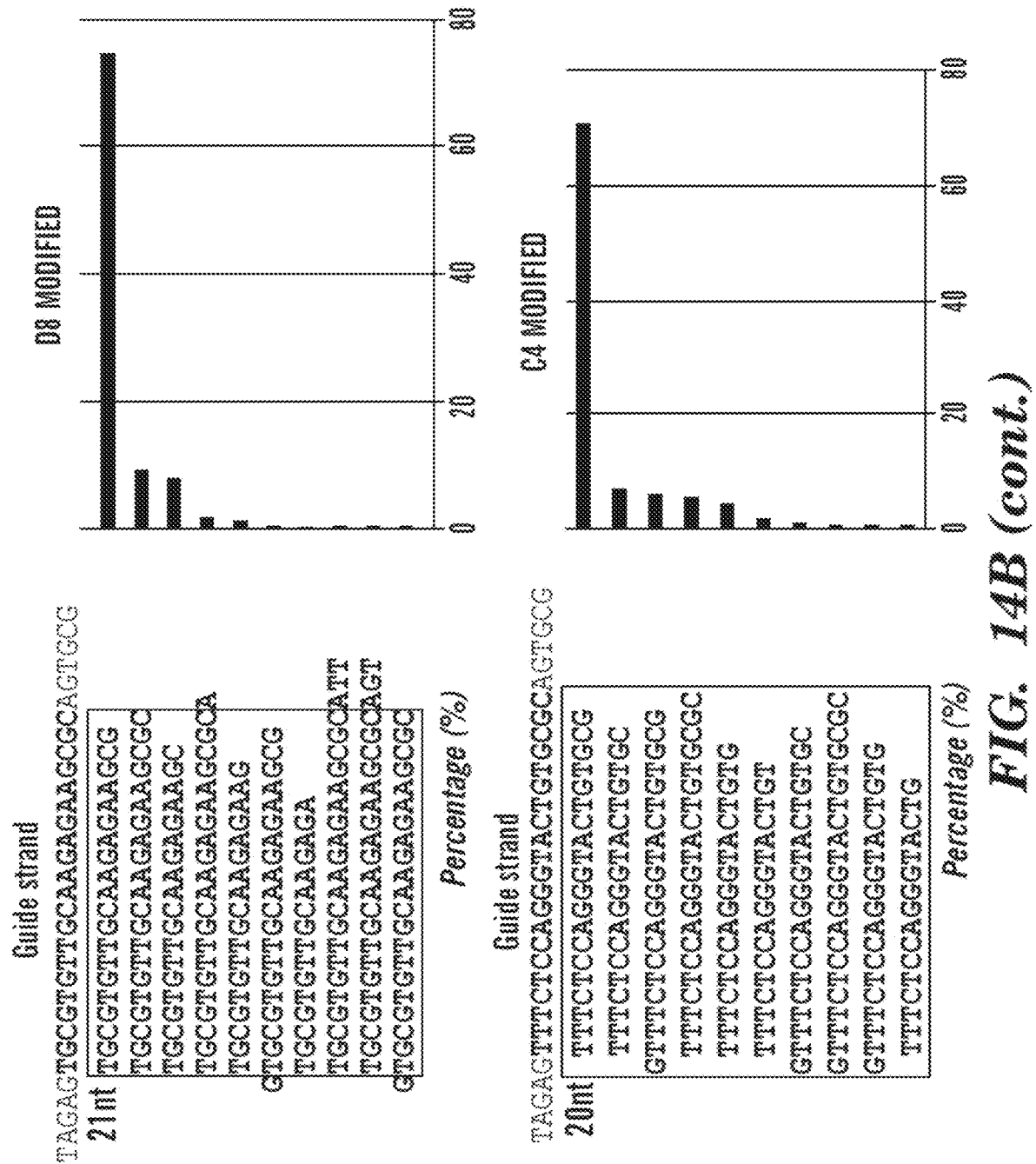
Figure 14B:
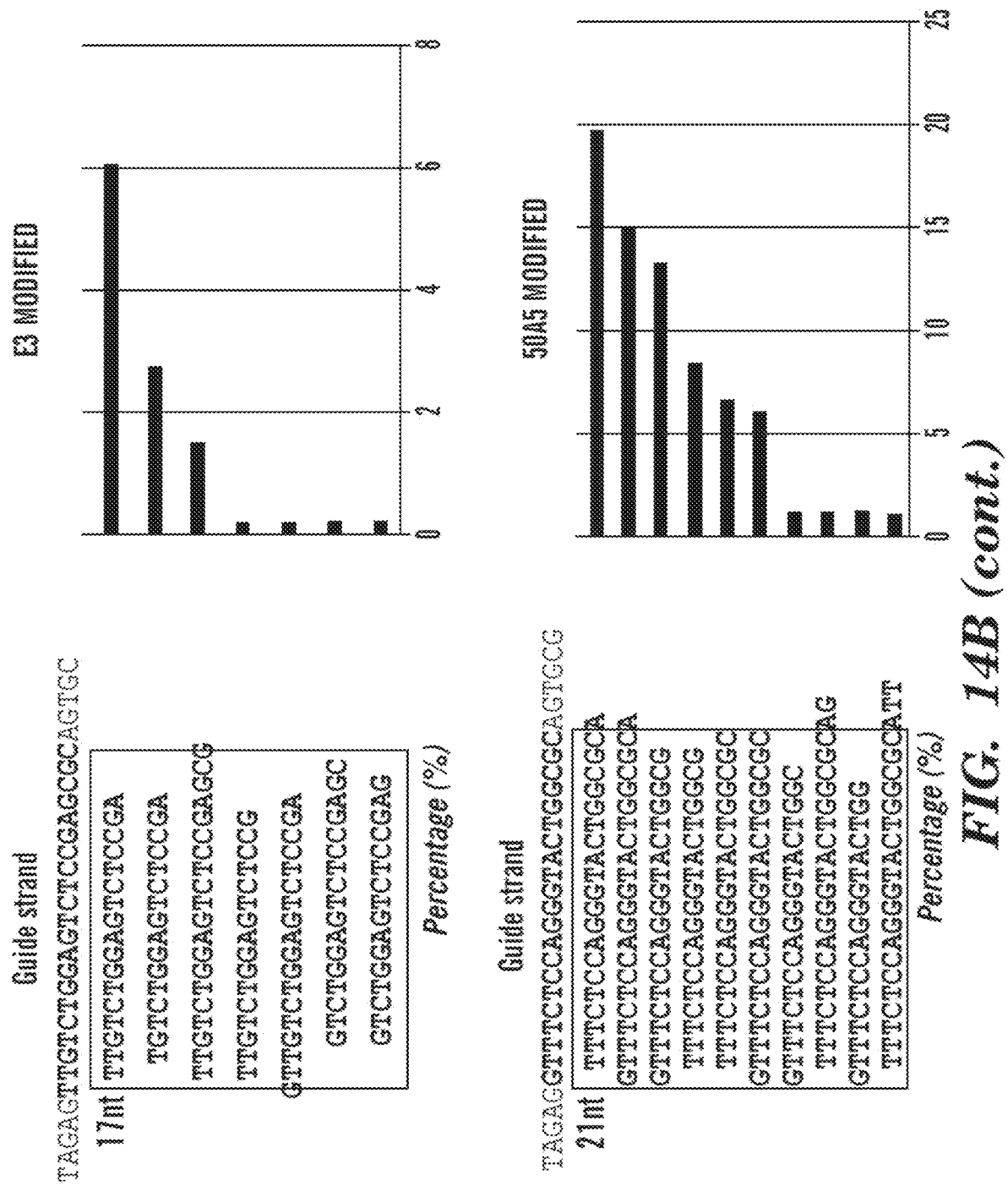
Figure 14B:
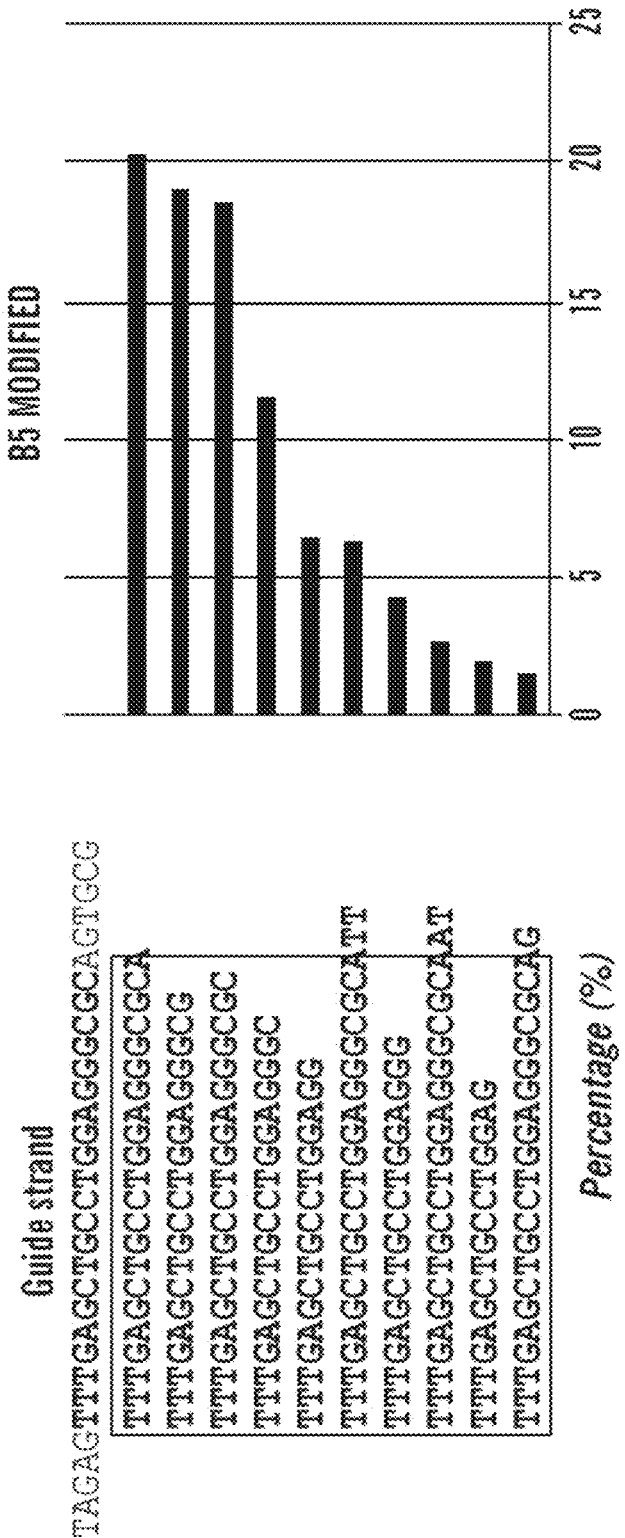
Figure 15:
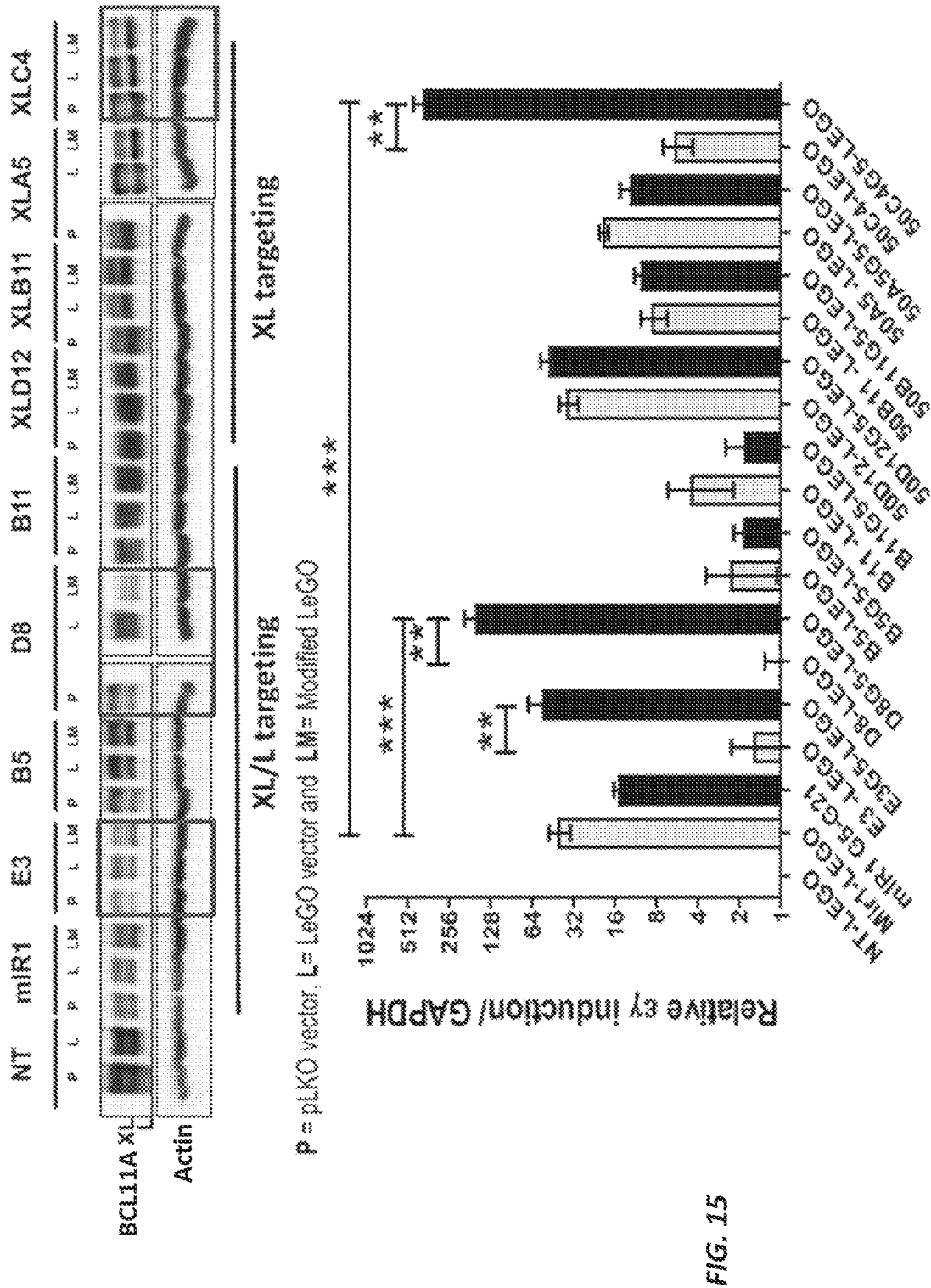
FIG. 15. Comparison of BCL11A knockdown with modified Guide sequences. Comparison of knockdown efficiency of modified and parent shRNA sequences. Western blot showing BCL11A expression (XL and L-isoforms, top panel). Red circles indicate shRNAs where an improved BCL11A knockdown was achieved upon introduction of a 4 bp shift. Bottom panel: Fold induction of normalized expression of ε-γ by modified/unmodified ShRNA sequences were compared to nontargeting control as measured by qPCR.
Figure 16:
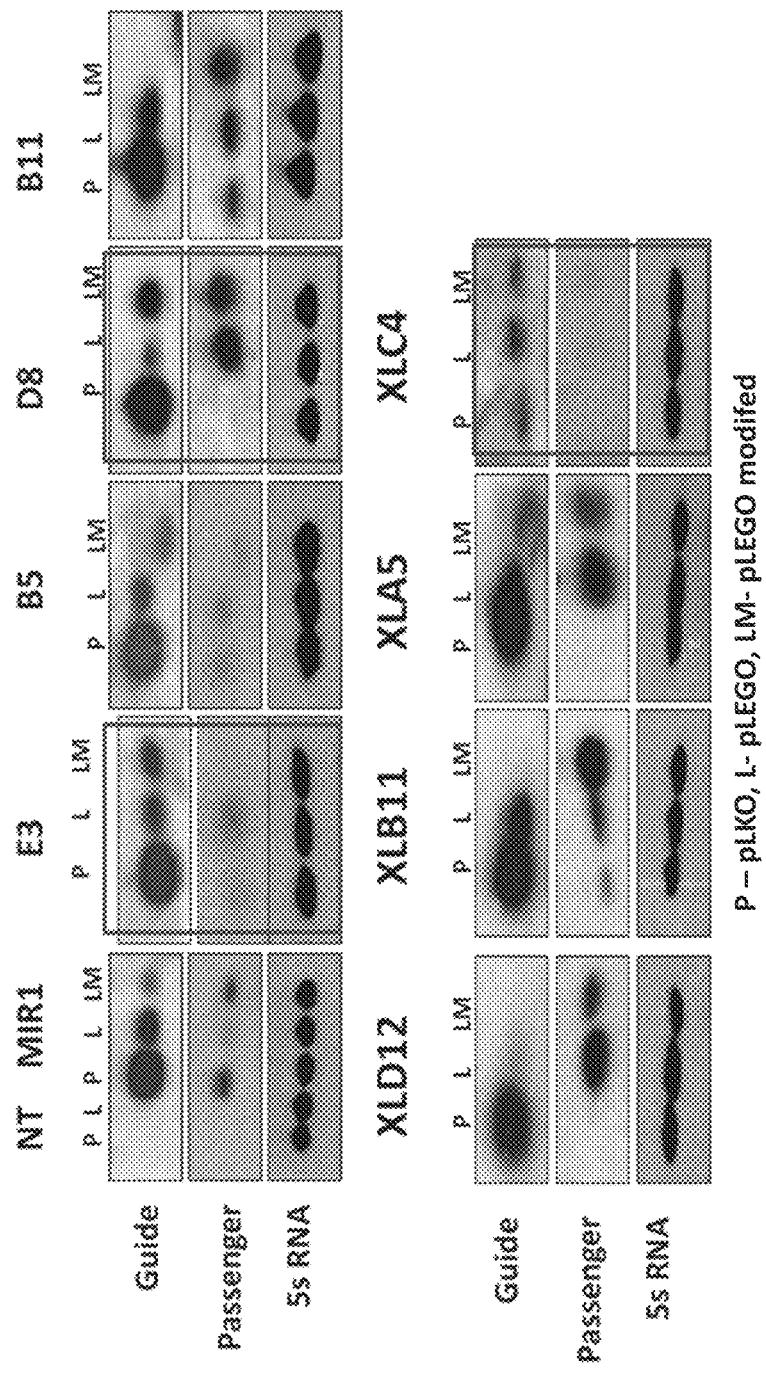
FIG. 16. Comparison of miR expression with modified Guide sequences. Consistent with the increase in knockdown efficiency and epsilon-y induction, the guide strand expression was high (which leads to increase in knockdown efficiency) when northern was performed in modified constructs compared to unmodified especially with E3G5, D8G5 and C4G5.
Figure 17:
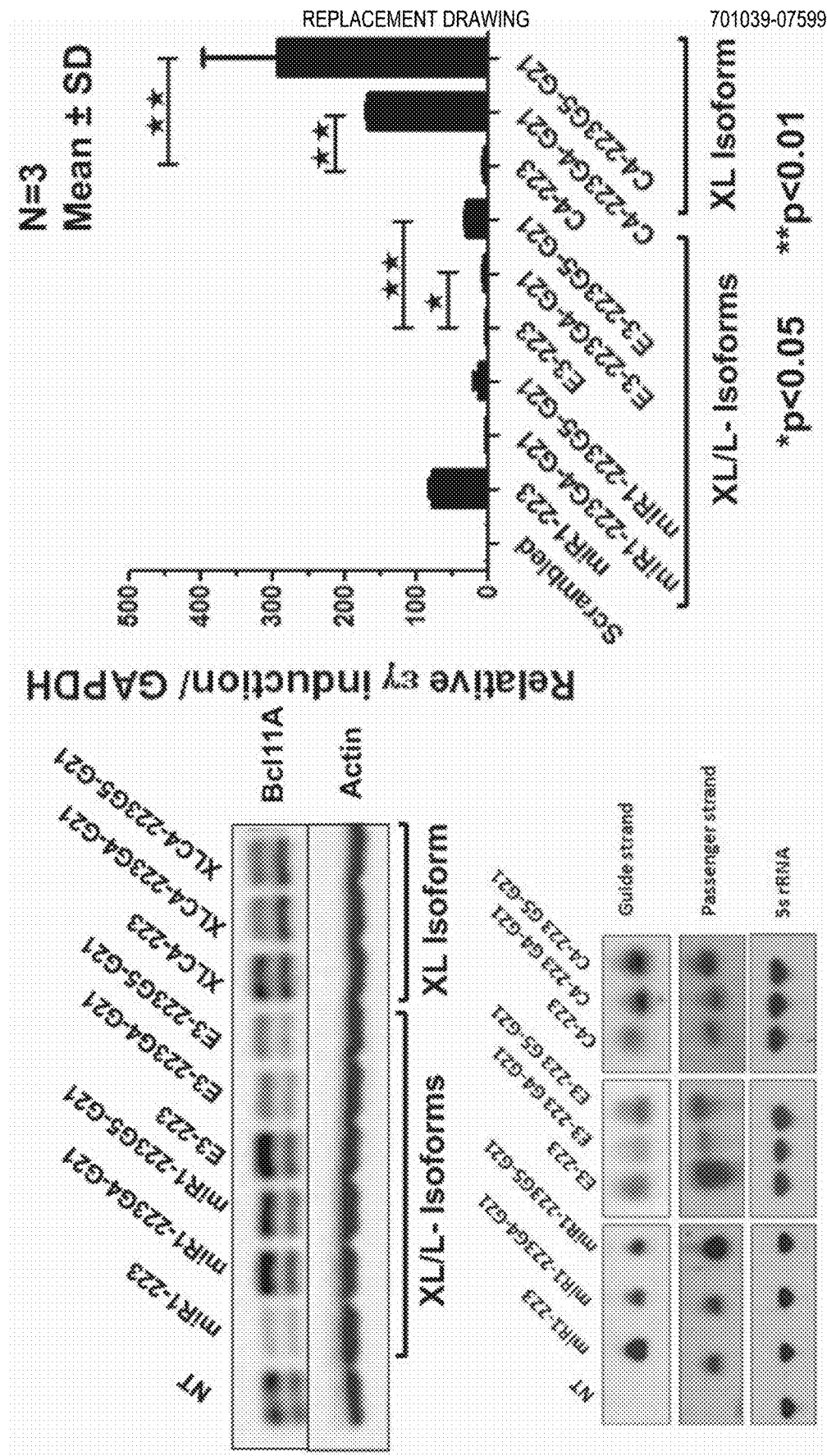
FIG. 17. BCL11A knockdown efficiency and εγ induction with LEGO vectors. Comparison of knockdown efficiency of selected shRNAs in pLKO pol III-based and pLEGO pol II-based systems. MEL cells were transduced with indicated shRNAs either in pLKO vector or with pLEGO vector and the transduced cells were selected either in the presence of puromycin (pLKO) or sorted for Venus expression (pLEGO). BCL11A protein levels were measured by immunoblot with β-actin as control. Fold induction of normalized ε-γ compared to non-targeting control is measured by qPCR. Non-targeting shRNA transduced MEL cells were used as negative controls. Frame shift has strong effect on both knockdown efficiency and εγ induction. shRNAs targeting XL isoform alone have strong effect on εγ induction. Data represent mean±SD from three independent experiments, each conducted in triplicates. * P<0.05.

Cord blood derived CD34+ human HSCs were transduced on fibronectin with SFFV-LVs (NT=scrambled shRNA, miR-1=targeting shRNA) at MOI=2 and sorted for Venus fluorescence. Cells were also visualized by fluorescent microscopy on MS-5 stroma. The cells were differentiated along the B-lymphopoietic path by methods modified from Luo et al. (Blood 2009). Cells were analyzed weekly for the acquisition of mature B-lymphocyte surface markers and loss of immature progenitor markers to identify a block in differentiation caused by the knock-down of BCL11A via SFFV-LVs. Cells were collected at weekly timepoints, and RNA extracted to verify BCL11A mRNA knockdown by shRNA targeting via SFFV-LV-miR-1 (FIG. 7).

Example 9

Optimization of Lentivirus Vector RNA Polymerase II Driven microRNA Embedded shRNAs for Enhanced Processing and Efficient Knockdown of BCL11A for Induction of Fetal Hemoglobin in Erythroid Cells.

RNA interference (RNAi) technology using short hairpin RNAs (shRNAs) expressed via pol III promoters has been widely exploited to modulate gene expression in a variety of mammalian cell types. To achieve lineage-specific targeting of mRNAs, expression of shRNAs via pol II promoters is required, necessitating embedding the shRNA in mammalian microRNA (shRNAmiR) sequences for expression and processing. Here, in order to achieve knockdown of the BCL11A transcription factor in hematopoietic cells, which has direct translational application in hemoglobinapathies, we compared the efficiency of mRNA modulation via pol III vs pol II based lentiviral vectors. Repression of the BCL11A protein could represent a therapeutic target for sickle cell disease and β-thalassemias, as its knock-down has been shown to induce the expression of the fetal HBG (γ-globin) gene ultimately leading to enhance levels of the fetal hemoglobin tetramer (HbF, α2γ2). In the mouse, BCL11A is a key repressor of murine Hbb-y gene representing a murine HBG homolog. The inventors demonstrate up to 100-1000 fold lower Hbb-y induction due to reduced BCL11A knockdown efficiency using shRNAmiR vs pol III mediated shRNA vector backbones. In order to understand the molecular basis for these differences, the inventors conducted small RNA sequence analysis of cells transduced by multiple shRNA-shRNAmiR pairs. The inventors show that shRNAs expressed via a U6 pol III promoter yield guide strand sequences that differ by a 4 bp shift compared to pol 11 driven (shRNAmiR) mature guide strand sequences. RNA sequencing demonstrated that the stretch of uridines making up part of the pol III termination signal is transcribed and included at the 3' end of the mature shRNA in a pol III vector backbone. The absence of these additional sequences is associated with a corresponding shift in the dicer cleavage site, thereby generating a different mature shRNA with an alternate seed sequence influencing the efficacy of target gene knockdown in pol II based vectors. In addition, both the absolute abundance and the ratio of guide to passenger strand are significantly different in cells transduced with either pol II or pol III based vectors. Incorporating a 4 bp shift in the guide strand of shRNAmiR resulted in a faithfully processed (a mature guide strand sequence identical to U6-driven sh-RNAs) shRNA sequence and improved knock-down efficiency of BCL11A by 50-70% at the protein level and was associated with a 100-300-fold enhancement of Hbb-y induction in murine erythroleukemia cells. The inventors have discovered a modified strategy for the prospective design of shRNAmiR vector backbones to achieve lineage-specific regulation of target genes.

Example 10

Optimization of miRNA-embedded shRNAs for Lineage-specific BCL11A Knockdown and Hemoglobin F Induction.
Materials and Methods
Design and Screening of shRNAs U6 promoter-driven lentiviral vectors (pol III-puro) expressing different shRNAs targeting BCL11A/BCL11A mRNA were obtained from the Broad Institute (Cambridge, Mass.). The pol III-puro has hPGK promoter driven puromycin selection marker. More than 100 shRNAs targeting either both XL/L forms or only XL form and 3'UTR region were screened in MEL cells in a 96 well format using a Qiagen Turbocapture plate and with a multiplexed Taqman qRT-PCR reaction measuring Gapdh and Hbb-y.
Construction of shRNAmiR Constructs The shRNAmiR, vectors were constructed by cloning the shRNA sequences with flanking mir223 sequences into the lentiviral LeGO-V2 vector containing a SFFV-driven Venus reporter (28). The shRNAmiR sequences with mir223 loop were synthesized by genscript USA Inc. (NJ, USA) and the resulting shRNA$^{miR}$s were cloned into the pol II backbone downstream of the Venus coding sequence using Xba1 and BamH1 sites. All the sequences of shRNAs are listed in FIG. 21A. A non-targeting control shRNA sequence was designed and named as SFFV-shRNAmiRNT or NT in short form. The SFFV-GFP vector, not containing any shRNA cassette and expressing GFP via an SFFV promoter, was used as a mock control (33).
Virus Production and Titration Lentiviral vector supernatants were generated by co-transfecting 10 μg of lentiviral transfer vectors, 10 μg of gag-pol, 5 μg of rev and 2 μg of VSVG packaging plasmids into HEK293T cells in a 10 cm culture dish using calcium phosphate reagent (INVITROGEN™). Supernatants were collected at 24 h and 48 h after transfection, filtered through a 0.4 micron membrane (CORNING®, NY, USA) and subsequently concentrated by ultracentrifugation at 23000 rpm for 2 h in a Beckmann XL-90 centrifuge using SW-28 swinging buckets. To determine the titer, NIH3T3 cells were infected with the virus in the presence of polybrene (8 μg/ml) and analyzed 48 h post-transduction by FACs for Venus expression (pol II constructs) or by puromycin selection (1 mg/ml, pol III constructs).
Cell Culture 3T3, 293T and MEL cells were maintained in DULBECCO's modified Eagle's or RPMI medium supplemented with 10% fetal calf serum, 2% penicillin-streptomycin and 2 mM glutamine, respectively.
In Vitro Erythroid Differentiation Culture Frozen stocks of primary human CD34+ cells were obtained from mobilized peripheral blood of healthy donors (Center of Excellence in Molecular Hematology at Fred Hutchinson Cancer Research Center, Seattle or the Flow Core at Boston Children's Hospital) according a protocol approved by the BCH Institutional Review Board. Erythroid differentiation protocol used is based on a 3-phase protocol adapted from (48). The cells were cultured in erythroid differentiation medium (EDM) based on IMDM (Iscove modified DULBECCO's medium), (CELLGRO®) supplemented with stabilized glutamine, 330 μg/mL holo-human transferrin (SIGMA®), 10 μg/mL recombinant human insulin (SIGMA®), 2 IU/mL heparin Choay (SIGMA®) and 5% solvent/detergent virus inactivated (S/D) plasma. During the first phase of expansion (days 0 to 7), CD34+ cells were cultured in EDM (erythroid differentiated medium) in the presence of 10-6 M hydrocortisone (HC) (SIGMA®), 100 ng/mL SCF (R&D SYSTEMS™), 5 ng/mL IL-3 (R&D SYSTEMS™), and 3 IU/mL Epo (AMGEN®). On day 4, cells were resuspended in EDM containing SCF, IL-3, Epo and HC. In the second phase (days 7 to 11), the cells were resuspended in EDM supplemented with SCF and Epo. In the third phase (day 11 to day 18), the cells were cultured in EDM supplemented with Epo alone. The cultures were maintained at 37° C. in 5% $CO_2$ in air.
Transduction and Flow Cytometry, for In Vitro Culture MEL and CD34+ cells were transduced with lentiviral vectors expressing U6-shRNA or SFFV-shRNAmiR in the presence of polybrene (8 μg/ml) (SIGMA-ALDRICH® Corp. St. Louis, Mo., US) for MEL cells and 10 μM prostaglandin E2 and 2 μg/ml polybrene for CD34+ cells rand centrifuged for two hours at (2000 rpm) at room temperature. Live cells were either sorted for Venus expression (pol II vectors) 48h post transduction by using BD FACS Aria II (BD BIOSCIENCES®) or cells were selected in the presence of puromycin (1 mg/ml, pol III constructs). For FACS analysis 7AAD (INVITROGEN™) was included as dead cell marker. CD34+ cells were labeled with Allo-phycocyanin (APC), phycoerythrin (PE), and PE-Cyanine7 conjugated antibodies. Anti-CD235 (glycophorin A)-PE, anti-CD71-APC, or anti-CD71-PE-Cyanine7 antibodies and DRAQ-5 (all EBIOSCIENCE®) were used for phenotyping. Analyses were performed on LSR-II flow cytometer (BECTON DICKINSON®) using Diva or FloJoX (TREESTAR™) software.

Isolation, Transduction and Flow Cytometry for Mouse Transplantation Experiments Lineage negative mouse bone marrow cells were isolated by flushing femur, tibia and hip of CD45.1 BoyJ (B6.SJL-Ptprca Pepcb/BoyJ) and CD45.2 B6 mice (C57BL/6J) followed by lineage depletion using the Mouse Lineage Cell depletion kit (Miltenyi, Biotec Inc., San Diego, USA). Cells were cultured at a density of 0.2-1×10$^6$ cells/ml in 100 ng/ml mSCF, 20 ng/ml mIL-3 (both PEPROTECH®, Rocky Hill, USA), 100 ng/ml hFlt3-L and 100 ng/ml hTPO (both CELLGENIX®, Portsmouth, USA) in STEMSPAN™ SFEM medium (STEMCELL® Technologies, Vancouver, CA). Following 24 h pre-stimulation cells were transduced at a density of 1×10$^6$ cells/ml at an MOI of 40 and transplanted into lethally irradiated (7+4Gy, split dose) recipients three days after isolation. For competitive repopulation experiments, equal numbers of cells from different transduction groups were mixed prior to transplantation into CD45.2 or heterozygous CD45.1/CD45.2 double positive recipients (0.4-1×10$^6$ per animal). Cell mixtures were analyzed via flow cytometry to confirm equal contributions of both competitor cell fractions, and readjusted if required. Analysis of peripheral blood, bone marrow and spleen was performed at multiple time points using the following antibodies: CD45.1, CD45.2, B220, CD11b, CD3, CD71, Ter119 and fixable viability dye EFLUOR780®. For analysis of the erythroid lineage red blood cell lysis was omitted. Analyses were performed on LSR-II or LSRFortessa flow cytometers (BECTON DICKINSON®) and Diva or FloJoX (Treestar™) software. Data analyses and statistics were done using Excel (MICROSOFT®) and GRAPHPAD PRISM® 5.

For transplantation of hCD34 cells ~10 week old female NSG-mice (NOD/LtSz-scid Il2rg−/−) (Jackson Laboratory, Bar Harbor, Me.) were irradiated with 2.7Gy followed by injection of ~10$^6$ cells per animal three days post isolation. Irradiated mice were fed BAYTRIL® supplemented water for 14 days.

RNA Extraction and qRT-PCR

Total RNA was extracted from MEL cells 7 days after sorting/post selection with puromycin, or freshly sorted cells on day 18 of erythroid differentiation of CD34+ cells, using the QIAGEN® RNA Plus micro kit (Valencia, Calif.). CDNA was generated using random hexamer primers and superscript III (INVITROGEN™, Carlsbad, Calif.). Quantitative PCR was performed using SYBR® Green PCR master mix (APPLIED BIOSYSTEMS®, Warrington UK) with intron spanning mouse Hbb-y and Gapdh primers (Hbb-y forward 5'-TGGCCTGTGGAGTAAGGTCAA-3', reverse 5'-GAAGCAGAGGACAAGTTCCCA-3'(SEQ. ID. NO:69)), (Gapdh forward 5'-TCACCACCATGGA-GAAGGC-3' (SEQ. ID. NO:70, reverse 5'-GCTAAGCA-GTTGGTGGTGCA-3' (SEQ. ID. NO:71)) and human HBG, HBB and GAPDH primers (HBG forward 5'-TGGAT-GATCTCAAGGGCAC-3' (SEQ. ID. NO:72), reverse 5'-TCAGTGGTATCTGGAGGACA-3' (SEQ. ID. NO:73)) (HBB forward 5'-CTGAGGAGAAGTCTGCCGTTA-3' (SEQ. ID. NO:74), reverse 5'-AGCATCAGGAGTGGACA-GAT-3' (SEQ. ID. NO:75)) and GAPDH forward 5'-AC-CCAGAAGACTGTGGATGG-3' (SEQ. ID. NO:76), reverse 5'-TTCAGCTCAGGGATGACCTT-3' (SEQ. ID. NO:77)). The PCR amplification conditions were: 95° C. for 10 min, followed by 40 cycles of 15 sec at 95° C. and 1 min at 60° C. The qPCRs were performed on a ABI® 7500 machine (APPLIED BIOSYSTEMS®, Foster City, Calif.). A standard curve using serial dilutions of cDNAs was used to determine the precise amplification efficacy for each reaction. Hbb-y and γ-globin expression levels were normalized to GAPDH as an internal control, and relative gene expression (ΔΔCt method) was used for analysis of PCR data, including correction for differential amplification efficiencies.

Northern Blot Analysis

MEL cells transduced with U6-shRNAs and SFFV-shRNA$^{miR}$s were sorted and collected after puromycin selection culturing for 7 days. Total RNA was isolated using 1 ml TRIZOL® reagent (AMBION®), and 15 μg were resolved on a 15% acrylamide gel. Small transcript sizes were determined using the Decade Ladder (AMBION®, Austin, Tex.). RNA was transferred to HYBOND™-XL membrane (AMERSHAM™, Piscataway, N.J.) and UV-crosslinked. Blots were pre-hybridized using UltraHyb-Oligo (AMBION®, Austin, Tx) at 35° C., probed with γ-32P-labeled oligonucleotides (4 polynucleotide kinase; AMERSHAM™, Piscataway, N.J.) at 37° C. for one hour, washed in 2× sodium citrate, 0.1% sodium dodecyl sulphate at 30-35° C., and exposed to film. Probe sequences for detecting mature miRNA were as follows: shRNA1, 5' CGGAGACTCCA-GACAATCGC 3' (SEQ. ID. NO:78); shRNA2, 5'CTCCA-GGCAGCTCAAAGATC 3' (SEQ. ID. NO:79); shRNA3, 5' TCTCTTGCAACACGCACAGA 3' (SEQ. ID. NO:80); shRNA4, 5' CAGGACTAGGTGCAGAATGT 3' (SEQ. ID. NO:81); shRNA5, 5' ATCGAGTGTTGAATAATGAT 3' (SEQ. ID. NO:82); shRNA6, 5' GTACCCTGGAGAAACA-CAT 3' (SEQ. ID. NO:83); shRNA7, 5' ACTGTCCACAG-GAGAAGCCA 3' (SEQ. ID. NO:84); shRNA8, 5' CAG-TACCCTGGAGAAACACA 3' (SEQ. ID. NO:85).

Western Blot Analysis

Transduced MELs and CD34+ cells were lysed in lysis buffer (RIPA) with protease (ROCHE®) and phosphatase inhibitors (SANTA CRUZ BIOTECHNOLGY®), pepstatin and leupeptin (SIGMA). Protein lysates were estimated by BCA protein assay (THERMO SCIENTIFIC). 25 μg of protein was suspended in 2× Laemmli sample buffer, boiled and loaded on to a 8% SDS-poly-acrylamide gel and subsequently transferred to a Polyvinylidene fluoride (PVDF) membrane (MILLIPORE®). Following blocking in PBS with 0.1% Triton-X100 and 5% nonfat dry milk, the PVDF membrane was incubated with a monoclonal mouse anti-BCL11A antibody (ABCAM®) or mouse anti-β-actin (SIGMA®). Anti-mouse IgG HRP-linked secondary antibody (CELL SIGNALING®) was used for detection by chemiluminescence 20× LUMIGLO® Reagent and 20× Peroxide (CELL SIGNALING®).

HPLC Analysis

Hemolysates were prepared from cells on day 18 of differentiation using osmotic lysis in water and three rapid freeze-thaw cycles. Hemoglobin electrophoresis with cellulose acetate and high performance liquid chromatography (HPLC) were carried out with the lysates, in the clinical laboratories of the Brigham and Women's Hospital using clinically-calibrated standards for the human hemoglobins.

RNA Sequencing and Analysis

Small RNAs were extracted from 6×10$^6$ MEL cells using mirVana miRNA isolation kit (INVITROGEN™) according to the manufacturer's instructions and sent out for deep RNA sequencing using ILLUMINA® Hiseq2000. A self-developed PERL script was used to remove the adaptor sequence, and 19-25 nt small RNAs were used for further analysis. The BOWTIE software (obtained from the internes website at bowtie-bio period sourceforge period net) was used for alignment, and 1 mismatch was permitted. Expression level of small RNAs was normalized to one million of total reads of each library for comparison between different samples. For the experiment with 250 TRC shRNAs in 4 cell lines, lentivirus was prepared by the Broad Institute using a high-throughput virus preparation protocol and cells were infected at high MOI with a single shRNA per well in 96 well plates (the protocols are obtained from the internes website of the Broad Institute at Cambridge, Mass., USA, at the RNAi public resources section under "puromycin") was added at 1 day post-infection and cells were lysed in TRIZOL® at 4 days post-infection. All lysates were pooled for each cell line, followed by total RNA extraction and small RNA library preparation (49). ILLUMINA® reads were trimmed, collapsed to unique reads (>17 nt) with counts, and mapped to TRC shRNA expression vector sequences allowing no mismatches. Mature shRNA sequence distributions were calculated for each shRNA before averaging across shRNAs.

Statistical Analysis

The GRAPHPAD PRISM® 5.0 software package was used for statistical analysis. Results are expressed as mean±standard deviation (SD). Statistical significance was assessed by t-test.

Results

Figure 19:
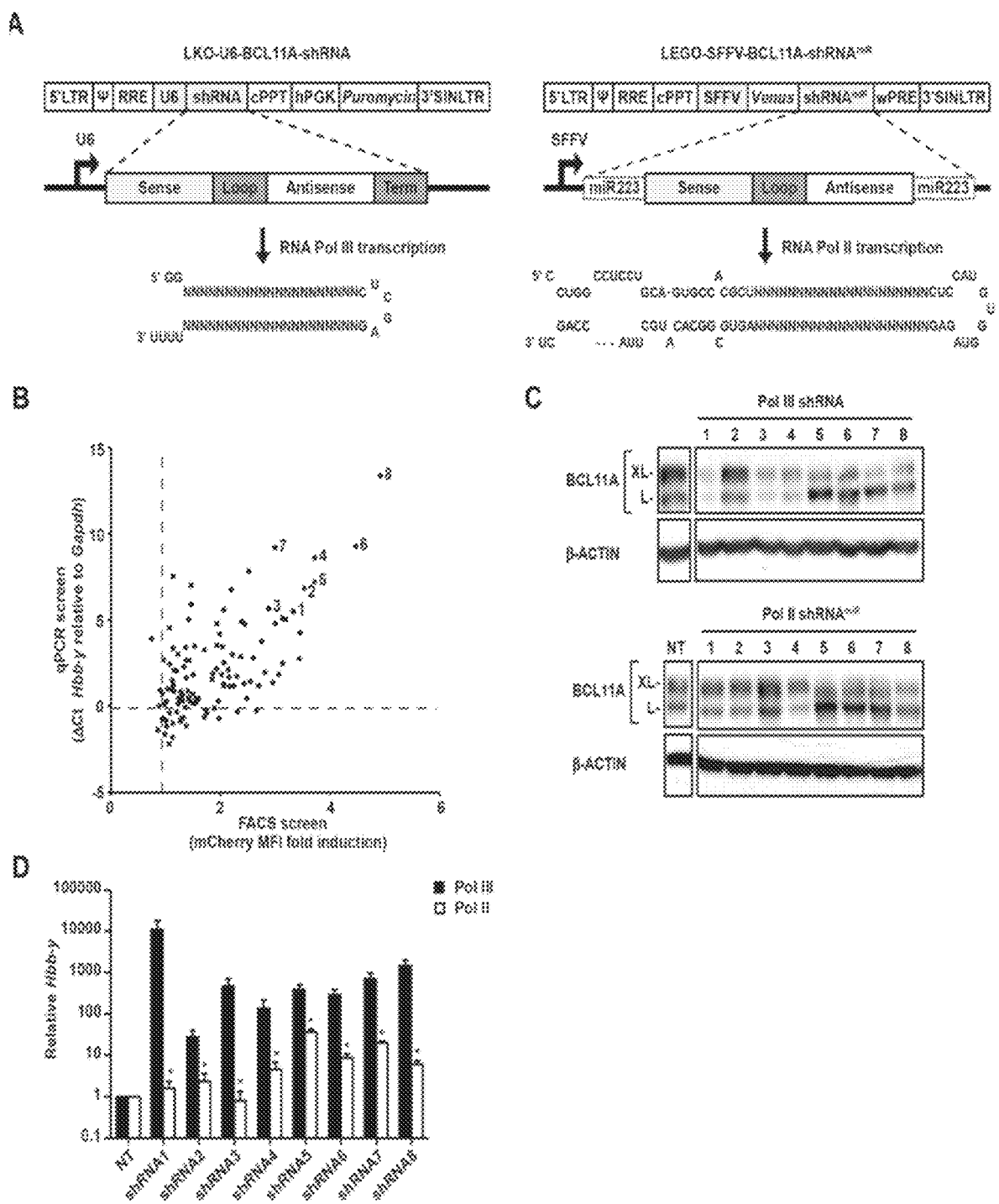
FIGS. 19A-19D show the screening and evaluation of shRNAs targeting BCL11A in pol III and pol II expression systems.

Decreased Knockdown Efficiency of BCL11A by shRNAs Embedded in a microRNA Scaffold (shRNAmiR) Compared to Simple Stem-Loop shRNAs To identify candidate shRNAs mediating effective knockdown of BCL11A, a lentiviral library of 118 shRNAs targeting coding sequences of BCL11A mRNA conserved between humans and mice was screened in MEL cells. ShRNAs were expressed from a pol III based U6 promoter (FIG. 19A, left panel) in the LKO lentivirus backbone (26) containing a puromycin resistance gene for selection named LKO-U6-BCL11A-shRNA$^{miR}$ (hereafter U6-shRNA). MEL cells, a commonly used cell line for the study of globin gene regulation, were transduced with the lentivirus vectors expressing shRNAs at a multiplicity of infection (MOI) of 2. The normalized expression of embryonic mouse Hbb-y mRNA, which serves as a functional homolog of the human γ-globin gene (27) provides an indirect readout of BCL11A knockdown (FIG. 19B, y-axis). As a second readout, the shRNA pool was also screened using a MEL-reporter cell line harboring a mCherry knock-in at the Hbb-y locus (D. Bauer, unpublished). Fluorescent reporter induction was analyzed by flow cytometry (FIG. 19B, x-axis). Eight shRNAs (labeled and named as shRNA1 through 8 in FIG. 19B) that consistently induced Hbb-y and mCherry reporter expression in MEL cells were cloned into human microRNA223 (miR-223) flanking and loop sequences to create synthetic microRNAs (shRNAmiR) with the goal of developing lineage-specific expression vectors for knockdown of BCL11A. For initial analysis, this cassette was incorporated in the pLeGO lentiviral vector (28) (FIG. 19A, right panel) into the 3' untranslated region of the Venus fluorescent reporter under control of the strong and ubiquitously expressed spleen focus forming virus (SFFV) promoter/enhancer named LEGO—SFFV-BCL11A-shRNAmiR (hereafter SFFV-shRNAmiR).

The knockdown efficacy of shRNAs that incorporated the same 21-base target-matching sequences was directly compared, but in the context of the pol III and pol II expression cassettes (i.e. U6-shRNAs vs SFFV-shRNAmiRs.) in MEL cells using a non-targeting (NT) shRNA as negative control. BCL11A protein was detected by immunoblot in cell lysates from MEL-cells transduced at an MOI of 2 (FIG. 19C). Knockdown of BCL11A was consistently less efficient in cells expressing SFFV-shRNAmiR compared to U6-shRNAs (FIG. 19C). To confirm the functional significance of this difference, the inventors measured induction of Hbb-y mRNA levels by qRT-PCR (FIG. 19D) in homogeneous populations of transduced cells obtained either by puromycin selection or by fluorescence-activated cell sorting (FACS). The reduced knockdown efficiency of SFFV-shRNAmiRs as compared to U6-shRNAs (see FIG. 19C) translated into significantly less induction of Hbb-y by SFFV-shRNAmiRs (FIG. 19D) and the differences in Hbb-y induction appear more pronounced than the differences in BCL11A knockdown.

Figure 20A:
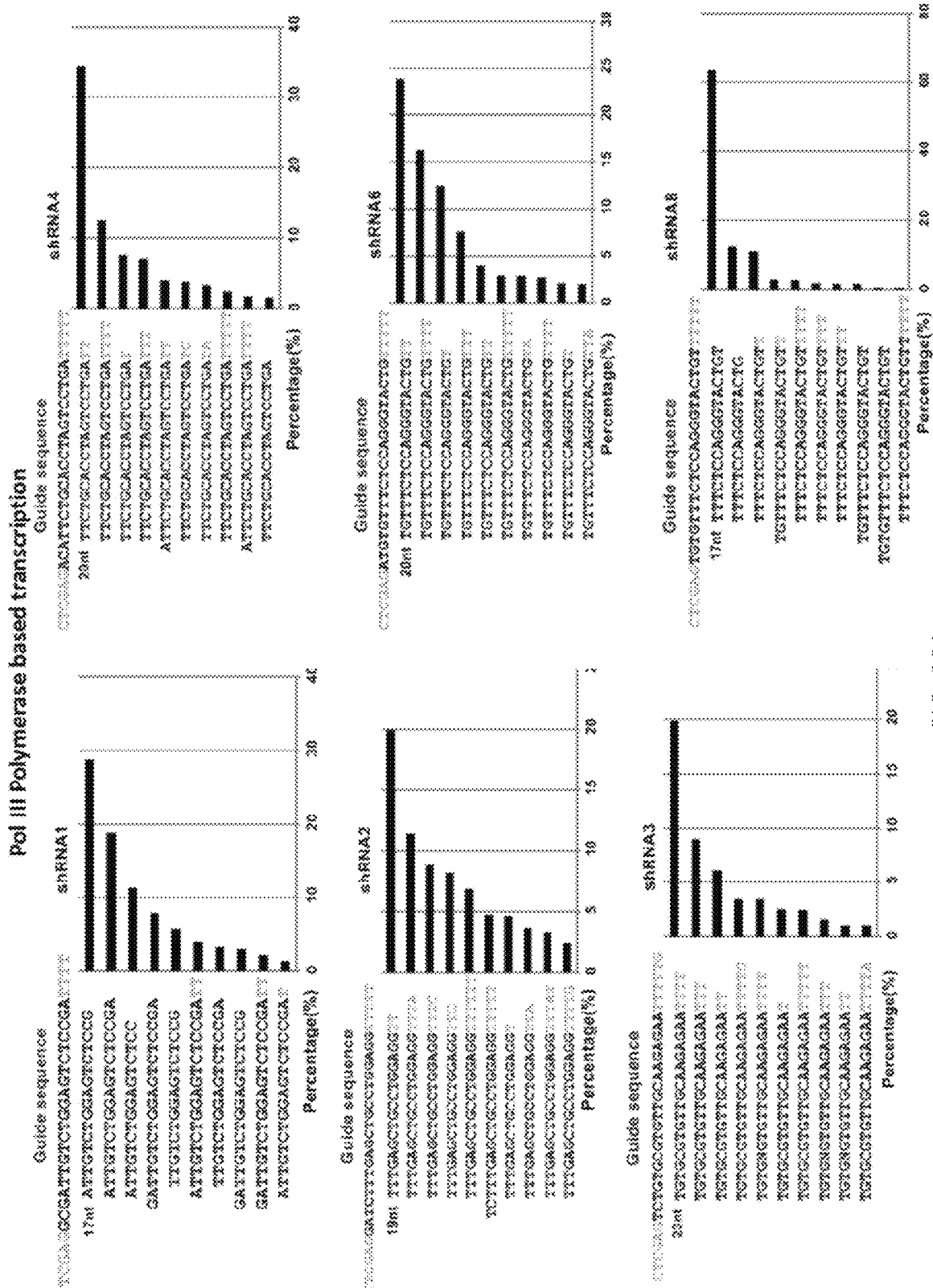
FIGS. 20A and 20B shows the small RNA sequencing analysis reveals differential processing between pol III versus pol II transcripts. Small RNA sequencing results of MEL cells transduced with U6-shRNAs and SFFV-shRNAmiRs1, 2, 3, 4, 7, or 8. The RNA sequences were aligned to the corresponding reference guide strand sequence, shown at the top of each panel in bold and the flanking sequences in grey. Different variants of guide strands produced from (FIG. 20A) U6-shRNAs or (FIG. 20B) SFFV-shRNAmiRs are plotted on the y-axis. The relative % contribution of each variant is indicated on the x-axis calculated based on the total number of reads matching the reference shRNA sequence.
Figure 20B:
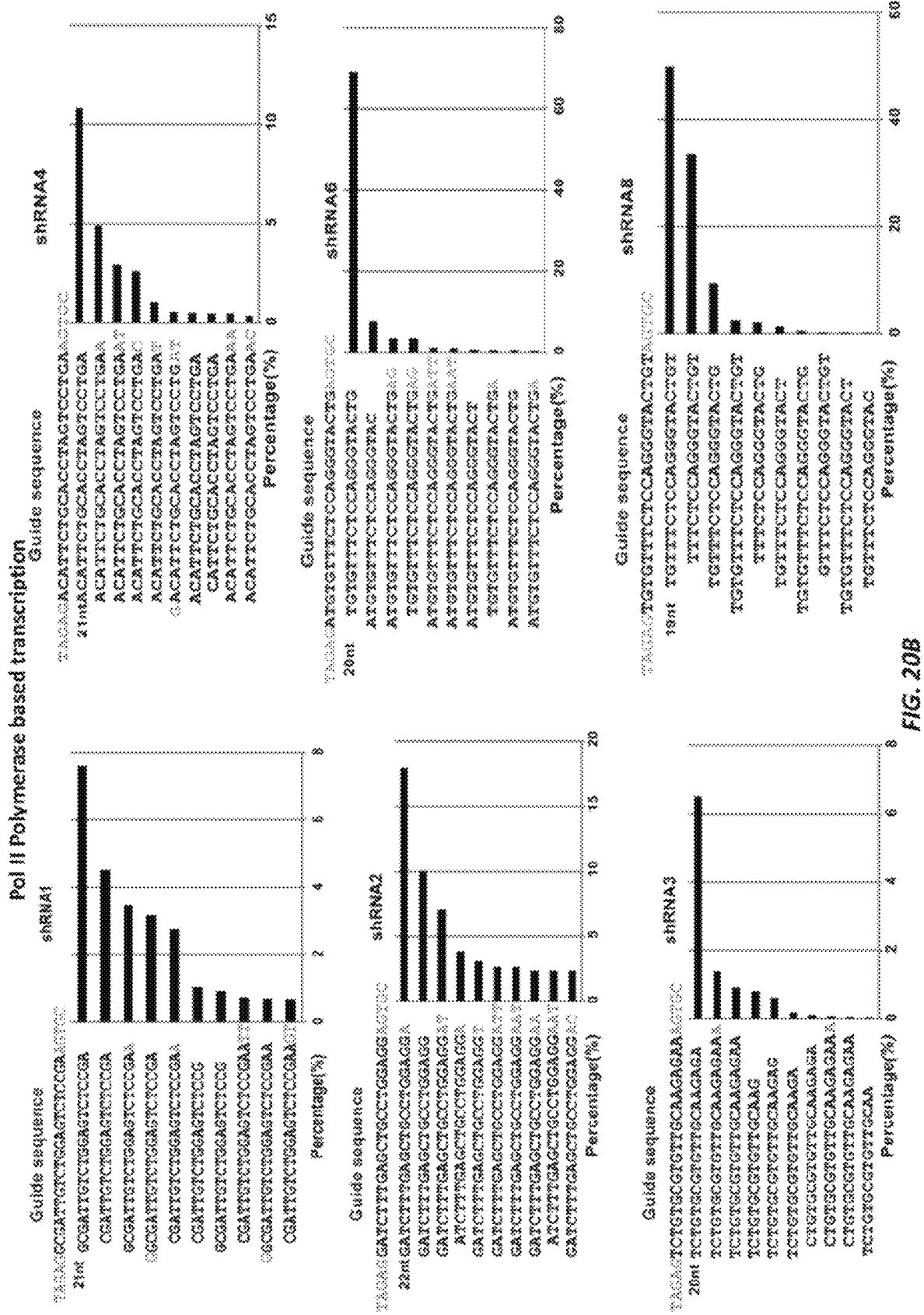
Figure 25:
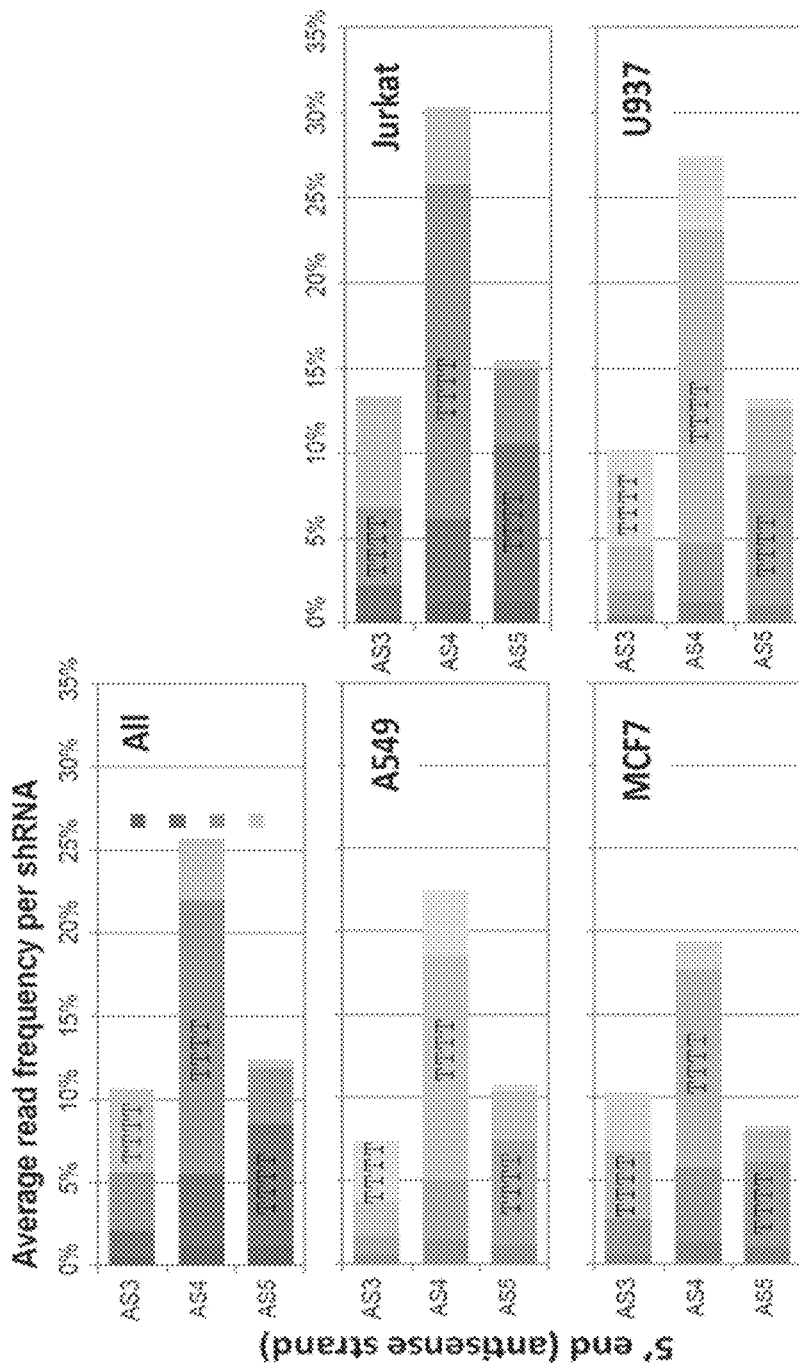
FIG. 25 shows the deep sequencing of 247 processed TRC shRNA products in four cell lines.

SFFV-shRNAmiR and U6-shRNAs Give Rise to Different Mature Guide Strand Sequences To understand the molecular basis for these differences, sequencing of small RNAs from cells transduced with various U6-shRNAs were performed and their corresponding SFFV-shRNAmiR counterparts. It was hypothesized that significant differences in Hbb-y induction were due to the production of different mature guide strands from the distinct shRNA-containing transcripts that are produced from the pol II and pol III contexts. The processed guide strand sequences from both the U6-shRNAs and SFFV-shRNAmiR contexts were therefore assessed (FIGS. 20A and B). The most abundantly found mature guide RNAs produced from SFFV-shRNAmiRs closely corresponded to the in silico predicted mature sequence (FIG. 20B). In contrast, most of the U6-shRNAs yielded mature guide strand sequences that match the predicted Dicer product consisting of ~22 nt of the 3' end of the pol III transcript, including a stretch of 3-5 nt derived from the pol III termination signal, but lacking a corresponding number of nucleotides of the target matched sequence at the 5' end. A similar distribution of processed products were observed in a large scale screen of 247 different U6-shRNAs in A549, MCF7, Jurkat and U937 cell lines, in which the predominant guide strand sequence has an average length of 22 nt with its 5' end starting 4 bases from the constant loop sequence. Deep sequencing of 247 processed TRC shRNA products in these four cell lines were performed (FIG. 25). The results indicate that the predominant mature guide strand starts at position 4 of the antisense sequence of the shRNA and includes four 3'-terminal U residues. Processing was generally consistent among cell lines and among different shRNA sequences. The average read frequency for each mature sequence is weighted equally across shRNAs, although some shRNAs generated >1,000-fold more reads than others. The semiquantitative nature of small RNA sequencing, due to strong RNA ligase biases during library preparation, make comparisons of relative expression or processing levels impossible, but consistent trends across cell lines and shRNAs demonstrate the likely predomonant guide strand identity. Sense strand reads were also detected (<30% per shRNA on average), with the vast majority starting with 'GG' and extending 20 nt into the sense strand sequence. These mature sequences are exactly consistent with a Dicer product of the primary hU6 shRNA transcript, with no need to invoke a Drosha/DCGR8 processing step. Taken together with, these findings indicate the importance of considering the processing events that generate mature sequences from pol II shRNAmiR and pol III shRNA transcripts when transferring shRNA sequences between vectors. The very similar distributions of mature sequences observed for the four cell types that were studied suggests that these processing patterns will generalize across different cellular contexts. The differences in the mature guide strand sequence generated in pol III vs pol II based vectors contribute substantially to differential BCL11A down regulation observed with U6-shRNAs compared to SFFV-shRNAmiRs. These data suggest predicted conversions between pol III and pol II vectors may be possible by considering the Drosha and Dicer cleavage of pol II shRNAs compared to the Dicer cleavage of pol III shRNAs.

Figures 21A, 21B:
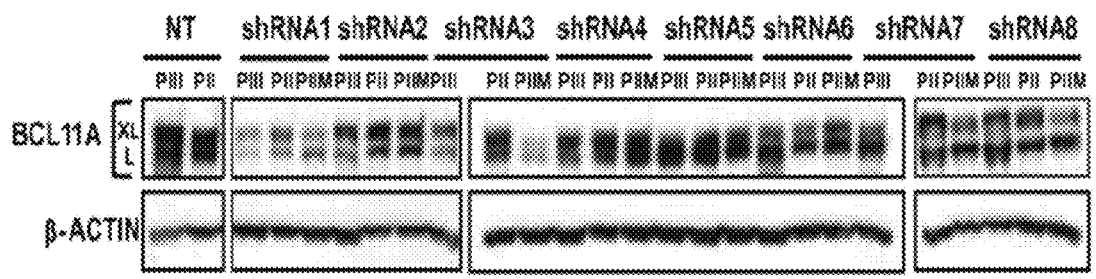
FIGS. 21A-21E show the modification of shRNA sequences leads to increased knockdown and improved guide vs. passenger strand ratio in MEL cells.
Figure 21C:
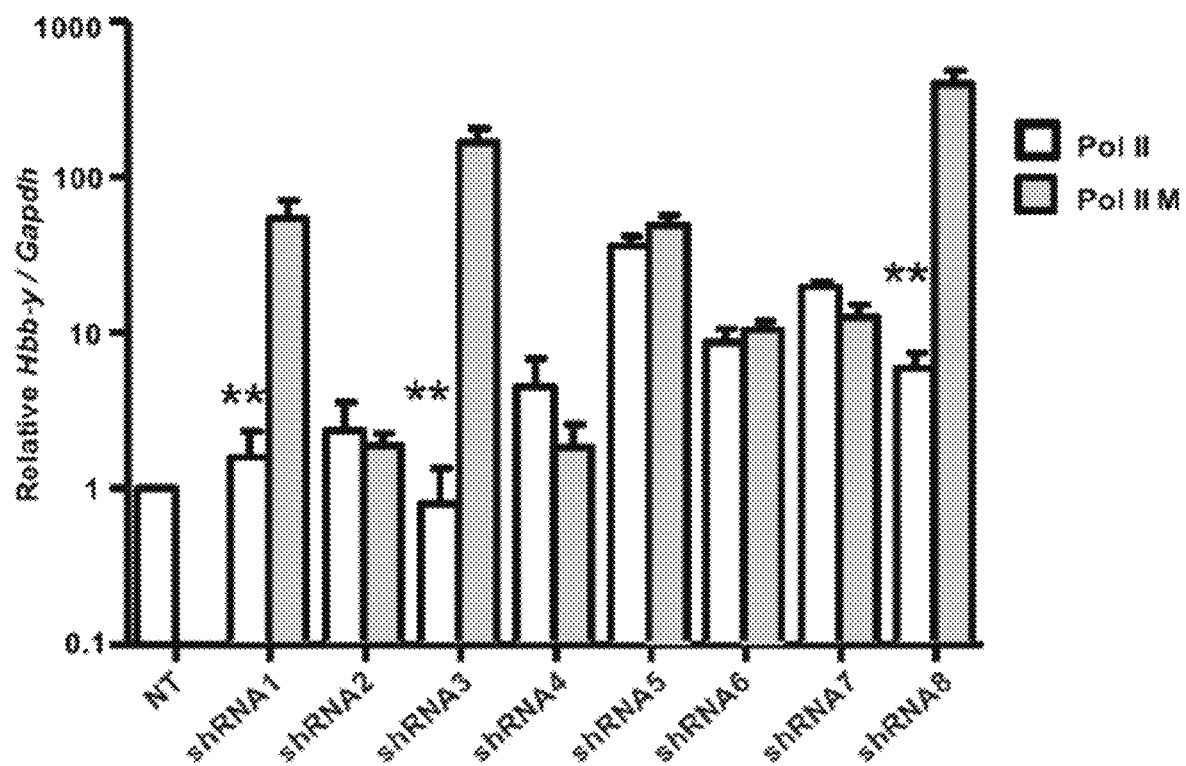
Figure 21D:
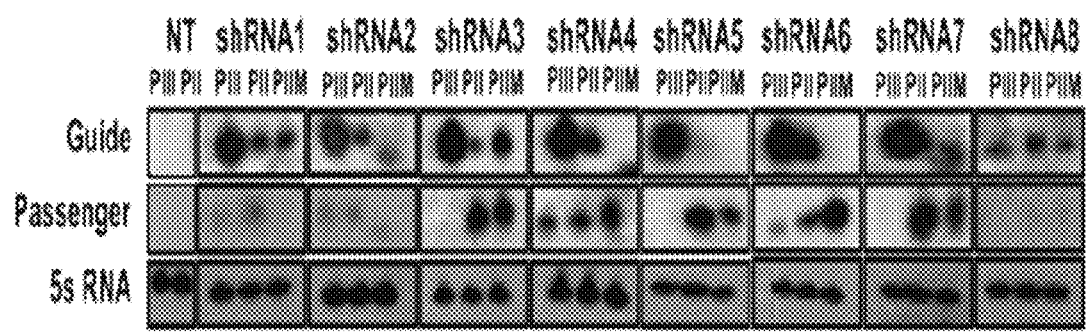
Figure 21E:
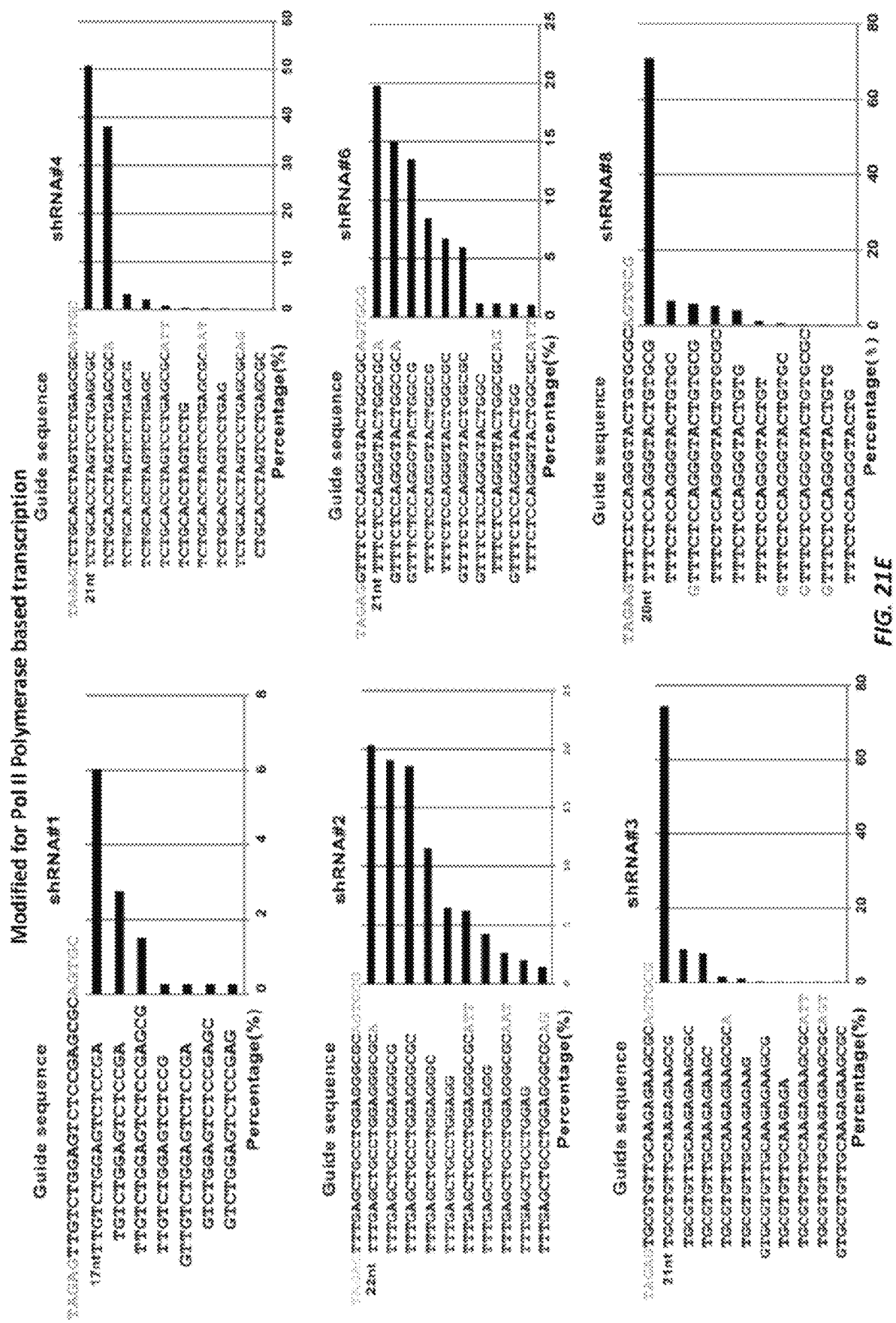

Modification of shRNA Sequences in a Pol II Based Vector Leads to Improved Knockdown Efficiency Based on these findings, the inventors hypothesized that using the predicted mature sequence from pol III shRNA vectors when transferring sequences into SFFV-shRNAmiR would lead to enhanced knockdown efficiency. Therefore, a set of SFFV-shRNAmiRs containing a 4-nucleotide shift in the 5' end of the guide strand sequence were designed (FIG. 21A). At the 3'-end the nucleotides GCGC were added to achieve higher 3'-end thermodynamic stability in the siRNA duplex which should promote preferential RISC-loading of the intended guide strand. The effect of modifications on knockdown efficiency and Hbb-y induction was evaluated in MEL cells by immunoblot and qRT-PCR, respectively. Improved knockdown efficiency of BCL11A protein was observed with SFFV-shRNAmiR1, 3 and 8 (FIG. 21B). The enhanced knockdown correlated with a 200 to 400 fold increased induction of Hbb-y transcripts (FIG. 21C). The other SFFV-shRNAmiRs did not show an appreciable increase in knockdown efficiency. To understand more fully the mechanism underlying the improved efficiency of modified SFFV-shRNAmiRs 1, 3 and 8 were analyzed the abundance of guide and passenger strand small RNAs and their ratios by Northern blot. First, a higher abundance of guide strand was seen for pol III versus pol II vectors in all cases. Furthermore, particularly for modified SFFV-shRNAmiRs 1 and 3 a higher abundance and higher guide to passenger strand ratios were found versus the unmodified shRNAmiRs, while these parameters were not affected for SFFV-shRNA8 (FIG. 21D). Deep sequencing of small RNAs was performed to evaluate the impact of the modification on guide strand sequences and to correlate it with the changes observed in BCL11A knockdown. Generally, the resulting processed sequences reflected the introduced 4 nt shift, resulting in a guide strand with seed regions similar to the sequences obtained from pol III shRNAs expressed in the LKO backbone. For SFFV-shRNAmiRs 1, 3 and 8, a single dominant sequence was found, which contrasts the less effective SFFV-shRNAmiRs which showed a broader distribution of sequences.

Figure 22:
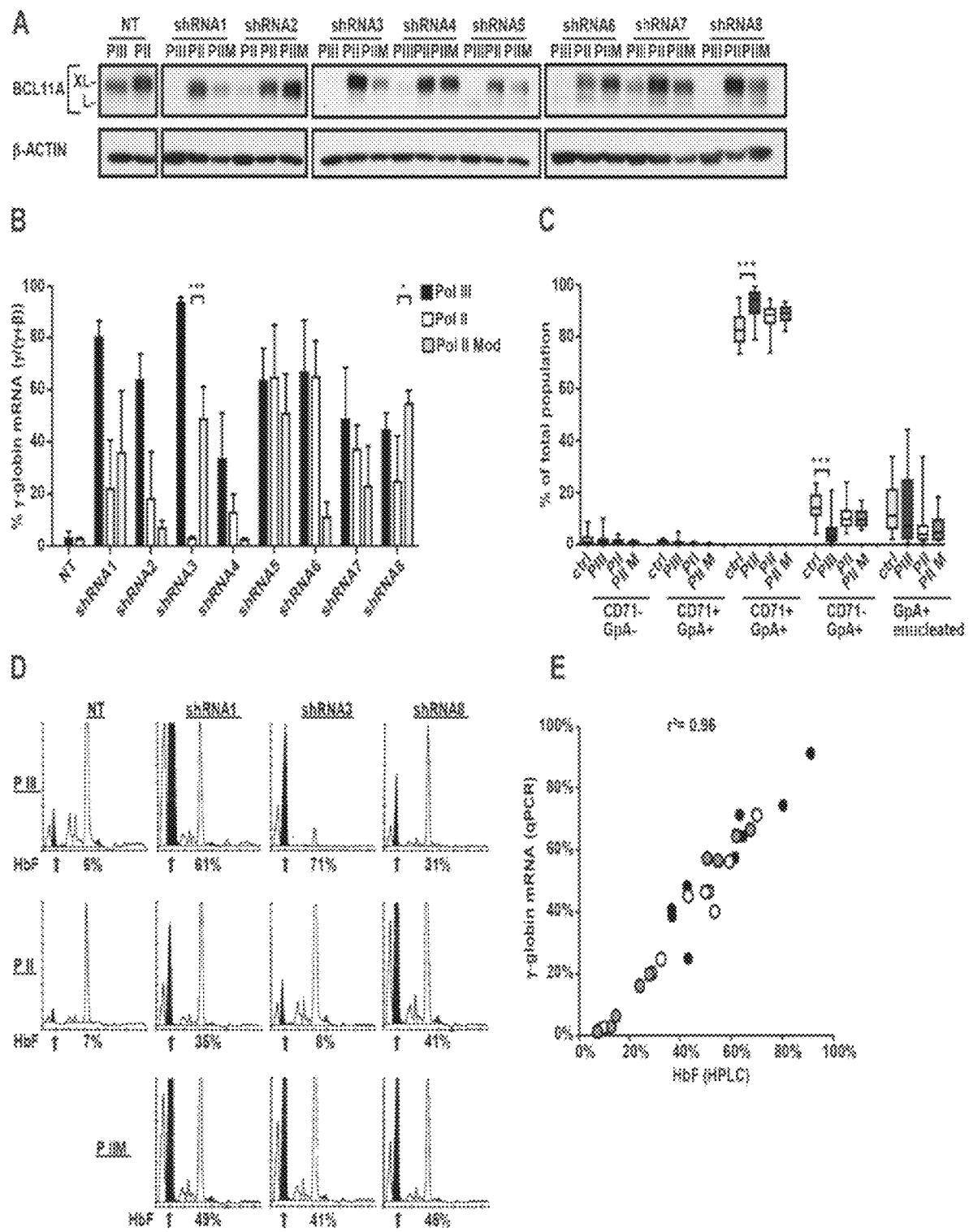
FIGS. 22A-22E show the modified shRNAmiRs lead to increased BCL11A knockdown efficiency and gamma globin induction in human CD34+ derived erythroid cells.

Effect of shRNAmiR Modification on BCL11A Knockdown and γ-Globin Induction in Primary Human CD34+ Derived Erythroid Cells Reactivation of fetal globin with BCL11A knockdown has therapeutic potential for the treatment of sickle cell disease and β-thalassemia. To evaluate the effect of modified SFFV-shRNAmiR on knockdown efficiency of BCL11A and induction of γ-globin and HbF expression in primary human cells, G-CSF mobilized peripheral blood (mPB) CD34+ HSPCs from healthy volunteers were transduced with vectors expressing U6-shRNAs, SFFV-shRNAmiR and modified SFFV-shRNAmiR and then subjected to erythroid differentiation. After eleven days in culture, BCL11A levels were determined via western blot (FIG. 22A). Consistent with findings in MEL cells, enhanced knockdown was observed with modified SFFV-shRNAmiRs 1, 3, and 8, which also led to increased induction of γ-globin transcripts (FIG. 22B). The status of erythroid differentiation was assessed at day 18 of culture by flow cytometric analysis for surface expression of CD71 and GpA and enucleation. No significant differences were observed between SFFV-shRNAmiRs and control vector transduced samples (FIG. 22C). In contrast, U6-shRNAs led to mild delay in the acquisition of differentiation markers during the later phases of maturation, which could indicate toxicity due to U6-promoter mediated shRNA overexpression. The observations of high γ-globin mRNA induction were confirmed by increased HbF protein measured by high performance liquid chromatography (HPLC). All three tested modified shRNAmiRs yielded increased HbF output compared to unmodified SFFV-shRNAmiRs (FIG. 22D), where between 40-50% of total hemoglobin in the erythroid cells was HbF. The correlation between γ-globin mRNA and HbF protein was high (r2=0.96), supporting the reliability of the analyses (FIG. 22E).

In summary, the inventors have demonstrated that shRNAs embedded into a miRNA scaffold and expressed via pol II promoters are processed to yield differing mature siRNAs in transduced cells compared with siRNA expressed from the U6 promoter. The target-matched sequence in the mature shRNA derived from the pol III promoter construct is uniformly shifted 3' by 3-5 nt and this difference was associated with significant differences in knockdown efficiency of the target transcript. In the case of BCL11A, a potential therapeutic target, this led to appreciable differences in the reactivation of γ-globin expression. These data demonstrate the importance of design optimization when transferring shRNA sequences into a microRNA scaffold to allow for pol II mediated expression.

Figure 23A:
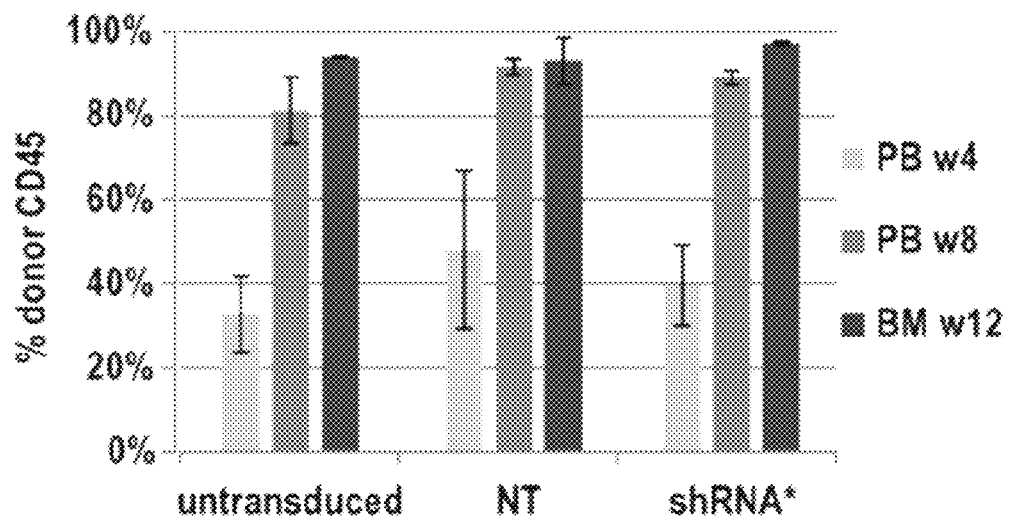
FIGS. 23A-23I show the negative impact of BCL11A knockdown on HSCs in vivo is prevented by restricting expression to erythroid cells.
Figure 23B:
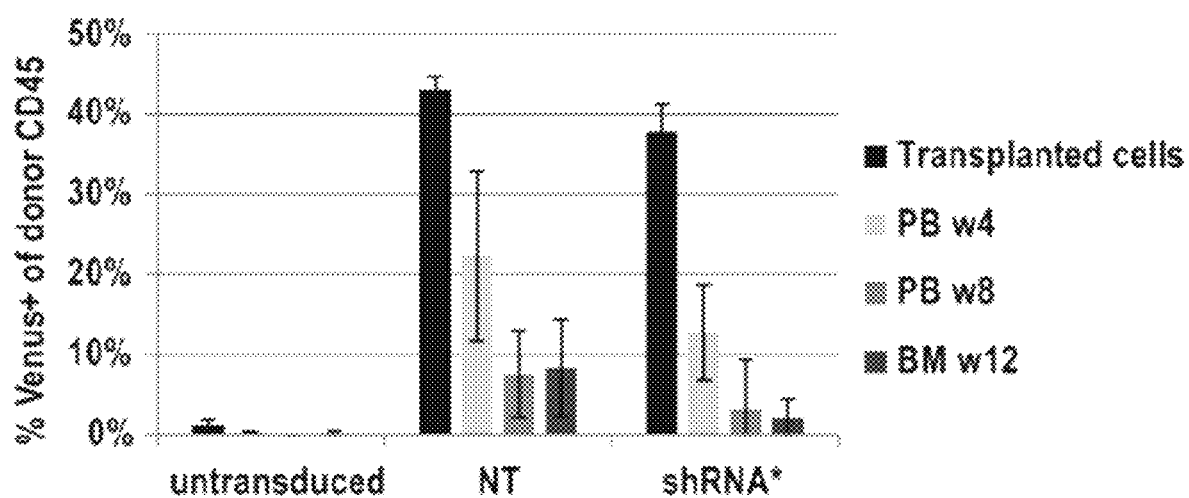
Figure 23C:
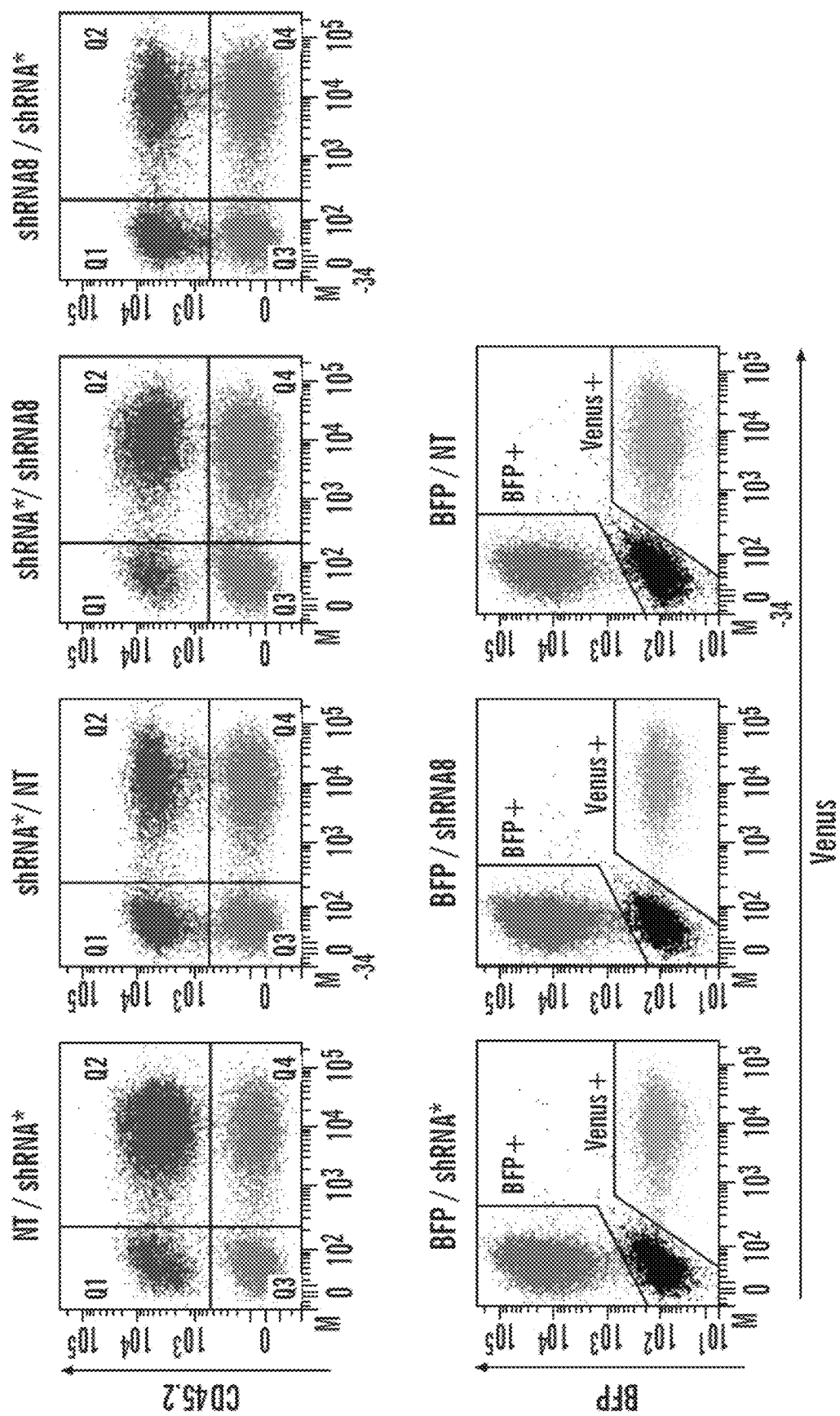
Figure 23D:
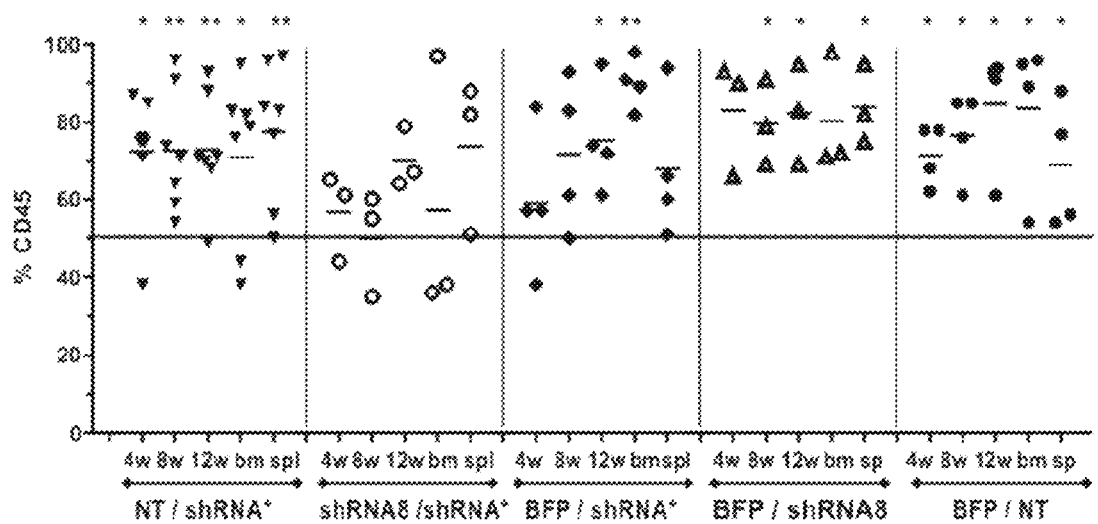

Ubiquitous Knockdown of BCL11A in Hematopoietic Stem and Progenitor Cells (HSPCs) Impairs Hematopoietic Reconstitution and can be Circumvented by Targeting shRNAmiR Expression to Erythroid Cells The impact of SFFV-shRNAmiR expression in vivo was assessed in a mouse model of HSPC transduction and transplantation. Lineage-negative (lin−) HSPCs from the bone marrow of β-YAC mice expressing the CD45.2 cell surface maker were transduced ex vivo with SFFV-shRNAmiR vectors or a non-targeting vector (SFFV-shRNAmiRNT) and transplanted into lethally irradiated CD45.1 BoyJ-recipient mice. Untransduced cells were transplanted in a control group. β-YAC mice harbor the human β-globin locus as a transgene that is developmentally regulated in the mouse environment, showing differential expression of fetal and adult β-globin genes. For validation purposes and for better comparison with previously published data a well described shRNA (23, 27, 29) (here termed shRNAmiR*) embedded into miRNA223 flanking sequences was employed. At 4, 8 and 12 weeks after transplantation, donor cell engraftment was determined based on CD45.1 and CD45.2 chimerism (FIG. 23A). Donor cell engraftment followed the expected pattern with near complete engraftment in peripheral blood (PB) and bone marrow (BM) after 8 weeks. However, unexpectedly, the fraction of gene modified cells steeply declined over time (FIG. 23B). Despite initial transduction rates of ~40% using the BCL11A knockdown vector, gene marking at week 12 was only 2-3% of total donor derived CD45 cells. Overexpression of the SFFV-shRNAmiR NT was also associated with reduced engraftment of gene modified cells but to a lesser extent, indicating both sequence-specific and non-specific toxicity in the engrafting HSPC cells. The timing of the loss of donor cells expressing shRNAs suggests an effect on the more primitive hematopoietic stem cell compartment.

Figure 23E:
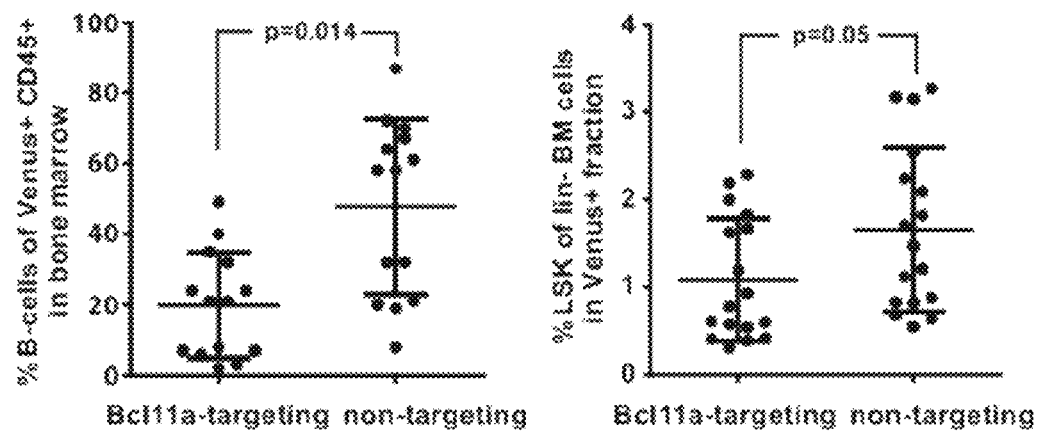

To further investigate the negative impact on hematopoietic reconstitution, quantitative competitive repopulation experiments were performed (FIG. 23C-23F). Lineage negative cells from CD45.1 (BoyJ) and CD45.2 (B1\6) donor animals were transduced with various vectors expressing SFFV-shRNAmiRs against BCL11A, a shRNA$^{miR}$NT or only a blue fluorescent protein (BFP) reporter under control of the ubiquitously expressed SFFV-promoter (SFFV-BFP). Cells were transplanted into congenic CD45.1/CD45.2 animals, allowing for identification of both donor populations and the recipient cells. In experiments in which the SFFV-BFP vector was employed, CD45.1 donor cells were transplanted into CD45.2 animals and the transduced donor cell populations were identified and compared based on fluorescence. Prior to transplantation, equal numbers of cells of the two populations transduced with competing vectors were mixed. The final ratio of gene modified cells obtained with both vectors in the transplanted population was analyzed via flow cytometry which confirmed comparable transduction rates ranging from 55-70% (FIG. 22C). The contribution of gene modified cells was assessed in transplanted animals in peripheral blood, bone marrow and spleen 4, 8 and 12 weeks after transplantation (FIG. 23D) and minor differences in the ratio of the infused transduced cells were taken into account for this analysis. In all instances and at each time point, cells transduced with vectors targeting BCL11A were outcompeted by cells transduced with the NT or SFFV-BFP vector, indicating a selective disadvantage upon BCL11A knockdown. No significant differences in reconstitution of hematopoietic cells compared to the ratio of the initially transplanted population was observed when two BCL11A targeting vectors competed against each other. Consistent with the findings in FIG. 23B, the overexpression of shRNAmiRNT also had a negative impact on hematopoietic reconstitution, as this group was outcompeted by cells transduced by a vector expressing only SFFV-BFP and not expressing a shRNA. The inventors performed a more detailed analysis of the B lymphocyte and more primitive HSC compartment within the transduced fraction of bone marrow cells (FIG. 23E). As anticipated from previous studies showing an absence of B cells in BCL11A−/− mice (30, 31) the number of B220 positive B-cells was significantly reduced upon BCL11A knockdown. Although not reaching significance, there was a trend toward loss of more primitive lin−, Sca-1+, c-kit+(LSK) cells that include the engrafting HSC compartment.

Figure 23F:
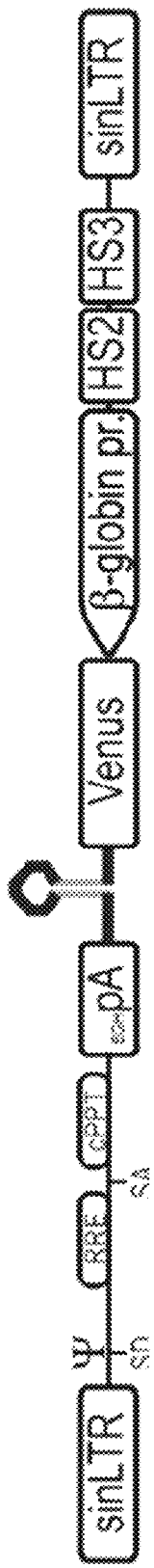
Figure 26:
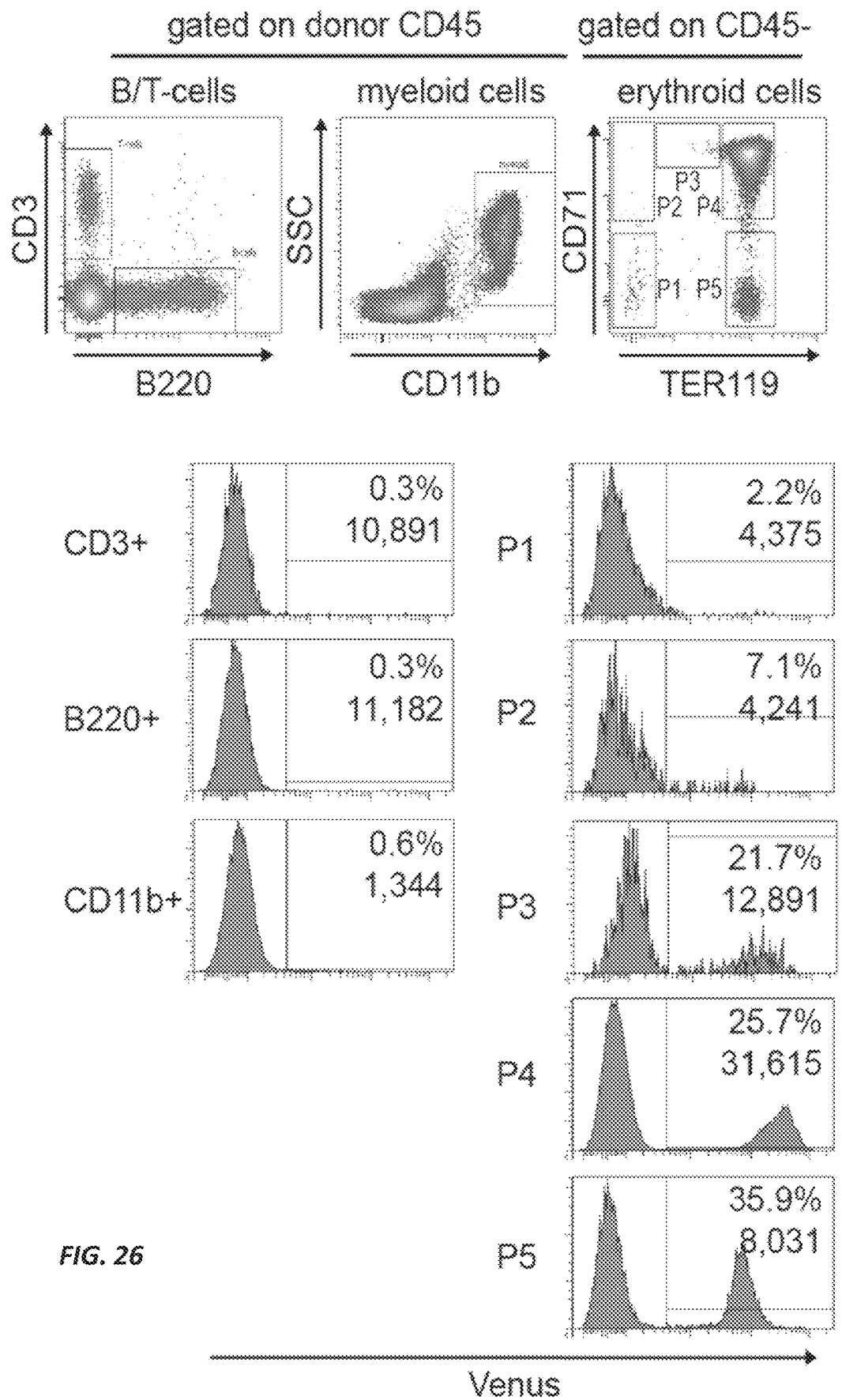
FIG. 26 shows the in vivo expression profile of the LCR-shRNA$^{miR}$ vector.

Erythroid specific knockdown of BCL11A could potentially circumvent the adverse effect of BCL11A knockdown on HSCs and B cells, while maintaining the therapeutic effect of γ-globin induction in erythroid cells. To direct knockdown selectively to erythroid cells, a lentivirus vector was generated in which the shRNAmiR cassette and the Venus fluorescent reporter is expressed under the control of the minimal β-globin proximal promoter linked to hypersensitive sites 2 and 3 (HS2 and HS3) of the β-globin locus control region (LCR) (32) (FIG. 23F) named LV-LCR-BCL11A-shRNAmiR (hereafter LCR-shRNAmiR). The expression profile of the Venus reporter transgene in the engrafted hematopoietic cell populations in vivo was first assessed in mice transplanted with transduced HSPC (FIG. 23G and FIG. 26). In FIG. 26, lineage negative cells were transduced using the LCR-shRNAmiR vector and engrafted into lethally irradiated recipient mice. Twelve weeks later donor cells and different hematopoietic cell types were identified using surface markers. Shown here is a representative gating scheme and histogram blots showing Venus expression in various lineages. Numbers in blots indicate the percentage of venus positive cells and mean fluorescence intensities (MFI). Expression of the transgene was tightly regulated; with no detectable expression in LSK and B cell fractions, very low levels of expression in T-cells and low levels of expression in myeloid cells in some animals. In contrast, transgene expression was strongly upregulated during erythroid differentiation, beginning in CD71+/Ter119− cells representing erythroid progenitors and proerythroblasts and peaking in the CD71+/Ter119+ double positive stage, representing basophilic erythroblasts. During final stages of erythroid maturation, a large fraction of CD71−/Ter119+ cells representing reticulocytes and mature erythrocytes expressed the reporter at a similar percentage compared to CD71+/Ter119+ cells.

Figure 23H:
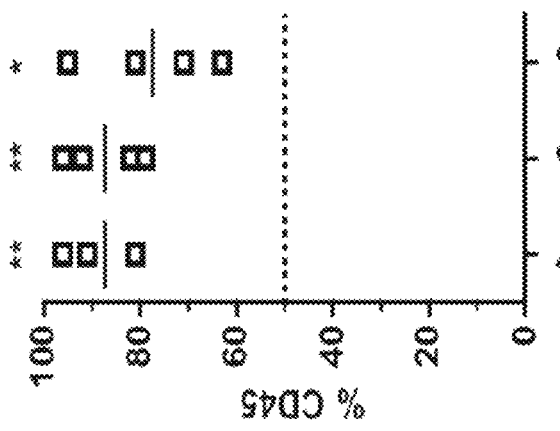
Figure 23G:
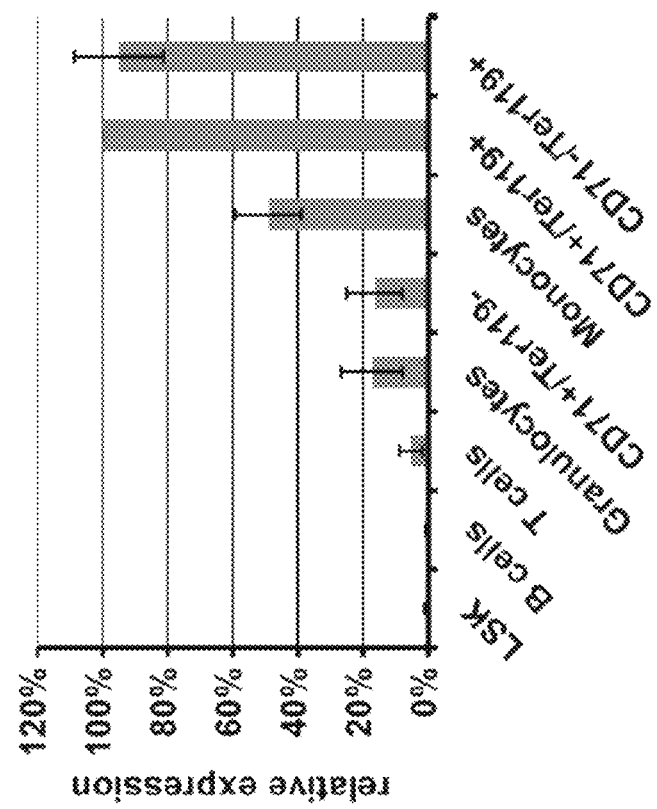

Next, to determine whether use of the LCR-vector circumvents the reconstitution defect observed upon ubiquitous SFFV- shRNAmiR overexpression, a competitive transplantation experiment was performed using LCR-shRNAmiR and SFFV-shRNAmiR (FIG. 23H). As the LCR-vector is transcriptionally silent in lin− cells, an aliquot of cells to be used for transplantation was subjected to in vitro erythroid differentiation and the ratio of Venus+ cells measured in the transcriptional permissive CD71+/Ter119+ population and used for normalization of the ratio of SFFV vs. LCR-transduced cells. Venus expression in transplanted animals was compared in erythroid cells, as this is the only population that is equally permissive for expression from both vectors. Reconstitution of transplanted mice demonstrated a clear dominance of cells derived from HSPc transduced with the LCR-vector, suggesting less toxicity in the HSPCs associated with erythroid lineage specific expression of the LCR-shRNAmiR (FIG. 23H). In summary, these data demonstrate that the adverse effect of BCL11A knockdown on HSC engraftment/function may be circumvented by erythroid specific miRNA expression.

Figure 23I:
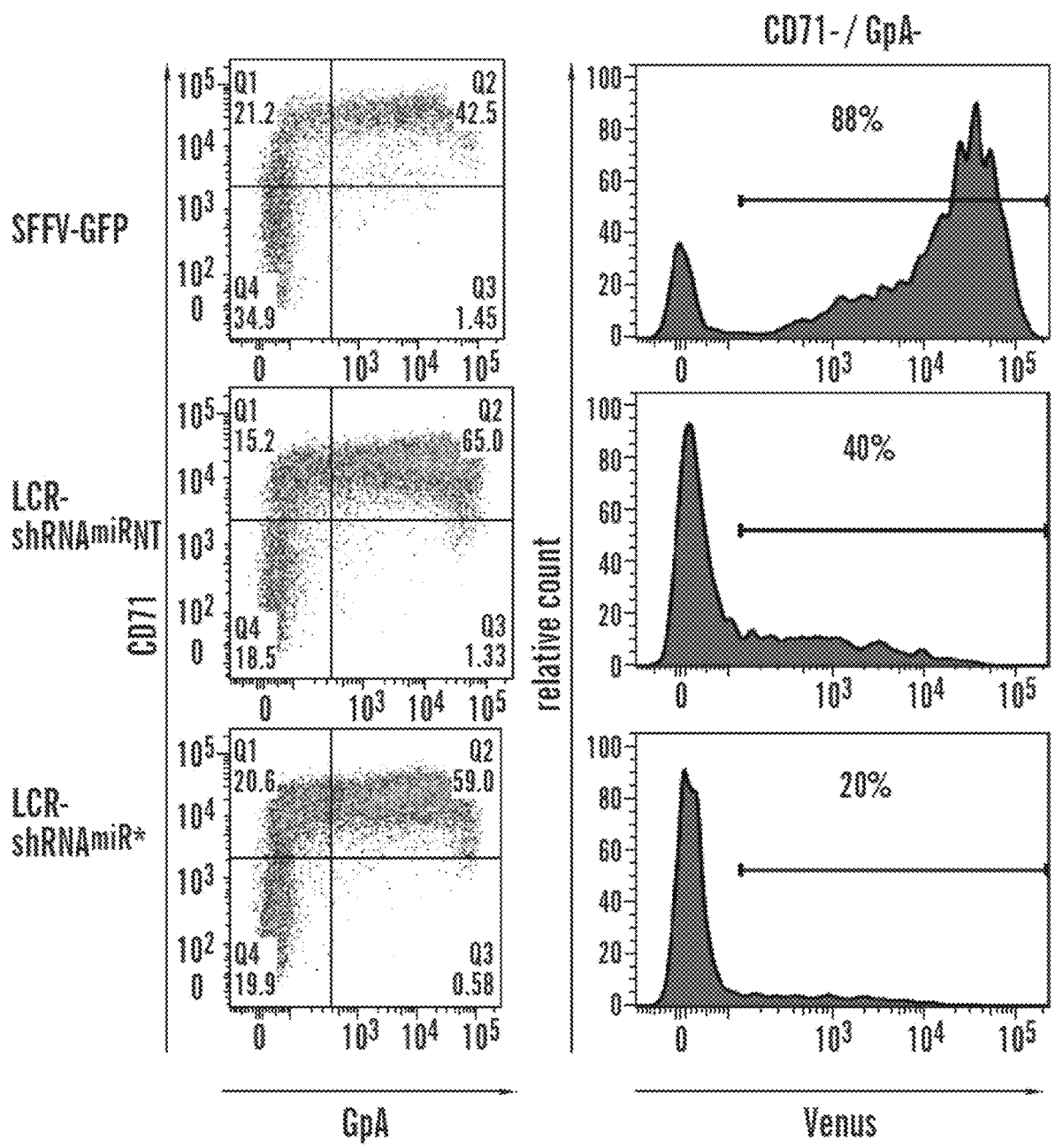
Figure 23I:
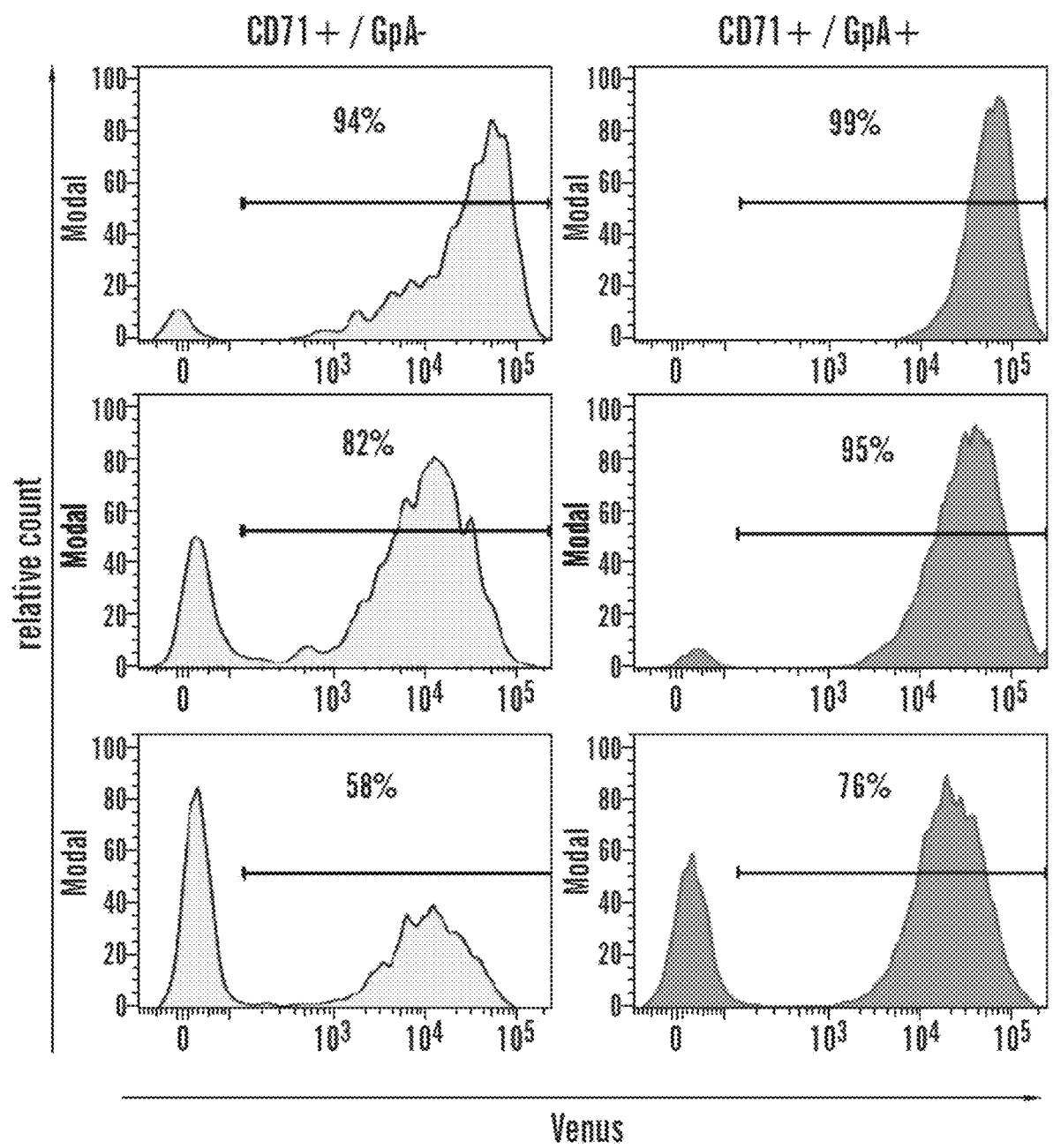
Figure 23I:
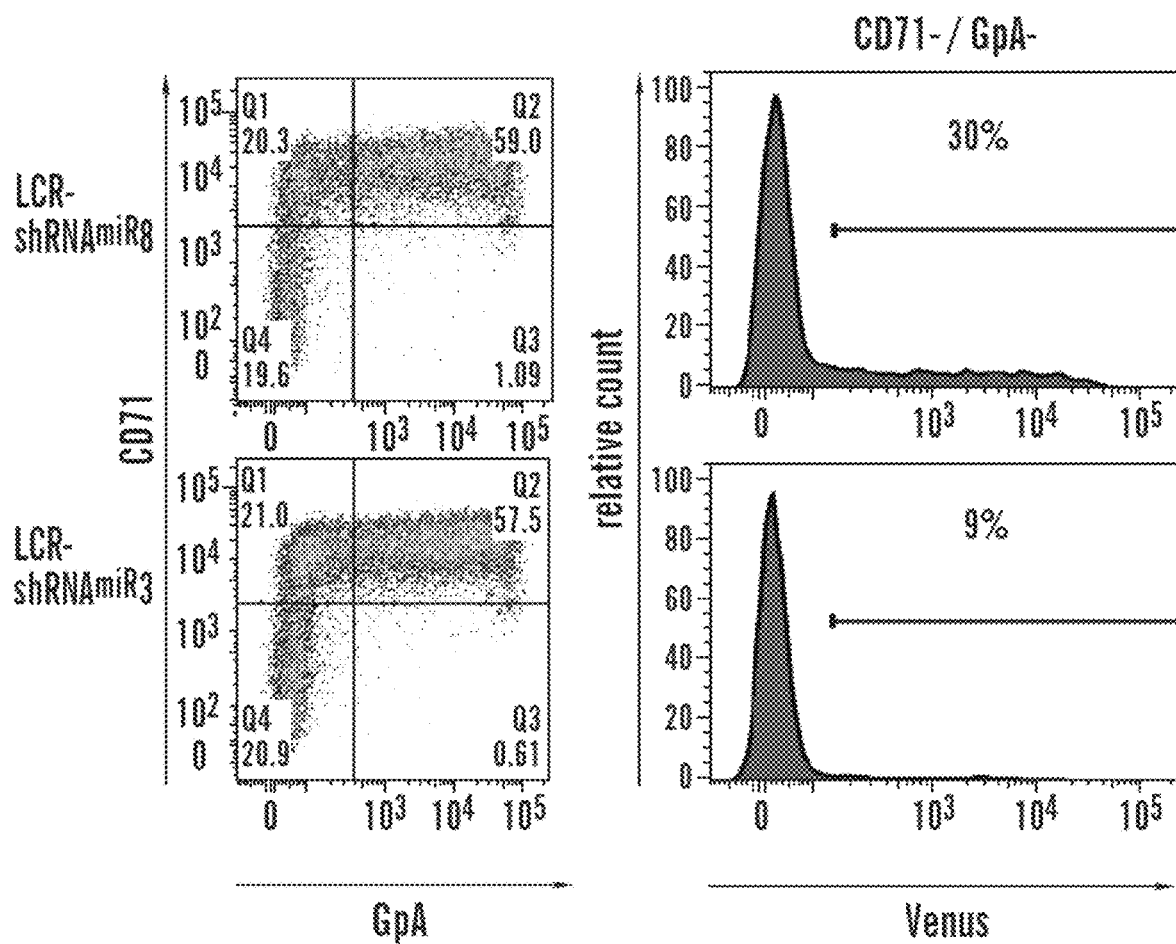
Figure 23I:
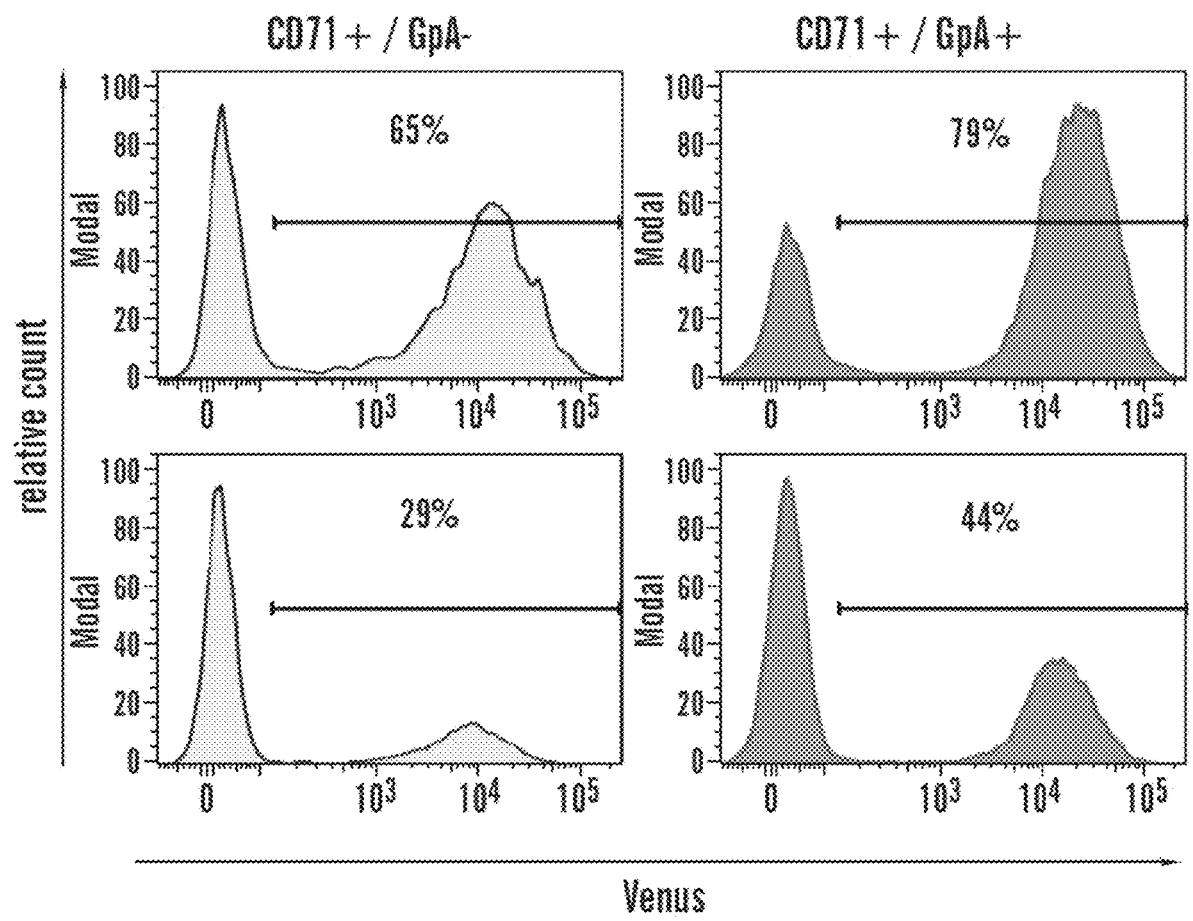
Figure 24:
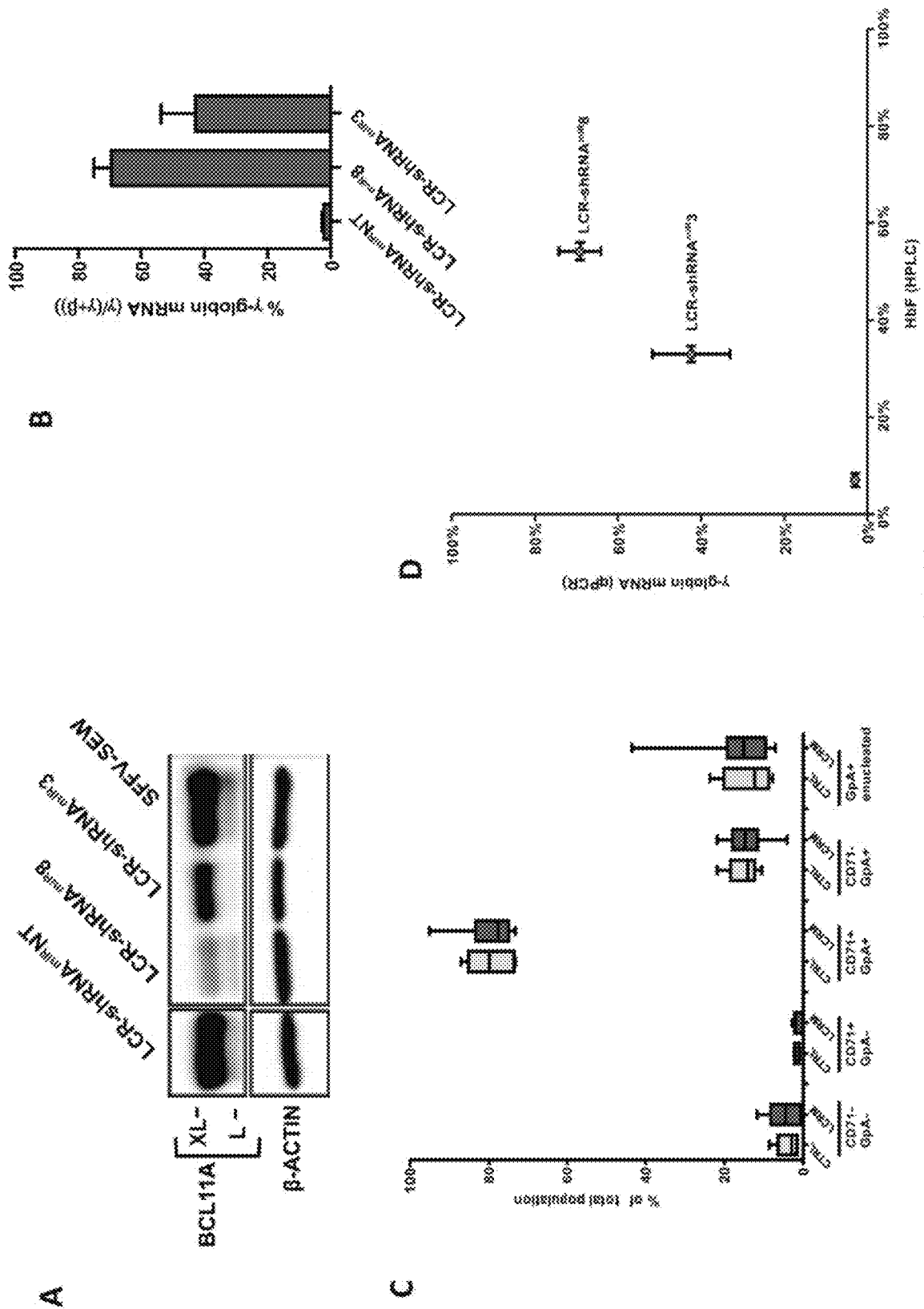
FIGS. 24A-24F show the lineage specific BCL11A knockdown and gamma globin induction by modified shRNAmiRs.
Figure 24:
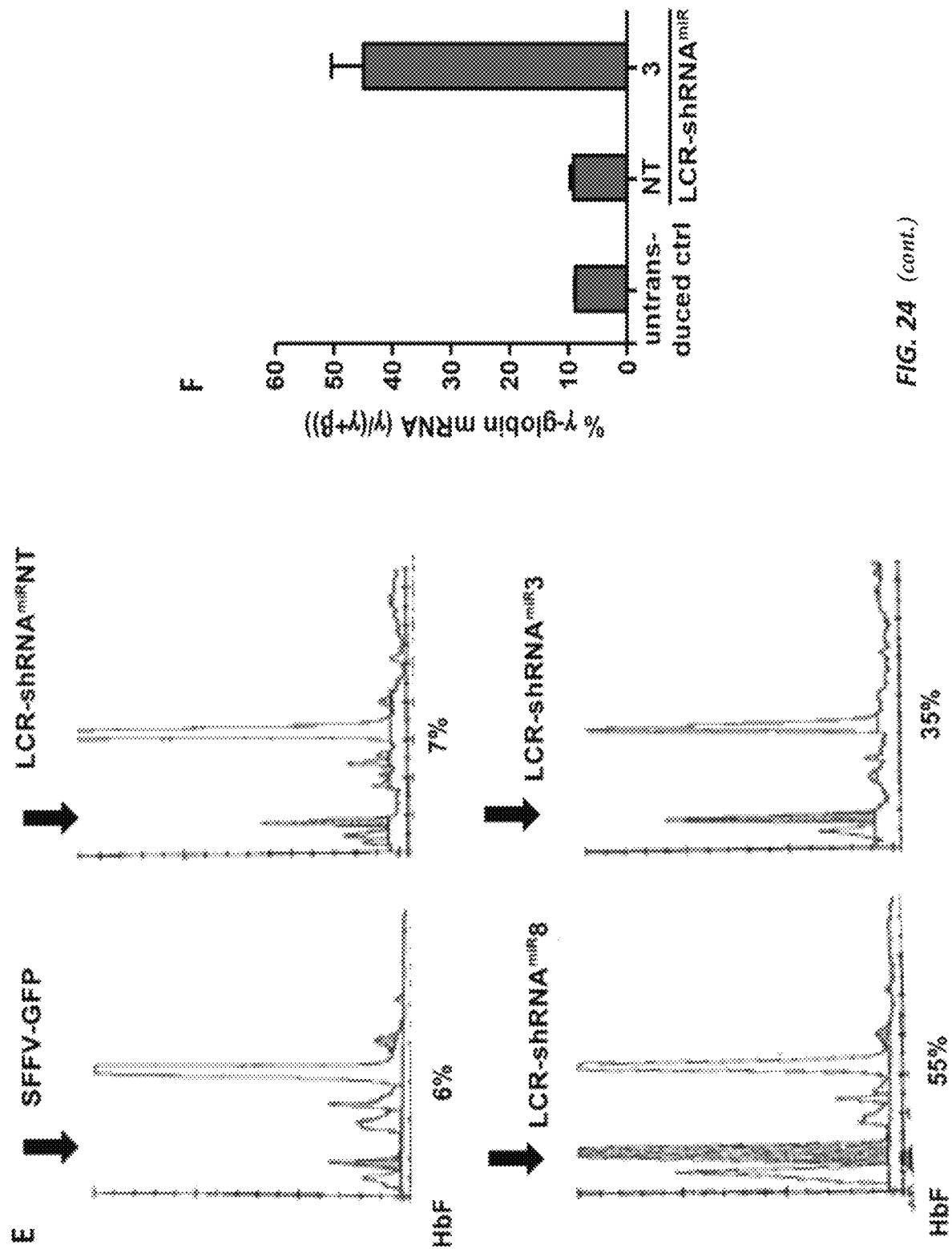

LCR-vector Mediated Erythroid Specific Knockdown of BCL11A Using Modified shRNAmiRs Yields High Levels of HbF in Human Erythroid Cells To test the efficacy of LCR-mediated erythroid specific knockdown of BCL11A in a human experimental system, CD34+ cells were transduced with LCR-shRNAmiR vectors containing modified shRNAmiRs 3 or 8 (FIG. 23F). The inventors first confirmed the expression profile of several LCR-shRNAmiR vectors (LCR-shRNA*, LCR-shRNAmiR3 and 8) in human cells during in vitro erythroid differentiation of human mPB CD34+ cells. Venus expression by the LCR-vectors and a SFFV-driven control vector without shRNAmiR-cassette (SFFV-GFP) (33) was evaluated at different stages of erythroid maturation, as defined by CD71 and GpA staining (FIG. 23I). Consistent with the findings in mouse cells shown in FIG. 23G, low levels of expression were observed in CD71−/GpA− immature erythroid cells. There was a strong upregulation of expression in CD71+ single positive cells with the highest level of transgene expression in the more mature CD71+/GpA+ double positive cells. As expected, the SFFV-GFP control drove high level constitutive expression in all subpopulations. Following the previously described differentiation protocol, BCL11A protein levels were measured on day 11 of culture and compared with non-targeting and mock control vectors (LCR-shRNAmiRNT and SFFV-GFP). Significant reduction in BCL11A was observed in the cells expressing the modified shRNAmiR compared to the cells expressing the non-targeting (NT) and control vector (SEW) (FIG. 24A). Gamma globin mRNA constituted 40 and 70% of total β-like globins in cells derived from CD34+ cells transduced with vectors expressing shRNAmiR3 and 8, respectively (FIG. 24B). No differences in cell growth were observed between cells transduced with LCR-shRNAmiRs or control vectors. Erythroid differentiation, as evaluated by surface expression of CD71, GpA and by enucleation was indistinguishable from controls (FIG. 24C), suggesting no negative impact of BCL11A knockdown upon lineage-specific expression of the BCL11A shRNAmiRs. Strong correlation was observed between the levels of γ-globin mRNA (qRT-PCR) and HbF as assessed by HPLC (FIG. 24D). HbF contributed to 35% and 55% of total hemoglobin in cells transduced with LCR-shRNAmiR3 and LCR-shRNAmiR8, representing levels comparable to SFFV-promoter mediated expression (FIG. 22D and FIG. 24E). Finally, to show in proof of principle that LCR-shRNAmiR mediated knockdown allows for efficient engraftment of hCD34+ cells and induction of γ-globin, transplantation of bone marrow derived CD34+ HSPCs transduced with LCR-shRNAmiR3 or NT vectors were performed into sub-lethally irradiated NSG-mice. Due to poor development of human erythroid cells in this xenograft model, CD34+ HSPCs were isolated from the bone marrow of transplanted animals 14 weeks after transplantation and subjected to erythroid differentiation in vitro. Venus+ cells were enriched by FACS and expression of γ- and β-globin was determined by RT-PCR (FIG. 24F). Consistent with previous data, the fraction of γ-globin of total β-globin locus output was 44.9%±5.5% for cells transduced with LCR-shRNAmiR3, compared to ~9%±0.5% in the two control groups consisting of untransduced or LCR-shRNAmiRNT transduced cells.

ShRNAs have been used extensively to analyze gene functions in biological studies, and there is increasing interest in the use of RNAi for therapeutic purposes. BCL11A represents an attractive therapeutic target for RNAi based modulation. BCL11A is a repressor of γ-globin expression and thus acts as a major regulator of the fetal to adult hemoglobin switch in erythroid cells. Importantly high levels of fetal hemoglobin are associated with milder disease phenotypes in sickle cell disease (SCD) and β-thalassemias and lineage-specific knockout of BCL11A has been validated as a therapeutic strategy in models of SCD. In the studies reported here, our goal was to develop a clinically applicable vector to reactivate fetal hemoglobin expression by RNAi mediated suppression of BCL11A. Using an optimized lentiviral vector containing a miRNA adapted shRNA (shRNAmiR) expressed from an erythroid lineage specific pol II promoter the inventors achieved HbF levels of >50% of total hemoglobin in primary erythroid cells derived from transduced CD34+ HSPCs. This level of HbF induction is likely to be clinically effective and compares favorably with previously published vectors (23, 27, 29) utilizing pol III driven expression cassettes that lack lineage specificity and the safety profile of SIN lentivirus vectors reported here.

Curative treatment for SCD can be attained with hematopoietic stem cell transplantation (HSCT). Favorable outcomes in SCD are largely dependent on the availability of matched sibling donors. Fewer than 10% of SCD patients have unaffected HLA-matched sibling potential donors (34). Gene therapy for hemoglobinopathies offers the clear advantage of eliminating the risk of GVHD by the use of autologous cells. The long-term aim of our studies is to modulate the hemoglobin switch, leading to the endogenous and physiologic induction of the protective HbF and suppression of the sickle globin. The inventors hypothesize this dual manipulation of expression will be the most effective therapeutic approach to prevent toxicities in SCD including hemolysis and end organ damage of the mutant, polymerizing hemoglobin. To realize the goal of therapeutic benefit, sufficient knockdown of BCL and induction of HbF on a per cell basis must occur and sufficient numbers of gene modified long-lived HSC must engraft in order for chimerism of the red cell compartment to attenuate the disease phenotype. Thus optimization of BCL11A knockdown and preservation of reconstitution capacity of transduced HSCP as shown here is critical to the long-term success of genetic therapy in SCD. As relates to the second point, the inventors believe this is currently attainable, as previous data from allogeneic transplants resulting in mixed chimerism have demonstrated that as low as 10% chimerism of the myeloid compartment is associated with peripheral blood red cell chimerism of 80-100% (35). The skewing of red cell mass after engraftment is most likely attributable to the enhanced survival of normal red cells compared with sickled cells. This level of marking of long-lived myeloid cells has recently been attained in a human trials utilizing lentivirus vector (36-38), including in βe-thalassemia (39).

Pol III driven shRNAs are the most commonly utilized vector systems to effect gene knockdown by RNAi, but these vectors mediate ubiquitous expression that may be associated with both non-specific toxicities from high expression levels and sequence-specific toxicities in certain cell types. Here the inventors demonstrate that BCL11A knockdown in HSCs impairs engraftment of these cells in transplant settings and B cell development in vivo. Although reduced engraftment in the absence of BCL11A is an unreported phenomenon, the data reported here are consistent with known expression of BCL11A in early HSPCs and with the report of a ~two-fold reduced HSC content in mice upon genetic deletion of BCL11A (31, 40, 41). The negative impact of BCL11A knockdown on engrafting HSCs may be more evident in the assays reported here due to increased selective pressure present in this experimental setting. Limiting numbers of HSCs are generally present following ex vivo culture and transduction of these cells and competition with control HSCs utilized in the assays used here may enhance the detection of toxicity at the HSC level. Within the erythroid lineage BCL11A is dispensable (24). In the data reported here, use of the erythroid specific LCR-vector, containing regulatory sequences derived from the β-globin locus (32, 42) circumvented the negative effects of BCL11A knockdown on HSC engraftment. The LCR-vector displayed a high degree of lineage fidelity in expression of the shRNAmiR targeting BCL11A. In addition, this vector architecture has been demonstrated to reduce the risk of transactivation of neighboring cellular genes when used to express other transgenes (43), an important feature for clinical translation. Thus, transcriptional targeting of shRNAmiRs appears critical in the case of BCL11A, underscoring the importance of developing effective pol II based knockdown vectors. This approach bypasses the negative impact of knockdown of BCL11A on HSPCs and also lymphoid cell development (30, 31), avoids toxicity related to shRNA overexpression (9, 11, 19) and improves the safety profile of the vector system, while maintaining the therapeutic efficacy.

The use of pol II promoters for shRNA expression necessitates embedding the shRNA in microRNA sequences. As the majority of previously validated effective shRNA sequences are derived from analyses performed using pol III promoters and the majority of commercially available knockdown systems are based on pol III promoters, conversion of shRNA sequences into a pol II configuration is important. In spite of significant research in this area, guidelines for conversion of shRNA sequences derived from effective pol III based vectors into pol II based shRNAmiR vectors are lacking. Here by comparing the results of RNA processing from cells transduced with both types of vectors in parallel the inventors confirmed that different small RNA products are generated with respect to the target matched sequences resulting in a markedly reduced efficiency of target knockdown via pol II based vectors. The mature guide strand sequences produced from pol II versus pol III systems containing identical target mRNA matched sequences are generally shifted by 3-5 nt relative to each other. Addition of 3-5 U-residues from the pol III termination signal to the 3' end of the shRNA transcript leads to a corresponding shift of the Dicer cleavage site, proving the dominant role of the 3'-counting rule for Dicer cleavage (44, 45). The shift of the guide strand in pol III versus pol II has a major impact on knockdown efficiency, as the seed region is altered and the thermodynamical properties and terminal nucleotide identity of the small RNA duplex changes, thereby impacting guide strand incorporation into the RISC-effector complex (4, 5, 46, 47). Re-engineering shRNAmiRs to mimic the mature guide strand sequences produced by pol III-driven shRNAs led to enhanced processing and improved knockdown of the target mRNA. This approach should be applicable for the development of vectors targeting other genes using pol II promoters, including other lineage specific expression cassettes.

In summary, the data demonstrate critical features of RNA processing relevant to the use of shRNA in different vector contexts, and also provide a strategy for lineage-specific gene knockdown that circumvents adverse consequences of widespread expression. The findings have important implications for design of microRNA embedded shRNAs and their application in RNAi based gene therapy approaches.

Example 11

Efficacy Studies of Transduction of BCL11A shRNAmiR in Health Donor Human CD34+ Cells.

The transcriptional repressor BCL11A represents a therapeutic target for β-hemoglobinopathies. The selectively suppression of BCL11A in erythroid cells via pol II promoter expressed microRNA adapted shRNAs (shRNAmiRs) resulted in effective knockdown of BCL11A in both murine and human cells. Expressing the modified shRNAmiRs in an erythroid-specific fashion circumvented the adverse effects on murine HSC engraftment and B cell development (see EXAMPLE 10 supra) and led to efficient BCL11A knock-down and high levels of HbF in primary human CD34- derived erythroid cells and in human erythroid cells differentiated in vitro after full engraftment of modified CD34+ cells in murine xenografts. The inventors also demonstrated effective induction of HbF in erythroid cells derived from transduced CD34 cells obtained from a donor with sickle cell disease.

In a series of experiments, GCSF mobilized CD34 from healthy donors were transduced with a vector expressing a non-targeting shRNA (LCR-NT) or BMS11-D12G5, and subjected to erythroid in vitro differentiation.

BCL11A D12G5-2 shRNA: Sense
(SEQ. ID. NO: 43)
ACGCTCGCACAGAACACTCATGGATTctccatgtggtagagAATCCATGA

GTGTTCTGTGCGAG

Anti-sense
(SEQ. ID. NO: 44)
CGCACTCGCACAGAACACTCATGGATTactaccacatggagAATCCATGA

GTGTTCTGTGCGA

Figure 27:
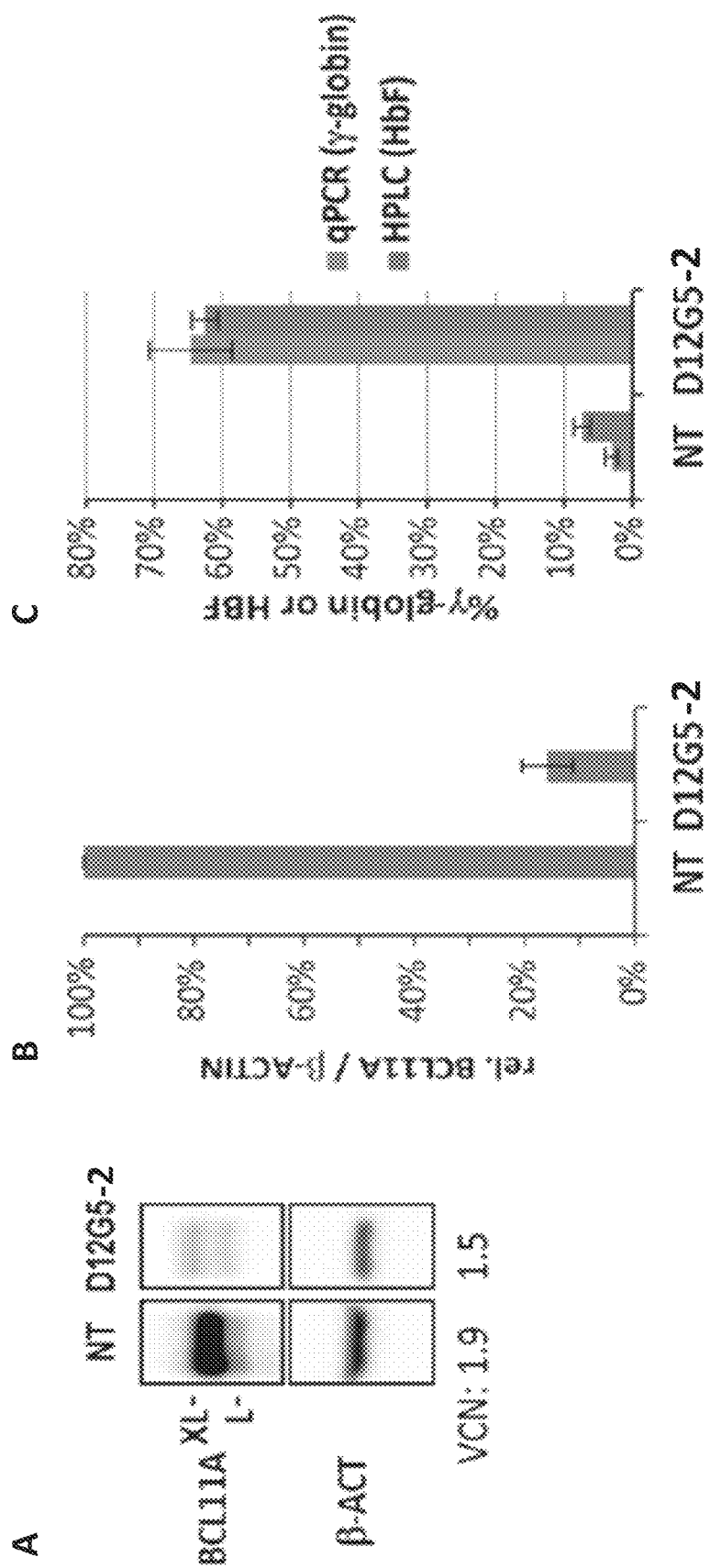
FIG. 27A is a Western blot of in vitro differentiated erythroid cells derived from transduced CD34+ cells from healthy donors showing BCL11A isoforms (L and XL) and β-ACTIN as loading control and demonstrating effective knock-down of BCL11A XL. VCN determined by DNA PCR is show below each lane.
FIG. 27B shows quantification of BCL11A knock down in erythroid cells. Data is derived from Western blots as shown in FIG. 27A. Data summarizes three independent experiments using cells from a single donor. (Error bars: SD)
FIG. 27C shows induction of gamma globin in erythroid cells as assessed by RT-qPCR and hemoglobin (HbF) assessed by HPLC. (Error bars: SD)

FIG. 27A is a Western blot of in vitro differentiated erythroid cells derived from transduced CD34 cells showing BCL11A isoforms (L and XL) and β-ACTIN as loading control and demonstrating effective knock-down of BCL11A XL. FIG. 27B shows quantification of BCL11A knock down in erythroid cells. Data is derived from Western blots as shown in FIG. 27A. Data summarizes three independent experiments using cells from a single donor. (Error bars: SD)

FIG. 27C shows induction of gamma globin in erythroid cells as assessed by RT-qPCR and hemoglobin (HbF) assessed by HPLC.

Example 12

Quantification of BCL11A Knock Down in Erythroid Cells.

Figure 28:
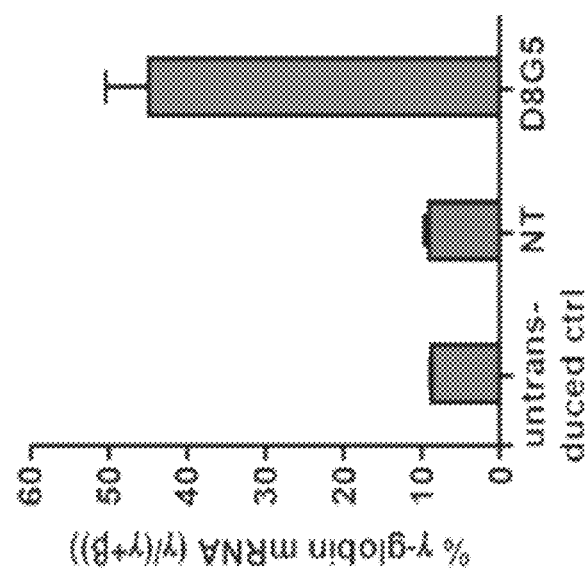
FIG. 28 shows induction of gamma globin in erythroid cells as assessed by RT-qPCR. The amount of gamma globin induction in the erythroid cells is a measure of the in vivo BCL11A knockdown in the cells. Error bars: SD. Data from three transplanted animals per group is shown.

The engraftment of the transduced CD34+ cells into NSG immunodeficient mice were studied, including the effectiveness of the in vivo knockdown of the BCL11A expression. Human CD34 were transduced with LCR-NT or BMS11-D8G5 and injected into sublethally irradiated NSG-recipient mice. Bone marrow CD34+ were isolated 14 weeks later and subjected to erythroid in vitro differentiation. FIG. 28 shows induction of gamma globin in erythroid cells as assessed by RT-qPCR.

Example 13

Knockdown of BCL11A and Induction of Fetal Hemoglobin in Erythroid Cells Derived from Transduced CD34 Cells from a Sickle Cell Patient.

Bone marrow CD34 were isolated from a SCD-patient which received HU treatment and had high baseline HBF. The cells were tranduced with LCR-NT or LCR-D12G5 and subjected to erythroid in vitro differentiation.

Figure 29:
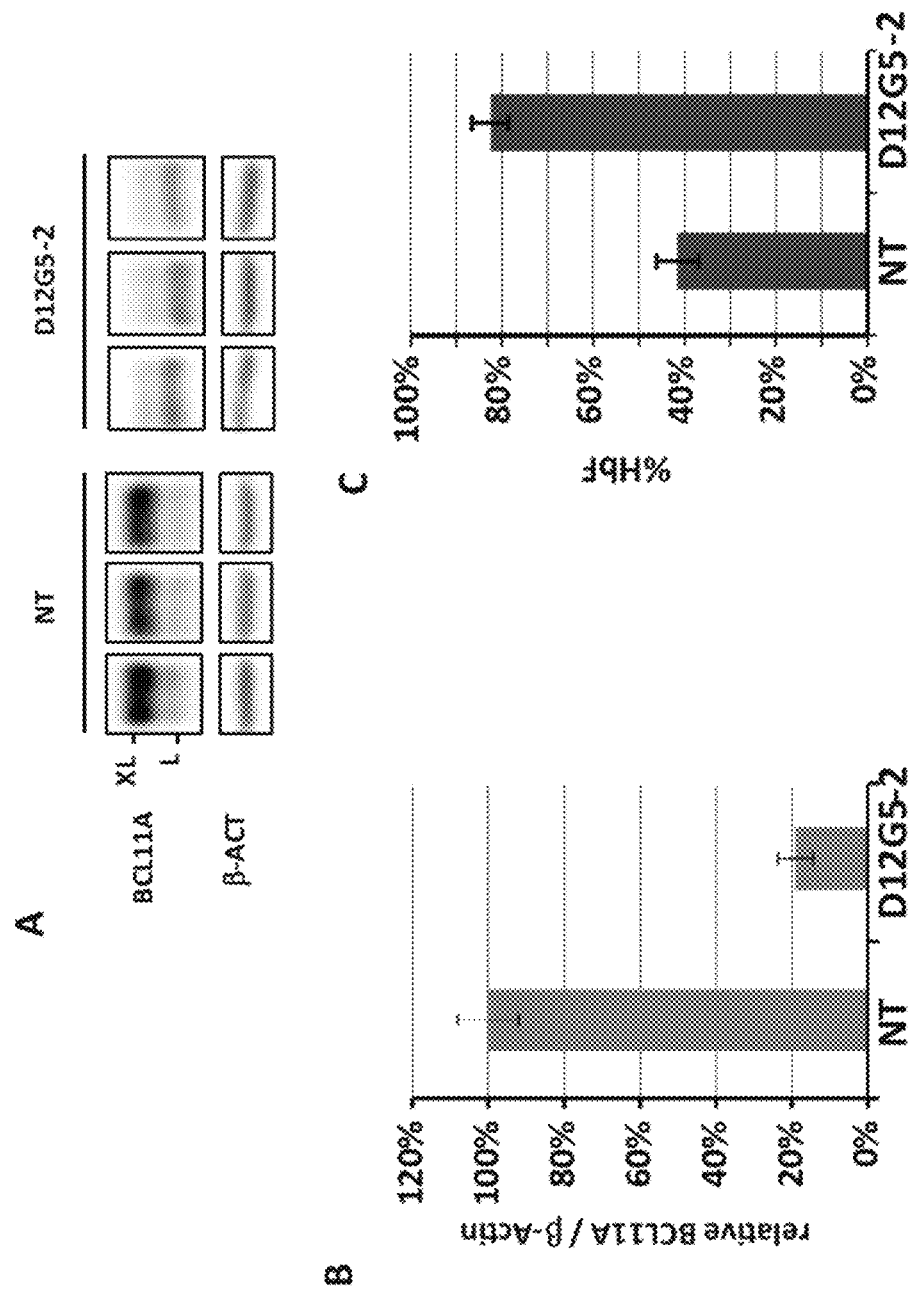
FIG. 29A shows Western blots showing of BCL11A (L and XL isoforms) and 13-ACTIN as loading control and demonstrates effective knock-down of BLC11A-XL. Each panel (labeled 1-6 below the lane) represents an independent experiment using cells from a single donor.
FIG. 29B shows quantification of BCL11A knock down in erythroid cells. Data is derived from Western blots shown in FIG. 29A. (Error bar: SD)
FIG. 29C shows resulting induction of HF by HPLC. (Error bars: SD)

BCL11A knock-down was studied in sickle cell patient cells. Bone marrow CD34 were isolated from a sickle cell patient and the cells were transduced with LCR-NT or LCR-D12G5-2 (untransduced cells used as an additional control) and subjected to erythroid differentiation in vitro. FIG. 29A shows Western blots showing of BCL11A (L and XL isoforms) and β-ACTIN as loading control and demonstrates effective knock-down of BLC11A-XL. Each panel (labeled 1-6 below the lane) represents an independent experiment using cells from a single donor. FIG. 29B shows quantification of BCL11A knockdown in erythroid cells. Data is derived from Western blots shown in FIG. 29A. FIG. 29C shows resulting induction of HF by HPLC. This patient was receiving hydroxyurea treatment which accounts for the high baseline Hb F level.

Example 14

An Embodiment of a Treatment Protocol
Initial Evaluation

Patients will undergo standard work-up for autologous bone marrow transplantation according to institutional guidelines, and then undergo two bone marrow harvests at a minimum of 4 weeks apart that will be used for a back-up marrow (minimum of $2 \times 10^6$ CD34+ cells/kg) and for a harvest of autologous bone marrow for gene transfer (target of $5 \times 10^6$ CD34+ cells/kg with a minimum of $4 \times 10^6$ CD34+ cells/kg).

Harvest of a Back-up Autologous Graft

Hematopoietic cells will be collected from the patient in advance of the treatment, to serve as a salvage procedure ("back-up graft"), should there be no hematopoietic recovery observed 6 weeks following the injection of genetically-manipulated cells, or should manipulated cells fail to meet release criteria. Bone marrow (up to 20 cc/kg) will be harvested from the patient under general anesthesia from the posterior iliac crests on both sides by multiple punctures at a minimum of 4 weeks prior to gene therapy. A portion of the bone marrow containing $2 \times 10^6$ CD34+ cells/kg will be frozen and stored unmanipulated in liquid nitrogen vapors (162° C. and -180° C.) according to standard clinical procedures for autologous bone marrow collection to constitute the back-up graft. The remainder of the harvest will be selected for CD34+ cells (described below) and utilized for gene modification (described below).

Bone Marrow Harvest

The remainder of the first bone marrow harvest in excess of the needed back up marrow will be utilized with a second bone marrow harvest for gene transfer. The second harvest will occur no sooner than 4 weeks after the initial harvest (described above). For the second harvest, bone marrow will again be harvested from the patient under general anesthesia from the posterior iliac crests on both sites by multiple punctures. The amount of marrow collected will be up to 20 ml/kg of body weight. This will give a total nucleated cell count of greater than ~$4 \times 10^8$ cells/kg. This in turn should yield a CD34+ cell dose of greater than $4 \times 10^6$ cells/kg after CD34+ cell selection.

Subjects from whom the estimated CD34+ count of both harvests is <$4 \times 10^6$ cells/kg will not receive conditioning. After a period of at least 6 weeks, if the subject wishes to remain on study, he may be harvested again. If the subject does not wish to be harvested again, he will be withdrawn from the study.

Subjects withdrawn from the study prior to administration of transduced CD34+ cells will resume normal clinical care (supportive care and/or allogeneic HSCT). Efficacy and safety assessments will not be carried out from the point of withdrawal and data will not be collected for the database.

CD34+ Cell Isolation, Pre-stimulation, and Transduction

CD34+ Cell Purification.

To allow sufficient time for clearance of conditioning agents and minimize the time of pre-stimulation and culture, whole bone marrow will be held overnight. All the manufacturing steps are performed in the Connell & O'Reilly Families Cell Manipulation Core Facility at the DFCI. The bone marrow will be red cell-depleted by density gradient centrifugation. CD34+ cells will be positively selected from the bone marrow mononuclear cells using the CliniMACS reagent and instrument. Quality control (QC) samples are taken to assess purity and sterility. Purified cells will be immediately processed for pre-stimulation and transduction.

CD34+ Pre-stimulation and Transduction

Transduction will be carried out on one or both harvests. Transduction of cells in excess of the back-up marrow target from the first harvest will be transduced and frozen for future use. The second harvest will be used for gene transfer in its entirety and the transduced product of the second harvest will be infused with the thawed transduced cells from the first harvest after conditioning.

Purified CD34+ cells are seeded in closed culture bags at a density of $0.5-1 \times 10^6$/ml in serum-free medium supplemented with growth factors (IL-3, SCF, FLT3L, TPO) and placed in an incubator at 37° C., 5% $CO_2$. After 24-30 hours, cells are harvested and counted. Additional QC testing includes cell viability, and Colony Forming Unit (CFU) assay. Cells are transferred to a new culture bag and treated with lentiviral supernatant. For this first round of transduction, cells are incubated for 18-24 hours. Cells are then harvested, counted, and transferred to a new bag, with lentiviral supernatant for a second round of transduction.

Final Harvest and Formulation

After the second round of transduction, cells are harvested, washed in plasmalyte and resuspended in their final formulation (PLASMALYTE, 1% HSA) in a volume of 50-100 mL. All cells available after removal of the QC samples will be infused into the patient. QC includes cell count, viability, sterility on wash supernatant, Mycoplasma, Endotoxin on supernatant, phenotype, CFU, RCL (samples taken and archived), insertional analysis, and average vector copy number by qPCR (cultured cells). A sample for Gram stain is taken from the product immediately before delivery to the patient.

Testing Prior to Subject Re-infusion

Samples are collected during and at the end of the procedure for cell count and viability (trypan blue exclusion or equivalent), sterility, mycoplasma, transduction efficiency (vector copy number), Gram stain, endotoxin and RCL testing. Of these only cell viability, sterility (in process, 72 hours), Gram stain and endotoxin measurements will be available prior to infusion.

If microbiological cultures reveal transient bacterial contamination, by Gram stain or positive culture at 72 hours, Cell Manipulation Core Facility staff will contact the PI, the assistant medical director and attending physician to decide whether to infuse the back-up harvest or infuse the product with antibiotic coverage. If back-up harvest is infused, the subject will be withdrawn from the protocol. If the cell viability is <70%, sterility testing is positive, or endotoxin is >5 EU/kg/hr, the cells will not be returned, back-up harvest will be infused and the subject will be withdrawn from the protocol.

If viable cell count from both harvests/transductions is greater than or equal to $4 \times 10^6$ CD34+ cells/kg at the end of transduction, cells will be infused. If viable cell count from both harvests/transductions is less than $4 \times 10^6$ CD34+ cells/kg at the end of transduction, cells will not be infused and back-up harvest will be infused 48 hours later.

Subject Conditioning Regimen

Subjects will receive myeloablative conditioning with Busulfan (~4 mg/kg intravenously daily, adjusted for weight, (given over 3 hours once daily) administered on days −4 to −2, prior to infusion of transduced cells. Conditioning will occur concurrent with purification and transduction of bone marrow cells. Busulfan levels will be drawn on all 3 days of administration, and levels on days 1 and 2 will be used to adjust the area under the curve target.

Infusion of Transduced Cells

Cells will be infused intravenously over 30-45 minutes after standard prehydration and premedication according to Boston Children's Hospital Hematopoietic Stem Cell Transplantation Unit standard guidelines. This standard requires that the patient be on continuous cardiac, respiratory and oxygen saturation monitor throughout the infusion and for 30 minutes afterwards. Vital signs will be measured and recorded pre-transfusion, 15 minutes into transfusion, every hour for duration of infusion, and end of transfusion. The RN will stay with the patient for the first 5 minutes of the transfusion. If two transduction products are administered, the second transduced product will be administered without delay after the first.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Lee, Y. et al., The nuclear RNase III Drosha initiates microRNA processing. Nature 425, 415-419 (2003).
2. Ha, M. and Kim, V. N., Regulation of microRNA biogenesis. Nature reviews. Molecular cell biology 15, 509-524 (2014).
3. Winter, J. et al., Many roads to maturity: microRNA biogenesis pathways and their regulation. Nature cell biology 11, 228-234 (2009).
4. Khvorova, A. et al., Functional siRNAs and miRNAs exhibit strand bias. Cell 115, 209-216 (2003).
5. Schwarz, D. S. et al., Asymmetry in the assembly of the RNAi enzyme complex. Cell 115, 199-208 (2003).
6. Lai, E. C., Micro RNAs are complementary to 3' UTR sequence motifs that mediate negative post-transcriptional regulation. Nature genetics 30, 363-364 (2002).
7. Lewis, B. P. et al., Prediction of mammalian microRNA targets. Cell 115, 787-798 (2003).
8. Park, J. E. et al., Dicer recognizes the 5' end of RNA for efficient and accurate processing. Nature 475, 201-205 (2011).
9. Grimm, D. et al., Fatality in mice due to oversaturation of cellular microRNA/short hairpin RNA pathways. Nature 441, 537-541 (2006).
10. McBride, J. L. et al., Artificial miRNAs mitigate shRNA-mediated toxicity in the brain: implications for the therapeutic development of RNAi. Proc Natl Acad Sci USA 105, 5868-5873 (2008).
11. Khan, A. A. et al., Transfection of small RNAs globally perturbs gene regulation by endogenous microRNAs. Nat Biotechnol 27, 549-555 (2009).
12. Yi, R. et al., Overexpression of exportin 5 enhances RNA interference mediated by short hairpin RNAs and microRNAs. RNA 11, 220-226 (2005).
13. Borner, K. et al., Robust RNAi enhancement via human Argonaute-2 overexpression from plasmids, viral vectors and cell lines. Nucleic Acids Res 41, e199 (2013).
14. Grimm, D. et al., Argonaute proteins are key determinants of RNAi efficacy, toxicity, and persistence in the adult mouse liver. The Journal of clinical investigation 120, 3106-3119 (2010).
15. Diederichs, S. and Haber, D. A., Dual role for argonautes in microRNA processing and posttranscriptional regulation of microRNA expression. Cell 131, 1097-1108 (2007).
16. Persengiev, S. P. et al., Nonspecific, concentration-dependent stimulation and repression of mammalian gene expression by small interfering RNAs (siRNAs). RNA 10, 12-18 (2004).
17. Fish, R. J. and Kruithof, E. K., Short-term cytotoxic effects and long-term instability of RNAi delivered using lentiviral vectors. BMC Mol Biol 5, 9 (2004).
18. Jackson, A. L. and Linsley, P. S., Recognizing and avoiding siRNA off-target effects for target identification and therapeutic application. Nat Rev Drug Discov 9, 57-67 (2010).
19. Martin, J. N. et al., Lethal toxicity caused by expression of shRNA in the mouse striatum: implications for therapeutic design. Gene Ther 18, 666-673 (2011).
20. Zeng, Y. et al., Both natural and designed micro RNAs can inhibit the expression of cognate mRNAs when expressed in human cells. Molecular cell 9, 1327-1333 (2002).
21. Fellmann, C. et al., An optimized microRNA backbone for effective single-copy RNAi. Cell Rep 5, 1704-1713 (2013).
22. Amendola, M. et al., Regulated and multiple miRNA and siRNA delivery into primary cells by a lentiviral platform. Mol Ther 17, 1039-1052 (2009).
23. Sankaran, V. G. et al., Human fetal hemoglobin expression is regulated by the developmental stage-specific repressor BCL11A. Science (New York, N.Y. 322, 1839-1842 (2008).
24. Xu, J. et al., Correction of sickle cell disease in adult mice by interference with fetal hemoglobin silencing. Science 334, 993-996 (2011).
25. Cullen, B. R., Derivation and function of small interfering RNAs and microRNAs. Virus Res 102, 3-9 (2004).
26. Moffat, J. et al., A lentiviral RNAi library for human and mouse genes applied to an arrayed viral high-content screen. Cell 124, 1283-1298 (2006).
27. Xu, J. et al., Transcriptional silencing of {gamma}-globin by BCL11A involves long-range interactions and cooperation with SOX6. Genes Dev 24, 783-798 (2010).
28. Weber, K. et al., Lentiviral gene ontology (LeGO) vectors equipped with novel drug-selectable fluorescent proteins: new building blocks for cell marking and multigene analysis. Gene Ther 17, 511-520 (2010).
29. Wilber, A. et al., Therapeutic levels of fetal hemoglobin in erythroid progeny of beta-thalassemic CD34+ cells after lentiviral vector-mediated gene transfer. Blood 117, 2817-2826 (2011).
30. Liu, P. et al., BCL11A is essential for normal lymphoid development. Nat Immunol 4, 525-532 (2003).
31. Yu, Y. et al., BCL is essential for lymphoid development and negatively regulates p53. J Exp Med 209, 2467-2483 (2012).
32. Miccio, A. et al., In vivo selection of genetically modified erythroblastic progenitors leads to long-term correction of beta-thalassemia. Proceedings of the National Academy of Sciences of the United States of America 105, 10547-10552 (2008).
33. Demaison, C. et al., High-level transduction and gene expression in hematopoietic repopulating cells using a human immunodeficiency [correction of imunodeficiency] virus type 1-based lentiviral vector containing an internal spleen focus forming virus promoter. Hum Gene Ther 13, 803-813 (2002).
34. Hansbury, E. N. et al., Bone marrow transplant options and preferences in a sickle cell anemia cohort on chronic transfusions. Pediatr Blood Cancer 58, 611-615 (2012).
35. Andreani, M. et al., Quantitatively different red cell/nucleated cell chimerism in patients with long-term, persistent hematopoietic mixed chimerism after bone marrow transplantation for thalassemia major or sickle cell disease. Haematologica 96, 128-133 (2011).
36. Cartier, N. et al., Hematopoietic stem cell gene therapy with a lentiviral vector in X-linked adrenoleukodystrophy. Science (New York, N.Y. 326, 818-823 (2009).
37. Biffi, A. et al., Lentiviral Hematopoietic Stem Cell Gene Therapy Benefits Metachromatic Leukodystrophy. Science (New York, N.Y., (2013).

38. Aiuti, A. et al., Lentiviral hematopoietic stem cell gene therapy in patients with Wiskott-Aldrich syndrome. Science 341, 1233151 (2013).
39. Cavazzana-Calvo, M. et al., Transfusion independence and HMGA2 activation after gene therapy of human beta-thalassaemia. Nature 467, 318-322 (2010).
40. Wu, X. et al., BCL11A controls Flt3 expression in early hematopoietic progenitors and is required for pDC development in vivo. PLoS One 8, e64800 (2013).
41. Ippolito, G. C. et al., Dendritic cell fate is determined by BCL11A. Proc Natl Acad Sci USA 111, E998-1006 (2014).
42. Roselli, E. A. et al., Correction of beta-thalassemia major by gene transfer in haematopoietic progenitors of pediatric patients. EMBO Mol Med 2, 315-328 (2010).
43. Zychlinski, D. et al., Physiological promoters reduce the genotoxic risk of integrating gene vectors. Mol Ther 16, 718-725 (2008).
44. Zhang, H. et al., Single processing center models for human Dicer and bacterial RNase III. Cell 118, 57-68 (2004).
45. Vermeulen, A. et al., The contributions of dsRNA structure to Dicer specificity and efficiency. RNA 11, 674-682 (2005).
46. Chiang, H. R. et al., Mammalian microRNAs: experimental evaluation of novel and previously annotated genes. Genes Dev 24, 992-1009 (2010).
47. Frank, F. et al., Structural basis for 5'-nucleotide base-specific recognition of guide RNA by human AGO2. Nature 465, 818-822 (2010).
48. Giarratana, M. C. et al., Proof of principle for transfusion of in vitro-generated red blood cells. Blood 118, 5071-5079 (2011).
49. Grimson, A. et al., Early origins and evolution of microRNAs and Piwi-interacting RNAs in animals. Nature 455, 1193-1197 (2008).

List of synthetic miR oligonucleotides

```
BCL11A miR1 oligos:
Sense
                                                         (SEQ ID NO: 1)
ACGCTCGCACAGAACACTCATGGATTctccatgtggtagagAATCCATGAGTGTTCTGTGCGag Anti-sense
                                                         (SEQ ID NO: 2)
CGCActCGCACAGAACACTCATGGATTctctaccacatggagAATCCATGAGTGTTCTGTGCGa BCL11A miR2 oligos:
Sense
                                                         (SEQ ID NO: 3)
ACGCTCCAGAGGATGACGATTGTTTActccatgtggtagagTAAACAATCGTCATCCTCTGGag Anti-sense
                                                         (SEQ ID NO: 4)
CGCActCCAGAGGATGACGATTGTTTActctaccacatggagTAAACAATCGTCATCCTCTGGa BCL11A E3 oligos:
Sense
                                                         (SEQ ID NO: 5)
ACGCTTCGGAGACTCCAGACAATCGCctccatgtggtagagGCGATTGTCTGGAGTCTCCGAag Anti-sense
                                                         (SEQ ID NO: 6)
CGCActTCGGAGACTCCAGACAATCGCctctaccacatggagGCGATTGTCTGGAGTCTCCGAa BCL11A D8 oligos:
Sense
                                                         (SEQ ID NO: 7)
ACGCTTTCTCTTGCAACACGCACAGActccatgtggtagagTCTGTGCGTGTTGCAAGAGAAag Anti-sense
                                                         (SEQ ID NO: 8)
CGCActTTCTCTTGCAACACGCACAGActctaccacatggagTCTGTGCGTGTTGCAAGAGAAa BCL11A XLC4 or C4 oligos:
Sense
                                                         (SEQ ID NO: 9)
ACGCTACAGTACCCTGGAGAAACACActccatgtggtagagTGTGTTTCTCCAGGGTACTGTag Anti-sense
                                                        (SEQ ID NO: 10)
CGCActACAGTACCCTGGAGAAACACActctaccacatggagTGTGTTTCTCCAGGGTACTGTa Non-targeting oligos:
Sense
                                                        (SEQ ID NO: 11)
ACGCTCAACAAGATGAAGAGCACCAActccatgtggtagagTTGGTGCTCTTCATCTTGTTGag Anti-sense
                                                        (SEQ ID NO: 12)
CGCActCAACAAGATGAAGAGCACCAActctaccacatggagTTGGTGCTCTTCATCTTGTTGa
```

BCL11A E3G5 or E3 mod oligos: (modified version)
Sense
(SEQ ID NO: 13)
ACGCTGCGCTCGGAGACTCCAGACAActccatgtggtagagTTGTCTGGAGTCTCCGAGCGCag Antisense
(SEQ ID NO: 14)
CGCActGCGCTCGGAGACTCCAGACAActctaccacatggagTTGTCTGGAGTCTCCGAGCGC a BCL11A D8G5 or D8 mod oligos: (modified version)
Sense
(SEQ ID NO: 15)
ACGCTGCGCTTCTCTTGCAACACGCActccatgtggtagagTGCGTGTTGCAAGAGAAGCGCag Antisense
(SEQ ID NO: 16)
CGCActGCGCTTCTCTTGCAACACGCActctaccacatggagTGCGTGTTGCAAGAGAAGCGC a BCL11A XLC4G5 oligos: (modified version)
Sense
(SEQ ID NO: 17)
ACGCTGCGCACAGTACCCTGGAGAAActccatgtggtagagTTTCTCCAGGGTACTGTGCGCag Antisense
(SEQ ID NO: 18)
CGCActGCGCACAGTACCCTGGAGAAActctaccacatggagTTTCTCCAGGGTACTGTGCGCa mIR1
(SEQ ID NO: 25)
CGCACAGAACACTCATGGATTctccatgtggtagagAATCCATGAGTGTTCTGTGCG (shRNA1 or E3)
(SEQ ID NO: 26)
TCGGAGACTCCAGACAATCGCctccatgtggtagagGCGATTGTCTGGAGTCTCCGA (shRNA2 or B5)
(SEQ ID NO: 27)
CCTCCAGGCAGCTCAAAGATCctccatgtggtagagGATCTTTGAGCTGCCTGGAGG (shRNA3 or D8)
(SEQ ID NO: 28)
TTCTCTTGCAACACGCACAGActccatgtggtagagTCTGTGCGTGTTGCAAGAGAA (shRNA4 or B11)
(SEQ ID NO: 29)
TCAGGACTAGGTGCAGAATGTctccatgtggtagagACATTCTGCACCTAGTCCTGA (shRNA5 or 50D12 or D12)
(SEQ ID NO: 30)
GATCGAGTGTTGAATAATGATctccatgtggtagagATCATTATTCAACACTCGATC (shRNA6 or 50A5 or A5)
(SEQ ID NO: 31)
CAGTACCCTGGAGAAACACATctccatgtggtagagATGTGTTTCTCCAGGGTACTG (shRNA7 or 50B11)
(SEQ ID NO: 32)
CACTGTCCACAGGAGAAGCCActccatgtggtagagTGGCTTCTCCTGTGGACAGTG (shRNA8 or 50C4)
(SEQ ID NO: 33)
ACAGTACCCTGGAGAAACACActccatgtggtagagTGTGTTTCTCCAGGGTACTGT mIR1G5
(SEQ ID NO: 34)
gcgcCGCACAGAACACTCATGctccatgtggtagagCATGAGTGTTCTGTGCGgcgc (shRNA1mod or E3G5)
(SEQ ID NO: 35)
gcgcTCGGAGACTCCAGACAActccatgtggtagagTTGTCTGGAGTCTCCGAgcgc (shRNA2mod or B5G5)
(SEQ ID NO: 36)
gcgcCCTCCAGGCAGCTCAAActccatgtggtagagTTTGAGCTGCCTGGAGGgcgc (shRNA3mod or D8G5)
(SEQ ID NO: 37)
gcgcTTCTCTTGCAACACGCActccatgtggtagagTGCGTGTTGCAAGAGAAgcgc (shRNA4mod or B11G5)

-continued

```
                                                 (SEQ ID NO: 38)
gcgcTCAGGACTAGGTGCAGActccatgtggtagagTCTGCACCTAGTCCTGAgcgc (shRNA5mod or 50D12G5 or D12G5)
                                                 (SEQ ID NO: 39)
gcgcGATCGAGTGTTGAATAActccatgtggtagagTTATTCAACACTCGATCgcgc (shRNA6mod or 50A5G5)
                                                 (SEQ ID NO: 40)
gcgcCAGTACCCTGGAGAAACctccatgtggtagagGTTTCTCCAGGGTACTGgcgc (shRNA7mod or 50B11G5)
                                                 (SEQ ID NO: 41)
gcgcCACTGTCCACAGGAGAActccatgtggtagagTTCTCCTGTGGACAGTGgcgc (shRNA8mod or 50C4G5 or C4G5)
                                                 (SEQ ID NO: 42)
gcgcACAGTACCCTGGAGAAActccatgtggtagagTTTCTCCAGGGTACTGTgcgc (BCL11A D12G5-2 shRNA):
Sense
                                                (SEQ. ID. NO: 43)
ACGCTCGCACAGAACACTCATGGATTctccatgtggtagagAATCCATGAGTGTTCTGTGCGAG (BCL11A D12G5-2 shRNA):
Anti-sense
                                                (SEQ. ID. NO: 44)
CGCACTCGCACAGAACACTCATGGATTctctaccacatggagAATCCATGAGTGTTCTGTGCGA (SEQ. ID. NO: 86)
5'-CCGGCGCACAGAACACTCATGGATTCTCGAGAATCCATGAGTGTTCTGTGCGTTTTTT-3'

(SEQ. ID. NO: 87)
5' CGCTCGCACAGAACACTCATGGATTctccatgtggtagagAATCCATGAGTGTTCTGTGCGA
GTG-3'

(SEQ. ID. NO: 88)
5' CGCTGCGCCGCACAGAACACTCATGctccatgtggtagagCATGAGTGTTCTGTGCGGCGCA
GTG-3'

(SEQ. ID. NO: 89)
5'-CCGGACAGTACCCTGGAGAAACACACTCGAGTGTGTTTCTCCAGGGTACTGTTTTTT-3'

(SEQ. ID. NO: 90)
5'-CGCTACAGTACCCTGGAGAAACACActccatgtggtagagTGTGTTTCTCCAGGGTACTGT
AGTG-3'

(SEQ. ID. NO: 91)
5' CGCTGCGCACAGTACCCTGGAGAAActccatgtggtagagTTTCTCCAGGGTACTGTGCGCA
GTG-3'

(SEQ. ID. NO: 92)
5'-CCGGTTCTCTTGCAACACGCACAGACTCGAGTCTGTGCGTGTTGCAAGAGAATTTTT-3'

(SEQ. ID. NO: 93)
5' CGCTTTCTCTTGCAACACGCACAGActccatgtggtagagTCTGTGCGTGTTGCAAGAGAAA
GTG-3'

(SEQ. ID. NO: 94)
5' CGCTGCGCTTCTCTTGCAACACGCActccatgtggtagagTGCGTGTTGCAAGAGAAGCGCA
GTG-3'

(SEQ. ID. NO: 95)
5'-CCGGGATCGAGTGTTGAATAATGATCTCGAGATCATTATTCAACACTCGATCTTTTT-3'

(SEQ. ID. NO: 96)
5'-CGCTGATCGAGTGTTGAATAATGATctccatgtggtagagATCATTATTCAACACTCGATC
AGTG-3'

(SEQ. ID. NO: 97)
5' CGCTGCGCGATCGAGTGTTGAATAActccatgtggtagagTTATTCAACACTCGATCGCGCA
GTG-3'
```

| New name | Old name |
|---|---|
| shRNA1 | E3 |
| shRNA2 | B5 |
| shRNA3 | D8 |
| shRNA4 | B11 |
| shRNA5 | 50D12 or D12 |
| shRNA6 | 50A5 or A5 |
| shRNA7 | 50B11 |
| shRNA8 | 50C4 |
| shRNA1mod | E3G5 |
| shRNA2mod | B5G5 |

-continued

| New name | Old name |
|---|---|
| shRNA3mod | D8G5 |
| shRNA4mod | B11G5 |
| shRNA5mod | 50D12G5 or D12G5 |
| shRNA6mod | 50A5G5 |
| shRNA7mod | 50B11G5 |
| shRNA8mod | 50C4G5 or C4G5 |

What is claimed is:

1. A hematopoietic stem or progenitor cell comprising a lentiviral vector that comprises a nucleic acid encoding:
   a) a first BCL11A segment that comprises a BCL11A sequence, a loop segment; and
   b) a second BCL11A segment arranged in tandem in a 5' to 3' direction,
   wherein the loop segment is between and directly linked to the first and second BCL11A segments,
   wherein the second BCL11A segment is complementary to the first BCL11A segment so that the first and second BCL11A segments base pair to form a hairpin loop with the loop segment forming the loop portion of the hairpin loop thus formed; and
   wherein the first BCL11A segment starts with a -GCGC- at the 5' end and the second BCL11A segment ends with a -GCGC- at the 3' end.

2. The hematopoietic stem or progenitor cell of claim 1, wherein the cell is a hematopoietic stem cell.

3. The hematopoietic stem or progenitor cell of claim 1, wherein the cell is a hematopoietic progenitor cell.

4. The hematopoietic stem or progenitor cell of claim 1, wherein the cell is an erythroid cell.

5. The hematopoietic stem or progenitor cell of claim 1, wherein the first and second BCL11A segments are about 18 to 25 nucleotides long.

6. The hematopoietic stem or progenitor cell of claim 1, wherein the first BCL11A segment contains a sequence derived from a BCL11A mRNA sequence.

7. The hematopoietic stem or progenitor cell of claim 1, wherein the first BCL11A segment is complementary to the second BCL11A segment.

8. The hematopoietic stem or progenitor cell of claim 1, wherein the first BCL11A segment comprises the nucleotide sequence set forth in any one of SEQ ID NOs: 57, 58, 59, 60, 61, 62, 63, 64, and 65.

9. The hematopoietic stem or progenitor cell of claim 1, wherein the first BCL11A segment comprises the nucleotide sequence set forth in SEQ ID NO: 61.

10. The hematopoietic stem or progenitor cell of claim 1, wherein the loop segment is derived from a microRNA.

11. The hematopoietic stem or progenitor cell of claim 1, wherein the loop segment is derived from a microRNA selected from the group consisting of: miR-142, miR-155, miR-181 and miR-223.

12. The hematopoietic stem or progenitor cell of claim 1, wherein the loop segment is derived from miR223.

13. The hematopoietic stem or progenitor cell of claim 1, wherein the loop segment comprises the polynucleotide sequence set forth in SEQ ID NO: 68.

14. The hematopoietic stem or progenitor cell of claim 1, wherein the nucleic acid comprises a polynucleotide sequence selected from the group consisting of SEQ ID NOs: 34, 35, 36, 37, 38, 39, 40, 41, and 42.

15. The hematopoietic stem or progenitor cell of claim 1, wherein the nucleic acid comprises the polynucleotide sequence set forth SEQ ID NO: 39.

16. A composition comprising the hematopoietic stem or progenitor cell of any one of claims 1 to 15.

17. A composition comprising a pharmaceutically acceptable carrier or diluent and the hematopoietic stem or progenitor cell of any one of claims 1 to 15.

* * * * *